(12) United States Patent
Christensen et al.

(10) Patent No.: US 10,240,166 B2
(45) Date of Patent: Mar. 26, 2019

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: Ceres, Inc., Thousands Oaks, CA (US)

(72) Inventors: Cory Christensen, Simi Valley, CA (US); Jack Okamuro, Oak Park, CA (US); Shing Kwok, Woodland Hills, CA (US); Roger Pennell, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 171 days.

(21) Appl. No.: 15/362,633

(22) Filed: Nov. 28, 2016

(65) Prior Publication Data

US 2017/0166917 A1 Jun. 15, 2017

Related U.S. Application Data

(60) Division of application No. 11/779,266, filed on Jul. 17, 2007, which is a continuation-in-part of application No. 11/778,060, filed on Jul. 15, 2007, which is a continuation-in-part of application No. 11/248,547, filed on Oct. 12, 2005, now Pat. No. 7,244,879, which is a continuation-in-part of application No. 11/779,266, which is a continuation-in-part of application No. 11/248,547.

(51) Int. Cl.
| | |
|---|---|
| C12N 15/82 | (2006.01) |
| C07K 14/415 | (2006.01) |
| A01H 1/02 | (2006.01) |
| C12Q 1/6895 | (2018.01) |

(52) U.S. Cl.
CPC ........... C12N 15/8273 (2013.01); A01H 1/02 (2013.01); C07K 14/415 (2013.01); C12Q 1/6895 (2013.01); C12Q 2600/13 (2013.01); C12Q 2600/156 (2013.01)

(58) Field of Classification Search
None
See application file for complete search history.

(56) References Cited

U.S. PATENT DOCUMENTS

| | | | |
|---|---|---|---|
| 5,990,387 A | 11/1999 | Tomes et al. | |
| 2006/0107345 A1* | 5/2006 | Alexandrov | C07K 14/415 800/278 |
| 2006/0150283 A1* | 7/2006 | Alexandrov | C07K 14/415 800/288 |
| 2009/0094717 A1 | 4/2009 | Troukhan et al. | |
| 2009/0265815 A1* | 10/2009 | Alexandrov | C07K 14/415 800/298 |
| 2010/0083407 A1 | 4/2010 | Feldmann et al. | |
| 2016/0369294 A9* | 12/2016 | Nadzan | C07K 14/415 |
| 2018/0223303 A1* | 8/2018 | Alexandrov | C07K 14/415 |

FOREIGN PATENT DOCUMENTS

| | | | |
|---|---|---|---|
| EP | 1033405 | 9/2000 | |
| EP | 1033405 A2 * | 9/2000 | C07K 14/415 |

OTHER PUBLICATIONS

Wells, Biochemistry 29:8509-8517, 1990.*
Guo et al. (PNAS, 101: 9205-9210, 2004.*
Keskin et al. (Protein Science, 13:1043-1055, 2004.*
Thornton et al. (Nature structural Biology, structural genomics supplement, Nov. 2000).*
Ngo et al., Computational Complexity, Protein Structure Prediction, and the Levinthal Pradox, The Protein Folding Problem and Tertiary Structure Prediction, K. Merz and S. Le Grand (eds.), pp. 492-495, 1994.*
Kim et al., "Molecular cloning of low temperature-inducible ribosomal proteins from soybean," *Journal of Experimental Botany* 55:1153-1155, 2004.
Lu et al., "*Arabidopsis* Mutants Deficient in Diacylglycerol Acyltransferase Display Increased Sensitivity to Abscisic Acid, Sugars, and Osmotic Stress during Germination and Seedling Development," *Plant Physiology* 129:1352-1358, 2002.
Ngo et al., "Computational Complexity, Protein Structure Prediction, and the Levinthal Pradox," *The Protein Folding Problem and Tertiary Structure Prediction*, K. Merz and S. Le Grand (eds.), pp. 492-495, 1994.
Guo et al., "Protein tolerance to random amino acid change," *PNAS* 101:9205-9210, 2004.
GenBank Accession No. AY117196, dated Sep. 18, 2002.
Keskin et al., "A new, structurally nonredundant, diverse data set of protein-protein interfaces and its implications," *Protein Science* 13:1043-1055, 2004.
Thornton et al., "From structure to function: Approaches and limitations," *Nature Structural Biology, Structural Gemonics Supplement*, Nov. 2000.
Wells, "Additivity of Mutational Effects in Proteins," *Biochemistry* 29:8509-8517, 1990.

* cited by examiner

*Primary Examiner* — Vinod Kumar
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased levels of cold tolerance and plant products produced from plants having increased cold tolerance levels.

7 Claims, 8 Drawing Sheets
Specification includes a Sequence Listing.

FIGURE 1

| | | | | | | |
|---|---|---|---|---|---|---|
| SEQ-ID-NO-4-GI-62526422 | MAL----SHPM | T-FSLFLTFL | ALTAAQSPMM | APT----MPP | PPS------T | 33 |
| SEQ-ID-NO-5-CLONE-1606506 | MAV----SRYI | LLLSFFTYLA | AFSTAQAPSM | SPM-MMPMAP | MSSGGGSSVP | 40 |
| SEQ-ID-NO-2-CLONE-30087 | MASSF-SSQAF | FLLTLSMVLI | PFSLAQAPMM | APSGSMSMPP | MPSGGS---P | 50 |
| SEQ-ID-NO-52-CLONE-1382611 | MAS----SSQAF | LLLTLSMVLV | HFSLAQSPMM | APSGSMSMPP | | 45 |

| | | | | | | |
|---|---|---|---|---|---|---|
| SEQ-ID-NO-4-GI-62526422 | -------S | TMSMPPTTST | TTPPPM-SSM | SPPPSAMSPT | P---SITMSPPP | 71 |
| SEQ-ID-NO-5-CLONE-1606506 | MPMTPPPSIM | PMTPPPTPMT | MTPPPMMMPM | TPPPMPMAPP | PMTMPMGPPP | 90 |
| SEQ-ID-NO-2-CLONE-30087 | PPVMS---M | PMMTPP-PP | MTPSPM-PM | TPPPMPMAPP | P---MPMASPP | 92 |
| SEQ-ID-NO-52-CLONE-1382611 | MPMMTPPP-M | PMMTPP-PPM | MAPPPM-PM | TPPPMPMAPM | P---MTPSSSP | 89 |

| | | | | | | |
|---|---|---|---|---|---|---|
| SEQ-ID-NO-4-GI-62526422 | MSPMTPSMSP | MGPMTPTMSP | MDSPPPAPAGP | GMAPGMSTPG | P---APGPMG | 118 |
| SEQ-ID-NO-5-CLONE-1606506 | MMMP----MSP | ------GPSMMP | -ASPPPPMGP | SMA-----PE | PATMSPGPSM | 127 |
| SEQ-ID-NO-2-CLONE-30087 | MMPMTPSTSP | ------SPLTVP | DMPSPPMPS | GME-----SSI | P---SPGP-M | 128 |
| SEQ-ID-NO-52-CLONE-1382611 | MSPPT-TMAP | ------SPETVP | DMASPPMMP | GMD-----SSI | P---SPGP-M | 124 |

| | | | | | |
|---|---|---|---|---|---|
| SEQ-ID-NO-4-GI-62526422 | GESMASPPPS | SCFVHGISIS | MAMV--ALC | SVALFF | 152 |
| SEQ-ID-NO-5-CLONE-1606506 | TPA--ETPAS | CATMQYSSIT | MLGI------V | | 150 |
| SEQ-ID-NO-2-CLONE-30087 | PPAMAASPDS | GAFNVRNNVV | TLSCVVGVVA | AHFLLV | 164 |
| SEQ-ID-NO-52-CLONE-1382611 | PPAM-ASPDS | GAFNVRNDVV | ALSF----VA | AHLLV | 156 |

FIGURE 2

| | | | | | | |
|---|---|---|---|---|---|---|
| SEQ-ID-NO-17-CLONE-839727 | MSAAE---GA | VVFSEEKEAL | VLKSWAIMKK | DSANLGLRFF | LKIFEIAPSA | 47 |
| SEQ-ID-NO-16-CLONE-1554560 | MALAE-ADDGA | VVFGEEQEAL | VLKSWAVMKK | DAANLGLRFF | LKVFEIAPSA | 50 |
| SEQ-ID-NO-60-CLONE-1802327 | MALAE---GN | VIFGEEQEAL | VLKSWALMKK | DSADLGLRFF | LKIFEIAPSA | 47 |
| SEQ-ID-NO-9-CLONE-30469-FL | -MESE---GK | VFTEEEQEAL | VVKSWSVMKK | NSAELGLKLF | LKIFEIAPTI | 46 |
| SEQ-ID-NO-10-GI-30909306 | -MESE---GK | VFTEEEQEAL | VVKSWSVMKK | NSADLGLKLF | LKIFEIAPTA | 46 |
| SEQ-ID-NO-13-CLONE-546001 | -MTT-LERG--- | -FSEEEQEAL | VVKSWNVMKK | NSCELGLKFF | LKIFEIAPSA | 46 |
| SEQ-ID-NO-70-CLONE-1916866 | MATYE---GK | -VFTEEEQEAL | VVKSWTVMKK | NAAELGLKFF | LKIFEIAPSA | 46 |
| | | | | | | |
| SEQ-ID-NO-17-CLONE-839727 | RQMFPFLRDS | DVPLETNPKL | KTHAVSVFVM | TCEAAAQLRK | AGKITVRETT | 97 |
| SEQ-ID-NO-16-CLONE-1554560 | KQMFSFLRDS | DVPLEKNPKL | KTHAMSVFVM | TCEAAAQLRK | AGKVTVRETT | 100 |
| SEQ-ID-NO-60-CLONE-1802327 | KQMFSFLRDS | DVPLEKNPKL | KNHAMSVFVM | TCESAAQLRK | AGKVTVRETT | 97 |
| SEQ-ID-NO-9-CLONE-30469-FL | KKMFSFLRDS | PIPAEQNPKL | KPHAMSVFVM | CCESAVQLRK | TGKVTVKETT | 96 |
| SEQ-ID-NO-10-GI-30909306 | KKLFSFLRDS | PIPAEQNPKL | KPHAMSVFVM | CCESAVQLRK | AGKVTVRETT | 96 |
| SEQ-ID-NO-13-CLONE-546001 | QKLFSFLRDS | TVPLEQNPKL | KPHAVSVFVM | TCDSAVQLRK | AGKVTVRESN | 96 |
| SEQ-ID-NO-70-CLONE-1916866 | KKLFSFLRDS | NVPLEQNTKL | KPHAMSVFVM | TCESAVQLRK | AGKVTVRESN | 96 |
| | | | | | | |
| SEQ-ID-NO-17-CLONE-839727 | LKRLGCTHLK | YGVADGHFEV | TRFALLETIK | EALPADMWGP | EMRNAWGEAY | 147 |
| SEQ-ID-NO-16-CLONE-1554560 | LKRLGATHLR | YGVADGHFEV | TGFALLETIK | EALPADMWSL | EMKKAWAEAY | 150 |
| SEQ-ID-NO-60-CLONE-1802327 | LKRLGATHFK | YGVADGHFEV | TRFALLETIK | EALPADMWSP | EMKNAWSEAY | 147 |
| SEQ-ID-NO-9-CLONE-30469-FL | LKRLGASHSK | YGVDEHFEV | AKYALLETIK | EAVP-EMWSP | EMKVAWGQAY | 145 |
| SEQ-ID-NO-10-GI-30909306 | LKRLGANHSK | YGVDEHFEV | TKYALLETIK | EAVP-EMWSP | EMKSAWGQAY | 145 |
| SEQ-ID-NO-13-CLONE-546001 | LKRLGATHFR | TGVANEHFEV | TKFALLETIK | EAVP-EMWSP | AMKNAWGEAY | 145 |
| SEQ-ID-NO-70-CLONE-1916866 | LKRLGATHFK | YGVDEHFEV | TKFALLETIK | EAVP-DMWSD | EMKNAWGEAY | 145 |
| | | | | | | |
| SEQ-ID-NO-17-CLONE-839727 | DQLVAAIKQE | MKPSE--- | | | | 162 |
| SEQ-ID-NO-16-CLONE-1554560 | SQLVAAIKRE | MKPDA--- | | | | 165 |
| SEQ-ID-NO-60-CLONE-1802327 | NQLVAAIKQE | MKPAA--- | | | | 162 |
| SEQ-ID-NO-9-CLONE-30469-FL | DHLVAAIKAE | MNLSN--- | | | | 160 |
| SEQ-ID-NO-10-GI-30909306 | DHLVDAIKAE | MKPSH--- | | | | 160 |
| SEQ-ID-NO-13-CLONE-546001 | DQLVAAIKSE | MKPPSS--- | | | | 161 |
| SEQ-ID-NO-70-CLONE-1916866 | DRLVAAIKE | MKACSQAA | | | | 163 |

FIGURE 3

| | | | | | | |
|---|---|---|---|---|---|---|
| SEQ-ID-NO-221-CLONE-839727-T | MSAAE---GA | VVFSEEKEAL | VLKSWAIMKK | DSANLGLRFF | LKIFEIAPSA | 47 |
| SEQ-ID-NO-207-CLONE-1554560-T | MALAEADDGA | VVFGEEQEAL | VLKSWAVMKK | DAANLGLRFF | LKVFEIAPSA | 50 |
| SEQ-ID-NO-208-CLONE-1802327-T | MALAE---GN | VIFGEEQEAL | VLKSWALMKK | DSADLGLRFF | LKIFEIAPSA | 47 |
| SEQ-ID-NO-7-CLONE-30469 | MESE---GK | LVFTEEQEAL | VVKSWSVMKK | NSAELGLKLF | KIFEIAPSA | 46 |
| SEQ-ID-NO-227-GI-30909306-T | MESE---GK | LVFTEEQEAL | VVKSWSVMKK | NSADLGLKLF | KIFEIAPTA | 46 |
| SEQ-ID-NO-219-CLONE-546001-T | MTIT---LE | RGFSEEEQEAL | VVKSWNVMKK | NSCELCLKFF | LKIFEIAPSA | 46 |
| SEQ-ID-NO-212-CLONE-1916866-T | MATY---EG | KVFTEEQEAL | VVKSWTVMKK | NAAELGLKFF | LKIFEIAPSA | 46 |

| | | | | | | |
|---|---|---|---|---|---|---|
| SEQ-ID-NO-221-CLONE-839727-T | RQMFPFLRDS | DVPLETNPKL | KTHAVSVFVM | --- | | 77 |
| SEQ-ID-NO-207-CLONE-1554560-T | KQMFSFLRDS | DVPLEKNPKL | KTHAMSVFVM | --- | | 80 |
| SEQ-ID-NO-208-CLONE-1802327-T | KQMFSFLRDS | DVPLEKNPKL | KNHAMSVFVM | --- | | 77 |
| SEQ-ID-NO-7-CLONE-30469 | KKMFSFLRDS | PIPAEQNPKL | KPHAMSVFVM | YN | | 78 |
| SEQ-ID-NO-227-GI-30909306-T | KKLFSFLRDS | PIPAEQNPKL | KPHAVSVFVM | --- | | 76 |
| SEQ-ID-NO-219-CLONE-546001-T | QKLFSFLRDS | TVPLEQNPKL | KPHAVSVFVM | --- | | 76 |
| SEQ-ID-NO-212-CLONE-1916866-T | KKLFSFLRDS | NVPLEQNTKL | KPHAMSVFVM | --- | | 76 |

FIGURE 4

| SEQ-ID-NO | Sequence (1-50) | |
|---|---|---|
| SEQ-ID-NO:20-CLONE:271922   | MAKRTKKVGI VGKYGTRYGA SLRKQI KKME VSQHSKYFCE FCGKYGVKRK | 50 |
| SEQ-ID-NO:54-CLONE:1627907  | MTKRTKKAGI VGKYGTRYGA SLRKQI KKME VSQHAKYFCE FCGKYAVKRQ | 50 |
| SEQ-ID-NO:25-CLONE:664936   | MTKRTKKAGI VGKYGTRYGA SLRKQI KKME VSQHSKFFCE FCGKYAVKRK | 50 |
| SEQ-ID-NO:28-CLONE:632613   | MTKRTKKAGI VGKYGTRYGA SLRKQI KKME VSQHSKYFCE FCGKYAVKRK | 50 |
| SEQ-ID-NO:29-CLONE:1390976  | MTKRTKKAGI VGKYGTRYGA SLRKQI KKME VSQHSKYFCE FCGKFAVKRK | 50 |
| SEQ-ID-NO:58-CLONE:1783890  | MTKRTKKAGI VGKYGTRYGA SLRKQI KKME VSQHSKYFCE FCGKFAVKRK | 50 |

| SEQ-ID-NO | Sequence (51-92) | |
|---|---|---|
| SEQ-ID-NO:20-CLONE:271922   | AVGI WGCKDC GKVKAGGAYT MNTASAVTVR STI RRLREQI EG | 92 |
| SEQ-ID-NO:54-CLONE:1627907  | AVGI WGCKDC GKVKAGGAYT LNTASAVTVR STI RRLREQT ES | 92 |
| SEQ-ID-NO:25-CLONE:664936   | AVGI WGCKDC GKVKAGGAYT LNTASAVTVR STI RRLREQT EG | 92 |
| SEQ-ID-NO:28-CLONE:632613   | AVGI WGCKDC GKVKAGGAYT MNTASAVTVR STI RRLREQT EA | 92 |
| SEQ-ID-NO:29-CLONE:1390976  | AVGI WGCKDC GKVKAGGAYT MNTASAVTVR STI RRLREQT EA | 92 |
| SEQ-ID-NO:58-CLONE:1783890  | AVGI WGCKDC GKVKAGGAYT MNTASAVTVR STI RRLREQT EA | 92 |

FIGURE 5

```
SEQ-ID-NO-34-CLONE-2403-FL    MQIFVKTLTG KTITLEVESS DTIDNVKAKI QDKEGIPPDQ QRLIFAGKQL  50
SEQ-ID-NO-35-CLONE-1482731    MQIFVKTLTG KTITLEVESS DTIDNVKAKI QDKEGIPPDQ QRLIFAGKQL  50
SEQ-ID-NO-36-CLONE-522921     MQIFVKTLTG KTITLEVESS DTIDNVKAKI QDKEGIPPDQ QRLIFAGKQL  50
SEQ-ID-NO-37-CLONE-1036726    MQIFVKTLTG KTITLEVESS DTIDNVKAKI QDKEGIPPDQ QRLIFAGKQL  50
SEQ-ID-NO-68-CLONE-1884696    MQIFVKTLTG KTITLEVESS DTIDNVKAKI QDKEGIPPDQ QRLIFAGKQL  50
SEQ-ID-NO-80-CLONE-2034916    MQIFVKTLTG KTITLEVESS DTIDNVKAKI QDKEGIPPDQ QRLIFAGKQL  50

SEQ-ID-NO-34-CLONE-2403-FL    EDGRTLADYN QKESTLHLV LRLRGGTMI K VKTLTGKEI E DIEPTDTI D  100
SEQ-ID-NO-35-CLONE-1482731    EDGRTLADYN QKESTLHLV LRLRGGTMI K VKTLTGKEI E DIEPTDTI D  100
SEQ-ID-NO-36-CLONE-522921     EDGRTLADYN QKESTLHLV LRLRGGTMI K VKTLTGKEI E DIEPTDTI D  100
SEQ-ID-NO-37-CLONE-1036726    EDGRTLADYN QKESTLHLV LRLRGGTMI K VKTLTGKEI E DIEPTDTI D  100
SEQ-ID-NO-68-CLONE-1884696    EDGRTLADYN QKESTLHLV LRLRGGMQ F VKTLTGKT T LEVESSDTI D  100
SEQ-ID-NO-80-CLONE-2034916    EDGRTLADYN QKESTLHLV LRLRGGMQ F VKTLTGKT T LEVESSDTI D  100

SEQ-ID-NO-34-CLONE-2403-FL    RIKERVEEKE GIPPVQQRLI YAGKQLADDK TAKDYAI EGG SVLHLVLALR  150
SEQ-ID-NO-35-CLONE-1482731    RIKERVEEKE GIPPVQQRLI YAGKQLADDK TAKDYNI EGG SVLHLVLALR  150
SEQ-ID-NO-36-CLONE-522921     RIKERVEEKE GIPPVQQRLI YAGKQLADDK TAKEYNI EGG SVLHLVLALR  150
SEQ-ID-NO-37-CLONE-1036726    RIKERVEEKE GIPPVQQRLI YAGKQLADDK TXKOYNI EGG SVSA        144
SEQ-ID-NO-68-CLONE-1884696    NVKAKI QDKE GIPPDQQRLI FAGKQLEDGR TLADYNI QKD STLHLVRLR   152
SEQ-ID-NO-80-CLONE-2034916    NVKVKI QDKE GIPPDQQRLI FAGKQLEDGR TLADYNI QKE STLHLVRLR   150

SEQ-ID-NO-34-CLONE-2403-FL    GGL ---------- ---------- ---------- ----------  153
SEQ-ID-NO-35-CLONE-1482731    GGS ---------- ---------- ---------- ----------  153
SEQ-ID-NO-36-CLONE-522921     GGT ---------- ---------- ---------- ----------  153
SEQ-ID-NO-37-CLONE-1036726    -SG ---------- ---------- ---------- ----------  146
SEQ-ID-NO-68-CLONE-1884696    -SG ---------- ---------- ---------- ----------  152
SEQ-ID-NO-80-CLONE-2034916    GGMQIFVKTL TGKTITLEVE SSDTIDNVKA KIQDKEGIPP DQQRLIFAGK  200

SEQ-ID-NO-34-CLONE-2403-FL    ---------- ---L                                       154
SEQ-ID-NO-35-CLONE-1482731    ---------- ---D                                       154
SEQ-ID-NO-36-CLONE-522921     ---------- ---Y                                       154
SEQ-ID-NO-37-CLONE-1036726    ---------- ---S                                       147
SEQ-ID-NO-68-CLONE-1884696    ---------- ---F                                       153
SEQ-ID-NO-80-CLONE-2034916    QLEDGRTLAD YNI                                        213
```

| SEQ-ID-NO-40-CLONE-2403 | MQI FVKTLTG | KTI TLEVESS | DTI DNVKAKI | QDK | 33 |
| SEQ-ID-NO-205-CLONE-1036726-T | MQI FVKTLTG | KTI TLEVESS | DTI DNVKAKI | QDK | 33 |
| SEQ-ID-NO-211-CLONE-1884696-T | MQI FVKTLTG | KTI TLEVESS | DTI DNVKAKI | QDK | 33 |
| SEQ-ID-NO-213-CLONE-1950105-T | MQI FVKTLTG | KTI TLEVESS | DTI DNVKAKI | QDK | 33 |
| SEQ-ID-NO-218-CLONE-522921-T | MQI FVKTLTG | KTI TLEVESS | DTI DNVKAKI | QDK | 33 |
| SEQ-ID-NO-206-CLONE-1482731-T | MQI FVKTLTG | KTI TLEVESS | DTI DNVKSKI | QDK | 33 |

| SEQ ID | | | | | | |
|---|---|---|---|---|---|---|
| SEQ-ID-NO-46-CLONE:1055099 | MRKARPPQPQ | P------- | -------- | ------QPSQQ | ELPYRGVRKR | PSCRYAAEIR | 38 |
| SEQ-ID-NO-56-CLONE:1761125 | MMRDTAAMAV | A------- | -------- | ---------SP | APRYRGVRKR | PWGRFAAEIR | 31 |
| SEQ-ID-NO-83-GI:125550159 | MCEAAA---- | -------- | -------- | ---------- | -LRFRGVRKR | PWGRFAAEIR | 25 |
| SEQ-ID-NO-45-CLONE:273307 | MRRGVAAAD- | A------- | -------V | ------GD--- | ELPYRGVRKR | PWGRFAAEIR | 35 |
| SEQ-ID-NO-62-CLONE:1838364 | MRRGRGAAAA | NAVARRPALQ | -------- | ---------PS | EPRYRGVRKR | PWGRFAAEIR | 46 |
| SEQ-ID-NO-50-CLONE:1240330 | MRKGRGGAS- | A------- | --AAVDVN | GSI------LK | EPRYRGVRKR | PWGRFAAEIR | 42 |
| SEQ-ID-NO-42-CLONE:674166 | MGRGCTAAA- | A------- | -EVAEPGLR | -PV------YFK | EQPYRGVRKR | PWGRFAAEIR | 44 |
| SEQ-ID-NO-86-GI:56384582 | MGRTRTTTKQ | A------- | ---AVE-- | -PV------FFK | EPRYRGVRKR | PWGRFAAEIR | 39 |
| SEQ-ID-NO-48-ANNOT:1441430 | MRRGRAAAAP | ATQNMLVIAK | -VDPNGS | GG------- | EPRYRGVRKR | PWGRFAAEIR | 47 |
| SEQ-ID-NO-87-GI:57012880 | MRRGRCSSAV | APVTGEPNGS | -------- | ---------SK | ELPYRGVRKR | PWGRFAAEIR | 44 |
| SEQ-ID-NO-44-CLONE:975672 | MRKGRCSSAV | P-------- | -------- | -PALP----GS | ELPYRGVRKR | PWGRFAAEIR | 39 |
| SEQ-ID-NO-84-GI:15223609 | MRRCRGSSAV | AGPTVVAAIN | -------- | ---------VK | ETRFRGVRKR | PWGRFAAEIR | 44 |

| | | | | | | |
|---|---|---|---|---|---|---|
| SEQ-ID-NO-46-CLONE:1055099 | DPAKKT-PIWL | GTFDCAEDAA | RAYDSAARSL | RGPTARTNFP | PSSATQPPPR | | 88 |
| SEQ-ID-NO-56-CLONE:1761125 | DPAKRARVWL | CTFDSAEEAA | RAYDVAARTL | RGPLARTNFP | CASSRLPLPS | | 81 |
| SEQ-ID-NO-83-GI:125550159 | DPAKRARVWL | CTYDSAEEAA | RAYDAAARTL | RGPKARTNFP | LVSSLPLPSP | | 75 |
| SEQ-ID-NO-45-CLONE:273307 | DPWKKT-RVWL | CTFDSAEEAA | RAYDAAARML | RGPKAKTNFP | LPAAALHHP | | 85 |
| SEQ-ID-NO-62-CLONE:1838364 | DPLKKARVWL | GTFDSAEEAA | RAYDAAARTL | RGPKAKTNFP | NSSNIPAFP | | 96 |
| SEQ-ID-NO-50-CLONE:1240330 | DPLKKARVWL | GTFDSAEEAA | RAYDAAARTL | RGPKAKTNFP | P---LSPFC | | 88 |
| SEQ-ID-NO-42-CLONE:674166 | DPLKKARVWL | GTFDSAEEAA | RAYDTAARTL | RGPKAKTNFP | L-----SPPFY | | 90 |
| SEQ-ID-NO-86-GI:56384582 | DPWKKT-RVWL | GTFDSAEEAA | RAYDTAARNL | RGPKAKTNFP | L-----AQPFY | | 85 |
| SEQ-ID-NO-48-ANNOT:1441430 | DPLKKARVWL | GTFDSAEEAA | RAYDAAARAL | RGAKAKTNFP | STTNQLFNH | | 97 |
| SEQ-ID-NO-87-GI:57012880 | DPWKKT-RVWL | GTFDSAEEAA | RAYDAAARNL | RGPKAKTNFP | PYAHHHOFN | | 94 |
| SEQ-ID-NO-44-CLONE:975672 | DPLKKSRVWL | GTFDSAEEAA | RAYDAAARNL | RGPKAKTNFQ | DCSPSSPLQ | | 89 |
| SEQ-ID-NO-84-GI:15223609 | DPMKKARVWL | GTFDSAEEAA | RAYDSAARNL | RGPKAKTNFP | DSSPPPPN | | 94 |

| | | | | | | |
|---|---|---|---|---|---|---|
| SEQ-ID-NO-46-CLONE:1055099 | ---------- | ---------- | ---------- | -----AAAA | AAAITSSQSST | | 106 |
| SEQ-ID-NO-56-CLONE:1761125 | ---------- | ---------- | ---------- | ---------- | APTCSS--SST | | 106 |
| SEQ-ID-NO-83-GI:125550159 | ---------- | ---------- | ---------- | ---------- | GPACSAL-SST | | 100 |
| SEQ-ID-NO-45-CLONE:273307 | -HMPAAA--- | AAAAPPY--- | RHOCCC--- | GGGLVAPPPA | RPACSLSLSST | | 124 |
| SEQ-ID-NO-62-CLONE:1838364 | -FETN----- | HHHNEGF--- | -HYALPG--- | KAAAAAPPVA | RPTRISSGMSST | | 137 |
| SEQ-ID-NO-50-CLONE:1240330 | ----YP---- | HPTTDPF--FYT | --TTYPTA | TGVVSTPPVA | RPTSSCMSST | | 128 |
| SEQ-ID-NO-42-CLONE:674166 | ---------- | -HPDPF---- | GFH-DQHHHH | EFHDPEVNPQ | RPTSSGMSST | | 122 |
| SEQ-ID-NO-86-GI:56384582 | ---------ON | PEAGNPF--- | SDH-RHFA-N | NNNNL--NNPQI | RPTSSGMSST | | 122 |
| SEQ-ID-NO-48-ANNOT:1441430 | -QNQN----- | QSPTDPF--- | GEL-RFYAGG | TGEDF-HDHR | RPTSSLSST | | 127 |
| SEQ-ID-NO-87-GI:57012880 | -QGHN----- | PNN-DPF--- | LDHHSINP-- | AGEGF--QDHR | RPTSSSMSST | | 129 |
| SEQ-ID-NO-44-CLONE:975672 | -PLHH----- | RNQI-DPF--- | VDS-RFYP--- | -QDNP--IIS | RPASSSMSST | | 126 |
| SEQ-ID-NO-84-GI:15223609 | LRFNQIRNON | QNQVDPF--- | MDH-RLYG--- | -GEQEVVIS | | | |
| | | | MDH-RLET-D | HQQQF-PIVN | RPTSSSMSST | | 138 |

FIGURE 7 (cont)

SEQUENCE LISTING

```
<160> NUMBER OF SEQ ID NOS: 229

<210> SEQ ID NO 1
<211> LENGTH: 828
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451
<220> FEATURE:
<221> NAME/KEY: misc_feature
<223> OTHER INFORMATION: Encodes the protein at SEQ ID NO: 2

<400> SEQUENCE: 1 aactttctc tcccactctt tcttttacta ctctcacaca tatctctgtc tatatatcac      60
tttacataaa ccactattcc acacacaaac acacatagcc atggcctctt ctttctcttc     120
acaagccttc ttcttgctca cattgtctat ggttttaatt cctttctctt tagctcaagc     180
tcccatgatg gctccttctg gctcaatgtc catgccgcct atgtctagcg gcggtggaag     240
ctcggttcct cctccagtga tgtctccgat gccaatgatg actccaccac ctatgcctat     300
gactccatca cccatgccca tgactccacc acctatgcct atggctccac caccaatgcc     360
```

-continued

```
catggcttca ccaccaatga tgccaatgac tccatctaca agcccaagcc cattaacagt    420
tccggatatg ccttcgccgc cgatgccatc cggaatggaa tcttcacctt ctccaggacc    480
catgccaccg gcaatggcgg cttcgccgga ttcgggagct ttcaatgtta gaaacaacgt    540
cgtaacactt tcatgcgttg ttggagttgt tgcagctcat tttctcctcg tttgaaatga    600
ttattgaatt ggtcagcctc gatcgttttc ttgtaattta ctttcatatt ttttttccct    660
caaattatta gtggtcatca ttttataata tttgagtttg tgtttgatgt acgattcaga    720
catttgtttg cattatgtgc ttaataagtt tatcgttgac tctacttgaa gagagacttt    780
gtgtgtgatg taaatttctt ctatctatgg aacattgcat tcgtagcc                828
```

```
<210> SEQ ID NO 2
<211> LENGTH: 164
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30087
<220> FEATURE:
<221> NAME/KEY: misc_feature
<223> OTHER INFORMATION: Ceres SEED LINE ID no. ME01451

<400> SEQUENCE: 2

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Val Met Ser Pro Met Pro Met Met Thr Pro Pro Pro
    50                  55                  60

Met Pro Met Thr Pro Ser Pro Met Pro Met Thr Pro Pro Pro Met Pro
65                  70                  75                  80

Met Ala Pro Pro Met Pro Met Ala Ser Pro Pro Met Met Pro Met
                85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val
```

```
<210> SEQ ID NO 3
<211> LENGTH: 155
<212> TYPE: PRT
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 3

Met Ala Ala Ser Gln Ala Phe Leu Leu Leu Thr Leu Ser Met Ala Leu
1               5                   10                  15
```

Val His Phe Ser Leu Ala Gln Ser Pro Met Met Ala Pro Ser Gly Ser
            20                  25                  30

Met Ser Met Pro Pro Met Pro Ser Gly Gly Ser Pro Met Pro Met Met
        35                  40                  45

Thr Pro Pro Pro Met Pro Met Thr Pro Pro Met Pro Met Ala Met Ala
    50                  55                  60

Pro Pro Pro Met Pro Met Thr Pro Pro Met Pro Met Ala Pro Met
65                  70                  75                  80

Pro Met Thr Pro Ser Ser Ser Pro Met Ser Pro Pro Thr Thr Met Ala
                85                  90                  95

Pro Ser Pro Glu Thr Val Pro Asp Met Ala Ser Pro Met Met Pro
            100                 105                 110

Gly Met Glu Ser Ser Pro Ser Pro Gly Pro Met Pro Pro Ala Met Ala
            115                 120                 125

Ser Pro Asp Ser Gly Ala Phe Asn Val Arg Asn Asp Val Val Ala Ile
130                 135                 140

Ser Phe Leu Val Ala Ala His Leu Leu Leu Val
145                 150                 155

<210> SEQ ID NO 4
<211> LENGTH: 152
<212> TYPE: PRT
<213> ORGANISM: Brassica napus
<220> FEATURE:
<221> NAME/KEY: misc_feature
<223> OTHER INFORMATION: Public GI no. 62526422
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 4

Met Ala Leu Ser His Pro Met Thr Ile Phe Ser Leu Phe Leu Thr Phe
1               5                   10                  15

Leu Ala Leu Thr Ala Ala Gln Ser Pro Met Met Ala Pro Thr Met Pro
            20                  25                  30

Pro Ser Thr Met Ser Met Pro Pro Thr Thr Ser Thr Thr Thr Pro Pro
        35                  40                  45

Pro Met Ser Ser Met Ser Pro Pro Pro Ser Ala Met Ser Pro Thr Pro
    50                  55                  60

Ser Thr Met Ser Pro Pro Pro Met Ser Pro Met Thr Pro Ser Met Ser
65                  70                  75                  80

Pro Met Gly Pro Met Thr Pro Thr Met Ser Pro Met Asp Ser Pro Pro
                85                  90                  95

Ala Pro Ala Gly Pro Gly Met Ala Pro Gly Met Ser Thr Pro Gly Pro
            100                 105                 110

Ala Pro Gly Pro Met Gly Gly Glu Ser Met Ala Ser Pro Pro Pro Ser
            115                 120                 125

Ser Gly Phe Val His Gly Ile Ser Ile Ser Met Ala Met Val Ala Ile
130                 135                 140

Ile Gly Ser Val Ala Leu Phe Phe
145                 150

<210> SEQ ID NO 5
<211> LENGTH: 150
<212> TYPE: PRT
<213> ORGANISM: Parthenium argentatum
<220> FEATURE:

```
<221> NAME/KEY: misc_feature
<223> OTHER INFORMATION: Ceres CLONE ID no. 1606506
<220> FEATURE:
<221> NAME/KEY: misc_feature
<223> OTHER INFORMATION: Functional homolog of Ceres Clone ID no. 30087
      given in SEQ ID NO: 2

<400> SEQUENCE: 5

Met Ala Val Ser Arg Tyr Ile Ile Leu Leu Ser Phe Thr Tyr Leu
1               5                   10                  15

Ala Ala Phe Ser Thr Ala Gln Ala Pro Ser Met Ser Pro Met Met Met
                20                  25                  30

Pro Met Ala Pro Pro Pro Ser Thr Met Pro Met Thr Pro Pro Ser
            35                  40                  45

Thr Met Pro Met Thr Pro Pro Pro Thr Pro Met Thr Met Thr Pro Pro
        50                  55                  60

Pro Met Met Met Pro Met Thr Pro Pro Pro Met Pro Met Gly Thr Pro
65                  70                  75                  80

Pro Met Thr Met Pro Met Gly Pro Pro Pro Met Met Pro Met Ser
                85                  90                  95

Pro Gly Pro Ser Met Met Pro Ala Ser Pro Pro Ser Pro Met Gly Pro
                100                 105                 110

Ser Met Ala Pro Glu Pro Ala Thr Met Ser Pro Gly Pro Ser Met Thr
                115                 120                 125

Pro Ala Glu Thr Pro Ala Ser Gly Ala Ile Met Gln Tyr Ser Ser Ile
            130                 135                 140

Thr Met Leu Gly Ile Val
145                 150

<210> SEQ ID NO 6
<211> LENGTH: 586
<212> TYPE: DNA
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<223> OTHER INFORMATION: Encodes the protein at SEQ ID NO: 7

<400> SEQUENCE: 6
aaaagatcta caaaacagag agttgtatac tttaaatcat ttagaggttg tgaaatatta      60
tggagagtga aggaaagatt gtgttcacag aagagcaaga ggctcttgta gtgaagtctt    120
ggagtgtcat gaagaaaaac tcagctgaat taggtctcaa actcttcatc aagatctttg    180
agattgcacc aacaacgaag aagatgttct ctttcttgag agactcacca attcctgctg    240
agcaaaatcc aaagctcaag cctcacgcaa tgtctgtttt tgtcatgtac aactgaggaa    300
aacagggaaa gttacggtga gggagactac tttgaagaga cttggagcca gccattctaa    360
atacggtgtc gttgacgaac actttgaggt ggccaagtat gcattgttgg agacgataaa    420
ggaggcagtg ccggagatgt ggtcaccgga gatgaaggtg gcttggggtc aggcttatga    480
tcaccttgtt gctgccatta agctgaaat gaatctttcc aactaaaaaa tcatatacta    540
ttatatagtt gtaaacttgt aataaatatt tcattttgaa ttgttc                  586

<210> SEQ ID NO 7
<211> LENGTH: 78
<212> TYPE: PRT
```

```
<213> ORGANISM: Artificial Sequence
<220> FEATURE:
<223> OTHER INFORMATION: Ceres CLONE ID no. 30469
<220> FEATURE:
<221> NAME/KEY: misc_feature
<223> OTHER INFORMATION: Ceres SEED LINE ID no. ME02779
<220> FEATURE:
<221> NAME/KEY: misc_feature
<222> LOCATION: (13)..(74)
<223> OTHER INFORMATION: Pfam Name: Globin
      Pfam Description: Globin

<400> SEQUENCE: 7

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Tyr Asn
65                  70                  75

<210> SEQ ID NO 8
<211> LENGTH: 483
<212> TYPE: DNA
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<223> OTHER INFORMATION: Encodes the protein at SEQ ID NO: 9

<400> SEQUENCE: 8
atggagagtg aaggaaagat tgtgttcaca gaagagcaag aggctcttgt agtgaagtct      60
tggagtgtca tgaagaaaaa ctcagctgaa ttaggtctca aactcttcat caagatcttt     120
gagattgcac caacaacgaa gaagatgttc tctttcttga gagactcacc aattcctgct     180
gagcaaaatc caaagctcaa gcctcacgca atgtctgttt ttgtcatgtg ttgtgaatca     240
gcagtacaac tgaggaaaac agggaaagtt acggtgaggg agactacttt gaagagactt     300
ggagccagcc attctaaata cggtgtcgtt gacgaacact tgaggtggc caagtatgca     360 ttgttggaga cgataaagga ggcagtgccg gagatgtggt caccggagat gaaggtggct     420
tggggtcagg cttatgatca ccttgttgct gccattaaag ctgaaatgaa tctttccaac     480
taa 483

<210> SEQ ID NO 9
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres CLONE ID no. 30469_FL
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
```

<400> SEQUENCE: 9

```
Met Glu Ser Glu Gly Lys Ile Val Phe Thr Glu Glu Gln Ala Leu
1               5                   10                  15

Val Val Lys Ser Trp Ser Val Met Lys Lys Asn Ser Ala Glu Leu Gly
            20                  25                  30

Leu Lys Leu Phe Ile Lys Ile Phe Glu Ile Ala Pro Thr Thr Lys Lys
                35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
                100                 105                 110

His Phe Glu Val Ala Lys Tyr Ala Leu Leu Glu Thr Ile Lys Glu Ala
                115                 120                 125

Val Pro Glu Met Trp Ser Pro Glu Met Lys Val Ala Trp Gly Gln Ala
        130                 135                 140

Tyr Asp His Leu Val Ala Ala Ile Lys Ala Glu Met Asn Leu Ser Asn
145                 150                 155                 160
```

<210> SEQ ID NO 10
<211> LENGTH: 160
<212> TYPE: PRT
<213> ORGANISM: Raphanus sativus
<220> FEATURE:
<221> NAME/KEY: misc_feature
<223> OTHER INFORMATION: Public GI no. 30909306
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 10

```
Met Glu Ser Glu Gly Lys Ile Val Phe Thr Glu Glu Gln Ala Leu
1               5                   10                  15

Val Val Lys Ser Trp Ser Val Met Lys Lys Asn Ser Ala Asp Leu Gly
            20                  25                  30

Leu Lys Leu Phe Ile Lys Ile Phe Glu Ile Ala Pro Thr Ala Lys Lys
                35                  40                  45

Leu Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Ala Gln Leu Arg Lys Thr Gly Lys Val Thr Val Lys Glu Thr Thr
                85                  90                  95

Leu Lys Arg Leu Gly Ala Asn His Ser Lys Tyr Gly Val Val Asp Glu
                100                 105                 110

His Phe Glu Val Thr Lys Tyr Ala Leu Leu Glu Thr Ile Lys Glu Ala
                115                 120                 125

Val Pro Glu Met Trp Ser Pro Glu Met Lys Ser Ala Trp Gly Gln Ala
        130                 135                 140
```

Tyr Asp His Leu Val Ala Ala Ile Lys Ala Glu Met Lys Pro Ser His
145                 150                 155                 160

<210> SEQ ID NO 11
<211> LENGTH: 158
<212> TYPE: PRT
<213> ORGANISM: Arabidopsis thaliana
<220> FEATURE:
<221> NAME/KEY: misc_feature
<223> OTHER INFORMATION: Public GI no. 37903656
<220> FEATURE:
<221> NAME/KEY: misc_feature
<222> LOCATION: (10)..(149)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 11

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
                20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
        50                  55                  60

Pro His Ala Met Ser Val Phe Val Met Thr Cys Glu Ser Ala Val Gln
65                  70                  75                  80

Leu Arg Lys Ala Gly Lys Val Thr Val Arg Glu Ser Thr Leu Lys Arg
                85                  90                  95

Leu Gly Gly Val His Phe Lys Ser Gly Val Val Asp Glu His Tyr Glu
                100                 105                 110

Val Thr Lys Phe Ala Leu Leu Glu Thr Ile Lys Glu Ala Leu Pro Glu
            115                 120                 125

Met Trp Ser Pro Glu Met Lys Asn Ala Trp Gly Glu Ala Tyr Asp Gln
        130                 135                 140

Leu Val Ala Ala Ile Lys Ser Glu Met Lys Pro Pro Leu Asn
145                 150                 155

<210> SEQ ID NO 12
<211> LENGTH: 163
<212> TYPE: PRT
<213> ORGANISM: Arabidopsis thaliana
<220> FEATURE:
<221> NAME/KEY: misc_feature
<223> OTHER INFORMATION: Public GI no. 15824736
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 12

Met Ala Thr Tyr Glu Gly Lys Val Phe Thr Glu Glu Gln Glu Ala Leu
1               5                   10                  15

Val Val Lys Ser Trp Thr Val Met Lys Lys Thr Ala Glu Leu Gly
                20                  25                  30

-continued

```
Leu Lys Phe Phe Leu Lys Ile Phe Glu Ile Ala Pro Ser Ala Lys Lys
             35                  40                  45

Leu Phe Ser Phe Leu Arg Asp Ser Asn Val Pro Leu Glu Gln Asn Thr
 50                  55                  60

Lys Leu Lys Pro His Ala Met Ser Val Phe Val Met Thr Cys Glu Ser
 65                  70                  75                  80

Ala Val Gln Leu Arg Lys Ala Gly Lys Val Thr Val Arg Glu Ser Asn
             85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
            115                 120                 125

Val Pro Asp Met Trp Ser Asp Glu Met Lys Asn Ala Trp Gly Glu Ala
130                 135                 140

Tyr Asp Arg Leu Val Ala Ala Ile Lys Ile Glu Met Lys Ala Cys Ser
145                 150                 155                 160

Gln Ala Ala
```

<210> SEQ ID NO 13
<211> LENGTH: 161
<212> TYPE: PRT
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 13

```
Met Thr Thr Thr Leu Glu Arg Gly Phe Ser Glu Gln Glu Ala Leu
 1                   5                  10                  15

Val Val Lys Ser Trp Asn Val Met Lys Lys Asn Ser Gly Glu Leu Gly
             20                  25                  30

Leu Lys Phe Phe Leu Lys Ile Phe Glu Ile Ala Pro Ser Ala Gln Lys
             35                  40                  45

Leu Phe Ser Phe Leu Arg Asp Ser Thr Val Pro Leu Glu Gln Asn Pro
 50                  55                  60

Lys Leu Lys Pro His Ala Val Ser Val Phe Val Met Thr Cys Asp Ser
 65                  70                  75                  80

Ala Val Gln Leu Arg Lys Ala Gly Lys Val Thr Val Arg Glu Ser Asn
             85                  90                  95

Leu Lys Lys Leu Gly Ala Thr His Phe Arg Thr Gly Val Ala Asn Glu
            100                 105                 110

His Phe Glu Val Thr Lys Phe Ala Leu Leu Glu Thr Ile Lys Glu Ala
            115                 120                 125

Val Pro Glu Met Trp Ser Pro Ala Met Lys Asn Ala Trp Gly Glu Ala
130                 135                 140

Tyr Asp Gln Leu Val Asp Ala Ile Lys Ser Glu Met Lys Pro Pro Ser
145                 150                 155                 160

Ser
```

```
<210> SEQ ID NO 14
<211> LENGTH: 160
<212> TYPE: PRT
<213> ORGANISM: Glycine max
<220> FEATURE:
<221> NAME/KEY: misc_feature
<223> OTHER INFORMATION: Public GI no. 11095158
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 14
```

Met Gly Thr Leu Asp Thr Lys Gly Phe Thr Glu Glu Gln Glu Ala Leu
1               5                   10                  15

Val Val Lys Ser Trp Asn Ala Met Lys Lys Asn Ser Ala Glu Leu Gly
            20                  25                  30

Leu Lys Leu Phe Leu Lys Ile Phe Glu Ile Ala Pro Ser Ala Gln Lys
        35                  40                  45

Leu Phe Ser Phe Leu Lys Asp Ser Lys Val Pro Leu Glu Gln Asn Thr
    50                  55                  60

Lys Leu Lys Pro His Ala Met Ser Val Phe Leu Met Thr Cys Glu Ser
65                  70                  75                  80

Ala Val Gln Leu Arg Lys Ser Gly Lys Val Thr Val Arg Glu Ser Ser
                85                  90                  95

Leu Lys Lys Leu Gly Ala Asn His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Glu Met Trp Ser Pro Ala Met Lys Asn Ala Trp Gly Glu Ala
    130                 135                 140

Tyr Asp Gln Leu Val Asn Ala Ile Lys Ser Glu Met Lys Pro Ser Ser
145                 150                 155                 160

```
<210> SEQ ID NO 15
<211> LENGTH: 152
<212> TYPE: PRT
<213> ORGANISM: Glycine max
<220> FEATURE:
<221> NAME/KEY: misc_feature
<223> OTHER INFORMATION: Public GI no. 12963875
<220> FEATURE:
<221> NAME/KEY: misc_feature
<222> LOCATION: (8)..(147)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 15
```

Met Ser Ser Phe Ser Glu Glu Gln Glu Ala Leu Val Val Lys Ser Trp
1               5                   10                  15

Gly Ser Met Lys Lys Asp Ala Gly Glu Trp Gly Leu Lys Phe Phe Leu
            20                  25                  30

Lys Ile Phe Glu Ile Ala Pro Ser Ala Lys Lys Met Phe Ser Phe Leu
        35                  40                  45

Lys Asp Ser Asn Val Pro Leu Asp Gln Asn Pro Lys Leu Lys Ile His

```
                    50                  55                  60
Ala Lys Ser Val Leu Val Met Thr Cys Glu Ala Ala Val Gln Leu Arg
 65                  70                  75                  80

Lys Ala Gly Lys Val Val Arg Asp Ser Thr Leu Lys Lys Ile Gly
                 85                  90                  95

Ala Thr His Phe Lys Tyr Gly Val Val Asp Glu His Phe Glu Val Thr
                100                 105                 110

Lys Tyr Ala Leu Leu Glu Thr Ile Lys Glu Ala Ser Gln Glu Met Trp
                115                 120                 125

Ser Val Glu Met Lys Asn Ala Trp Gly Glu Ala Tyr Asp Gln Leu Val
            130                 135                 140

Ser Ala Ile Lys Thr Glu Met Lys
145                 150
```

```
<210> SEQ ID NO 16
<211> LENGTH: 165
<212> TYPE: PRT
<213> ORGANISM: Zea mays
<220> FEATURE:
<221> NAME/KEY: misc_feature
<223> OTHER INFORMATION: Ceres CLONE ID no. 1554560
<220> FEATURE:
<221> NAME/KEY: misc_feature
<222> LOCATION: (17)..(157)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 16
```

```
Met Ala Leu Ala Glu Ala Asp Asp Gly Ala Val Val Phe Gly Glu Glu
  1               5                  10                  15

Gln Glu Ala Leu Val Leu Lys Ser Trp Ala Val Met Lys Lys Asp Ala
                 20                  25                  30

Ala Asn Leu Gly Leu Arg Phe Phe Leu Lys Val Phe Glu Ile Ala Pro
             35                  40                  45

Ser Ala Lys Gln Met Phe Ser Phe Leu Arg Asp Ser Asp Val Pro Leu
 50                  55                  60

Glu Lys Asn Pro Lys Leu Lys Thr His Ala Met Ser Val Phe Val Met
 65                  70                  75                  80

Thr Cys Glu Ala Ala Gln Leu Arg Lys Ala Gly Lys Val Thr Val
                 85                  90                  95

Arg Glu Thr Thr Leu Lys Arg Leu Gly Ala Thr His Leu Arg Tyr Gly
                100                 105                 110

Val Ala Asp Gly His Phe Glu Val Thr Gly Phe Ala Leu Leu Glu Thr
            115                 120                 125

Ile Lys Glu Ala Leu Pro Ala Asp Met Trp Ser Leu Glu Met Lys Lys
130                 135                 140

Ala Trp Ala Glu Ala Tyr Ser Gln Leu Val Ala Ala Ile Lys Arg Glu
145                 150                 155                 160

Met Lys Pro Asp Ala
                165
```

```
<210> SEQ ID NO 17
<211> LENGTH: 162
<212> TYPE: PRT
<213> ORGANISM: Triticum aestivum
<220> FEATURE:
```

-continued

```
<221> NAME/KEY: misc_feature
<223> OTHER INFORMATION: Ceres CLONE ID no. 839727
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 17

Met Ser Ala Ala Glu Gly Ala Val Val Phe Ser Glu Glu Lys Glu Ala
1               5                   10                  15

Leu Val Leu Lys Ser Trp Ala Ile Met Lys Lys Asp Ser Ala Asn Leu
            20                  25                  30

Gly Leu Arg Phe Phe Leu Lys Ile Phe Glu Ile Ala Pro Ser Ala Arg
        35                  40                  45

Gln Met Phe Pro Phe Leu Arg Asp Ser Asp Val Pro Leu Glu Thr Asn
    50                  55                  60

Pro Lys Leu Lys Thr His Ala Val Ser Val Phe Val Met Thr Cys Glu
65                  70                  75                  80

Ala Ala Ala Gln Leu Arg Lys Ala Gly Lys Ile Thr Val Arg Glu Thr
                85                  90                  95

Thr Leu Lys Arg Leu Gly Gly Thr His Leu Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Gly Pro Glu Met Arg Asn Ala Trp Gly
    130                 135                 140

Glu Ala Tyr Asp Gln Leu Val Ala Ala Ile Lys Gln Glu Met Lys Pro
145                 150                 155                 160

Ser Glu

<210> SEQ ID NO 18
<211> LENGTH: 169
<212> TYPE: PRT
<213> ORGANISM: Triticum aestivum
<220> FEATURE:
<221> NAME/KEY: misc_feature
<223> OTHER INFORMATION: Public GI no. 14701800
<220> FEATURE:
<221> NAME/KEY: misc_feature
<222> LOCATION: (21)..(161)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 18

Met Ala Leu Val Glu Gly Asn Asn Gly Val Ser Gly Gly Ala Val Ser
1               5                   10                  15

Phe Ser Glu Glu Gln Glu Ala Leu Val Leu Lys Ser Trp Ala Ile Met
            20                  25                  30

Lys Lys Asp Ser Ala Asn Ile Gly Leu Arg Phe Phe Leu Lys Ile Phe
        35                  40                  45

Glu Val Ala Pro Ser Ala Ser Gln Met Phe Ser Phe Leu Arg Asn Ser
    50                  55                  60

Asp Val Pro Leu Glu Lys Asn Pro Lys Leu Lys Thr His Ala Met Ser
```

```
                65                  70                  75                  80
Val Phe Val Met Thr Cys Glu Ala Ala Gln Leu Arg Lys Ala Gly
                        85                  90                  95
Lys Val Thr Val Arg Asp Thr Thr Leu Lys Arg Leu Gly Ala Thr His
                    100                 105                 110
Phe Lys Tyr Gly Val Gly Asp Ala His Phe Glu Val Thr Arg Phe Ala
                115                 120                 125
Leu Leu Glu Thr Ile Lys Glu Ala Val Pro Val Asp Met Trp Ser Pro
            130                 135                 140
Ala Met Lys Ser Ala Trp Ser Glu Ala Tyr Asn Gln Leu Val Ala Ala
        145                 150                 155                 160
Ile Lys Gln Glu Met Lys Pro Ala Glu
                    165

<210> SEQ ID NO 19
<211> LENGTH: 416
<212> TYPE: DNA
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<223> OTHER INFORMATION: Encodes the protein at SEQ ID NO: 20

<400> SEQUENCE: 19
gctcattagg gtttctcatc tacgacggcg tggtgttcct ccttcctgct ctgaaaaatg      60
gcgaagagaa cgaagaaggt tggaatcgtc ggcaaatacg gaacacgtta tggtgcgagt     120
atcaggaagc agattaagaa gatggaggtc agccagcaca gcaagtactt ctgtgagttc     180
tgtggcaagt acggagtgaa gcgaaaggct gttggtatct ggggttgcaa ggattgtggc     240
aaggtcaagg caggtggtgc ttacacaatg aacaccgcca gtgcggtcac tgttagaagc     300
acgatcagaa ggttgaggga gcagatcgag ggttaaaagt ctgctggctt tttatatttg     360
gtttccttgt tttgacaatt taagttttgc atcaacagtg agaacatgtt ttgatt         416

<210> SEQ ID NO 20
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 271922
<220> FEATURE:
<221> NAME/KEY: misc_feature
<223> OTHER INFORMATION: Ceres SEED LINE ID no. ME03944
<220> FEATURE:
<221> NAME/KEY: misc_feature
<222> LOCATION: (2)..(91)
<223> OTHER INFORMATION: Pfam Name: Ribosomal_L37ae;
      Pfam Description: Ribosomal L37ae protein family

<400> SEQUENCE: 20

Met Ala Lys Arg Thr Lys Lys Val Gly Ile Val Gly Lys Tyr Gly Thr
1               5                   10                  15
Arg Tyr Gly Ala Ser Ile Arg Lys Gln Ile Lys Lys Met Glu Val Ser
            20                  25                  30
Gln His Ser Lys Tyr Phe Cys Glu Phe Cys Gly Lys Tyr Gly Val Lys
        35                  40                  45
```

```
Arg Lys Ala Val Gly Ile Trp Gly Cys Lys Asp Cys Gly Lys Val Lys
         50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Ile Glu Gly
                 85                  90

<210> SEQ ID NO 21
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4090257
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 21

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Phe Phe Cys Glu Phe Cys Gly Lys Phe Ala Val Lys
             35                  40                  45

Arg Lys Ala Val Gly Ile Trp Gly Cys Lys Asp Cys Gly Lys Val Lys
         50                  55                  60

Ala Gly Gly Ala Tyr Thr Leu Asn Thr Pro Ser Ala Val Thr Val Arg
 65                  70                  75                  80

Ser Thr Ile Arg Arg Leu Arg Glu Gln Thr Glu Gly
                 85                  90

<210> SEQ ID NO 22
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 4741896
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 22

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Tyr Ala Val Lys
             35                  40                  45

Arg Lys Ala Val Gly Ile Trp Gly Cys Lys Ala Cys Gly Lys Val Lys
         50                  55                  60
```

```
Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90
```

<210> SEQ ID NO 23
<211> LENGTH: 92
<212> TYPE: PRT
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<222> LOCATION: (45)..(45)
<223> OTHER INFORMATION: Xaa is any aa, unknown, or other
<220> FEATURE:
<221> NAME/KEY: misc_feature
<222> LOCATION: (49)..(49)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 23

```
Met Ala Lys Arg Thr Lys Lys Val Gly Ile Val Gly Lys Tyr Gly Thr
  1               5                  10                  15

Arg Tyr Gly Ala Ser Ile Arg Lys Gln Ile Lys Lys Met Glu Val Ser
                 20                  25                  30

Gln His Ser Lys Tyr Phe Cys Glu Phe Cys Gly Lys Xaa Gly Val Lys
             35                  40                  45

Xaa Lys Ala Val Gly Ile Trp Gly Cys Lys Asp Cys Gly Lys Val Lys
 50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Ile Glu Gly
                 85                  90
```

<210> SEQ ID NO 24
<211> LENGTH: 92
<212> TYPE: PRT
<213> ORGANISM: Arabidopsis thaliana
<220> FEATURE:
<221> NAME/KEY: misc_feature
<223> OTHER INFORMATION: Public GI no. 6016699
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 24

```
Met Thr Lys Arg Thr Lys Lys Ala Arg Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Asn Lys Tyr Phe Cys Glu Phe Cys Gly Lys Tyr Ser Val Lys
```

```
                35                  40                  45
Arg Lys Val Val Gly Ile Trp Gly Cys Lys Asp Cys Gly Lys Val Lys
     50                  55                  60

Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ser
                 85                  90

<210> SEQ ID NO 25
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 664936
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 25

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Phe Phe Cys Glu Phe Cys Gly Lys Tyr Ala Val Lys
             35                  40                  45

Arg Lys Ala Val Gly Ile Trp Gly Cys Lys Asp Cys Gly Lys Val Lys
     50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Gly
                 85                  90

<210> SEQ ID NO 26
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 26

Met Thr Lys Arg Thr Lys Lys Ala Gly Ile Val Gly Lys Tyr Gly Thr
 1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
```

```
Ala Gly Gly Ala Tyr Thr Met Asn Thr Ala Ser Ala Val Thr Val Arg
 65                  70                  75                  80

Ser Thr Ile Arg Arg Leu Arg Glu Gln Thr Glu Ala
                 85                  90
```

<210> SEQ ID NO 27
<211> LENGTH: 92
<212> TYPE: PRT
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 27

```
Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Lys Phe Phe Cys Glu Phe Cys Gly Lys Tyr Ala Val Lys
             35                  40                  45

Arg Lys Ala Val Gly Ile Trp Gly Cys Lys Asp Cys Gly Lys Val Lys
     50                  55                  60

Ala Gly Gly Ala Tyr Thr Leu Asn Thr Ala Ser Ala Val Thr Val Arg
 65                  70                  75                  80

Ser Thr Ile Arg Arg Leu Arg Glu Gln Thr Glu Ser
                 85                  90
```

<210> SEQ ID NO 28
<211> LENGTH: 92
<212> TYPE: PRT
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 28

```
Met Thr Lys Arg Thr Lys Lys Ala Gly Ile Val Gly Lys Tyr Gly Thr
  1               5                  10                  15

Arg Tyr Gly Ala Ser Leu Arg Lys Gln Ile Lys Lys Met Glu Val Ser
                 20                  25                  30

Gln His Ser Lys Tyr Phe Cys Glu Phe Cys Gly Lys Phe Ala Val Lys
             35                  40                  45

Arg Lys Ala Val Gly Ile Trp Gly Cys Lys Asp Cys Gly Lys Val Lys
     50                  55                  60

Ala Gly Gly Ala Tyr Thr Met Asn Thr Ala Ser Ala Val Thr Val Arg
```

```
                 65                  70                  75                  80

Ser Thr Ile Arg Arg Leu Arg Glu Gln Thr Glu Ala
                 85                  90

<210> SEQ ID NO 29
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 29

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 30
<211> LENGTH: 92
<212> TYPE: PRT
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 30

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
        50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90
```

```
                    85                  90

<210> SEQ ID NO 31
<211> LENGTH: 92
<212> TYPE: PRT
<213> ORGANISM: Zea mays
<220> FEATURE:
<221> NAME/KEY: misc_feature
<223> OTHER INFORMATION: Public GI no. 56202147
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 31

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Lys Tyr Phe Cys Glu Phe Cys Gly Lys Phe Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
                85                  90

<210> SEQ ID NO 32
<211> LENGTH: 92
<212> TYPE: PRT
<213> ORGANISM: Zea mays
<220> FEATURE:
<221> NAME/KEY: misc_feature
<223> OTHER INFORMATION: Public GI no. 58578274
<220> FEATURE:
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional homolog of Ceres Clone ID no. 271922
      given in SEQ ID NO: 20

<400> SEQUENCE: 32

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
                20                  25                  30

Gln His Ser Glu Tyr Phe Cys Glu Phe Cys Gly Lys Tyr Ala Val Lys
            35                  40                  45

Arg Lys Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90
```

```
<210> SEQ ID NO 33
<211> LENGTH: 632
<212> TYPE: DNA
<213> ORGANISM: Arabidopsis thaliana
<220> FEATURE:
<221> NAME/KEY: misc_feature
<223> OTHER INFORMATION: Ceres CLONE ID no. 2403_FL
<220> FEATURE:
<221> NAME/KEY: misc_feature
<223> OTHER INFORMATION: Encodes the protein at SEQ ID NO: 34

<400> SEQUENCE: 33
attccccatc gcacagaccc gcctaagaat ccgagagaga agaagagata atgcagatct      60
tcgtcaaaac cctcaccggc aaaactataa ccctagaggt tgagagcagc gacaccatcg     120
acaatgttaa agccaaaatc caggacaaat agggcatacc acctgatcaa cagaggctga     180 ttttttgctgg taagcaattg gaagatggcc ggacctttagc tgactacaac atccagaaag    240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcatc tatgccggaa     420
aacagcttgc tgatgacaaa acggccaaag attatgcgat agagggaggc tctgttcttc     480
atttggttct tgctcttagg ggtggtcttc tctgatctga ataaataagc ttttcaacaa     540
acatctttcc cctcactatt gtcctccttt tgtggaattc atgacacaca aaaattgcta     600
tgggaaattg gaatattatg atgttttttc tc                                   632

<210> SEQ ID NO 34
<211> LENGTH: 154
<212> TYPE: PRT
<213> ORGANISM: Arabidopsis thaliana
      220>
<221> NAME/KEY: misc_feature
<223> OTHER INFORMATION: Ceres CLONE ID no. 2403_FL
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 34

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
```

```
                    100                 105                 110

Pro Pro Val Gln Gln Arg Leu Ile Tyr Ala Gly Lys Gln Leu Ala Asp
        115                 120                 125

Asp Lys Thr Ala Lys Asp Tyr Ala Ile Glu Gly Gly Ser Val Leu His
    130                 135                 140

Leu Val Leu Ala Leu Arg Gly Gly Leu Leu
145                 150

<210> SEQ ID NO 35
<211> LENGTH: 154
<212> TYPE: PRT
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 35

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Val Leu Ala Leu Arg Gly Gly Ser Asp
145                 150

<210> SEQ ID NO 36
<211> LENGTH: 154
<212> TYPE: PRT
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
```

```
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 36

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Glu Tyr Asn Ile Glu Gly Gly Ser Val Leu His
    130                 135                 140

Leu Val Leu Ala Leu Arg Gly Gly Thr Tyr
145                 150

<210> SEQ ID NO 37
<211> LENGTH: 147
<212> TYPE: PRT
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(142)
<223> OTHER INFORMATION: Pfam Name: ubiquitin
      Pfam Description: Ubiquitin family
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 37

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Thr Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Xaa Lys Asp Tyr Asn Ile Glu Gly Gly Ser Val Ser Ala
    130                 135                 140

Ser Gly Ser
145

<210> SEQ ID NO 38
<211> LENGTH: 153
<212> TYPE: PRT
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 38

Met Gln Ile Phe Val Lys Thr Leu Thr Gly Lys Thr Ile Thr Leu Glu
1               5                   10                  15

Val Glu Ser Ser Asp Thr Val Asp Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ala Asp Tyr Asn Ile Gln Lys Glu
        50                  55                  60

Ser Thr Leu His Leu Val Leu Arg Leu Arg Gly Gly Thr Met Ile Lys
65                  70                  75                  80

Val Lys Thr Leu Thr Gly Lys Glu Ile Glu Ile Asp Ile Glu Pro Thr
                85                  90                  95

Asp Ser Ile Asp Arg Ile Lys Glu Arg Val Glu Glu Lys Glu Gly Ile
            100                 105                 110

Pro Pro Val Gln Gln Arg Leu Ile Tyr Ala Gly Lys Gln Leu Ala Asp
        115                 120                 125

Asp Lys Thr Ala Lys Asp Tyr Asn Ile Glu Gly Gly Ser Val Leu His
    130                 135                 140

Leu Xaa Leu Ala Leu Arg Gly Gly Tyr
```

<210> SEQ ID NO 39
<211> LENGTH: 620
<212> TYPE: DNA
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<223> OTHER INFORMATION: Encodes the protein at SEQ ID NO: 40

<400> SEQUENCE: 39

```
attccccatc gcacagaccc ccctaagaat ccgagagaga agaagagata atgcagatct      60
tcgtcaaaac cctcaccggc aaaactataa ccctagaagt tgagagcagc gacaccatcg     120
acaatgttaa agccaaaatc caggacaaag agggcatacc acctgatcaa cagaggctga     180
ttttgctgg taagcaattg gaagatggcc ggaccttagc tgattacaac atccagaaag      240
agtctactct tcatcttgtc ctcaggctca gaggtggaac catgatcaag gtgaagacac     300
tcactggaaa agaaatcgag attgatatcg aaccaaccga cactattgat cggatcaaag     360
aacgtgttga agagaaagaa ggcatccctc ctgttcaaca aaggctcata tatgccggaa     420
aacagcttgc tgatgacaaa acggccaaag attatgcgat agaggaggc tctgttcttc      480
atttggttct tgctcttagg ggtggtcttc tctgatctta ataaataagc ttttcaacaa     540
acatcttttc cctcactatt gtcctcctta tgtggaattc atgacacacc aaaattgcta     600
tgggaaattg gaatattatg                                                 620
```

<210> SEQ ID NO 40
<211> LENGTH: 33
<212> TYPE: PRT
<213> ORGANISM: Artificial Sequence
<220> FEATURE:
<223> OTHER INFORMATION: Ceres CLONE ID no. 2403
<220> FEATURE:
<221> NAME/KEY: misc_feature
<223> OTHER INFORMATION: Ceres SEED LINE ID no. ME05304
<220> FEATURE:
<221> NAME/KEY: misc_feature
<222> LOCATION: (1)..(33)
<223> OTHER INFORMATION: Pfam Name: ubiquitin
    Pfam Description: Ubiquitin family

<400> SEQUENCE: 40

```
Met Gln Ile Phe Val Lys Thr Leu Thr Gly Lys Thr Ile Thr Leu Glu
1               5                   10                  15
Val Glu Ser Ser Asp Thr Ile Asp Asn Val Lys Ala Lys Ile Gln Asp
            20                  25                  30
Lys
```

<210> SEQ ID NO 41
<211> LENGTH: 1106
<212> TYPE: DNA
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<223> OTHER INFORMATION: Encodes the protein at SEQ ID NO: 42

<400> SEQUENCE: 41

```
atatttttgt gtagatgaag atcaacaaga gaaggtgttg ttgtgagttg tgttgttatg      60
gtaccttcct tcaaccacaa aacctctctc cctctaccac ccattctctt ctctctctct     120
ctctcccgtc ctccatctct caccttctca atctcttcac caccaccatc atcatcatta     180
tcttctccaa tctctataac ctcgaaatcc ctcaaaacct ctccctcaaa ccaaatgaaa     240
tgacccttt  gtgagaacat ttttccccc  ttaagaaaag gtcaaaggct gcaacttttt     300
cttaaccaat ctcacatttt tttatttttc aacgtatttt ggccaggttt ggttttctgg     360
gttgtcttgg aattcaaaaa agattccaac tttgaagatg ggtagggtg  gaaccgccgc     420
ggcggcggcg gaggtcgccg aacccggttt aaggccggtt tatttcaaag aacagcgata     480
tagggcgtc  agaaaaagac cgtggggccg gttcgctgcc gaaatcagag acccttgaa      540
gaaagccagg gtttggctcg gaacctttga caccgccgag gaggcggcgc gtgcctacga     600
cacggcggcg agaaccctcc ggggaccaaa ggcgaagacc aatttccctc tttctccgcc     660
gttctaccat cccgatccat tttccgatca ccggcacttc gccaacaccg gcgaagattt     720
ccacgatcac cggcgaccaa catccagtgg catgagcagc accgtagagt ccttcagcgg     780
cccccgtgct gccgtgccgg cgacagcgcc ggtggccacc ggccggagat atccccggac     840
gccaccgtt  atccccgagg actgccgcag cgactgcgat tcgtcgtcct ccgtcgttga     900
cgacggcgaa ggcgacaacg tggcgtcgtc gttcccgcga gaaccgttgc cgtttgatct     960
aaacgcgttg ccgttagacg atgctgacgt ggcaaccgat gatctgttct gcaccgttct    1020
ttgcctctga tgagaaaaaa tgaaaaaacg gaacgaaatg atgtatttgg ttcgttgacg    1080
gaattattat tatttttttc tttctt                                        1106
```

<210> SEQ ID NO 42
<211> LENGTH: 210
<212> TYPE: PRT
<213> ORGANISM: Glycine max
<220> FEATURE:
<221> NAME/KEY: misc_feature
<223> OTHER INFORMATION: Ceres CLONE ID no. 674166
<220> FEATURE:
<221> NAME/KEY: misc_feature
<223> OTHER INFORMATION: Ceres SEED LINE ID no. ME03186
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<222> LOCATION: (26)..(89)
<223> OTHER INFORMATION: Pfam Name: AP2;
      Pfam Description: AP2 domain

<400> SEQUENCE: 42

Met Gly Arg Gly Gly Thr Ala Ala Ala Ala Glu Val Ala Glu Pro
1               5                   10                  15

Gly Leu Arg Pro Val Tyr Phe Lys Glu Gln Arg Tyr Arg Gly Val Arg
                20                  25                  30

Lys Arg Pro Trp Gly Arg Phe Ala Ala Glu Ile Arg Asp Pro Leu Lys
            35                  40                  45

Lys Ala Arg Val Trp Leu Gly Thr Phe Asp Thr Ala Glu Glu Ala Ala
        50                  55                  60

Arg Ala Tyr Asp Thr Ala Ala Arg Thr Leu Arg Gly Pro Lys Ala Lys

```
                65                  70                  75                  80
Thr Asn Phe Pro Leu Ser Pro Pro Phe Tyr His Pro Asp Pro Phe Ser
                    85                  90                  95
Asp His Arg His Phe Ala Asn Thr Gly Glu Asp Phe His Asp His Arg
                    100                 105                 110
Arg Pro Thr Ser Ser Gly Met Ser Ser Thr Val Glu Ser Phe Ser Gly
                    115                 120                 125
Pro Arg Ala Ala Val Pro Ala Thr Ala Pro Val Ala Thr Gly Arg Arg
                    130                 135                 140
Tyr Pro Arg Thr Pro Pro Val Ile Pro Glu Asp Cys Arg Ser Asp Cys
145                 150                 155                 160
Asp Ser Ser Ser Val Val Asp Asp Gly Glu Gly Asp Asn Val Ala
                    165                 170                 175
Ser Ser Phe Pro Arg Glu Pro Leu Pro Phe Asp Leu Asn Ala Leu Pro
                    180                 185                 190
Leu Asp Asp Ala Asp Val Ala Thr Asp Asp Leu Phe Cys Thr Val Leu
                    195                 200                 205
Cys Leu
    210

<210> SEQ ID NO 43
<211> LENGTH: 225
<212> TYPE: PRT
<213> ORGANISM: Glycine max
<220> FEATURE:
<221> NAME/KEY: misc_feature
<223> OTHER INFORMATION: Public GI no. 12322345
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 43

Met Arg Arg Gly Arg Gly Ser Ser Ala Val Ala Gly Pro Thr Val Val
1               5                   10                  15
Ala Ala Ile Asn Gly Ser Val Lys Glu Ile Arg Phe Arg Gly Val Arg
                    20                  25                  30
Lys Arg Pro Trp Gly Arg Phe Ala Ala Glu Ile Arg Asp Pro Trp Lys
                    35                  40                  45
Lys Ala Arg Val Trp Leu Gly Thr Phe Asp Ser Ala Glu Glu Ala Ala
                    50                  55                  60
Arg Ala Tyr Asp Ser Ala Ala Arg Asn Leu Arg Gly Pro Lys Ala Lys
65                  70                  75                  80
Thr Asn Phe Pro Ile Asp Ser Ser Pro Pro Pro Asn Leu Arg
                    85                  90                  95
Phe Asn Gln Ile Arg Asn Gln Asn Gln Asn Val Asp Pro Phe Met
                    100                 105                 110
Asp His Arg Leu Phe Thr Asp His Gln Gln Gln Phe Pro Ile Val Asn
                    115                 120                 125
Arg Pro Thr Ser Ser Ser Met Ser Ser Thr Val Glu Ser Phe Ser Gly
                    130                 135                 140
Pro Arg Pro Thr Thr Met Lys Pro Ala Thr Thr Lys Arg Tyr Pro Arg
145                 150                 155                 160
```

```
Thr Pro Pro Val Val Pro Glu Asp Cys His Ser Asp Cys Asp Ser Ser
            165                 170                 175

Ser Ser Val Ile Asp Asp Asp Asp Ile Ala Ser Ser Arg Arg
        180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225

<210> SEQ ID NO 44
<211> LENGTH: 215
<212> TYPE: PRT
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<222> LOCATION: (174)..(174)
<223> OTHER INFORMATION: Xaa is any aa, unknown, or other
<220> FEATURE:
<221> NAME/KEY: misc_feature
<222> LOCATION: (194)..(194)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (209)..(209)
<223> OTHER INFORMATION: Xaa is any aa, unknown, or other
<220> FEATURE:
<221> NAME/KEY: misc_feature
<222> LOCATION: (214)..(214)
<223> OTHER INFORMATION: Xaa is any aa, unknown, or other
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 44

Met Arg Lys Gly Arg Gly Ser Ser Ala Val Pro Pro Ala Leu Pro Gly
1               5                   10                  15

Ser Val Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ser Arg Val Trp
        35                  40                  45

Leu Gly Thr Phe Asp Ser Ala Glu Glu Ala Ala Arg Ala Tyr Asp Ala
    50                  55                  60

Ala Ala Arg Asn Leu Arg Gly Pro Lys Ala Lys Thr Asn Phe Gln Ile
65                  70                  75                  80

Asp Cys Ser Pro Ser Ser Pro Leu Gln Pro Leu His His Arg Asn Gln
                85                  90                  95

Ile Asp Pro Phe Met Asp His Arg Leu Tyr Gly Gly Glu Gln Glu Val
            100                 105                 110

Val Ile Ile Ser Arg Pro Ala Ser Ser Met Ser Ser Thr Val Lys
        115                 120                 125
```

```
Ser Cys Ser Gly Val Arg Pro Ala Ser Ser Val Ala Lys Ala Ala
    130                 135                 140

Thr Lys Arg Tyr Pro Arg Thr Pro Pro Val Ala Pro Glu Asp Cys Arg
145                 150                 155                 160

Ser Asp Cys Asp Ser Ser Ser Val Val Glu Asp Gly Xaa Asp Ile
                165                 170                 175

Ala Ser Ser Ser Arg Arg Lys Pro Pro Phe Glu Phe Asp Leu Asn
            180                 185                 190

Phe Xaa Pro Leu Asp Gly Val Asp Leu Phe Val Gly Ala Asp Asp Xaa
        195                 200                 205

Xaa Cys Thr Asp Leu Xaa Leu
    210                 215

<210> SEQ ID NO 45
<211> LENGTH: 211
<212> TYPE: PRT
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional homolog of Ceres Clone ID no. 674166
      given in SEQ ID NO: 42

<400> SEQUENCE: 45

Met Arg Arg Arg Gly Val Ala Ala Ala Asp Ala Asp Gly Asp Val Glu
1               5                   10                  15

Leu Arg Phe Arg Gly Val Arg Lys Arg Pro Trp Gly Arg Tyr Ala Ala
            20                  25                  30

Glu Ile Arg Asp Pro Ala Lys Lys Ala Arg Val Trp Leu Gly Thr Phe
        35                  40                  45

Asp Ser Ala Glu Asp Ala Ala Arg Ala Tyr Asp Ala Ala Ala Arg Met
50                  55                  60

Leu Arg Gly Pro Lys Ala Arg Thr Asn Phe Pro Leu Pro Ala Ala Ala
65                  70                  75                  80

Ala Leu His His Pro His Met Pro Ala Ala Ala Ala Ala Ala Ala Pro
                85                  90                  95

Pro Tyr Thr Thr Tyr Pro Thr Ala Thr Gly Val Val Ser Thr Pro Pro
            100                 105                 110

Val Ala Arg Pro Ala Cys Ser Ser Leu Ser Ser Thr Val Glu Ser Phe
            115                 120                 125

Ser Gly Ala Arg Pro Arg Pro Val Leu Pro Pro Arg Phe Pro Pro Pro
    130                 135                 140

Ser Ile Pro Asp Gly Asp Cys Arg Ser Asp Cys Gly Ser Ser Ala Ser
145                 150                 155                 160

Val Val Asp Asp Asp Cys Thr Asp Ala Ala Ala Ser Ala Ser Cys Pro
                165                 170                 175

Phe Pro Leu Pro Phe Asp Leu Asn Leu Pro Pro Gly Gly Gly Gly Ala
            180                 185                 190

Gly Val Gly Phe Tyr Ala Asp Glu Glu Asp Glu Leu Arg Leu Thr Ala
        195                 200                 205

Leu Arg Leu
    210
```

<210> SEQ ID NO 46
<211> LENGTH: 194
<212> TYPE: PRT
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<222> LOCATION: (20)..(83)
<223> OTHER INFORMATION: Pfam Name: AP2
    Pfam Description: AP2 domain
<220> FEATURE:
<221> NAME/KEY: misc_feature
<223> OTHER INFORMATION: Functional homolog of Ceres Clone ID no. 674166
    given in SEQ ID NO: 42

<400> SEQUENCE: 46

Met Arg Lys Ala Arg Pro Pro Gln Pro Gln Pro Ser Gln Gln
1               5                  10                  15

Ser Pro Glu Ile Arg Tyr Arg Gly Val Arg Lys Arg Pro Ser Gly Arg
            20                  25                  30

Tyr Ala Ala Glu Ile Arg Asp Pro Ala Lys Lys Thr Pro Ile Trp Leu
        35                  40                  45

Gly Thr Phe Asp Cys Ala Glu Asp Ala Ala Arg Ala Tyr Asp Ser Ala
    50                  55                  60

Ala Arg Ser Leu Arg Gly Pro Thr Ala Arg Thr Asn Phe Pro Pro Ser
65                  70                  75                  80

Ser Ala Thr Gln Pro Pro Arg Pro Pro Pro Ala Ala Ala
                85                  90                  95

Ala Ala Ala Thr Ser Ser Gln Ser Ser Thr Val Glu Ser Trp Ser Gly
            100                 105                 110

Gly Gly Pro Arg Ala Pro Ala Arg Ala Arg Ser Ala Ala Arg Ala Gly
        115                 120                 125

Thr Ala Lys Glu Gly Glu Glu Asp Cys Arg Ser Tyr Cys Gly Ser Ser
    130                 135                 140

Ser Ser Val Leu Leu Glu Glu Gly Ala Asp Asp Ala Ala Ala Ser Arg
145                 150                 155                 160

Ser Pro Leu Pro Phe Asp Leu Asn Met Pro Pro Pro Gln Glu Gly Ala
                165                 170                 175

Leu Asp Ala Glu Ala Asp Gln Met Thr Cys Arg Tyr Asp Thr Leu Leu
            180                 185                 190

Arg Leu

<210> SEQ ID NO 47
<211> LENGTH: 660
<212> TYPE: DNA
<213> ORGANISM: Populus balsamifera subsp. trichocarpa
<220> FEATURE:
<221> NAME/KEY: misc_feature
<223> OTHER INFORMATION: Ceres ANNOT ID no.1441430
<220> FEATURE:
<221> NAME/KEY: misc_feature
<223> OTHER INFORMATION: Encodes the protein at SEQ ID NO: 48

<400> SEQUENCE: 47
atggggagaa caagaacaac aacaaaacag gctgttgacc caaatggatc tgcaacccaa      60
aatatgttag taattgcaaa agagcccaga tacagaggag tacgaaagag accatgggga     120
agattcgctg cggagattag agatccctgg aaaaagacca gagtttggct gggcacctc      180

```
gactctgcag aggatgcagc gcgtgcctac gatgcggctg ctcgcaccct ccgcggagca    240
aaggccaaga caaactttcc tatctccaca acgaaccagt tattcaatca tcaaaatcaa    300
aaccaaagcc caaccgatcc cttcttggat caccacagta taaatcccca agacccaca     360 tctagcagtt tgagcagtac agtggagtct ttcagcggtc ctaggcctcc gcagccaaca    420
acaacaacaa aatcgggaaa tgggccgagg agatctcatc cacggatccc accggttgtt    480
ccagaagatt gtcatagcga ttgcgattca tcttcttcgg tggttgatga cagagatgtc    540
gcatccgctg cttcttcttt gtgccgcaag cctttgcctt tcgatctaaa tttcccaccg    600
ttggaccagg ttgacttggg ctctggtgat gatctccact gcactgcttt atgcctttga    660
```

<210> SEQ ID NO 48
<211> LENGTH: 219
<212> TYPE: PRT
<213> ORGANISM: Populus balsamifera subsp. trichocarpa
<220> FEATURE:
<221> NAME/KEY: misc_feature
<223> OTHER INFORMATION: Ceres ANNOT ID no. 1441430
<220> FEATURE:
<221> NAME/KEY: misc_feature
<222> LOCATION: (29)..(92)
<223> OTHER INFORMATION: Pfam Name: AP2
    Pfam Description: AP2 domain
<220> FEATURE:
<221> NAME/KEY: misc_feature
<223> OTHER INFORMATION: Functional Homolog of Ceres CLONE ID no. 674166
    Given in SEQ ID NO: 42

<400> SEQUENCE: 48

Met Gly Arg Thr Arg Thr Thr Lys Gln Ala Val Asp Pro Asn Gly
1               5                   10                  15

Ser Ala Thr Gln Asn Met Leu Val Ile Ala Lys Glu Pro Arg Tyr Arg
            20                  25                  30

Gly Val Arg Lys Arg Pro Trp Gly Arg Phe Ala Ala Glu Ile Arg Asp
        35                  40                  45

Pro Trp Lys Lys Thr Arg Val Trp Leu Gly Thr Phe Asp Ser Ala Glu
    50                  55                  60

Asp Ala Ala Arg Ala Tyr Asp Ala Ala Ala Arg Thr Leu Arg Gly Ala
65                  70                  75                  80

Lys Ala Lys Thr Asn Phe Pro Ile Ser Thr Thr Asn Gln Leu Phe Asn
                85                  90                  95

His Gln Asn Gln Asn Gln Ser Pro Thr Asp Pro Phe Leu Asp His His
            100                 105                 110

Ser Ile Asn Pro Gln Arg Pro Thr Ser Ser Leu Ser Ser Thr Val
        115                 120                 125

Glu Ser Phe Ser Gly Pro Arg Pro Pro Gln Pro Thr Thr Thr Lys
    130                 135                 140

Ser Gly Asn Gly Pro Arg Arg Ser His Pro Arg Ile Pro Pro Val Val
145                 150                 155                 160

Pro Glu Asp Cys His Ser Asp Cys Asp Ser Ser Ser Val Val Asp
                165                 170                 175

Asp Arg Asp Val Ala Ser Ala Ala Ser Ser Leu Cys Arg Lys Pro Leu
            180                 185                 190

Pro Phe Asp Leu Asn Phe Pro Pro Leu Asp Gln Val Asp Leu Gly Ser
        195                 200                 205

Gly Asp Asp Leu His Cys Thr Ala Leu Cys Leu
    210                 215

```
<210> SEQ ID NO 49
<211> LENGTH: 985
<212> TYPE: DNA
<213> ORGANISM: Glycine max
<220> FEATURE:
<221> NAME/KEY: misc_feature
<223> OTHER INFORMATION: Ceres CLONE ID no.1240330
<220> FEATURE:
<221> NAME/KEY: misc_feature
<223> OTHER INFORMATION: Encodes the protein at SEQ ID NO: 50

<400> SEQUENCE: 49
attattcctc ttccatctct attctccata cacccacca caccacttgt gaaaaacctc      60
attaatatca cacactgaca tgtatctctg agctccaatc caatacaaga ccacaccttg     120
tcgtgtcgga cgaaccttgg tgtctgtttt tttttttttt tcattatttt ctccgaagag     180
atgaggaagg gcagaggtgg aggcgcctcg gcggcggcgg tggatgtgaa cggatccatt     240
ttaaaggagc tcggtaccg gggcgtgagg aagagaccgt gggggagatt cgccgcggag      300
atcagagacc cgttgaagaa agccagggtt tggttgggaa ccttcgattc tgccgaggat     360
gctgctcgtg cctacgacgc cgccgctcgg actctccgag gtcccaaggc caaaacaaat     420 ttccccctc tctcacctt ttgctatcca cacccacca ccgatccttt cttctacact       480
ggtttccacg atcaacacca ccaccacaac aacaacaacc ttaacaaccc tcaaagaccc     540
acttcaagtg gcatgagtag caccgttgag tccttcagtg ggccccgccc tccaccacc      600 accactacca ccacaaccac aactgcgacg ccgttttga ctgctacgcg gagatacccg      660
cgcactcccc ctcttgtccc tgaagactgc cacagtgact gcgactcttc ctcctccgtc     720
gttgacgacg gcgacgacaa catcgtttcg tcgtcgtttc gacctcccct gccgtttgat    780
ctcaacgcgc tgccgtttga tgatgctgcc gcggatgatg atctacgccg caccgcgctt    840
tgtctctgat gatgattatc gtgcgatgat gattttaat ttctcatttt tttacttgat     900 tttttttgtta ttgctatgca gaagaaatat atatttaaaa tgatgatcag atgtaagatt    960
atggtaatat gatcttaatt ctgtg                                          985

<210> SEQ ID NO 50
<211> LENGTH: 222
<212> TYPE: PRT
<213> ORGANISM: Glycine max
<220> FEATURE:
<221> NAME/KEY: misc_feature
<223> OTHER INFORMATION: Ceres CLONE ID no. 1240330
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 50

Met Arg Lys Gly Arg Gly Gly Gly Ala Ser Ala Ala Ala Val Asp Val
1               5                   10                  15

Asn Gly Ser Ile Leu Lys Glu Pro Arg Tyr Arg Gly Val Arg Lys Arg
            20                  25                  30

Pro Trp Gly Arg Phe Ala Ala Glu Ile Arg Asp Pro Leu Lys Lys Ala
        35                  40                  45

Arg Val Trp Leu Gly Thr Phe Asp Ser Ala Glu Asp Ala Ala Arg Ala
    50                  55                  60
```

Tyr Asp Ala Ala Ala Arg Thr Leu Arg Gly Pro Lys Ala Lys Thr Asn
65                  70                  75                  80

Phe Pro Pro Leu Ser Pro Phe Cys Tyr Pro His Pro Thr Thr Asp Pro
                85                  90                  95

Phe Phe Tyr Thr Gly Phe His Asp Gln His His His Asn Asn Asn
            100                 105                 110

Asn Leu Asn Asn Pro Gln Arg Pro Thr Ser Ser Gly Met Ser Ser Thr
            115                 120                 125

Val Glu Ser Phe Ser Gly Pro Arg Pro Pro Thr Thr Thr Thr Thr Thr
130                 135                 140

Thr Thr Thr Thr Ala Thr Pro Phe Leu Thr Ala Thr Arg Arg Tyr Pro
145                 150                 155                 160

Arg Thr Pro Pro Leu Val Pro Glu Asp Cys His Ser Asp Cys Asp Ser
                165                 170                 175

Ser Ser Ser Val Val Asp Asp Gly Asp Asp Asn Ile Val Ser Ser Ser
            180                 185                 190

Phe Arg Pro Pro Leu Pro Phe Asp Leu Asn Ala Leu Pro Phe Asp Asp
            195                 200                 205

Ala Ala Ala Asp Asp Asp Leu Arg Arg Thr Ala Leu Cys Leu
210                 215                 220

<210> SEQ ID NO 51
<211> LENGTH: 726
<212> TYPE: DNA
<213> ORGANISM: Zea mays
<220> FEATURE:
<221> NAME/KEY: misc_feature
<223> OTHER INFORMATION: Ceres CLONE ID no.1382611
<220> FEATURE:
<221> NAME/KEY: misc_feature
<223> OTHER INFORMATION: Encodes the protein at SEQ ID NO: 52

<400> SEQUENCE: 51
acttttctct cccattcttt tacaactcac gttgcacagc cttttctct atatattact      60 tgacataaac tactattcac aacacaaaca cacacataac catggcctct tcttcacaag    120
cttttccttt gctcacattg tctatggttt tagttcattt ctctttagct caatctccca    180
tgatggctcc ttctggctcc atgtccatgc cgccaatgcc tagcggcggc tctccaatgc    240
caatgatgac tccaccacct atgccaatga tgactccacc acctatggct atggctccac    300
cacctatgcc tatgactcca ccaccaatgc ccatggctcc gatgccaatg actccatctt    360
caagtccaat gagcccacca actactatgg ccccaagtcc agaaacagtc cctgatatgg    420
cttcgccacc gatgatgcca ggaatggatt cttctccttc tccgggaccc atgccaccgg    480
caatggcctc tccagattcc ggagcattca atgtaagaaa cgacgtcgta gcaatttcgt    540
tccttgttgc agctcatttg ctcctagttt gagattatta ttaaattggc cagcgtcgtg    600
tttgtgtaat ttactttcat tttttctcg agccattaat tttcatgttt tatcatatat    660
ttgggtttgt gtttgatatg gtacgattca gacatttgtt tgcttaataa gtttatcgtt    720
gactct                                                             726

<210> SEQ ID NO 52
<211> LENGTH: 156
<212> TYPE: PRT
<213> ORGANISM: Zea mays
<220> FEATURE:
<221> NAME/KEY: misc_feature
<223> OTHER INFORMATION: Ceres CLONE ID no. 1382611
<220> FEATURE:

<221> NAME/KEY: misc_feature
<223> OTHER INFORMATION: Functional Homolog of Ceres CLONE ID no. 30087
      Given in SEQ ID NO: 2

<400> SEQUENCE: 52

Met Ala Ser Ser Gln Ala Phe Leu Leu Leu Thr Leu Ser Met Val
1               5                   10                  15

Leu Val His Phe Ser Leu Ala Gln Ser Pro Met Met Ala Pro Ser Gly
            20                  25                  30

Ser Met Ser Met Pro Pro Met Pro Ser Gly Gly Ser Pro Met Pro Met
        35                  40                  45

Met Thr Pro Pro Pro Met Pro Met Met Thr Pro Pro Pro Met Ala Met
    50                  55                  60

Ala Pro Pro Pro Met Pro Met Thr Pro Pro Met Pro Met Ala Pro
65                  70                  75                  80

Met Pro Met Thr Pro Ser Ser Ser Pro Met Ser Pro Pro Thr Thr Met
            85                  90                  95

Ala Pro Ser Pro Glu Thr Val Pro Asp Met Ala Ser Pro Pro Met Met
                100                 105                 110

Pro Gly Met Asp Ser Ser Pro Ser Pro Gly Pro Met Pro Pro Ala Met
            115                 120                 125

Ala Ser Pro Asp Ser Gly Ala Phe Asn Val Arg Asn Asp Val Val Ala
            130                 135                 140

Ile Ser Phe Leu Val Ala Ala His Leu Leu Leu Val
145                 150                 155

<210> SEQ ID NO 53
<211> LENGTH: 580
<212> TYPE: DNA
<213> ORGANISM: Papaver somniferum
<220> FEATURE:
<221> NAME/KEY: misc_feature
<223> OTHER INFORMATION: Ceres CLONE ID no.1627907
<220> FEATURE:
<221> NAME/KEY: misc_feature
<223> OTHER INFORMATION: Encodes the protein at SEQ ID NO: 54

<400> SEQUENCE: 53
gcagaagcac aaggtaagat tgaaggagga gaccggaact cttcttcgcc aaaaccctag      60
ttcgagctca ccaacaacaa tctttcgcaa tgactaagcg taccaagaag gccggaattg     120
tgggtaaata tggtaccaga tatggagctt cattaaggaa acagattaag aagatggaag     180
tgagtcagca tgcaaagtac ttctgtgagt tctgcggaaa gtacgctgtg aagagacagg     240
ctgttggaat ctggggatgc aaggattgtg gcaaagttaa agctggtggt gcttacactt     300
tgaacaccgc cagtgccgtg acagttagaa gcaccattag aaggttgagg gagcaaactg     360
aatcttagat tgatctcgtt atctatattt tgtattttgg tactgggtga gaggtaccat     420
cagagctaat ttagtgttta tcaccttttc tggtcttcaa gaactagtta gtcattttgt     480
tattcagaga ttttttgataa tgtctagtat cttacatttg tgagcagact atttctttgt     540
ttcaaattat ggagttctga tgaatcttat atttattctc                           580

<210> SEQ ID NO 54
<211> LENGTH: 92
<212> TYPE: PRT
<213> ORGANISM: Papaver somniferum
<220> FEATURE:
<221> NAME/KEY: misc_feature
<223> OTHER INFORMATION: Ceres CLONE ID no. 1627907
<220> FEATURE:

```
<221> NAME/KEY: misc_feature
<222> LOCATION: (2)..(91)
<223> OTHER INFORMATION: Pfam Name: Ribosomal_L37ae
      Pfam Description: Ribosomal L37ae protein family
<220> FEATURE:
<221> NAME/KEY: misc_feature
<223> OTHER INFORMATION: Functional Homolog of Ceres CLONE ID no. 271922
      Given in SEQ ID NO: 20

<400> SEQUENCE: 54
```

Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ala Lys Tyr Phe Cys Glu Phe Cys Gly Lys Tyr Ala Val Lys
        35                  40                  45

Arg Gln Ala Val Gly Ile Trp Gly Cys Lys Asp Cys Gly Lys Val Lys
    50                  55                  60

Ala Gly Gly Ala Tyr Thr Leu Asn Thr Ala Ser Ala Val Thr Val Arg
65                  70                  75                  80

Ser Thr Ile Arg Arg Leu Arg Glu Gln Thr Glu Ser
                85                  90

```
<210> SEQ ID NO 55
<211> LENGTH: 983
<212> TYPE: DNA
<213> ORGANISM: Panicum virgatum
<220> FEATURE:
<221> NAME/KEY: misc_feature
<223> OTHER INFORMATION: Ceres CLONE ID no.1761125
<220> FEATURE:
<221> NAME/KEY: misc_feature
<223> OTHER INFORMATION: Encodes the protein at SEQ ID NO: 56

<400> SEQUENCE: 55
```

| | | | | | |
|---|---|---|---|---|---|
| accagaccac | accacaccac | accgcgtcca | catcctcccg | cgcttctccg | ctcagcccgc | 60 |
| gcgtttccgc | tgaggaggga | tagccgcgcg | gcgcgtcgag | gggtttgtct | ttgatcgggt | 120 |
| agctgaggct | gagcgggcgg | ggcaggatga | tgcgcgacac | ggcggccgtg | gccgtggcgg | 180 |
| cgccgcggta | caggggcgtg | cggaagcggc | cgtggggccg | gttcgcggcg | gagatccgcg | 240 |
| acccggcgaa | gcgcgcgcgc | gtctggctcg | gcaccttcga | ctccgccgag | gccgcggcgc | 300 |
| gcgcctacga | cgtcgccgcg | cggacccgc  | gcggcccgct | cgccaggacc | aacttcccct | 360 |
| gcgcctcctc | ccgcctcccg | ctgccctccc | gccaccaagg | cggctgtggc | ggcggcctcg | 420 |
| tcgcgccgcc | gcccgccgcg | ccgacgtgca | gctccagctc | caccgtcgag | tcctccagcg | 480 |
| gaccccgagg | ggcgcccagg | gctgctgcgg | cggcggcgcc | tcgaattcgg | aggcggtcgg | 540 |
| tgaaaaagcc | gcgccggca  | cgcccgaca  | tcgactgcca | cagcgactgc | gcctcgtcgg | 600 |
| cctccgtcgt | ggacgacggc | gacgacgcct | ccacggtccg | gtcgcgcgcg | ccgttcgacc | 660 |
| tcaacgtccc | ggctccggtg | gacggtgacc | acgcccctcga | cctctgcacg | gagctgcggc | 720 |
| tctgagcaat | atgatcctcg | aacaacaaca | acagcaaaac | attgaaggcg | attttttcccc | 780 |
| ggtcttcttt | tcctgactaa | attctgatat | gatcaatatg | ctcgagagtt | ctcgtttttct | 840 |
| ttaacgcctc | ttgtatttgg | atctgctacc | atcttctctg | cccattctat | ttgtacacca | 900 |
| gataacatgt | aagatgttca | cgaattaaca | catatctttt | cttaaaaaaa | tgaattaaca | 960 |
| cggaaaaaaa | aaaaaaaaaa | aaa | | | | 983 |

```
<210> SEQ ID NO 56
```

-continued

```
<211> LENGTH: 192
<212> TYPE: PRT
<213> ORGANISM: Panicum virgatum
<220> FEATURE:
<221> NAME/KEY: misc_feature
<223> OTHER INFORMATION: Ceres CLONE ID no. 1761125
<220> FEATURE:
<221> NAME/KEY: misc_feature
<222> LOCATION: (13)..(76)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 56

Met Met Arg Asp Thr Ala Ala Val Ala Val Ala Ala Pro Arg Tyr Arg
1               5                   10                  15

Gly Val Arg Lys Arg Pro Trp Gly Arg Phe Ala Ala Glu Ile Arg Asp
            20                  25                  30

Pro Ala Lys Arg Ala Arg Val Trp Leu Gly Thr Phe Asp Ser Ala Glu
        35                  40                  45

Ala Ala Ala Arg Ala Tyr Asp Val Ala Ala Arg Thr Leu Arg Gly Pro
    50                  55                  60

Leu Ala Arg Thr Asn Phe Pro Cys Ala Ser Ser Arg Leu Pro Leu Pro
65                  70                  75                  80

Ser Arg His Gln Gly Gly Cys Gly Gly Leu Val Ala Pro Pro
                85                  90                  95

Ala Ala Pro Thr Cys Ser Ser Ser Thr Val Glu Ser Ser Ser Gly
            100                 105                 110

Pro Arg Gly Ala Pro Arg Ala Ala Ala Ala Ala Pro Arg Ile Arg
        115                 120                 125

Arg Arg Ser Val Lys Lys Pro Arg Pro Ala Ala Pro Asp Ile Asp Cys
130                 135                 140

His Ser Asp Cys Ala Ser Ser Ala Ser Val Val Asp Asp Gly Asp Asp
145                 150                 155                 160

Ala Ser Thr Val Arg Ser Arg Ala Pro Phe Asp Leu Asn Val Pro Ala
                165                 170                 175

Pro Val Asp Gly Asp His Ala Leu Asp Leu Cys Thr Glu Leu Arg Leu
            180                 185                 190

<210> SEQ ID NO 57
<211> LENGTH: 594
<212> TYPE: DNA
<213> ORGANISM: Panicum virgatum
<220> FEATURE:
<221> NAME/KEY: misc_feature
<223> OTHER INFORMATION: Ceres CLONE ID no.1783890
<220> FEATURE:
<221> NAME/KEY: misc_feature
<223> OTHER INFORMATION: Encodes the protein at SEQ ID NO: 58

<400> SEQUENCE: 57
gagccctacc cgcacccgcg ccgccgccgc cccgcgcccc gtcgccgcag acgactccgc    60
cccgtcgccg cgatgacgaa gcgcaccaag aaggccggaa tcgtcggcaa atatggaact   120
aggtatggtg ctagcttgcg taagcaaatc aagaagatgg aggtgtctca gcactccaag   180
tacttctgcg agttctgtgg aaagtttgct gtgaaaagga aagcagttgg aatctgggga   240
tgcaaggact gcgggaaggt taaggctggt ggtgcttaca ccatgaacac tgctagtgca   300
gtcaccgtca ggagcacaat ccgtcgcttg agggagcaga ctgaagcata atcggagctc   360
```

-continued

```
ttctctgcag tagtcctgtg cttttttgtac cgtctaagac atatggctgt ttggcctaag      420
aacattcatg aatattctgg ttatgcttaa ggatatcaaa aattatggtg ctaaaatttg      480
tacttcgttg ctgttgcaaa gttgacctgt cttgatccat tcataatgta gaatttcctc      540
atggttctta tctccagttt gctactcttt ggccaaaaaa aaaaaaaaaa aaaa            594
```

<210> SEQ ID NO 58
<211> LENGTH: 92
<212> TYPE: PRT
<213> ORGANISM: Panicum virgatum
<220> FEATURE:
<221> NAME/KEY: misc_feature
<223> OTHER INFORMATION: Ceres CLONE ID no. 1783890
<220> FEATURE:
<221> NAME/KEY: misc_feature
<222> LOCATION: (2)..(91)
<223> OTHER INFORMATION: Pfam Name: Ribosomal_L37ae
    Pfam Description: Ribosomal L37ae protein family
<220> FEATURE:
<221> NAME/KEY: misc_feature
<223> OTHER INFORMATION: Functional Homolog of Ceres CLONE ID no. 271922
    Given in SEQ ID NO: 20

<400> SEQUENCE: 58

```
Met Thr Lys Arg Thr Lys Lys Ala Gly Ile Val Gly Lys Tyr Gly Thr
1               5                   10                  15

Arg Tyr Gly Ala Ser Leu Arg Lys Gln Ile Lys Lys Met Glu Val Ser
            20                  25                  30

Gln His Ser Lys Tyr Phe Cys Glu Phe Cys Gly Lys Phe Ala Val Lys
        35                  40                  45

Arg Lys Ala Val Gly Ile Trp Gly Cys Lys Asp Cys Gly Lys Val Lys
    50                  55                  60

Ala Gly Gly Ala Tyr Thr Met Asn Thr Ala Ser Ala Val Thr Val Arg
65                  70                  75                  80

Ser Thr Ile Arg Arg Leu Arg Glu Gln Thr Glu Ala
            85                  90
```

<210> SEQ ID NO 59
<211> LENGTH: 880
<212> TYPE: DNA
<213> ORGANISM: Panicum virgatum
<220> FEATURE:
<221> NAME/KEY: misc_feature
<223> OTHER INFORMATION: Ceres CLONE ID no.1802327
<220> FEATURE:
<221> NAME/KEY: misc_feature
<223> OTHER INFORMATION: Encodes the protein at SEQ ID NO: 60

<400> SEQUENCE: 59

```
acacagatac attcgtcgat ccaccactgt ccagtgcttg gcggttacgc acgcacgcac      60
acagatagga ttatctttta ctacaccaac tcaccaagat actagcaagc cgaatcgaca     120
aacaagcagc aggaagagga ggcatggcgc tcgcggaggg gaacgtcatc ttcggcgagg     180
agcaggaggc gctggtgctc aagtcgtggg ccctcatgaa gaaggactcg gccgacctcg     240
gcctccgctt cttcctcaag atcttcgaga tcgcgccgtc ggcgaagcag atgttctcgt     300
tcctgcgcga ctccgacgtg ccgctcgaga agaaccccaa gctcaagaac cacgccatgt     360
ccgtcttcgt catgaccctgc gaggcggcgg cgcagctacg gaaggccggg aagtcaccg      420 tcagggagac gacgctcaag cggctgggcg ccacgcactt caagtacggc gtcgccgacg     480
gccacttcga ggtgacgagg ttcgcgctgc tggagacgat aaaggaggcg cttcccgccg     540
```

```
acatgtggag cctggagatg aagaacgcct ggagcgaggc ttacaaccag ctggtggcgg      600
ccatcaagca ggagatgaag cctgccgcat gatgctgctg ctgctactga gatgaagcct      660
gcccgcatga tgctgctgct gctactcggc ctccgcgctg agttccccct acgatgcacc      720
accatctcca aattcttcat cgctgttttt ttttttttgc tgttttgact tgtattgtgc      780
attttccaaa tctctcgatg gagacaagtg tgatgactaa ttttttgagag catgtatata      840 tgttgtgatg agcattgaat aaaaaaaaaa aaaaaaaaa                              880
```

<210> SEQ ID NO 60
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1802327
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 60

```
Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Asn Ala Trp Ser
    130                 135                 140

Glu Ala Tyr Asn Gln Leu Val Ala Ala Ile Lys Gln Glu Met Lys Pro
145                 150                 155                 160

Ala Ala
```

<210> SEQ ID NO 61
<211> LENGTH: 1017
<212> TYPE: DNA
<213> ORGANISM: Gossypium hirsutum
<220> FEATURE:
<221> NAME/KEY: misc_feature
<223> OTHER INFORMATION: Ceres CLONE ID no.1838364
<220> FEATURE:
<221> NAME/KEY: misc_feature
<223> OTHER INFORMATION: Encodes the protein at SEQ ID NO: 62

<400> SEQUENCE: 61

```
cctgcccatt tccatcttcc ttctttcctt cctctttcct ttgtcttctt gctttatctt      60
```

-continued

```
ccctttatct tcaatctttt ctgttctgtt tttttcttag attcataggt aagttcgttt      120
tggttggctt gattatttcc tcacttccct tcttttttgg ttcatcgtga tcttttcatc      180 aaccccttt gattgttata tagattgtta ctattctttt aatctttaa atattttt         240 tccatgagga gagggagagg tgccgcagct gcaaacgccg tagctaggag accggcactg      300
caacccagcg gatctattaa agagccgaga tacagaggtg ttagaaaaag gccatggggc      360
agattcgcgg ccgagattcg agaccctggg aagaagacca gggtctggtt agggacgttc      420
gactcggccg aagaagccgc tcgagcctac gatacggcgg cgaggacgct ccgtggaccc      480
aaagctaaaa caaatttccc cataaattct tcaaatatcc cggcttttcc tttcgaaacc      540
aatcatcacc acaacgaagg gttcatcgac caacgccggt tatatccgat gggcgaattt      600
catgaccccg aagtgaatcc acagagaccc acgaggagta gcatgagtag cacggtggag      660
tcgtttagtg gacccagacc ggcccaacca ccgcaaaagt cggcggactt cgcggtggtt      720
tcgactagga agtactatcc gaggccgccg ccagtagagc cagaggattg tcatagtgac      780
tgtgattcat catcgtcggt ggttgatgat ggggatatcg cgttgtcttc ttgtcggaaa      840
actttgcctt tcgatctcaa ttttccaccc ttggatgaag atggaagatc tccagtgtac      900
tgctttatgt ctttgatcgc gatgccggtg atgaatgatg atgatcgatt attggatctc      960
tttttctttt ttaaaaaatg ttagcttttt taagcggaaa aaaaaaaaaa aaaaaaa       1017
```

<210> SEQ ID NO 62
<211> LENGTH: 246
<212> TYPE: PRT
<213> ORGANISM: Gossypium hirsutum
<220> FEATURE:
<221> NAME/KEY: misc_feature
<223> OTHER INFORMATION: Ceres CLONE ID no. 1838364
<220> FEATURE:
<221> NAME/KEY: misc_feature
<222> LOCATION: (28)..(91)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 62

```
Met Arg Arg Gly Arg Gly Ala Ala Ala Ala Asn Ala Val Ala Arg Arg
1               5                   10                  15

Pro Ala Leu Gln Pro Ser Gly Ser Ile Lys Glu Pro Arg Tyr Arg Gly
            20                  25                  30

Val Arg Lys Arg Pro Trp Gly Arg Phe Ala Ala Glu Ile Arg Asp Pro
        35                  40                  45

Trp Lys Lys Thr Arg Val Trp Leu Gly Thr Phe Asp Ser Ala Glu Glu
    50                  55                  60

Ala Ala Arg Ala Tyr Asp Thr Ala Ala Arg Thr Leu Arg Gly Pro Lys
65                  70                  75                  80

Ala Lys Thr Asn Phe Pro Ile Asn Ser Ser Asn Ile Pro Ala Phe Pro
                85                  90                  95

Phe Glu Thr Asn His His His Asn Glu Gly Phe Ile Asp Gln Arg Arg
            100                 105                 110

Leu Tyr Pro Met Gly Glu Phe His Asp Pro Glu Val Asn Pro Gln Arg
        115                 120                 125

Pro Thr Arg Ser Ser Met Ser Ser Thr Val Glu Ser Phe Ser Gly Pro
    130                 135                 140
```

-continued

Arg Pro Ala Gln Pro Pro Gln Lys Ser Ala Asp Phe Ala Val Val Ser
145                 150                 155                 160

Thr Arg Lys Tyr Tyr Pro Arg Pro Pro Val Glu Pro Glu Asp Cys
            165                 170                 175

His Ser Asp Cys Asp Ser Ser Ser Val Val Asp Asp Gly Asp Ile
            180                 185                 190

Ala Leu Ser Ser Cys Arg Lys Thr Leu Pro Phe Asp Leu Asn Phe Pro
        195                 200                 205

Pro Leu Asp Glu Asp Gly Arg Ser Pro Val Tyr Cys Phe Met Ser Leu
    210                 215                 220

Ile Ala Met Pro Val Met Asn Asp Asp Asp Arg Leu Leu Asp Leu Phe
225                 230                 235                 240

Phe Phe Phe Lys Lys Cys
                245

<210> SEQ ID NO 63
<211> LENGTH: 708
<212> TYPE: DNA
<213> ORGANISM: Panicum virgatum
<220> FEATURE:
<221> NAME/KEY: misc_feature
<223> OTHER INFORMATION: Ceres CLONE ID no.1876458
<220> FEATURE:
<221> NAME/KEY: misc_feature
<223> OTHER INFORMATION: Encodes the protein at SEQ ID NO: 64

<400> SEQUENCE: 63
acacagatac attcgtcgat ccaccactgt ccagtgcttg gcggttacgc acgcacgcac      60
acagatagga ttatctttta ctacaccaac tcaccaagat actagcaagc cgaatcgaca     120
aacaagcagc aggaagagga ggcatggcgc tcgcggaggg gaacgtcatc ttcggcgagg     180
agcaggaggc gctggtgctc aagtcgtggg ccctcatgaa gaaggactcg ccgacctcg      240 gcctccgctt cttcctcaag atcttcgaga tcgcgccgtc ggcgaagcag atgttctcgt     300
tcctgcgcga ctccgacgtg ccgctcgaga agaaccccaa gctcaagacc cacgccatgt     360
ccgtcttcgt catgacctgc gaggcggcgg cgcagctacg gaaggccggg aaggtcaccg     420
tcagggagac gacgctcaag cggctgggcg ccacgcactt caagtacggc gtcgccgacg     480
gccacttcga ggtgacgagg ttcgcgctgc tggagacgat aaaggaggcg cttcccgccg     540
acatgtggag cctggagatg aagtacgcct ggagcgaggc ttacaaccag cttgtggcgg     600
ccatcaagca ggagatgaag cctgccgcat gatgctgctg ctgctactcg gcctccgcgc     660
tgagttcccc ctacgatgca ccaccatctc caaattcttc atcgctgt                  708

<210> SEQ ID NO 64
<211> LENGTH: 162
<212> TYPE: PRT
<213> ORGANISM: Panicum virgatum
<220> FEATURE:
<221> NAME/KEY: misc_feature
<223> OTHER INFORMATION: Ceres CLONE ID no. 1876458
<220> FEATURE:
<221> NAME/KEY: misc_feature
<222> LOCATION: (14)..(154)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 64

Met Ala Leu Ala Glu Gly Asn Val Ile Phe Gly Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met Thr Cys Glu
65                  70                  75                  80

Ala Ala Ala Gln Leu Arg Lys Ala Gly Lys Val Thr Val Arg Glu Thr
                85                  90                  95

Thr Leu Lys Arg Leu Gly Ala Thr His Phe Lys Tyr Gly Val Ala Asp
            100                 105                 110

Gly His Phe Glu Val Thr Arg Phe Ala Leu Leu Glu Thr Ile Lys Glu
        115                 120                 125

Ala Leu Pro Ala Asp Met Trp Ser Leu Glu Met Lys Tyr Ala Trp Ser
    130                 135                 140

Glu Ala Tyr Asn Gln Leu Val Ala Ile Lys Gln Glu Met Lys Pro
145                 150                 155                 160

Ala Ala

<210> SEQ ID NO 65
<211> LENGTH: 712
<212> TYPE: DNA
<213> ORGANISM: Panicum virgatum
<220> FEATURE:
<221> NAME/KEY: misc_feature
<223> OTHER INFORMATION: Ceres CLONE ID no.1879148
<220> FEATURE:
<221> NAME/KEY: misc_feature
<223> OTHER INFORMATION: Encodes the protein at SEQ ID NO: 66

<400> SEQUENCE: 65
acacagatac attcgtcgat ccaccactgt ccagtgctcg gctcggttac gcacgcacgc     60
acacaaattg tagtacctgt gttttacacc accaaagata ctagcaagcc gagtcgacaa    120
acaaagcagc aggaagaggc atggcgctcg ctgacgggaa cggcgcggcc atcttcggcg    180
aggagcagga ggcgctggtg ctcaagtcgt gggccctcat gaagaaggac tcggccgacc    240
tcggcctccg cttcttcctc aagatcttcg agatcgcgcc gtcggcgaag cagatgttct    300
cgttcctgcg cgactccgac gtgccgctgg agaagaaccc caagctcaag cccacgcca    360 tgtccgtctt cgtcatgacc tgcgaggcgg cagcgcagct acggaaggcc gggaaggtca    420
ccgtcaggga gacgacgctc aagcggctgg gcgcaacgca cttcaagtac ggcgtcgccg    480
acggccactt cgaggtgaca aggttcgcgc tgctggagac gataaaggag gcgcttcccg    540
ccgacatgtg gagcctggag atgaagaacg cctggagcga ggcttacaac cagctcgtgg    600
cggccatcaa gcaggagatg aagcctgctg catgatgctg catgctgcta catactcggc    660
ctccgagttc ccctacgat gcaccaccat ctccaagttc ttcatcgcta tt             712

<210> SEQ ID NO 66
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1879148

```
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 66

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Gln Glu Met
145                 150                 155                 160

Lys Pro Ala Ala

<210> SEQ ID NO 67
<211> LENGTH: 1129
<212> TYPE: DNA
<213> ORGANISM: Gossypium hirsutum
<220> FEATURE:
<221> NAME/KEY: misc_feature
<223> OTHER INFORMATION: Ceres CLONE ID no.1884696
<220> FEATURE:
<221> NAME/KEY: misc_feature
<223> OTHER INFORMATION: Encodes the protein at SEQ ID NO: 68

<400> SEQUENCE: 67
atccgccccc atttgttcgc tctgtatatt gaacttttct ttctcgattt tctctttgaa    60
caaaaatgat gaagatcttc aaccagactc tcaccggcaa gactatcacg ctcgaggtcg   120
agagctccga caccatcgaa ggcgccaaca ccattctcca agatggaggg agcctccctc   180
cttaccgaac ccgactgatc ttcgccggac aacagcttga ggacggactg accttgtgcg   240
attacaacat cttaaaggag gtcaactctc cacctcttcc tccggttgcg cggtgggatg   300
cttaccttcc ggaggacctt gaccggcaat accatcactc tccaggtcta aagcgccgac   360
tcgatcaagt tcgttcacgc taacatccaa gactaggaag gcgtcccccc ataccaacta   420
cgactctgct tcgaccgaaa acaacttgaa gacggccgta ccttggccga ctacaacatc   480
cagaaggagt caacgctcca tcttgtcctt cgtttgcgtg gcgggatgca aatcttcgtt   540
aagacgctta cgggaaagac gatcactctc gaggtcgaga gctctgacac gatcgacaac   600
gtgaaagcca aaatccaaga caaggaaggc atcccgccag accagcaacg tctcatcttc   660
```

-continued

```
gccggaaagc aactcgagga cgggcggact ttagccgatt acaatatcca gaaggaatcg      720
actcttcatc tggtcctgcg tcttggaggt gggatgcaga tcttcgtcaa gactttgacc      780
ggtaagacga ttactttaga agtggagagc tcggatacga ttgataacgt gaaagcgaag      840
attcaggaca agaaggaat tccaccagat cagcaaaggt tgattttgc tgggaaacaa        900 ctggaagacg aaggacttt ggctgattac aatattcaaa aggattccac tcttcacctt      960
gttcttcgtc ttcgtggtgg gttctaagcc ttaaggtctc ccttaatgtg ggttttctgg     1020
ttttacgtga aggactgtgc cctgtaatgg ccttttaaat aatttctagt ctttgtttac     1080
cggttgcatc tatgtatggt ttctcttaga atggaattag catatttac                  1129
```

<210> SEQ ID NO 68
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 1884696
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 68

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Asp Ser Thr Leu His
    130                 135                 140

Leu Val Leu Arg Leu Arg Gly Gly Phe
145                 150
```

<210> SEQ ID NO 69
<211> LENGTH: 679
<212> TYPE: DNA
<213> ORGANISM: Gossypium hirsutum
<220> FEATURE:
<221> NAME/KEY: misc_feature

```
<223> OTHER INFORMATION: Ceres CLONE ID no.1916866
<220> FEATURE:
<221> NAME/KEY: misc_feature
<223> OTHER INFORMATION: Encodes the protein at SEQ ID NO: 70

<400> SEQUENCE: 69
aaatcaaata cctactgcaa ttaaaatccc ggaattactt aaacaacaat ggctacctat      60
gaaggtaaag ttttcactga agaacaagaa gctttggtgg tcaagtcatg gactgtaatg     120
aagaagaacg cagctgaatt gggtcttaaa ttcttcttga agatatttga gattgcacca     180
tcagccaaga aactattctc attcttgaga gactccaatg ttccattgga gcaaaacaca     240
aagctgaagc cccatgccat gtctgtcttt gtcatgacat gtgaatctgc agtgcaactg     300
cgtaaagcag gcaaagttac agtgagggaa tcaaatttga agaaattagg agctacccat     360
tttaagtatg gggtagttga tgaacatttt gaggtaacaa aatttgctct tttggagacc     420
ataaaagaag cagtaccaga tatgtggtca gatgagatga agaatgcatg gggtgaagcc     480
tatgatcgtt tggtcgcagc cattaaaata gaaatgaagg catgctcaca agctgcatga     540
tttcacaagt tccctacatt attgcttgtt aattttgggt ccaataagat tgaaagtttt     600
caatcattta aacatgtaat gtaacatagc tattgctcat cactactgtt ttttttcccct     660
agtttgtttg ctcctgttc                                                  679

<210> SEQ ID NO 70
<211> LENGTH: 163
<212> TYPE: PRT
<213> ORGANISM: Gossypium hirsutum
<220> FEATURE:
<221> NAME/KEY: misc_feature
<223> OTHER INFORMATION: Ceres CLONE ID no. 1916866
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 70

Met Ala Thr Tyr Glu Gly Lys Val Phe Thr Glu Glu Gln Glu Ala Leu
1               5                  10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
```

Gln Ala Ala

<210> SEQ ID NO 71
<211> LENGTH: 1003
<212> TYPE: DNA
<213> ORGANISM: Panicum virgatum
<220> FEATURE:
<221> NAME/KEY: misc_feature
<223> OTHER INFORMATION: Ceres CLONE ID no.1950105
<220> FEATURE:
<221> NAME/KEY: misc_feature
<223> OTHER INFORMATION: Encodes the protein at SEQ ID NO: 72

<400> SEQUENCE: 71

```
atcgccacaa gttcgcgatc tctcgatttc acaaatcgcc gagaagaccc gagcagagaa      60
gttccctccg atcgccttgc caagatgcag atctttgtga agacactcac tggcaagact     120
atcacccttg aggtggagtc ttctgacaca attgacaatg tcaaggcaaa gatccaggac     180
aaggaaggga ttcctccaga ccagcagcgc cttatcttcg ctggcaagca gcttgaggat     240
ggccgtacac ttgcagatta caacattcag aaggagtcca cactgcacct tgtcctcagg     300
ctgcgtggag gcatgcagat tttcgtgaag accctcactg caagacgat caccctggag      360
gtggagtcat ctgacaccat cgacaatgtg aaggcaaaga tccaggacaa ggagggcatc     420
cccctgacc agcagcgcct catctttgca ggcaagcagt tggaggatgg gcgaactctg       480
gctgactaya atatccagaa agaatcmacc ctgcacctsg tsctccgcct gcgtggtgga     540
atgcagatct ttgtgaagac gcttaccggc aagaccatca ccttggaggt ggagtcttcg     600
gacaccatcg acaatgtgaa ggcgaagatt caggacaagg agggcattcc tccggaccag     660
crgcgcctca tctttgctgg caagcagcta gaggacgggc gtaccctggc ggattacaac     720
atccagaagg agtccaccct ccaccttgtc ctgcgcctcc gtggtggttt ctgagcctag     780
tgctcctgag ttgccttttg tcgttatggt caacctctgg tttaagtcgt gtgaactctc     840
tgcattgcgt tgctagtgtc tggttgtggt tgtaataaga acatgaagaa catgttgctg     900
tggatcacat gacttttttt ttttgaaccg gaagatcaca tgactttcat ggctttaagt     960
tcctgaactc tgaaatctgg accccctttt aagctctgaa ctc                      1003
```

<210> SEQ ID NO 72
<211> LENGTH: 229
<212> TYPE: PRT
<213> ORGANISM: Panicum virgatum
<220> FEATURE:
<221> NAME/KEY: misc_feature
<223> OTHER INFORMATION: Ceres CLONE ID no. 1950105
<220> FEATURE:
<221> NAME/KEY: misc_feature
<222> LOCATION: (1)..(74)
<223> OTHER INFORMATION: Pfam Name: ubiquitin
    Pfam Description: Ubiquitin family
<220> FEATURE:
<221> NAME/KEY: misc_feature
<222> LOCATION: (77)..(150)
<223> OTHER INFORMATION: Pfam Name: ubiquitin
    Pfam Description: Ubiquitin family
<220> FEATURE:
<221> NAME/KEY: misc_feature
<222> LOCATION: (153)..(226)
<223> OTHER INFORMATION: Pfam Name: ubiquitin
    Pfam Description: Ubiquitin family
<220> FEATURE:
<221> NAME/KEY: misc_feature
<223> OTHER INFORMATION: Functional Homolog of Ceres CLONE ID no. 2403
    Given in SEQ ID NO: 40

<220> FEATURE:
<221> NAME/KEY: misc_feature
<222> LOCATION: (135)..(135)
<223> OTHER INFORMATION: Xaa is any aa, unknown, or other
<220> FEATURE:
<221> NAME/KEY: misc_feature
<222> LOCATION: (141)..(141)
<223> OTHER INFORMATION: Xaa is any aa, unknown, or other
<220> FEATURE:
<221> NAME/KEY: misc_feature
<222> LOCATION: (145)..(145)
<223> OTHER INFORMATION: Xaa is any aa, unknown, or other
<220> FEATURE:
<221> NAME/KEY: misc_feature
<222> LOCATION: (146)..(146)
<223> OTHER INFORMATION: Xaa is any aa, unknown, or other
<220> FEATURE:
<221> NAME/KEY: misc_feature
<222> LOCATION: (193)..(193)
<223> OTHER INFORMATION: Xaa is any aa, unknown, or other

<400> SEQUENCE: 72

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Xaa Asn Ile Gln Lys Glu Xaa Thr Leu His
130                 135                 140

Xaa Xaa Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Xaa Arg Leu Ile Phe Ala Gly Lys Gln Leu Glu Asp Gly Arg Thr Leu
        195                 200                 205

Ala Asp Tyr Asn Ile Gln Lys Glu Ser Thr Leu His Leu Val Leu Arg
    210                 215                 220

Leu Arg Gly Gly Phe
225

<210> SEQ ID NO 73
<211> LENGTH: 724
<212> TYPE: DNA
<213> ORGANISM: Panicum virgatum
<220> FEATURE:
<223> OTHER INFORMATION: Ceres CLONE ID no.1990746
<220> FEATURE:
<221> NAME/KEY: misc_feature
<222> LOCATION: (623)..(623)

```
<223> OTHER INFORMATION: n is a, c, t, g, unknown, or other
<220> FEATURE:
<221> NAME/KEY: misc_feature
<222> LOCATION: (624)..(624)
<223> OTHER INFORMATION: n is a, c, t, g, unknown, or other
<220> FEATURE:
<221> NAME/KEY: misc_feature
<222> LOCATION: (625)..(625)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 74

<400> SEQUENCE: 73
acacagatac actcgtcgat ccaccagacc accactgtcc agtgctcggc tcggttacgc      60
acgcacgcac acaaatagga gtacctgttt tacaccacca agatactagc aagcccaagc     120
cgagtcgaca acaagcagc aggaagaggc atggcgctcg cggaggggaa cggcgcggcc     180
atcttcggcg aggaacagga ggcgctggtg ctcaagtcgt gggccctcat gaagaaggac     240
tcggccgacc tcggcctccg cttcttcctc aagatcttcg agatcgcgcc gtcggcgaag     300
cagatgttct cgttcctgcg cgactccgac gtgccgctgg agaagaaccc caagctcaag     360
acccacgcca tgtccgtctt cgtcatgacc tgcgaggcgg cagtgcagct acggaaggcc     420
gggaaggtca ccgtcaggga cgacgctc aagcggctgg gcgcaacgca cttcaagtac     480
ggcgtcgccg acggccactt cgaggtgaca aggttcgcgc tgctggagac gataaaggag     540
gcgcttcccg ccgacatgtg gagcctggag atgaagaacg cctggagcga ggcttacaac     600
cagctcgtgg cggccatcaa gcnnnagatg aagcctgccg catgatgctg catgctgcta     660
catactcggc ctccgagtcc cccctacgat gcaccaccat ctcccagttc ttcatcgcta     720
tttt                                                                   724

<210> SEQ ID NO 74
<211> LENGTH: 164
<212> TYPE: PRT
<213> ORGANISM: Panicum virgatum
<220> FEATURE:
<221> NAME/KEY: misc_feature
<223> OTHER INFORMATION: Ceres CLONE ID no. 1990746
<220> FEATURE:
<221> NAME/KEY: misc_feature
<222> LOCATION: (16)..(156)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7
<220> FEATURE:
<221> NAME/KEY: misc_feature
<222> LOCATION: (158)..(158)
<223> OTHER INFORMATION: Xaa is any aa, unknown, or other
<220> FEATURE:
<221> NAME/KEY: misc_feature
<222> LOCATION: (159)..(159)
<223> OTHER INFORMATION: Xaa is any aa, unknown, or other

<400> SEQUENCE: 74

Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
```

```
              50                  55                  60
Lys Asn Pro Lys Leu Lys Thr His Ala Met Ser Val Phe Val Met Thr
 65                  70                  75                  80

Cys Glu Ala Ala Val Gln Leu Arg Lys Ala Gly Lys Val Thr Val Arg
                 85                  90                  95

Glu Thr Thr Leu Lys Arg Leu Gly Ala Thr His Phe Lys Tyr Gly Val
            100                 105                 110

Ala Asp Gly His Phe Glu Val Thr Arg Phe Ala Leu Leu Glu Thr Ile
        115                 120                 125

Lys Glu Ala Leu Pro Ala Asp Met Trp Ser Leu Glu Met Lys Asn Ala
    130                 135                 140

Trp Ser Glu Ala Tyr Asn Gln Leu Val Ala Ala Ile Lys Xaa Xaa Met
145                 150                 155                 160

Lys Pro Ala Ala

<210> SEQ ID NO 75
<211> LENGTH: 696
<212> TYPE: DNA
<213> ORGANISM: Panicum virgatum
<220> FEATURE:
<221> NAME/KEY: misc_feature
<223> OTHER INFORMATION: Ceres CLONE ID no.2007485
<220> FEATURE:
<221> NAME/KEY: misc_feature
<223> OTHER INFORMATION: Encodes the protein at SEQ ID NO: 76

<400> SEQUENCE: 75
agagcagggg gatggaagaa aataaactac tggccaaacc ctagccgagc cccgggtccg      60
ctcaccgcct tcccaccccc ccacccaccc acctgccccc cccccccccc cgccctcgcc     120
gtccgcgatg cgccgggcga agccgccgca gccgcagccg tcgccgtcgc cggagatccg     180
gtaccgcggc gtgcggaggc ggccatcggg gcgctacgcc gccgagatcc gggacccggc     240
caagaagacc ccgatctggc tcggcaccct cgactccgcc gaggccgccg cgcgcgccta     300
cgacgccgcc gcccgatccc tccgcgggcc caccgcccgc accaacttcc ccagcgccgc     360 ggccccgcg ccgcggcaca gcaggccccc cgccccctcc gccgccgcgc aggcggctgc     420
cgcggcggca gcggccacgt ccagccacag cagcaccata gagtcgtgga gcgacggcgc     480
gacccgcgcc gcgctggcgc gtagcgctgc ctccgtcctg gcgcgcagcg ccgctccgac     540
ggaggaggaa gacgaggact gccgcagcta ctgcggatcc tcgtcgtccg tcctctgcga     600
agacactggg ggcgacgatg cggccgcctc ccgcgcgccc ctgccgttcg atctgaacct     660
gccgccgcct catgacgcgg cctccgagac cgatca                              696

<210> SEQ ID NO 76
<211> LENGTH: 201
<212> TYPE: PRT
<213> ORGANISM: Panicum virgatum
<220> FEATURE:
<221> NAME/KEY: misc_feature
<223> OTHER INFORMATION: Ceres CLONE ID no. 2007485
<220> FEATURE:
<221> NAME/KEY: misc_feature
<222> LOCATION: (17)..(80)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 76
```

```
Met Arg Arg Ala Lys Pro Pro Gln Pro Gln Pro Ser Pro Ser Pro Glu
1               5                   10                  15

Ile Arg Tyr Arg Gly Val Arg Arg Pro Ser Gly Arg Tyr Ala Ala
            20                  25                  30

Glu Ile Arg Asp Pro Ala Lys Lys Thr Pro Ile Trp Leu Gly Thr Phe
        35                  40                  45

Asp Ser Ala Glu Ala Ala Arg Ala Tyr Asp Ala Ala Ala Arg Ser
    50                  55                  60

Leu Arg Gly Pro Thr Ala Arg Thr Asn Phe Pro Ser Ala Ala Ala Pro
65                  70                  75                  80

Ala Pro Arg His Ser Arg Pro Ala Pro Ser Ala Ala Ala Gln Ala
            85                  90                  95

Ala Ala Ala Ala Ala Ala Ala Thr Ser Ser His Ser Ser Thr Ile Glu
                100                 105                 110

Ser Trp Ser Asp Gly Ala Thr Arg Ala Ala Leu Ala Arg Ser Ala Ala
            115                 120                 125

Ser Val Leu Ala Arg Ser Ala Ala Pro Thr Glu Glu Glu Asp Glu Asp
        130                 135                 140

Cys Arg Ser Tyr Cys Gly Ser Ser Ser Val Leu Cys Glu Asp Thr
145                 150                 155                 160

Gly Gly Asp Asp Ala Ala Ala Ser Arg Ala Pro Leu Pro Phe Asp Leu
            165                 170                 175

Asn Leu Pro Pro Pro His Asp Ala Ala Ser Glu Thr Asp Gln Met Gly
            180                 185                 190

Ala Arg Tyr Asp Thr Leu Leu Arg Leu
            195                 200
```

<210> SEQ ID NO 77
<211> LENGTH: 698
<212> TYPE: DNA
<213> ORGANISM: Panicum virgatum
<220> FEATURE:
<221> NAME/KEY: misc_feature
<223> OTHER INFORMATION: Ceres CLONE ID no.2033803
<220> FEATURE:
<221> NAME/KEY: misc_feature
<223> OTHER INFORMATION: Encodes the protein at SEQ ID NO: 78

<400> SEQUENCE: 77

| | | | | | |
|---|---|---|---|---|---|
| acacagatac | attcgtcgat | ccaccagacc | accactgtcc | agtgctcggc | tcggttacgc | 60 |
| acgcacgcac | acaaatagga | gtacctgttt | tacaccaaga | tactagcaag | cccaagccga | 120 |
| gtcgacaaac | aagcagcagg | aagaggcatg | gcgctcgcgg | aggggaacgg | cgcggccatc | 180 |
| ttcggcgagg | agcaggaggc | gctggtgctc | aagtcgtggg | ccctcatgaa | gaaggactcg | 240 |
| gccgacctcg | gcctccgctt | cttcctcaag | atcttcgaga | tcgcgccgtc | ggcgaagcag | 300 |
| atgttctcgt | tcctgcgcga | ctccgacgtg | ccgctggaga | agaacccaa | gctcaagacc | 360 |
| cacgccatgt | ccgtcttcgt | catgacctgc | gaggcggcag | cgcagctacg | gaaggccggg | 420 |
| aaggtcaccg | tcagggagac | gacgctcaag | cggctgggcg | caacgcactt | caagtacggc | 480 |
| gtcgccgacg | gccacttcga | ggtgacaagg | ttcgcgcttc | ccgccgactt | gtggagcctg | 540 |
| gagatgaaga | acgcctggag | cgaggcttac | aaccagctcg | tggcggccat | caagcaggag | 600 |
| atgaagcctg | ccgcatgatg | ctgcatgctg | ctacatactc | ggcctccgag | ttccccctac | 660 |
| gatgcaccac | catctccaag | ttctttcatt | gtcttgtg | | | 698 |

-continued

```
<210> SEQ ID NO 78
<211> LENGTH: 156
<212> TYPE: PRT
<213> ORGANISM: Panicum virgatum
<220> FEATURE:
<221> NAME/KEY: misc_feature
<223> OTHER INFORMATION: Ceres CLONE ID no. 2033803
<220> FEATURE:
<221> NAME/KEY: misc_feature
<222> LOCATION: (16)..(148)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 78

Met Ala Leu Ala Glu Gly Asn Gly Ala Ala Ile Phe Gly Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
        50                  55                  60

Lys Asn Pro Lys Leu Lys Thr His Ala Met Ser Val Phe Val Met Thr
65                  70                  75                  80

Cys Glu Ala Ala Ala Gln Leu Arg Lys Ala Gly Lys Val Thr Val Arg
                85                  90                  95

Glu Thr Thr Leu Lys Arg Leu Gly Ala Thr His Phe Lys Tyr Gly Val
                100                 105                 110

Ala Asp Gly His Phe Glu Val Thr Arg Phe Ala Leu Pro Ala Asp Leu
            115                 120                 125

Trp Ser Leu Glu Met Lys Asn Ala Trp Ser Glu Ala Tyr Asn Gln Leu
    130                 135                 140

Val Ala Ala Ile Lys Gln Glu Met Lys Pro Ala Ala
145                 150                 155

<210> SEQ ID NO 79
<211> LENGTH: 724
<212> TYPE: DNA
<213> ORGANISM: Panicum virgatum
<220> FEATURE:
<221> NAME/KEY: misc_feature
<223> OTHER INFORMATION: Ceres CLONE ID no.2034916
<220> FEATURE:
<221> NAME/KEY: misc_feature
<223> OTHER INFORMATION: Encodes the protein at SEQ ID NO: 80

<400> SEQUENCE: 79
aatccaatct cccccgatcc ccaatcgcga attcccctct ccggcaggcg aagcaatcga      60 ggggcacccct ttcatctcgt caagatgcag atctttgtga agaccctcac tggtaagacc    120
atcaccctcg aggttgagtc ctcggatacc attgacaacg tcaaggctaa aatccaggac    180
aaggagggga tccctccgga ccagcagcgc ctcatctttg ccggcaagca gctcgaagat    240
gggaggacgc ttgctgacta caacatccag aaggagtcca ccctccacct cgtgctcagg    300 ctcagggggtg gtatgcagat ctttgtcaag actctcaccg gcaagacgat tactcttgag    360
gttgagtcct cggacacgat cgacaatgta aaggtgaaga tccaagacaa ggagggggatc    420 ccaccggacc agcagcgcct catctttgcc ggcaagcagc tcgaggatgg ccgcactctg    480
```

-continued

```
gctgactaca acattcagaa agagtcgacc cttcaccttg tgctcaggct gaggggaggc    540
atgcaaatat tgtcaagac tctgactggc aagaccatca cgcttgaggt ggagtcgtct    600
gacaccattg ataatgtgaa ggcgaagatc caagacaagg agggcatccc gccggaccag    660
cagcgcctga tctttgccgg taagcagctg gaggatggtc gtaccctggc agactataat    720
attc                                                                 724
```

<210> SEQ ID NO 80
<211> LENGTH: 213
<212> TYPE: PRT
<213> ORGANISM: Panicum virgatum
<220> FEATURE:
<221> NAME/KEY: misc_feature
<223> OTHER INFORMATION: Ceres CLONE ID no. 2034916
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<222> LOCATION: (153)..(213)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 80

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Val Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Ser Ser Asp Thr Ile Asp
                165                 170                 175

Asn Val Lys Ala Lys Ile Gln Asp Lys Glu Gly Ile Pro Pro Asp Gln
            180                 185                 190

Gln Arg Leu Ile Phe Ala Gly Lys Gln Leu Glu Asp Gly Arg Thr Leu
        195                 200                 205
```

Ala Asp Tyr Asn Ile
    210

<210> SEQ ID NO 81
<211> LENGTH: 1194
<212> TYPE: DNA
<213> ORGANISM: Glycine max
<220> FEATURE:
<221> NAME/KEY: misc_feature
<223> OTHER INFORMATION: Ceres CLONE ID no.651581
<220> FEATURE:
<221> NAME/KEY: misc_feature
<222> LOCATION: (678)..(678)
<223> OTHER INFORMATION: n is a, c, t, g, unknown, or other
<220> FEATURE:
<221> NAME/KEY: misc_feature
<222> LOCATION: (679)..(679)
<223> OTHER INFORMATION: n is a, c, t, g, unknown, or other
<220> FEATURE:
<221> NAME/KEY: misc_feature
<223> OTHER INFORMATION: Encodes the protein at SEQ ID NO: 82

<400> SEQUENCE: 81

| | | | | | |
|---|---|---|---|---|---|
| gtgtagttga | aggagcagaa | gaagaagaag | agaaggtggt | accgccttca | attctctttt | 60 |
| tctctctcca | tttctcatcc | tcatcatctt | attattcctc | ttccatctct | attctccata | 120 |
| acacccacca | caccacttgt | gaaaaacctc | attaatatca | cacactgaca | tgtatctctg | 180 |
| agctccaatc | caatacaaga | ccacaccttg | tcgtgtcgga | cgaaccttgg | tgtctgtttt | 240 |
| tttttttttt | tttcattatt | ttctccgaag | agatgaggaa | gggcaraggt | ggaggcgcct | 300 |
| cggcggcggc | ggtggatgtg | aacggatcca | ttttaaagga | gcctcggtac | cggggcgtga | 360 |
| ggaagagacc | gtgggggaga | ttcgccgcgg | agatcagaga | cccgttgaag | aaagccaggg | 420 |
| tttggttggg | aaccttcaat | tctgccgagg | atgctgctcg | tgcctacrac | gccgccgctc | 480 |
| ggactctccg | aggtcccaag | gccaaaacaa | atttcccccc | tctctcacct | ttttgctatc | 540 |
| cacaccccac | caccgatcct | tcttstaca | ctggtttcca | cgatcaacac | caccaccaca | 600 |
| acaacaacaa | ccttaacaac | cctcaaagac | ccacttcaag | tggcatgagt | agcmccgttg | 660 |
| agtccttcag | tgggcccnnc | ccttttttcc | ccaccaccac | cmctaccacc | acaaccacaa | 720 |
| ctgcgacgcc | gttttgact | gctacgcgga | gatacccgcg | cactccccct | cttgtccctg | 780 |
| aagactgcca | cagtgactgc | gactcttcct | cctccgtcgt | tgacgacggc | gacgacaaca | 840 |
| tcgtttcgtc | gtcgtttcga | cctcccttgc | cgtttgatct | caacgcgctg | ccgtttgatg | 900 |
| atgctgccgc | ggatgatgat | ctacgccgca | ccgcgctttg | tctctgatga | tgattatcgt | 960 |
| gcgatgatga | ttttaattt | ctcatttttt | tacttgattt | ttttgttatt | gctatgcaga | 1020 |
| agaaatatat | atttaaaatg | atgatcagat | gtaagattat | ggtaatatga | tcttaattct | 1080 |
| gtgagaggaa | gattccgtgt | tggttatatt | ttcttctttt | tattatttt | ttaaacattt | 1140 |
| ttatttagaa | ggaaatattg | aatgaaaaga | aaaagagaa | agtaattatg | atcg | 1194 |

<210> SEQ ID NO 82
<211> LENGTH: 224
<212> TYPE: PRT
<213> ORGANISM: Glycine max
<220> FEATURE:
<221> NAME/KEY: misc_feature
<223> OTHER INFORMATION: Ceres CLONE ID no. 651581
<220> FEATURE:
<221> NAME/KEY: misc_feature
<222> LOCATION: (24)..(87)
<223> OTHER INFORMATION: Pfam Name: AP2
      Pfam Description: AP2 domain
<220> FEATURE:

```
<221> NAME/KEY: misc_feature
<223> OTHER INFORMATION: Functional Homolog of Ceres CLONE ID no. 674166
      Given in SEQ ID NO: 42
<220> FEATURE:
<221> NAME/KEY: misc_feature
<222> LOCATION: (137)..(137)
<223> OTHER INFORMATION: Xaa is any aa, unknown, or other

<400> SEQUENCE: 82
```

| | | | | | | | | | | | | | | |
|---|---|---|---|---|---|---|---|---|---|---|---|---|---|---|
| Met | Arg | Lys | Gly | Arg | Gly | Gly | Ala | Ser | Ala | Ala | Val | Asp | Val | |
| 1 | | | | 5 | | | | | 10 | | | | | 15 |
| Asn | Gly | Ser | Ile | Leu | Lys | Glu | Pro | Arg | Tyr | Arg | Gly | Val | Arg | Lys | Arg |
| | | | | 20 | | | | | 25 | | | | | 30 | |
| Pro | Trp | Gly | Arg | Phe | Ala | Ala | Glu | Ile | Arg | Asp | Pro | Leu | Lys | Lys | Ala |
| | | 35 | | | | | 40 | | | | | 45 | | | |
| Arg | Val | Trp | Leu | Gly | Thr | Phe | Asn | Ser | Ala | Glu | Asp | Ala | Ala | Arg | Ala |
| | 50 | | | | | 55 | | | | | 60 | | | | |
| Tyr | Asp | Ala | Ala | Arg | Thr | Leu | Arg | Gly | Pro | Lys | Ala | Lys | Thr | Asn | |
| 65 | | | | | 70 | | | | | 75 | | | | | 80 |
| Phe | Pro | Pro | Leu | Ser | Pro | Phe | Cys | Tyr | Pro | His | Thr | Thr | Asp | Pro | |
| | | | | 85 | | | | | 90 | | | | | 95 | |
| Phe | Phe | Tyr | Thr | Gly | Phe | His | Asp | Gln | His | His | His | Asn | Asn | Asn | |
| | | | | 100 | | | | | 105 | | | | | 110 | |
| Asn | Leu | Asn | Asn | Pro | Gln | Arg | Pro | Thr | Ser | Ser | Gly | Met | Ser | Ser | Thr |
| | | 115 | | | | | 120 | | | | | 125 | | | |
| Val | Glu | Ser | Phe | Ser | Gly | Pro | Arg | Xaa | Phe | Ser | Pro | Thr | Thr | Thr | Thr |
| 130 | | | | | 135 | | | | | 140 | | | | | |
| Thr | Thr | Thr | Thr | Thr | Thr | Ala | Thr | Pro | Phe | Leu | Thr | Ala | Thr | Arg | Arg |
| 145 | | | | | 150 | | | | | 155 | | | | | 160 |
| Tyr | Pro | Arg | Thr | Pro | Pro | Leu | Val | Pro | Glu | Asp | Cys | His | Ser | Asp | Cys |
| | | | | 165 | | | | | 170 | | | | | 175 | |
| Asp | Ser | Ser | Ser | Ser | Val | Val | Asp | Asp | Gly | Asp | Asp | Asn | Ile | Val | Ser |
| | | | 180 | | | | | 185 | | | | | 190 | | |
| Ser | Ser | Phe | Arg | Pro | Pro | Leu | Pro | Phe | Asp | Leu | Asn | Ala | Leu | Pro | Phe |
| | | 195 | | | | | 200 | | | | | 205 | | | |
| Asp | Asp | Ala | Ala | Ala | Asp | Asp | Leu | Arg | Arg | Thr | Ala | Leu | Cys | Leu | |
| 210 | | | | | 215 | | | | | 220 | | | | | |

```
<210> SEQ ID NO 83
<211> LENGTH: 184
<212> TYPE: PRT
<213> ORGANISM: Oryza sativa subsp. indica
<220> FEATURE:
<221> NAME/KEY: misc_feature
<223> OTHER INFORMATION: Public GI ID no. 125550159
<220> FEATURE:
<221> NAME/KEY: misc_feature
<222> LOCATION: (7)..(70)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 83
```

| | | | | | | | | | | | | | | | |
|---|---|---|---|---|---|---|---|---|---|---|---|---|---|---|---|
| Met | Cys | Glu | Ala | Ala | Ala | Pro | Arg | Tyr | Arg | Gly | Val | Arg | Lys | Arg | Pro |
| 1 | | | | 5 | | | | | 10 | | | | | 15 | |
| Trp | Gly | Arg | Phe | Ala | Ala | Glu | Ile | Arg | Asp | Pro | Ala | Lys | Arg | Ala | Arg |
| | | 20 | | | | | 25 | | | | | 30 | | | |
| Val | Trp | Leu | Gly | Thr | Tyr | Asp | Ser | Ala | Glu | Ala | Ala | Ala | Arg | Ala | Tyr |

-continued

```
                35                  40                  45
Asp Val Ala Ala Arg Asn Leu Arg Gly Pro Leu Ala Arg Thr Asn Phe
 50                  55                  60

Pro Leu Val Ser Ser Leu Pro Leu Pro Ser Pro His Tyr His Leu Pro
 65                  70                  75                  80

Gly Lys Ala Ala Ala Ala Ala Pro Pro Val Ala Gly Pro Ala Cys Ser
                 85                  90                  95

Ala Ser Ser Thr Val Glu Ser Ser Ser Gly Pro Arg Gly Pro Arg Pro
            100                 105                 110

Ala Ala Thr Ala Ala Ala Val Pro Arg Arg Val Pro Arg Pro Ala
        115                 120                 125

Pro Pro Ala Pro Asp Ala Gly Cys His Ser Asp Cys Ala Ser Ser Ala
130                 135                 140

Ser Val Val Asp Asp Ala Asp Asp Ala Ser Thr Val Arg Ser Arg Val
145                 150                 155                 160

Ala Ala Phe Asp Leu Asn Leu Pro Pro Pro Leu Asp Arg Asp His Val
                165                 170                 175

Asp Leu Cys Thr Asp Leu Arg Leu
            180

<210> SEQ ID NO 84
<211> LENGTH: 225
<212> TYPE: PRT
<213> ORGANISM: Arabidopsis thaliana
<220> FEATURE:
<221> NAME/KEY: misc_feature
<223> OTHER INFORMATION: Public GI ID no. 15223609
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 84

Met Arg Arg Gly Arg Gly Ser Ser Ala Val Ala Gly Pro Thr Val Val
 1               5                  10                  15

Ala Ala Ile Asn Gly Ser Val Lys Glu Ile Arg Phe Arg Gly Val Arg
                20                  25                  30

Lys Arg Pro Trp Gly Arg Phe Ala Ala Glu Ile Arg Asp Pro Trp Lys
            35                  40                  45

Lys Ala Arg Val Trp Leu Gly Thr Phe Asp Ser Ala Glu Glu Ala Ala
 50                  55                  60

Arg Ala Tyr Asp Ser Ala Ala Arg Asn Leu Arg Gly Pro Lys Ala Lys
 65                  70                  75                  80

Thr Asn Phe Pro Ile Asp Ser Ser Pro Pro Pro Asn Leu Arg
                 85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
        115                 120                 125

Arg Pro Thr Ser Ser Ser Met Ser Ser Thr Val Glu Ser Phe Ser Gly
    130                 135                 140

Pro Arg Pro Thr Thr Met Lys Pro Ala Thr Thr Lys Arg Tyr Pro Arg
145                 150                 155                 160
```

-continued

```
Thr Pro Pro Val Val Pro Glu Asp Cys His Ser Asp Cys Asp Ser Ser
            165                 170                 175

Ser Ser Val Ile Asp Asp Asp Asp Ile Ala Ser Ser Arg Arg
        180                 185                 190

Arg Asn Pro Pro Phe Gln Phe Asp Leu Asn Phe Pro Pro Leu Asp Cys
        195                 200                 205

Val Asp Leu Phe Asn Gly Ala Asp Asp Leu His Cys Thr Asp Leu Arg
    210                 215                 220

Leu
225

<210> SEQ ID NO 85
<211> LENGTH: 164
<212> TYPE: PRT
<213> ORGANISM: Arabidopsis thaliana
<220> FEATURE:
<221> NAME/KEY: misc_feature
<223> OTHER INFORMATION: Public GI ID no. 30683885
<220> FEATURE:
<221> NAME/KEY: misc_feature
<223> OTHER INFORMATION: Functional Homolog of Ceres CLONE ID no. 30087
      Given in SEQ ID NO: 2

<400> SEQUENCE: 85

Met Ala Ser Ser Phe Ser Ser Gln Ala Phe Phe Leu Leu Thr Leu Ser
1               5                   10                  15

Met Val Leu Ile Pro Phe Ser Leu Ala Gln Ala Pro Met Met Ala Pro
            20                  25                  30

Ser Gly Ser Met Ser Met Pro Pro Met Ser Ser Gly Gly Gly Ser Ser
        35                  40                  45

Val Pro Pro Pro Val Met Ser Pro Met Pro Met Met Thr Pro Pro Pro
    50                  55                  60

Met Pro Met Thr Pro Pro Met Pro Met Thr Pro Pro Met Pro
65                  70                  75                  80

Met Ala Pro Pro Met Pro Met Ala Ser Pro Pro Met Pro Met
            85                  90                  95

Thr Pro Ser Thr Ser Pro Ser Pro Leu Thr Val Pro Asp Met Pro Ser
            100                 105                 110

Pro Pro Met Pro Ser Gly Met Glu Ser Ser Pro Ser Pro Gly Pro Met
        115                 120                 125

Pro Pro Ala Met Ala Ala Ser Pro Asp Ser Gly Ala Phe Asn Val Arg
    130                 135                 140

Asn Asn Val Val Thr Leu Ser Cys Val Val Gly Val Val Ala Ala His
145                 150                 155                 160

Phe Leu Leu Val

<210> SEQ ID NO 86
<211> LENGTH: 218
<212> TYPE: PRT
<213> ORGANISM: Pisum sativum
<220> FEATURE:
<221> NAME/KEY: misc_feature
<223> OTHER INFORMATION: Public GI ID no. 56384582
<220> FEATURE:
<221> NAME/KEY: misc_feature
<222> LOCATION: (21)..(84)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42
```

```
<400> SEQUENCE: 86

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
                85                  90                  95

Leu Arg Phe Tyr Ala Gly Ala Gly Glu Gly Phe Gln Asp His Arg
            100                 105                 110

Arg Pro Thr Ser Ser Gly Met Ser Ser Thr Val Glu Ser Phe Gly Gly
        115                 120                 125

Pro Arg Pro Val Arg Pro Met Pro Pro Ser Ala Val Thr Gly Arg
    130                 135                 140

Arg Tyr Pro Arg Thr Pro Val Ala Pro Gly Asp Cys Arg Ser Asp
145                 150                 155                 160

Cys Asp Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
            180                 185                 190

Leu Asn Ala Pro Pro Leu Glu Glu Gly Asp Val Ala Asn Gly Leu Gly
        195                 200                 205

Glu Asp Leu His Cys Thr Leu Leu Cys Leu
    210                 215

<210> SEQ ID NO 87
<211> LENGTH: 225
<212> TYPE: PRT
<213> ORGANISM: Nicotiana tabacum
<220> FEATURE:
<221> NAME/KEY: misc_feature
<223> OTHER INFORMATION: Public GI ID no. 57012880
<220> FEATURE:
<221> NAME/KEY: misc_feature
<222> LOCATION: (26)..(89)
<223> OTHER INFORMATION: Pfam Name: AP2
      Pfam Description: AP2 domain
<220> FEATURE:
<221> NAME/KEY: misc_feature
<223> OTHER INFORMATION: Functional Homolog of Ceres CLONE ID no. 674166
      Given in SEQ ID NO: 42

<400> SEQUENCE: 87

Met Arg Arg Gly Arg Ala Ala Ala Pro Ala Pro Val Thr Gly Glu
1               5                   10                  15

Pro Asn Gly Ser Gly Gly Ser Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Thr Arg Val Trp Leu Gly Thr Phe Asp Ser Ala Glu Asp Ala Ala
    50                  55                  60

Arg Ala Tyr Asp Ala Ala Ala Arg Ala Leu Arg Gly Pro Lys Ala Lys
65                  70                  75                  80
```

```
Thr Asn Phe Pro Leu Pro Tyr Ala His His His Gln Phe Asn Gln Gly
                85                  90                  95

His Asn Pro Asn Asn Asp Pro Phe Val Asp Ser Arg Phe Tyr Pro Gln
            100                 105                 110

Asp Asn Pro Ile Ile Ser Gln Arg Pro Thr Ser Ser Ser Met Ser Ser
        115                 120                 125

Thr Val Glu Ser Phe Ser Gly Pro Arg Pro Pro Ala Pro Arg Gln
    130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                165                 170                 175

His Gly Asp Cys Glu Lys Glu Asn Asp Asn Asp Asn Ile Ala
            180                 185                 190

Ser Ser Ser Phe Arg Lys Pro Leu Leu Phe Asp Leu Asn Leu Pro Pro
        195                 200                 205

Pro Met Asp Asp Ala Gly Ala Asp Asp Leu His Cys Thr Ala Leu Cys
    210                 215                 220

Leu
225

<210> SEQ ID NO 88
<211> LENGTH: 163
<212> TYPE: PRT
<213> ORGANISM: Gossypium hirsutum
<220> FEATURE:
<221> NAME/KEY: misc_feature
<223> OTHER INFORMATION: Public GI ID no. 62548111
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 88

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met Thr Cys Glu Ser
65                  70                  75                  80

Ala Val Gln Leu Arg Lys Ala Gly Lys Val Thr Val Arg Glu Ser Asn
                85                  90                  95

Leu Lys Lys Leu Gly Ala Thr His Phe Lys Tyr Gly Val Val Asp Glu
            100                 105                 110

His Phe Glu Val Thr Lys Phe Ala Leu Leu Glu Thr Ile Lys Glu Ala
        115                 120                 125

Val Pro Asp Met Trp Ser Asp Glu Met Lys Asn Ala Trp Gly Glu Ala
    130                 135                 140

Tyr Asp Arg Leu Val Ala Ala Ile Lys Ile Glu Met Lys Ala Cys Ser
```

<210> SEQ ID NO 89
<211> LENGTH: 153
<212> TYPE: PRT
<213> ORGANISM: Gossypium hirsutum
<220> FEATURE:
<221> NAME/KEY: misc_feature
<223> OTHER INFORMATION: Ceres CLONE ID no. 100021733
<220> FEATURE:
<221> NAME/KEY: misc_feature
<222> LOCATION: (1)..(74)
<223> OTHER INFORMATION: Pfam Name: ubiquitin
      Pfam Description: Ubiquitin family
<220> FEATURE:
<221> NAME/KEY: misc_feature
<222> LOCATION: (77)..(150)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional Homolog of Ceres CLONE ID no. 2403
      Given in SEQ ID NO: 40

<400> SEQUENCE: 89

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ala Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Ser Ser
                85                  90                  95

Asp Thr Ile Asp Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ala Asp Tyr Asn Ile Gln Lys Glu Ser Thr Leu His
    130                 135                 140

Leu Val Leu Arg Leu Arg Gly Gly Phe
145                 150

<210> SEQ ID NO 90
<211> LENGTH: 775
<212> TYPE: DNA
<213> ORGANISM: Brassica napus
<220> FEATURE:
<221> NAME/KEY: misc_feature
<223> OTHER INFORMATION: Ceres CLONE ID no. 947579
<220> FEATURE:
<221> NAME/KEY: misc_feature
<223> OTHER INFORMATION: Encodes the protein at SEQ ID NO: 3

<400> SEQUENCE: 90
ctctctagat cttggatcac tcggacgaca tgtgttggat cccagtgcac tggccctgcc      60
agcctactca aaaaaacswt samttttckc tcccattstt tkacractca tcgttggcac     120
wtcctwcttt ctstatatat tacttgacat wawcyrctmt ycacmwcaca wacacacacw     180

| | |
|---|---|
| taaccatggc cagcttcaca wgctttcctt tgctcacat tgyctatggc tttagytcat | 240 |
| ytctctttag ctcwatctcc catgatggct ccttctggct ccatgtccat gscgckchat | 300 |
| gccatagcgg cggctctcca atgccaatga tgactccacc acctatgcca atgatgactc | 360 |
| cmccgcctat ggctatggct ccaccaccta tgcctatgac tccaccacca atgcccatgg | 420 |
| ctccgatgcc aatgactcca tcttcaagtc caatgagccc accaactact atggccccaa | 480 |
| gtccagaaac agtccctgat atggcttcgc caccgatgat gccgggaatg gagtcttctc | 540 |
| cttctccggg acccatgcca ccggcaatgg cctctccaga ttccggagca ttcaatgtaa | 600 |
| gaaacgacgt cgtagcaatt tcgttccttg ttgcagctca tttgctccta gtttgagatt | 660 |
| attattaaat tggccagcgt cgtgttgtgt aatttacttt catttttttct cgagccatta | 720 |
| gttttcatgt tttatcatat atttgggttt gtgtttgata tggtacgatt cagmc | 775 |

<210> SEQ ID NO 91
<211> LENGTH: 1032
<212> TYPE: DNA
<213> ORGANISM: Arabidopsis thaliana
<220> FEATURE:
<221> NAME/KEY: misc_feature
<223> OTHER INFORMATION: Ceres CLONE ID no. 36046
<220> FEATURE:
<221> NAME/KEY: misc_feature
<223> OTHER INFORMATION: Encodes the protein at SEQ ID NO: 23

<400> SEQUENCE: 91

| | |
|---|---|
| gctcattagg gtttctcatc tacggcgtgg tgttcctcct tcctgctctg aaaaatggcg | 60 |
| aagagaacga agaaggttgg aatcgtcggc aaatacggaa cacgttatgg tgcgagtatc | 120 |
| aggaagcaga ttaagaagat ggaggtcagc cagcacagca agtacttctg tgagttctgt | 180 |
| ggcaagtacg gagtgaagcg aaaggctgtt ggtatctggg gttgcaagga ttgtggcaag | 240 |
| gtcaaggcag gtggtgctta cacaatgaac accgccagtg cggtcactgt tagaagcacg | 300 |
| atcagaaggt tgagggagca gatcgagggt taaaagtctg ctgaggaaga tgctgagaca | 360 |
| gtatacgctt gtatcgactt ggtatcaacg ataatacaga ggaagctgag gaagatcaag | 420 |
| gagaaggact cagaccatgg aaggcacatg aaaggtttca acagattgaa ggtaagggaa | 480 |
| ccagtgattg agccggttgt ggaggatgtt gaggacagta ctgactcgag cgtaggagaa | 540 |
| gaagaagaag aggatgattt gatcaaggag attgtccgta ccaagacttt cgagatgcca | 600 |
| ccattgactg tcgctgaggc agtcgagcag ctggaactag tcagtcacga cttctatggc | 660 |
| ttccaaaatg aaaactggtg agataaacat agtgtacaag agaaaagaag gaggttacgg | 720 |
| tctgataatc ccaaagaaag acgggaaggc cgagaaggtt gagccgcttc caaccgagca | 780 |
| attgaatgaa cactctttcg ccgagtagac tgcctctgca cacaccaaaa ccgataagct | 840 |
| catctctcct tacagtttac ctgtgtagga gttagggttc ttgaataaac aatgcaacaa | 900 |
| agattgtaga agtcagtgta cataaaaaaa tggccaacca ctctttgtta cttttgtggt | 960 |
| gaaaaggaag atcttaattc tctttccatc agatgatagc aatacatttt ttcataaaca | 1020 |
| agaatgttac at | 1032 |

<210> SEQ ID NO 92
<211> LENGTH: 492
<212> TYPE: DNA
<213> ORGANISM: Parthenium argentatum
<220> FEATURE:
<221> NAME/KEY: misc_feature
<223> OTHER INFORMATION: Ceres CLONE ID no. 1606506
<220> FEATURE:

```
<221> NAME/KEY: misc_feature
<223> OTHER INFORMATION: Encodes the protein at SEQ ID NO: 5

<400> SEQUENCE: 92
atctagcttc aacctttttt tcctctcact actcaattca atatggctgt ctcacgttac    60
attatcctac tcttatcctt cacctacttg gctgccttct ccaccgctca agctccatca   120
atgtcaccaa tgatgatgcc catggcacca ccaccatcga cgatgcccat gacaccacca   180
ccatcgacga tgcccatgac accaccacca acgcccatga ccatgacacc accaccaatg   240
atgatgccca tgacaccacc accaatgccc atggggacac caccaatgac aatgcccatg   300
ggaccgccac caatgatgat gcccatgagc ccaggaccat cctgatgcc agcctccccg    360 ccatcaccca tgggaccgtc catggcacct gaaccagcta ccatgtcgcc tggaccctcc   420
atgacgcctg ctgagacacc agccagtggc gctatcatgc agtattctag catcactatg   480
ttgggcattg tg                                                       492

<210> SEQ ID NO 93
<211> LENGTH: 970
<212> TYPE: DNA
<213> ORGANISM: Glycine max
<220> FEATURE:
<221> NAME/KEY: misc_feature
<223> OTHER INFORMATION: Ceres CLONE ID no. 546001
<220> FEATURE:
<221> NAME/KEY: misc_feature
<223> OTHER INFORMATION: Encodes the protein at SEQ ID NO: 13

<400> SEQUENCE: 93
agatataatc gaaaaaaatt actgtttgga tatattccac tatttagaaa gcaaaatgga    60
ctacgaaaac ttgagtaaca aggtaagcca cacaaatggg aatgactccc cattacaatg   120
aagggccaac ttcattttca atgaatccca ctataaaaac tttagcaatg caaaagctaa   180
aacatcaacc atttcctcat ccactttcac tggaatcaca atcctgaaac aaaaacatct   240
tagcatttaa catactacta gacaacatga ccaccacatt ggaaagaggt ttctcggaag   300
agcaagaagc tctggtggtg aagtcatgga atgtcatgaa gaagaattct ggagagttgg   360
gtctcaagtt tttcttgaaa atatttgaga ttgctccatc agctcagaaa ttgttctcat   420
tcttgagaga ttcaacggtt cctttggagc aaaatcccaa gctcaagccc catgccgtgt   480
ctgtctttgt aatgacctgt gattcagcag ttcagctgcg gaaggccggg aaagtcactg   540
tcagagaatc aaacttgaaa aaattaggtg ctacccattt tagaaccggc gtagcaaacg   600
agcatttcga ggtgacaaag tttgcactgt tggagaccat aaaagaagct gtaccagaaa   660
tgtggtcacc ggctatgaag aatgcatggg gagaagctta tgatcagctg gtcgatgcca   720
ttaaatctga aatgaaacca ccctcctctt agactccagt ttaagcagtt cctttccttc   780
cctctcaatt ctcaaattgt tatattaata aaagtgagaa agtttaggct tgtgcttta    840 ttttgtgtga atgtaatata ctttgtgtac gtagacttgg ctattgggag ttgctaggtt   900
gggaagtgtt tcgcattcaa caattctgta gttgaaggtg attaaatgaa ttatagctat   960
ttgtttcttc                                                          970

<210> SEQ ID NO 94
<211> LENGTH: 604
<212> TYPE: DNA
<213> ORGANISM: Zea mays
<220> FEATURE:
<221> NAME/KEY: misc_feature
<223> OTHER INFORMATION: Ceres CLONE ID no. 1554560
```

```
<220> FEATURE:
<221> NAME/KEY: misc_feature
<223> OTHER INFORMATION: Encodes the protein at SEQ ID NO: 16

<400> SEQUENCE: 94
tcgtatccac ccaacctccc actgtaaaaa agagcagcgg aacgtgcgtg catccatcca      60
attccaatcc cagtcccaat cccaccagtg tccagtgctc ggggaaccga cacagctcct     120
cagcagagaa gccagcccga tcagcagaca gcaggcatgg cgctcgcgga ggccgacgac     180
ggcgcggtgg tcttcggcga ggagcaggag gcgctggtgc tcaagtcgtg ggccgtcatg     240
aagaaggacg ccgccaacct gggcctccgc ttcttcctca aggtcttcga gatcgcgccg     300
tcggcgaagc agatgttctc gttcctgcgc gactccgacg tgccgctaga aagaaccccc     360
aagctcaaga cgcacgccat gtccgtcttc gtcatgacct cgaggcggc ggcgcagctc      420 cgcaaggccg ggaaggtcac cgtgagggag accacgctca agaggctggg cgccacgcac     480
ttgaggtacg gcgtcgcaga tggacacttc gaggtgacgg ggttcgcgct gcttgagacg     540
atcaaggagg cgctccccgc tgacatgtgg agcctcgaga tgaagaaagc ctgggccgag     600
gcct                                                                    604

<210> SEQ ID NO 95
<211> LENGTH: 846
<212> TYPE: DNA
<213> ORGANISM: Triticum aestivum
<220> FEATURE:
<221> NAME/KEY: misc_feature
<223> OTHER INFORMATION: Ceres CLONE ID no. 839727
<220> FEATURE:
<221> NAME/KEY: misc_feature
<223> OTHER INFORMATION: Encodes the protein at SEQ ID NO: 17

<400> SEQUENCE: 95
acgccgtccg tttctggctc atcaggaggt ccaaaggccg cgcaagtcga cctatataag      60
cgcctccgct ccagcttggg atcaaatcac gaccaacacg taccggatct tgaccgaccg     120
aaccattcag tgctcgcgct cactcacgca tcatagccaa gttaagcggg aaggaaggaa     180
ggaaggaagc catgtctgcc gcggagggag ccgtcgtgtt cagcgaggag aaggaggcgc     240
tggtgctcaa gtcatgggcc atcatgaaga aggattccgc caaccttggg ctccgcttct     300
tcctcaagat cttcgagatc gcgccgtcgg cgaggcagat gttcccgttc ctgcgcgact     360
ccgacgtgcc gctggagacc aaccccaagc tcaagaccca cgccgtgtcc gtcttcgtca     420
tgacgtgcga ggctgctgcg cagctgcgga aagccgggaa gatcaccgtc agggagacca     480
ccctgaagag gctgggcggc acgcacttga aatacggcgt ggcagatggc cactttgagg     540
tgacgcggtt cgctctgctc gagacgatca aggaggcgct tccggcggac atgtggggc      600 cggagatgag gaacgcgtgg ggcgaggcct acgaccaact ggtcgcggcc atcaagcaag     660
agatgaagcc ctctgagtag ctcatccatt gtactcatat catatgccac gcaacttccg     720
tccatatccg tccaactttc gttgcttgac cggttcactc atgtcaccat attgtgtttg     780
tattgtgtgt ttacgtgtac taacgcatat tgtaaaatgg gcattcaata aaggaacaaa     840
ttgtgc                                                                  846

<210> SEQ ID NO 96
<211> LENGTH: 440
<212> TYPE: DNA
<213> ORGANISM: Glycine max
<220> FEATURE:
<221> NAME/KEY: misc_feature
```

```
<223> OTHER INFORMATION: Ceres CLONE ID no. 664936
<220> FEATURE:
<221> NAME/KEY: misc_feature
<223> OTHER INFORMATION: Encodes the protein at SEQ ID NO: 25

<400> SEQUENCE: 96
ctcttgtctt agtctaataa acaacacgga cgcagagcct tcgatccaga aaccatgact      60
aagagaacga agaaggcagg cattgtcgga aaatatggta cccgatatgg tgctagtttg     120
cggaagcaga ttaagaagat ggaagttagt cagcatagca aattcttttg tgaattttgt    180
gggaagtatg ctgtgaagag aaggctgtg ggaatatggg gatgcaagga ttgtggtaaa     240
gtgaaagctg gcggtgccta cactttgaat actgcaagtg ctgtcactgt gcgcagcacc    300
atccggaggt tgagggaaca aaccgagggt tgagcttttt ggttgatgtt agattttgag    360
caaattaact ggagaaatga ttcgttttg tttaggaagc tgtattgttt caacttacaa     420
tgcagtgtga attgctttcg                                                440

<210> SEQ ID NO 97
<211> LENGTH: 463
<212> TYPE: DNA
<213> ORGANISM: Glycine max
<220> FEATURE:
<221> NAME/KEY: misc_feature
<223> OTHER INFORMATION: Ceres CLONE ID no. 658438
<220> FEATURE:
<221> NAME/KEY: misc_feature
<223> OTHER INFORMATION: Encodes the protein at SEQ ID NO: 26

<400> SEQUENCE: 97
atatawcttg actctccgca attccctgtc tcckccgccg cagcttccgt ctcccggatt      60
tcgccgcctg ccgcakccgc agcagctcgc cgsccacgcs tcctayccgt cgacgagatg     120
acgaascgca ccaagaaggc tggaattgtc ggcaaatatg gtacccgtta tggtgccagt    180
ttgcgtaagc agatcargaa gatgsaggtg tctcagcact ccaagtactt ckgtgagttc    240
tgtgggaagt ttgctgtgaa gaggaaagsa gttggaattt ggggatgcaa tggactgtgg    300
gaaggwsaag gaaaccttcg ccwkaaaccg tgagctcgaa gtgmggtcca ctccaggwgg    360
gccatgctcg gggccttggg swgcagtctt ccccgaagct attgtyccgc aacggggtca    420
agtttggaga agctgtgtgg ttcaaggccg ggtcccagat ctt                      463

<210> SEQ ID NO 98
<211> LENGTH: 458
<212> TYPE: DNA
<213> ORGANISM: Glycine max
<220> FEATURE:
<221> NAME/KEY: misc_feature
<223> OTHER INFORMATION: Ceres CLONE ID no. 1049262
<220> FEATURE:
<221> NAME/KEY: misc_feature
<223> OTHER INFORMATION: Encodes the protein at SEQ ID NO: 27
<220> FEATURE:
<221> NAME/KEY: misc_feature
<222> LOCATION: (224)..(224)
<223> OTHER INFORMATION: n is a, c, t, g, unknown, or other

<400> SEQUENCE: 98
aacaaaccct cgttcacggt tcaacttcag cagccgcgcc tctaacttgt agcagcgata      60
cctcttctct tatcactaaa aaatgaccaa gagaaccaag aaggccggta ttgttggaaa    120
atacggcacc cgatatggtg ctagtttaag gaagcaaatc aagaagatgg aagttagtca    180
gcacagtaaa ttcttttgtg agttctgtgg aaagtacgct gttnagagga aggccgtggg    240
```

```
tatttgggc tgcaaagatt gtggaaaagt gaaggctgga ggtgcttaca cattgaatac    300
tgcgagtgct gtcactgtcc ggagcaccat tcggaggctg agagagcaga ctgagagttg    360
aaagcagttt acacttttca tttgtttcca aagcttattt taaaattatc atacaatttt    420
ggcaggtcta tgttaggaat attagtaatg tgctactt                            458
```

```
<210> SEQ ID NO 99
<211> LENGTH: 600
<212> TYPE: DNA
<213> ORGANISM: Triticum aestivum
<220> FEATURE:
<221> NAME/KEY: misc_feature
<223> OTHER INFORMATION: Ceres CLONE ID no. 632613
<220> FEATURE:
<221> NAME/KEY: misc_feature
<223> OTHER INFORMATION: Encodes the protein at SEQ ID NO: 28

<400> SEQUENCE: 99
```

```
ctcaaaaccc taggcttcca tatataactt gactctccac aattccctgt ctccgccgcc     60
gcagctttcg tctcccggat ttcgccgccg cagccgctca ccgcccacgc ctcctacccg    120
tcgacgagat gacgaagcgc accaagaagg ctggtattgt cggcaaatat ggtacccgtt    180
atggtgccag tttgcgtaag cagatcaaga agatggaggt gtctcagcac tccaagtact    240
tctgtgagtt ctgtgggaag tttgctgtga agaggaaagc agttggaatt tggggatgca    300
aggactgtgg gaaggtgaag gctggcggtg cttacactat gaacactgcc agtgcggtca    360
ctgtcaggag cactatccgt cgtttgaggg agcagactga agcataagtt gctactagtg    420
ttttgtccta gtgaatcatc tgggatttcg cagtttagac gatactttgg attcagttcc    480
attggctgtt tagtcaagga ttatctttgt acttggtgcg atgatgttct gttatgttat    540
tctcccaccc ttttgttgcc tgattccact ctgatttact gtggattctg atttgccttc    600
```

```
<210> SEQ ID NO 100
<211> LENGTH: 546
<212> TYPE: DNA
<213> ORGANISM: Zea mays
<220> FEATURE:
<221> NAME/KEY: misc_feature
<223> OTHER INFORMATION: Ceres CLONE ID no. 1390976
<220> FEATURE:
<221> NAME/KEY: misc_feature
<223> OTHER INFORMATION: Encodes the protein at SEQ ID NO: 29

<400> SEQUENCE: 100
```

```
aagcatccac aattccacat aacctcgccc gcgccgcctc ccccacgaga cgccttcttg     60
ctctcgcttc cggtgacgcc cgccacttcc tccccgacga gatgacgaaa cgcaccaaga    120
aggcaggaat cgttggcaaa tatggtacca ggtatggtgc cagtttacgt aaacagatca    180
agaagatgga ggtctcgcag cactccaaat acttctgtga gttctgtggc aagtttgccg    240
tgaagaggaa agcagttggt atctggggat gcaaggactg tgggaaggtt aaggccggtg    300
gcgcctacac aatgaacact gctagtgcgg tcactgtgag aagcacaatc cggcgcctgc    360
gggagcagac cgaagcatga ttgcgggcag cttgaaaagg agtacctgga tttttgtagt    420
tcagccaaga gccgtgaacc attttgcctt tttagctaaa tgaacaagaa atgtttatct    480
atctgtagtg accactttgt actcatggtt tgtcatgcta aattgatggt atgcactatg    540
caatgc                                                              546
```

```
<210> SEQ ID NO 101
<211> LENGTH: 550
```

<212> TYPE: DNA
<213> ORGANISM: Zea mays
<220> FEATURE:
<221> NAME/KEY: misc_feature
<223> OTHER INFORMATION: Ceres CLONE ID no. 1457185
<220> FEATURE:
<221> NAME/KEY: misc_feature
<223> OTHER INFORMATION: Encodes the protein at SEQ ID NO: 30

<400> SEQUENCE: 101

| | | | | | |
|---|---|---|---|---|---|
| atatataact | tgactctccg | caattccctg | tctccgccgc | cgcagcttcc | gtctcccgga | 60 |
| tttcgccgcc | gccgcagccg | cagcagctcg | ccgcccacgc | ctcctacccg | tcgacgagat | 120 |
| gacgaagcgc | accaagaagg | ctggaattgt | cggcaaatat | ggtacccgtt | atggtgccag | 180 |
| tttgcgtaag | cagatcaaga | agatggaggt | gtctcagcac | tccaagtact | tctgtgagtt | 240 |
| ctgtgggaag | tttgctgtga | agaggaaagc | agttggaatt | tggggatgca | aggactgtgg | 300 |
| gaaggtgaag | gctggcggtg | cttacaccat | gaacactgcc | agtgcggtca | ctgtcaggag | 360 |
| cactatccgt | cgcttgaggg | agcagactga | agcataagtt | gctactagtg | ttttgtccta | 420 |
| gtgaatcatc | tgggattttg | cagtttagac | gatactttgg | attcagttct | gttggctgtt | 480 |
| tagtcaagga | ttatctttgt | acttggtgcg | atgatgttct | gttatgttat | tctctcaccc | 540 |
| tttttttgcc | | | | | | 550 |

<210> SEQ ID NO 102
<211> LENGTH: 668
<212> TYPE: DNA
<213> ORGANISM: Zea mays
<220> FEATURE:
<221> NAME/KEY: misc_feature
<223> OTHER INFORMATION: Ceres CLONE ID no. 1482731
<220> FEATURE:
<221> NAME/KEY: misc_feature
<223> OTHER INFORMATION: Encodes the protein at SEQ ID NO: 35

<400> SEQUENCE: 102

| | | | | | |
|---|---|---|---|---|---|
| aaaaattcat | tgatcgaaaa | aagaaaaaa | gaaagaaaag | aaaagatgca | gatcttcgtg | 60 |
| aaaaccttga | ccggcaaaac | cataacccta | gaggttgaaa | gcagcgacac | catcgacaat | 120 |
| gtcaaatcca | aaatccagga | caaagagggg | ataccacctg | atcaacagag | gctcatcttt | 180 |
| gctgggaaac | aacttgagga | tggtcgaacg | ctagctgact | acaacattca | gaaagagtcc | 240 |
| actcttcact | tggttctgag | gcttagggt | gggaccatga | tcaaggtcaa | gactctcact | 300 |
| ggtaaagaaa | tcgaaattga | tatcgaacct | accgatacta | ttgaccggat | caaggaacgt | 360 |
| gttgaggaga | agaaggcat | ccctcctgtt | caacaaggc | tcatctatgc | tgggaaacag | 420 |
| ctagctgatg | acaaaacggc | aaaggactac | aacatagagg | gaggctctgt | tcttcatctg | 480 |
| gtccttgctc | tcagggggtgg | ttctgactaa | ataactattt | gctctagagt | tcctttcaat | 540 |
| ggctttggtt | ggttgaatcc | atgagacaaa | gtgaatacaa | tttggatttc | gtgctttggt | 600 |
| tactatgatg | ctatttcagc | tggtttggat | caatttacca | aaaaaaaaa | aaaaaaaaa | 660 |
| aaaaaaag | | | | | | 668 |

<210> SEQ ID NO 103
<211> LENGTH: 752
<212> TYPE: DNA
<213> ORGANISM: Glycine max
<220> FEATURE:
<221> NAME/KEY: misc_feature
<223> OTHER INFORMATION: Ceres CLONE ID no. 522921
<220> FEATURE:
<221> NAME/KEY: misc_feature

```
<223> OTHER INFORMATION: Encodes the protein at SEQ ID NO: 36
<220> FEATURE:
<221> NAME/KEY: misc_feature
<222> LOCATION: (639)..(639)
<223> OTHER INFORMATION: n is a, c, t, g, unknown, or other
<220> FEATURE:
<221> NAME/KEY: misc_feature
<222> LOCATION: (674)..(674)
<223> OTHER INFORMATION: n is a, c, t, g, unknown, or other
<220> FEATURE:
<221> NAME/KEY: misc_feature
<222> LOCATION: (690)..(690)
<223> OTHER INFORMATION: n is a, c, t, g, unknown, or other
<220> FEATURE:
<221> NAME/KEY: misc_feature
<222> LOCATION: (697)..(697)
<223> OTHER INFORMATION: n is a, c, t, g, unknown, or other
<220> FEATURE:
<221> NAME/KEY: misc_feature
<222> LOCATION: (700)..(700)
<223> OTHER INFORMATION: n is a, c, t, g, unknown, or other
<220> FEATURE:
<221> NAME/KEY: misc_feature
<222> LOCATION: (714)..(714)
<223> OTHER INFORMATION: n is a, c, t, g, unknown, or other

<400> SEQUENCE: 103
aattacaaat acaaatacga ataccottct ctctcacaca aaacactagt ccctcccttc      60
ttccttgtct ctttctcttc tcaacaacat gcagatcttc gtcaagactt tgactggcaa    120
gaccatcacc ctcgaggtcg agagtagcga caccatcgac aacgtcaagg ccaagatcca    180
ggacaaggaa ggtatccctc ctgaccagca gagtttgatt tttgctggta agcagctgga    240
agatggtcgc actcttgctg attataacat acaaaaggaa tcaacacttc acttggtctt    300
gaggctcagg ggaggaacca tgattaaagt gaagactcta actggaaaag aaattgaaat    360
tgacattgag ccaactgata caatcgaccg gatcaaggaa cgcgttgaag aaaaagaggg    420
aattccacct gtgcagcaga gactcatata tgcaggtaaa cagcttgctg atgacaaaac    480
agctaaagag tacaacattg agggtggttc tgtacttcac ttggtgcttg cattgagggg    540
tggtacttat tagtgtagat gccatatcag aacccaaaga catgaaagga agctctattc    600
ctgccccgtc tctctgaaga catcattgtt cttttatgng cttggttttt gtaattgtgg    660
ctactattgg tggncagtaa ctcagtatcn ttttagntgn atgctattta aaanccctaa    720
ggtgggcctt tatatgaata tctgaaccaa tg                                  752

<210> SEQ ID NO 104
<211> LENGTH: 484
<212> TYPE: DNA
<213> ORGANISM: Brassica napus
<220> FEATURE:
<221> NAME/KEY: misc_feature
<223> OTHER INFORMATION: Ceres CLONE ID no. 1036726
<220> FEATURE:
<221> NAME/KEY: misc_feature
<223> OTHER INFORMATION: Encodes the protein at SEQ ID NO: 37

<400> SEQUENCE: 104
gaaatcaaat aaaaaaatct ttaagcaaga aagaaagaa aatgcagatc ttcgtcaaaa      60
ccctgacggg gaaaaccata accctggagg ttgaaagcag cgacaccatc gacaatgtca    120
aagccaaaat ccaggacaaa gaaggaatac cgccggatca gcagaggctg atcttcgctg    180
ggaagcaact agaagacggt agaacccttg cggactacaa catccagaaa gagtccactc    240
ttcacttggt cttgaggctt aggggtggca ccatgatcaa ggtcaagact ctcactggca    300
aagaaatcga gattgacatc gaacctaccg acaccattga tcgcatcaag gagcgtgttg    360
```

| | |
|---|---|
| aggagaaaga aggcatccct cctgttcaac agaggctcat ctacgctgga aaacagctag | 420 |
| ctgatgacaa gacggcmaaa gactacaaca tcgagggagg ctctgttcct gcatctggtt | 480 |
| cttg | 484 |

<210> SEQ ID NO 105
<211> LENGTH: 580
<212> TYPE: DNA
<213> ORGANISM: Glycine max
<220> FEATURE:
<221> NAME/KEY: misc_feature
<223> OTHER INFORMATION: Ceres CLONE ID no. 513071
<220> FEATURE:
<221> NAME/KEY: misc_feature
<223> OTHER INFORMATION: Encodes the protein at SEQ ID NO: 38
<220> FEATURE:
<221> NAME/KEY: misc_feature
<222> LOCATION: (543)..(543)
<223> OTHER INFORMATION: n is a, c, t, g, unknown, or other

<400> SEQUENCE: 105

| | |
|---|---|
| aagaaaaagg aaattttctt gggcgttctt cggcttcgtt gtcacaaggt tcgagttcgt | 60 |
| caccgtctag tacgactgtg cgagggagga agaggcgagg agaagatgca gatcttcgtg | 120 |
| aagaccctga cggggaagac catcaccctc gaggtggaga gcagcgacac cgtcgacaac | 180 |
| gtcaaagcca aatccagga caaggaaggg attccccag atcaacagcg actgatattc | 240 |
| gctggcaagc agctggagga tggacgcacg ctggctgact acaacatcca aaaggagtca | 300 |
| actcttcatt tggtcctcag gcttaggggt ggaaccatga tcaaggtcaa aactctcact | 360 |
| gggaaagaga tcgagatcga cattgaaccc actgactcga ttgacaggat caaggagcgt | 420 |
| gttgaagaga aagaaggcat tcctcccgtg cagcaaaggc tcatctatgc tggtaagcag | 480 |
| cttgctgatg acaagaccgc aaaggactac aacatcgagg gtggatctgt cctccatctt | 540 |
| gtncttgctc tgaggggtgg ttactagtct aaacctgatg | 580 |

<210> SEQ ID NO 106
<211> LENGTH: 987
<212> TYPE: DNA
<213> ORGANISM: Brassica napus
<220> FEATURE:
<221> NAME/KEY: misc_feature
<223> OTHER INFORMATION: Ceres CLONE ID no. 975672
<220> FEATURE:
<221> NAME/KEY: misc_feature
<223> OTHER INFORMATION: Encodes the protein at SEQ ID NO: 44

<400> SEQUENCE: 106

| | |
|---|---|
| attccatcaa cttcagacac acagatctct tctcaatcac attacttctg gttctcccac | 60 |
| catgaggaaa gggagaggct cttccgccgt tccacccgcc cttcccggat ctgtgaagga | 120 |
| gccgaggtac agaggcgtta ggaagagacc ttggggccgt ttcgccgccg agatccgtga | 180 |
| ccccttgaaa aaatcccgag tctggctcgg cacgttcgac tccgcggagg aagccgcacg | 240 |
| cgcctacgac gcagccgctc gtaacctccg cggtccaaag gccaagacca acttccaaat | 300 |
| cgactgttct ccttcctctc ctctccaacc actccatcat cggaaccaga tcgatccctt | 360 |
| tatgaccacc cggttatacg gcggagagca ggaggttgtt atcatcagcc ggccggcgag | 420 |
| tagcagcatg agcagcaccg ttaagtcgtg cagcggagtg agaccagcgt cttcttccgt | 480 |
| ggcgaaggcg gcgacgaaga gatatccacg gactccgccg gtggcgccgg aggattgccg | 540 |
| cagcgactgc gattcgtcgt cgtcggtggt tgaagacgga sacgacatag cttcgtcgtc | 600 |

```
ttcgcggcgg aaaccgccgt ttgagtttga tcttaatttt ccsccgttgg atggcgttga      660
cttattcgta ggcgcggacg atctccactg caccgatctg cgtctttgat ctttgagcac      720
aatgacaaca aagatgatga agaagtgata gggagagaga gtttgtgtta agatctgttg      780
ttgtaagaac cagatctgtg tttcattcac ttgtctgttt cttataaaga tcaaaccttt      840
gttacatgta acacttatat agctgctgat gattcttaat tattcaaaat ccaaagtctg      900
tagaatttat acagtatcta tcactgatgt gcttatggat ggtttggagt atgaggctac      960
attttcataa atacattcaa tgtgtgt                                          987

<210> SEQ ID NO 107
<211> LENGTH: 1034
<212> TYPE: DNA
<213> ORGANISM: Zea mays
<220> FEATURE:
<221> NAME/KEY: misc_feature
<223> OTHER INFORMATION: Ceres CLONE ID no. 273307
<220> FEATURE:
<221> NAME/KEY: misc_feature
<223> OTHER INFORMATION: Encodes the protein at SEQ ID NO: 45

<400> SEQUENCE: 107
ctctccttcc ttcacggatt cccaaatact cgcttccaat accaattctc cgatccacgt       60
tcgttcccgc accctcgcgc tccgctgatc cggcggcatg cggcgccgcg gcgtggcggc      120
ggctgatgcg gacggtgacg tggagttgcg cgttccgcgg gtgcggaaga ggccgtgggg      180
ccggtacgca gcggagatcc gggacccggc gaagaaggcg cgcgtctggc tcggcacatt      240
cgactccgcc gaggacgccg cccgcgccta cgacgccgca gcgcggatgc tgcgcgggcc      300
caaggccagg accaacttcc cgctccccgc cgcagccgcc ctccaccacc cccacatgcc      360
cgctgctgcc gccgcagcag ctccaccata cacaacatat cccaccgcca cgggcgtcgt      420
ctcgacgccg ccggtcgcca gaccggcttg cagcagcctc agctccaccg tggagtcctt      480
cagcggcgcg cggccgcggc ctgtgctccc gccgcggttc cctccgccgt cgattcctga      540
tggcgactgc cgcagcgact gtggttcctc ggcctcggtc gtggacgacg actgcacgga      600
cgcggccgcc tctgcgtcgt gccccttccc gctcccgttc gacctcaacc tgcccccagg      660
cggcggcgga gccggcgtcg ggtttacgc cgatgaggag gatgagctca ggctcacggc      720
gctgcggctg tgacgtcgag ctcaatcgag ccgctgctta gaaagaggaa aaggagaaaa      780
atatttggtt cttcccttct cttgtagccg acacgaactc tccatccact acgatgttgt      840
tgtttacttg atctgattat gatatttgcc tgaatcctag tcaacttacc tgcatgcatg      900
cctgcttgtt ttctggcgat tgaggattat cgccaaacgc caaatcttgc agcagctgtt      960
gtactgtaat atatcaacat tttacttcct tcctcttatg aggaaagaga cagataaagt     1020
aacttatttc aatc                                                      1034

<210> SEQ ID NO 108
<211> LENGTH: 911
<212> TYPE: DNA
<213> ORGANISM: Triticum aestivum
<220> FEATURE:
<221> NAME/KEY: misc_feature
<223> OTHER INFORMATION: Ceres CLONE ID no. 1055099
<220> FEATURE:
<221> NAME/KEY: misc_feature
<223> OTHER INFORMATION: Encodes the protein at SEQ ID NO: 46

<400> SEQUENCE: 108
aaacaaaaaa ccaccagggg aagaagggaa agacacacgc cactgtgacc aaaccctagg       60
```

```
ccggccgcga tgcgcaaggc gaggccgccg cagccccagc cgcagccgtc gcagcagtcg      120
ccggagatcc ggtaccgcgg cgtgcggaag cgccctcgg gccgctacgc cgccgagatc       180
cgggaccccg ccaagaagac gccgatctgg ctcggcacct tcgactgcgc cgaggacgcc      240
gcccgcgcct acgactccgc cgcccgatcc ctccgcgggc ccaccgcccg caccaacttc      300
ccgccctcct ccgccacgca gccgccgccg aggccccctc ccccgcggc gcggccgcg        360 gccgccacgt ccagccagag cagcaccgtc gagtcctgga gcggcggcgg gccccgcgcc     420
cccgccaggg cccgcagcgc cgcccgagcg ggcacggcca aggaggggga ggaggactgc      480
cgcagctact gcggctcctc gtcctccgtc ctcctcgagg agggcgcgga cgacgcggcc     540
gcctcccgct cccgctgcc cttcgatctg aacatgccgc cccgcagga gggggcgctt        600 gacgccgagg ccgatcagat gacctgccgg tacgacacgc tgctccgcct ctagctccac      660
gacgacgaga gcaaggattc gtgggagggg aactgggaaa aggaacgaga aaagcgcttg      720 ccccgctcc gctccggtcc gtcttccgat gatctcgtgg tgttctctct ttgttagaaa        780
tggataattc ttgccatttt tttttcttac tttctttcct tcttcttttt ttttttcttct    840 taccactttg attcgatatg tgaataattg agtcatgtaa gctgcgagca aggaaatctg      900
agcttttcct t                                                          911
```

<210> SEQ ID NO 109
<211> LENGTH: 160
<212> TYPE: PRT
<213> ORGANISM: Arabidopsis thaliana
<220> FEATURE:
<221> NAME/KEY: misc_feature
<223> OTHER INFORMATION: Ceres GI ID no. GI_15226675
<220> FEATURE:
<221> NAME/KEY: misc_feature
<222> LOCATION: (13)..(152)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 109

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
        35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met Cys Cys Glu Ser
65                  70                  75                  80

Ala Val Gln Leu Arg Lys Thr Gly Lys Val Thr Val Arg Glu Thr Thr
                85                  90                  95

Leu Lys Arg Leu Gly Ala Ser His Ser Lys Tyr Gly Val Val Asp Glu
            100                 105                 110

His Phe Glu Val Ala Lys Tyr Ala Leu Leu Glu Thr Ile Lys Glu Ala
        115                 120                 125

Val Pro Glu Met Trp Ser Pro Glu Met Lys Val Ala Trp Gly Gln Ala
    130                 135                 140

Tyr Asp His Leu Val Ala Ala Ile Lys Ala Glu Met Asn Leu Ser Asn 145          150          155          160

<210> SEQ ID NO 110
<211> LENGTH: 1823
<212> TYPE: DNA
<213> ORGANISM: Arabidopsis thaliana
<220> FEATURE:
<221> NAME/KEY: misc_feature
<223> OTHER INFORMATION: Ceres Promoter 28176

<400> SEQUENCE: 110

| | | | | | | |
|---|---|---|---|---|---|---|
| gtctcttaaa | aaggatgaac | aaacacgaaa | ctggtggatt | atacaaatgt | cgccttatac | 60 |
| atatatcggt | tattggccaa | aagagctatt | ttaccttatg | gataatggtg | ctactatggt | 120 |
| tggagttgga | ggtgtagttc | aggcttcacc | ttctggttta | agccctccaa | tgggtaatgg | 180 |
| taaatttccg | gcaaaaggtc | ctttgagatc | agccatgttt | tccaatgttg | aggtcttata | 240 |
| ttccaagtat | gagaaaggta | aaataaatgc | gtttcctata | gtggagttgc | tagatagtag | 300 |
| tagatgttat | gggctacgaa | ttggtaagag | agttcgattt | tggactagtc | cactcggata | 360 |
| cttttttcaat | tatggtggtc | ctggaggaat | ctcttgtgga | gtttgatatt | tgcgagtata | 420 |
| atctttgaac | ttgtgtagat | tgtacccaaa | accgaaaaca | tatcctatat | aaatttcatt | 480 |
| atgagagtaa | aattgtttgt | tttatgtatc | atttctcaac | tgtgattgag | ttgactattg | 540 |
| aaaacatatc | ttagataagt | ttcgttatga | gagttaatga | tgattgatga | catacacact | 600 |
| cctttatgat | ggtgattcaa | cgttttggag | aaaatttatt | tataatctct | cataaattct | 660 |
| ccgttattag | ttgaataaaa | tcttaaatgt | ctccttaac | catagcaaac | caacttaaaa | 720 |
| atttagattt | taaagttaag | atggatattg | tgattcaacg | attaattatc | gtaatgcata | 780 |
| ttgattatgt | aaaataaaat | ctaactaccg | gaatttattc | aataactcca | ttgtgtgact | 840 |
| gcatttaaat | atatgtttta | tgtcccatta | attaggctgt | aatttcgatt | tatcaattta | 900 |
| tatactagta | ttaatttaat | tccatagatt | tatcaaagcc | aactcatgac | ggctagggtt | 960 |
| ttccgtcacc | ttttcgatca | tcaagagagt | tttttttataa | aaaaatttat | acaattatac | 1020 |
| aatttcttaa | ccaaacaaca | cataattata | agctatttaa | catttcaaat | tgaaaaaaaa | 1080 |
| aatgtatgag | aattttgtgg | atccattttt | gtaattcttt | gttgggtaaa | ttcacaacca | 1140 |
| aaaaaataga | aaggcccaaa | acgcgtaagg | gcaaattagt | aaaagtagaa | ccacaaagag | 1200 |
| aaagcgaaaa | ccctagacac | ctcgtagcta | taagtaccct | cgagtcgacc | aggattaggg | 1260 |
| tgcgctctca | tatttctcac | attttcgtag | ccgcaagact | cctttcagat | tcttacttgc | 1320 |
| aggttagata | ttttctctct | ttagtgtctc | cgatcttcat | cttcttatga | ttattgtagc | 1380 |
| tgtttagggt | ttagattctt | agttttagct | ctatattgac | tgtgattatc | gctattcttt | 1440 |
| tgctgttgtt | atactgcttt | tgattctcta | gctttagatc | cgtttactcg | tcgatcaata | 1500 |
| ttgttcctat | tgagtctgat | gtataatcct | ctgattaatt | gatagcgttt | agttttgata | 1560 |
| tcgtcttcgc | atgttttta | tcatgtcgat | ctgtatctgc | tctggttata | gttgattctg | 1620 |
| atgtatttgg | ttggtgatgt | tccttagatt | tgatatacct | gttgtctcgt | ggtttgatat | 1680 |
| gatagctcaa | ctggtgatat | gtggttttgt | ttcagtggat | ctgtgtttga | ttatattgtt | 1740 |
| gacgttttgg | ttgttgtatg | gttgatggtt | gatgtatttt | tgttgattct | gatgtttcga | 1800 |
| tttttgtttt | tgtttttgaca | gct | | | | 1823 |

<210> SEQ ID NO 111
<211> LENGTH: 1000
<212> TYPE: DNA

<213> ORGANISM: Arabidopsis thaliana
<220> FEATURE:
<221> NAME/KEY: misc_feature
<223> OTHER INFORMATION: Ceres Promoter PT0668

<400> SEQUENCE: 111

| | | | | | |
|---|---|---|---|---|---|
| atagagtttt | actatgcttt | tggaatcttt | cttctaatgt | gccaactaca | gagaaataca | 60 |
| tgtattacca | ctaggaatcg | gaccatatca | tagatatcag | gattagataa | ctagttctcg | 120 |
| tcgctatcac | ttcgcattaa | gttctagtaa | ttgttaaaga | ttctaatttt | ttactaaaca | 180 |
| aaaactaaat | caacatcaaa | tatgcaaagt | gtgtgttgtc | cacacaagtg | actcaaagta | 240 |
| tacgcaggtg | ggattggacc | atattattgc | aaatcgtttc | cgaaccactc | atatttcttt | 300 |
| ttttctctcc | tttttttatc | cggagaatta | tggaaccact | tcatttcaac | ttcaaaacta | 360 |
| attttttggt | tcagtgatca | aatacaaaaa | aaaaaaaaa | gttatagata | ttaaatagaa | 420 |
| aactattcca | atcttaaaaa | tacaaatgaa | accataattt | taatttatac | aaaactattt | 480 |
| aattagctaa | gggttgtctt | aacgtttaga | aaataaaaaa | ttatgattgt | ctgtttaaaa | 540 |
| ttacaatgaa | tgaataaaaa | aaatatgcaa | tgaatgaaag | aataaatttt | gtacatccga | 600 |
| tagaatgaga | aaatgaattt | tgtacaaacc | actcaagaat | tcaaaacaat | tgtcaaagtt | 660 |
| ttcttctcag | ccgtgtgtcc | tcctctccta | gccgccacat | ctcacacact | aatgctaacc | 720 |
| acgcgatgta | accgtaagcg | ctgagttttt | gcatttcaga | tttcacttcc | accaaacaaa | 780 |
| actcgccacg | tcatcaatac | gaatcattcc | gtataaacgt | ctagattctt | tacagcctac | 840 |
| aatgttctct | tctttggtcg | gccattattt | aacgctttga | acctaaatct | agcccagcca | 900 |
| acgaagaaga | cgaagcaaat | ccaaaccaaa | gttctccatt | ttcgtagctt | ctttaagctt | 960 |
| tttcagtatc | atagagacac | ttttttttttt | ttgattagaa | | | 1000 |

<210> SEQ ID NO 112
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0535

<400> SEQUENCE: 112

| | | | | | |
|---|---|---|---|---|---|
| ttagtgaaat | tatgcacatta | agtaaggttt | tcttagttag | ctaatgtatg | gctattcaat | 60 |
| tgttatgtta | ggctatttta | gttagtatat | gaatttaggc | agtctatgca | aatgatttcg | 120 |
| ttttcatttt | ttcatatgta | aacatcaaga | tcaagtaacg | ccattcgagt | tgatattttt | 180 |
| tttttaaatt | agtgtgtgta | aatttggac | cgcttatttg | agtttgctaa | tgaagttgca | 240 |
| tatatattac | gttaaaccat | aggcaaacta | atttgaaaca | tccgattcga | tttcctgtaa | 300 |
| tttttcttgg | ttaattgacc | aaaatcaaga | tcttcagaaa | taaaataaaa | gacgaaagaa | 360 |
| agctgtcgca | aagcagattg | tgttaaaaaa | aagtggattg | ggctcaaacg | caacttgtcc | 420 |
| agcccgtgac | aattacccta | tacgcaagta | agagtaacgt | atcactggca | aaagttggta | 480 |
| ttagttacga | tatctttgtc | atgggggcat | gcatgggcat | ggcttaagag | ttaagcctta | 540 |
| agaagagtcc | cacactcgtg | actctcatga | tcacttgttg | tttcttacgg | gcaaatacat | 600 |
| ttaactttat | tcttcattta | ttcacctata | ttcttttgga | taataacttt | tctctatata | 660 |
| aaataacaaa | catcgtacgt | ttcatttatt | tacaacaagc | gatgagaatt | aaaaggagac | 720 |
| cttaattgat | gatactcttc | ttttctctcg | gttacaacgg | gattattaca | gataatgata | 780 |
| atctatatgg | atgctgacgt | ggaaaaacaa | aatttggtga | aacacgtcaa | ttaagcacga | 840 |

```
cttttccatg gctagtggct aagatcgttt catcacatgg ctatatcata taatacttgg    900
atgaattcaa aataaacgac tgagaaaatg tccacgtcac ggcgcaccgc tttggactta    960
agtctcctat aataaataca acaccaaaca ttgcattcca                         1000
```

<210> SEQ ID NO 113
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0585

<400> SEQUENCE: 113

```
tgaagtcatt taatatgagt ttgacattag gtaaacctaa tctatgagat tatagaatgt     60
agcaaaacta tcaatgtttc ttttccaaaa tattttgtgg tttttctttt tggttcatta    120
tgttttgtta tttgtgaatt attttaatat gaagtaatta tattgatttt atatgatata    180
catattattt tgatataaaa tttaacactt atccattaaa atagcatggg cataatcaaa    240
atcgggacta ttacgatgaa aaagatagtt aaattgtatg ataaaataaa atgtgtaaga    300
ttaaaatttt gggttttaga aaattactaa acaaatatat gacaaagtat gttgactatt    360
atttaaaatt taaatatcat caataagata tagttaaagt cattaagtgt atagcaaaat    420
gaaaattcta agattaaaat tcgattaaaa tttttttttac taaattaaat atttaaaaat    480
agggattatc atttactatt tacaattcta atatcatggg taaaaattga taacttttttt    540 taaacccgcc tatctaggtg ggcctaacct agtttactaa ttactatatg attaacttat    600
taccactttt acttcttctt ttttggtcaa attactttat tgttttttat aaagtcaaat    660
tactctttgc attgtaaata atagtagtaa ctaaaatctt aaaacaaaat attcaacctt    720
tcccattatt ggaatggtaa tgtcttcaac accattgacc aacgttaagg aatgtctttt    780
aatatttttg gaacctaaat gctaatactg tataccacaa tcacttatga gtattgaagt    840
tgagatagag gaggtacaag gagaccttat ctgcagaaga caaaaagcca ttttttagcaa    900 aactaaagaa agaaaaaaga ttgaaacaca aatatgcgcc actcgtagtc caccccctatc    960 tctttggcaa aagccacttc actctttttc ccttttttat                          999
```

<210> SEQ ID NO 114
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0613

<400> SEQUENCE: 114

```
ttaatactaa cattgtagaa agccacaaaa aagaaattga aatgtgagta gatgctgagt     60
cagaggtttg gtcaatacac aacagctaat tgagataata ttatacacgt cacgatgact    120
tgttttttct cctcccaact tgttaatttc tttattctta aaattaaacc atcgcaaaaa    180
cagaagaaca cagctgtttt tctcgactcc caatttctat tttgctgcta aggacatttc    240
atttcattat ttcccaattc aggactcctt agattttcct aaatttgttt tcctaacttg    300
ctctctctca ttctaacatt ttctcatttt tttagattat cttgtacttt ttagtagatt    360
attttatcag gttttacaaa catacattga cattctaaaa agggcttcta aaaattcagt    420
gtggaatgct gatatactaa aaaaaggtca tgcaaaatta tctacgattt atctaaaatt    480
```

```
agataatttg ccatatataa ctattaacta ataatcgatc ctttgatttt ttgtttagat      540
aaaacgaaac agctatatct ttttttttg ttatcggatt ttaatcgaat aaaagctgaa       600
aaataacagt tatatcttct tctttttaa ctaatgaaac agttatatct taaacaaaca       660
acagaaacag taaatatta atgcaaatcc gcgtcaagag ataaatttta acaaactaat       720
aacaattgag ataagattag cgcaaaagaa actctaattt tagagcgtgt aaacacaaac      780
acgtcttgaa agtaaacgtg aattacacgc ttctaaaacg agcgtgagtt ttggttataa      840
cgaagatacg gtgaagtgtg acacctttct acgttaattt cagtttgagg acacaactca      900
agttatgttt gatatctaag gacttgcact gtctccaaat ctgcaggaag gacttttga      960 ttggatcaat ataaatacca tctccattct cgtctccttc                           1000
```

<210> SEQ ID NO 115
<211> LENGTH: 351
<212> TYPE: DNA
<213> ORGANISM: Arabidopsis thaliana
<220> FEATURE:
<221> NAME/KEY: misc_feature
<223> OTHER INFORMATION: Ceres Promoter PT0625

<400> SEQUENCE: 115

```
gatcatgatc agtttcaact cgctgtgccc acgtgtcgag agatcggcac gtgcctgagc       60
tctcagccgc tcataaatac acttgtttag tagcaacagt atactatagt agtcctctcc      120
tgtttggctt ttagcttgca tcgatggatg gatggatgga tcgcatgaga gggcttcgcg      180
aaggtacgga accttacaca acgcgtgtcc tttctacgtg gccatcgtgt aggcgtctcg      240
ccatgctacg tgtcccggag gatgtctcga tgccaaccct tataaatact gttccattcc      300
aatcccatcg ccacagccag tgcaaatctg atcgatcaag ataatcgagc a              351
```

<210> SEQ ID NO 116
<211> LENGTH: 1022
<212> TYPE: DNA
<213> ORGANISM: Arabidopsis thaliana
<220> FEATURE:
<221> NAME/KEY: misc_feature
<223> OTHER INFORMATION: Ceres Promoter PT0633

<400> SEQUENCE: 116

```
cccgatcggc cttaatctga gtcctaaaaa ctgttatact taacagttaa cgcatgattt       60
gatggaggag ccatagatgc aattcaatca aactgaaatt tctgcaagaa tctcaaacac      120
ggagatctca agtttgaaa gaaaatttat ttcttcgact caaaacaaac ttacgaaatt      180
taggtagaac ttatatacat tatattgtaa tttttttgtaa caaaatgttt ttattattat     240
tatagaattt tactggttaa attaaaaatg aatagaaaag gtgaattaag aggagagagg      300
aggtaaacat tttcttctat tttttcatat tttcaggata aattattgta aaagtttaca      360
agatttccat ttgactagtg taaatgagga atattctcta gtaagatcat tatttcatct      420
acttctttta tcttctacca gtagaggaat aaacaatatt tagctccttt gtaaatacaa      480
attaattttc gttcttgaca tcattcaatt ttaattttac gtataaaata aaagatcata      540
cctattagaa cgattaagga gaaatacaat tcgaatgaga aggatgtgcc gtttgttata      600
ataaacagcc acacgacgta aacgtaaaat gaccacatga tgggccaata gacatggacc      660
gactactaat aatagtaagt tacatttag gatggaataa atatcatacc gacatcagtt       720
tgaaagaaaa gggaaaaaaa gaaaaaataa ataaagata tactaccgac atgagttcca      780
aaaagcaaaa aaaagatca agccgacaca gacacgcgta gagagcaaaa tgactttgac      840
```

```
gtcacaccac gaaaacagac gcttcatacg tgtcccttta tctctctcag tctctctata    900
aacttagtga gaccctcctc tgttttactc acaaatatgc aaactagaaa acaatcatca    960
ggaataaagg gtttgattac ttctattgga agaaaaaaa tctttggaaa aggcctgcag   1020
gg                                                                  1022
```

<210> SEQ ID NO 117
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0650

<400> SEQUENCE: 117

```
catacttaat tctaaaaaaa caacacttat agtttataag cagctcttat gataaaaatc     60
tttctgagtt atagctctgt taaacttgta ttcaccccaa aaacggatgt ttcatttctt    120 atttttact tggagtattt tattgtaatt tgtaaaaaaa aatgtaaagt gggggatatc    180
atgaaaaaca acgtcacttt gtttggtcac aatatacatt tgataaaata atggtcgtcg    240
cgtgatttag ttgattttg ttttatcaac cacgtgtttc acttgatgag tagtttatat    300
agttaacatg attcggccac ttcagatttg ggtttgccca catatgacat accgacatag    360
aaggttaaat ccacgtggga aatgccaata ttcaatgttt ggttttcaaa agagaatcat    420
ttctttatat gatctcaaaa gtatggaatt gaaatgacta atgagcacat gcaattggtg    480
ctatcttaaa aaccgaacgt ctttgaattt aatttgtttt tcaccaaagg tacctaatga    540
aaccctttca ttaaaaaata aaggtaacaa acaaaatttt gtattggaaa aaacattttt    600
tggaatatat aattttggtaa tagaattatg agcaaaaag aaaaagaaaa gaaagaataa    660
tgagcataat aaagccttta cagtattact aattgggccg agcagttttg ggctcttgat    720
catgtctagt aatcttaaac agacgataaa gttaactgca atttagttgg ttcaggtgag    780
ctaccaaatc caaaaatacg cagattaggt tcaccgtacc ggaacaaacc ggatttatca    840
aaatccttaa gttatacgaa atcacgcttt tccttcgatt tctccgctct tctccactct    900
tcttctctgt tctatcgcag acattttgt ttatatgcat acataataat aatacactct    960
tgtcaggatt tttgattctc tctttggttt tctcggaaaa                        1000
```

<210> SEQ ID NO 118
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter PT0660

<400> SEQUENCE: 118

```
caagtcaagt tccaatattc taaggagaaa taatagtata ctaaacatac attagagagg     60
ttaaacttct ttttggattt aagtgtgtat gcataggcta tttattctta agtataacta    120
ttaactgtag ctagatttat acaagaaata cataaaactt tatgcatgtg aggtagccat    180
gaatatacgt acatgttgca atcgattata catgttgtat ttggatttct ctatacatgt    240
tttaacttgt cattctctaa gtatatacat accattaata ctgtgggcat gagtttatga    300
taagactttt cttttgaga ccagtttgt tttcctttcc acctatattt gtctataggc    360
ttcacggtac actagtttac aagtgttttt atatgttcta aataaaattg agattttccg    420
```

```
gaacggtatg atctgtttgc aaataaggac gtatatataa cagtatcaaa tatatttgtt      480
gttataaggc aataatatat tttctgagat attgcgtgtt acaaaaaaga aatatttgtt      540
aagaaaaaaa aagatggtcg aaaaagggga gtaggtgggg gcggtcggct tttgattagt      600
aataaaagaa accacacgag tgacctaccg attcgactca acgagtctac cgagctaaca      660
cagattcaac tcgctcgagc ttcgttttat gacaagttgg tttttttttt ttttttaat       720 tttttcatct tcttgggttt ggttgggtca ctcttcaggt caggtgtgta aaaagaaag       780 aaagaaaaga gagattgttg tgttgtaacc cctttgacta aaatctaatg aacttttta       840 acacaacaaa actccttcag atctgaaagg gttcttcttc tctcttagtc tcttcgtcct      900
tttattctcc gtcgtcgttt catgatctga ctctctggtc ttctcttctt cttcttcttc      960
ttctattttt tcttacttcg tcactgttgt gtctgaac                             998
```

<210> SEQ ID NO 119
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0665

<400> SEQUENCE: 119

```
aaaaaggatg ggtaatggga cctatttttcc ccaacatccc acatgcacac ttccctctcc      60
attctctcac atttatttct ttcattctaa tttatccatt ccgtgtgtaa catattcact      120
aataatctca tctcactaac tcattcattg attgtgatat gtttatctag aattagtgtt      180
ttaacactgt gtctacatat gatttccttt tcattgtatg tgaacatgtt aactcactaa      240
tcattttgta ttttcgagtt aacatgagtc tccacttcgg tagactaaag taaagatagg      300
tttgagtata ataaagttta aaatttgctt taaaatcaat atttataaat aagtttttat      360
cataagtgat ttttgtatgt tatattggac cttgtataaa cagactacag aagaaaatta      420
tttatgagaa cttgtaatgt tagagtggac ctcgtataaa ctaattatgt gggcttttac      480
cataaactat ttatgaaaat tattatggcc cacaccacta taactaaagc ccacatattt      540
agcagcccag tttcattgta agagacatgt tcgctctgga actagaattt tctggttttt      600
gggtatttgt tttcttatgt gtagagaaat gatggtaacg attaaatgtt gtgtattaca      660
atttacaatg gtaagacgat taatatattt acacacaatt ttgttgttgc tgtaacacgt      720
tagtgtgtgt gatgatagaa tttcataaag ctttaactac gaggggcaaa atgttaattc      780
taaatagttg acagcagaaa aagatatgta tacataatat aaggattaaa acgtaaataa      840
taataaataa ggcgagttaa attaaaaccc tgttaaaacc ctagcttgaa acacatgtat      900
aaaaacactt gcgagcgcag cttcatcgcc atcgccattc tctctctcat caaaagcttt      960
tctccttgat tttcgcattc tttagagtct taacgcaaag                           1000
```

<210> SEQ ID NO 120
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter PT0672

<400> SEQUENCE: 120

```
cagccgtaaa tcctccataa atttattttg caagttttgc tcattatata atgagcggaa       60
tttatgatat aatcgtttgt aataatgtta tgttttgatc aaaatttgaa attaaaagta      120
```

```
ggtgagaact tgttatacag tgtagataag gtggatcttg aatataaaaa taaaatttat    180
aagatgtatt taaagcagaa aagcataaaa ctttagataa aataatgtaa aaatgtgtta    240
gcatcaatgt tgggatattg gccgacccga acttaatcaa tgtcggaagc cattacttct    300
ctcccaaaag accttttttcc ttcggagaac taggaacttc ctcactacct ttcgcttaac    360
gtgaaagcca taaatttcat atattcataa aaatcagaaa atctaaaact gtttagtatc    420
acctgttttt ggtatagact attggttttg tgttacttcc taaactatat gatttcgtac    480
ttcattggat cttatagaga tgaatattcg taaaaagata agttatctgg tgaaacgtta    540
cttcagtcat gttgggtcta gattacata ctactatgaa acattttaag ataataatta    600
tcctagccaa ctatatgttc tatattatgg gccaagaaga tatagaacta aagttcaga    660 atttaacgat ataaattact agtatattct aatacttgaa tgattactgt tttagttgtt    720
tagaataaat agtagcgtgt tggttaagat accatctatc cacatctata tttgtgtggg    780
ttacataaaa tgtacataat attatataca tatatatgta tatttttgat aaagccatat    840
attactcctt gacctctgcc cccatttcct tttactataa ataggaatac tcatgatcct    900
ctaattcagc aatcaacacc aacgaacaca accttttcca aagccaataa taaaagaaca    960
aaagctttta gtttcatcaa agacgaagct gccttagaa                          999
```

<210> SEQ ID NO 121
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0676

<400> SEQUENCE: 121

```
aagatagtac agtttcagtg ttttgagaaa aaaagctgaa ctaaaactaa aatgtttaag     60
gacacaatat ttagtttcaa ttagataatt caacagtttg aacaattttt tttttttttt    120
tttgaagtca tttatttata caatgtttta aaacgcatta agcatttagg cagccgacaa    180
acgcctattg tctaactgta aataggcgct tccacttagg ttcatattgc atatttacta    240
tatgtgtata gtgacaaaaa ccaatatttc tcttattttg gatgaaggta tagtagttgt    300
taaatgttca atataattaa gcattaatga caaataaaat aaaattaatt tagttgataa    360
aaagataatc ttataaaaag atcgatgaat agatataatg gtttactgaa ttctatagct    420
cttaccttgc acgactatgt cccaaggaga ggaagtacct taactataat tctgaacata    480
attttgtcta tcttggtgag tattatatga cctaaacccct ttaataagaa aaagtataat    540
actggcgtaa cgtaataaat taacacaatc ataagttgtt gacaagcaaa aaaacataca    600
taatttgttt aatgagatat attagttata gttcttatgt caaagtacaa ttatgcctac    660
caaaattaat taatgatttc aacaggaagt ctgagatgat gggccgacgt gtagttacgt    720
ttcttgaatt gtgagagatg gtatttatta tactgaagaa aacattattt actaaataaa    780
ttttcatttc acatcttctg taatcaatgc gggtagatga agaagttgtt aatacgatgg    840
ccaaccatat ggatctcttt tttggcgttt ctatatatag taacctcgac tccaaaggca    900
ttacgtgact caataaaatc aagtcttttg tttccttttta tccaaaaaaa aaaaaaagtc    960
ttgtgtttct cttaggttgg ttgagaatca tttcatttca                         1000
```

<210> SEQ ID NO 122
<211> LENGTH: 998

```
<212> TYPE: DNA
<213> ORGANISM: Arabidopsis thaliana
<220> FEATURE:
<221> NAME/KEY: misc_feature
<223> OTHER INFORMATION: Ceres Promoter PT0678

<400> SEQUENCE: 122
aattaaatga aaccgcccct aaattaggag ggatttgggt aagtggtaac acattcactg       60
gaaacatgtg aagaaaggag gatgtcaagt agctgaaaac tcagtatagt aaccaacggc      120
ttctcaccaa cctttcatta ataatttggt catccctata tttttattca acattttgtt      180
tttcaatagc ttagagcacc ttaatacctt tcagtgtttt tttataaaaa aaacaaaaat      240
tgggattaat catcaatccc caaatgtaac gtttacttag attatgttca tttttctata      300
cacacaaatc atattctttt gttttaatct tcgaaaaacg agaggacatt aaatacccct      360
aaaaaaggag gggacattac taccaacgta cattaacatg tttgatagca aacgattat       420 tttgttcgtt ttgaaaaggg gaaagtaatg tgtaaattat gtaaagatta ataaactttt      480
atggtatagt aacattttcg aataataaga gagggaaaac actcgccatt gtcggcaatt      540
tagaaccaat attagaaggg ttttttttaga gaaaaaggac ttaaaagttt agagaccta      600 acaacaactt atttagaaat agacatgctt aagttgacaa cagcgagttt attttctata      660
tcgaagaaaa atacgaactt tttcttaatt agatttcgaa tgcatgcact atcgagaatc      720
gaccgtcaca agaaaaaact aatatacata ctgtacatat ctatattcaa tattggtggg      780
gatgggttta atgtgtattt ataattcatg gataaattca cacaataagg tccatgaaac      840
tagaaggtac caaaaataag cattaatgac tctttgccac ttatatatat gattctctca      900
tagtaccatt ttattctccc aaacctatct tcttcttcct ctcttgtctc tctcgctctc      960
tctcttctac attgtttctt gaggtcaatc tattaaaa                             998

<210> SEQ ID NO 123
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0683

<400> SEQUENCE: 123
gattgaatga tgagtgtgca cccttgtatt actaataaaa aatttagcaa cagttataag       60
ctaacgtcat ccatgagtca ttcattagat tcactatttg cgttctcaaa aatcgaattg      120
ttaaaatttg agaagctcta atatacgagt caatgagatg tggcaaaagc atgtccttga      180
ccataaaatt tcgagggtc aactcattag ataaggacaa gaatcaacca attgaaggcg       240
tcttctataa caagtttctt tattactaat attaaagtcc aatggggtga gggggagaag      300
aacttaaata aaaggaaata attggtaagt gaataaaatc taaatacgat actagatgat      360
tgatttgtgc tagtgcatgg tattagatca gatatgtgtt actattcgaa ttcaaattgg      420
catattccat gttgttgata agaaaattgt agaagtgtaa aagctgagtt actatattca      480
aactagtggt ttacataaag tgagacaaca actgtttcac aaaaatgact ataaaatagt      540
aagtagtatt aggtcaattg attttaaaat tttaatcaaa ttcaaatttg tgatataatc      600
aaatttgttt atagaaaatg ttaagaaatc aattttggca gaactaattc agtgagaaac      660
aatcatttac aaaaacaatt ttaacattat ttaacagtaa gatttgacat ttaacccgtt      720
cgtgtgaacc catcatatct aacatggctc tacccatgac gcctccatgc catggacaat      780
```

| | |
|---|---|
| tttgacagat cagaagttct gaacgtggac gaggtaagaa caccatgatg atacgattgg | 840 |
| agttagttat gtcgccaccg acatcactgc caatctcatt aataaaagtg gtactaaatc | 900 |
| tctaatctct attaactata aatataacaa agaaccaaaa gaaagtttct tatctctctt | 960 |
| atctttcata atttccaaga aacacaaacc ttttctacta | 1000 |

<210> SEQ ID NO 124
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0688

<400> SEQUENCE: 124

| | |
|---|---|
| acgttcagag gcatcgcttt tgtacaaatt gaagcgggtt tgttcaatat ttaaaataac | 60 |
| acaggaaaca ttcaaatgta ttattgatgt tgcttaggtt tgtgaaatga tatgaaccat | 120 |
| atcgtatata ttactagatt tttcttatat gttttaaggg tagtggggct gacctatcat | 180 |
| tctgtttggc attaccaatc agactatcag agtattcacc attcaggatt ccataactag | 240 |
| aaaaagaagg ggtttacatt ttctcatact gtataatttt ctactatcag agattttatc | 300 |
| gattacatta atctcatagt gattattctg atttataaaa aagttgacaa ataattaaa | 360 |
| accagtattt tataacaaga ttgtctctct cccatggcca ttattttgac ctctgactta | 420 |
| tttaaatctt aattaacagc ataatactgt attaagcgta tttaaatgaa acaaaataaa | 480 |
| agaaaaaaag aacaaaacga aagagtggac cacatgcgtg tcaagaaagg ccggtcgtta | 540 |
| ccgttaaggt gtgtcgaact gtgattgggc cacgttaacg gcgtatccaa aagaaagaaa | 600 |
| gggcacgtgt atagatctag gaaaaaagaa agaatggacg gtttagattg tatctaggta | 660 |
| ccaggaaatg gaacgtcaca ccaaacggta cgtgtcggat cctgcccgtt gatgctgacg | 720 |
| gtcagcaact tccccttatt catgcccccc tgcccgttaa ttacgtgtaa cccttccatg | 780 |
| cgaaaatcaa acccttttt ttttttgcgt tcttcttcaa cttttctttt taaatcaaac | 840 |
| cttttctttt taaatcaca ttgcatttcc taacgctcaa caaaatctct ctctactaat | 900 |
| atctctctct ctctctctct attgttgaag aagactcata atcggagatt gtttgttttt | 960 |
| ggtttgctct gtaaattgga gaagttttgt tagagatcaa | 1000 |

<210> SEQ ID NO 125
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0695

<400> SEQUENCE: 125

| | |
|---|---|
| aacatttct ttaacttact cttaaatttt aatagtaagt tgatgcatgt tatgttgatc | 60 |
| cgtcttgatc acaaatattg ttttatggac gaattctttg acagtaaatg gctatagtga | 120 |
| ctcagcttgg agcatcccga tatgaaaaca aagtgcagta ttgtgtcgtg gtcatcacta | 180 |
| acgcactttc ctagaactat cgcgcgtgtt tgacctatgc aacacaccag atgtcatgaa | 240 |
| cgtatactta aatagaaaca atgatataga caattggcta tattctgtca tggaacgcaa | 300 |
| accggataac atgtctatta gattcatcgg acttgatcat ggttatgtct taatagacga | 360 |
| attctttgtt aacgattggt taaacggct cacgttagag catcctacta tgacttcaaa | 420 |
| attgataaat attacatgga aatcacttta attttagtta gaaggtagtt aatttagata | 480 |

-continued

| | |
|---|---|
| ttcttattta ataaattaaa aaatagaaga aaaaaagatg agaagagttt ttgtttataa | 540 |
| aataagaaat atctttttatt gtaattttaa aattaaacaa atttaattta tattaaaatt | 600 |
| atctttgttt tattgttaag gcaataatta ttttttttggt gggaattgtt aaaacaataa | 660 |
| ttagtatact gttaagtggt cctttaataa taagataacg tgatttaaaa aagaacgaga | 720 |
| caggctaata tagtagagag gaaaaaatac aatttaggcc caataaagcc caatatagag | 780 |
| ttgtgctcaa acacaggtct tcgccagatt tcctatgacg ccgtgtgtca atcatgacgc | 840 |
| caagtgtcat tcaagaccgt cacgtggcgt tgtttctaca cataggcgat ccatacaaat | 900 |
| cagtaacaaa cacgaaaaga gcattcatat gtacgaaagt agaaaagaag agactctttg | 960 |
| tgataaaact aagtaagaaa tagcataaaa gtaaaaggga | 1000 |

<210> SEQ ID NO 126
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0708

<400> SEQUENCE: 126

| | |
|---|---|
| gtttccaaaa ctagtattct ttatttgctc tattcattat attttttatat ttgtaacgtc | 60 |
| ccgaccgtct ttattaggtt tcgacaatca cttctcggaa ggtcgtccat cctgaaatta | 120 |
| ctctatccta aacatgttta actataaaat tctctcgaaa cttttgtaac gtatataacc | 180 |
| acataaattc tcttaaactt atttgcatac accattatat ttctgaaatc gatatgttac | 240 |
| aatattattt aatatttaga ttacttttac tgaatcgaat taaatatcaa atcgaaacaa | 300 |
| atctaatcta ccaaaaataa tttttgttata aacatttctt gcctagttct acctcatata | 360 |
| cattttagtt aaagaaagaa atcacaacaa ttcccataat tcaataatta aatccacaaa | 420 |
| atcttggagt aagtaagaga aataaaaaga tagtatctta acataaacaa ttcaaagatg | 480 |
| ctctctcaca caattcacac acacttacaa aacaaaagac agaaacaatg ttttcattca | 540 |
| aatcaaaaga agttataaca ctagtacaaa aaaagctcaa attctaatag taactctttt | 600 |
| tatttcccaa ttacccaaag attctctctc acttcacaaa actagctttg agagtcgtgt | 660 |
| tccacaaaat ccattaaagc tgaaacggtt ttgctcacca ttcaaacaaa tacaaaattg | 720 |
| caaaacccca aattataaca aaataatata aaaattaaac cgctaaaaag agtgaaccaa | 780 |
| caaaaatcgc cgaatgtgtg tgtaatgaga aaaccgaccc atcatcccaa tcatctcttc | 840 |
| ccgtgtcact ctcttcctct cccacgtttc ttctctcttc cctttatggg ttttaacttc | 900 |
| tccttcttct tcttcttcaa tcttcagttt tcaaattcaa caacaattca cattttgatt | 960 |
| tcttcatcat ctctctctct ctcgcttctc tctcaaatcg | 1000 |

<210> SEQ ID NO 127
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0710

<400> SEQUENCE: 127

| | |
|---|---|
| tagtgcgcgt ggggagaggg aatggtgaaa ccttagtggt taagttatga ggaaaatgat | 60 |
| aaaaggataa aacaatcaaa tgcagcttga aacggccata acataaagta ccttatggtg | 120 |

| | | | | |
|---|---|---|---|---|
| gtgcgaatat | ttttgtgttt | ctttcactct | tttattgctg | aaagctacga cacttgtctt | 180 |
| aatatattgt | ttccgcaagt | cacatgatct | acttttttatt | taacgtctag aaacgccgag | 240 |
| atatatgatg | attagtatat | cacgtctatg | caaattgtta | gttcgtgttt ggccaaaaga | 300 |
| tatcgagaca | tgtctgaaga | accgagtctg | gttttgagat | atttcttcaa gcattactat | 360 |
| acaatagaaa | aaggagacac | gcgaatatga | taatagcaaa | aggcataaaa aggcgaaaat | 420 |
| taaagaaaaa | cgtaaagtga | tttggcctca | atcaacggga | acgtatctta attttagagg | 480 |
| ttcttcttt | acttttgaga | cgagagagtt | tgcgtctttg | cgagctgctt tggttgacta | 540 |
| aacattatca | tattgaaaac | caaaatacaa | cggaggaata | tttgtcacag tttcactttc | 600 |
| acattgtttc | cttaacgttt | aatcaaccctt | gttcaaaatt | tctatagttg taatcatcat | 660 |
| tgtttacaaa | atttttcgttc | aaagatgatt | ttaaataaaa | ttgtgaaaga aaaccttttc | 720 |
| tgaaataagg | attggatgat | agtgttaaaa | gaaaaatatg | aactgaggca aaaagaggag | 780 |
| tggtccccgg | aagattgtga | atgtgtcat | ctaaaccagc | cagacgtagt cacgtgttct | 840 |
| ctctagctttt | atgaacttcc | ttagccagca | ccatcattgt | gattgtagta tatatgtaac | 900 |
| cctaccttca | tctctcccat | tttccattct | ccatatagac | tcctttacaa tatacaaaac | 960 |
| ctatccaaaa | gcgaagaagc | caagcaaaca | tattataaaa | | 1000 |

<210> SEQ ID NO 128
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter PT0723

<400> SEQUENCE: 128

| | | | | |
|---|---|---|---|---|
| gtcatatctt | atcaacacgt | caacgatcaa | acctttagc | ctattaaatt caacggctta | 60 |
| gatcaaaacg | aaactaggtg | ggtcccactt | ttaatatcgt | ggctgcataa catttcctcg | 120 |
| ataactgaag | ccgttgtggt | ctttctcaga | atctggtgct | taaacactct ggtgagttct | 180 |
| agtacttctg | ctatgatcga | tctcattacc | atttcttaaa | tttctctccc taaatattcc | 240 |
| gagttcttga | tttttgataa | cttcaggttt | tctcttttg | ataaatctgg tctttccatt | 300 |
| tttttttttt | tgtggttaat | ttagtttcct | atgttcttcg | attgtattat gcatgatctg | 360 |
| tgtttggatt | ctgttagatt | atgttattgg | tgaatatgta | tgtgttttg catgtctggt | 420 |
| tttggtctta | aaaatgttca | aatctgatga | tttgattgaa | gcttttttag tgttggtttg | 480 |
| attcttctca | aaactactgt | taatttacta | tcatgttttc | caactttgat tcatgatgac | 540 |
| acttttgttc | tgctttgtta | taaaattttg | gttggtttga | ttttgtaatt atagtgtaat | 600 |
| tttgttagga | atgaacatgt | tttaatactc | tgttttrcga | tttgtcacac attcgaatta | 660 |
| ttaatcgata | atttaactga | aaattcatgg | ttctagatct | tgttgtcatc agattatttg | 720 |
| tttcgataat | tcatcaaata | tgtagtcctt | tgctgatttt | gcgactgttt cattttttct | 780 |
| caaaattgtt | ttttgttaag | tttatctaac | agttatcgtt | gtcaaaagtc tctttcattt | 840 |
| tgcaaaatct | tcttttttttt | tttgtttgta | actttgttttt | ttaagctaca catttagtct | 900 |
| gtaaaatagc | atcgaggaac | agttgtctta | gtagacttgc | atgttcttgt aacttctatt | 960 |
| tgtttcagtt | tgttgatgac | tgctttgatt | ttgtaggtca | aa | 1002 |

<210> SEQ ID NO 129
<211> LENGTH: 1001
<212> TYPE: DNA

<213> ORGANISM: Arabidopsis thaliana
<220> FEATURE:
<221> NAME/KEY: misc_feature
<223> OTHER INFORMATION: Ceres Promoter PT0740

<400> SEQUENCE: 129

| | | | | | |
|---|---|---|---|---|---|
| tgtggccact | aaagatttac | ccttaaccgg | gcccatataa | gcccacgtca | agtggcgctt | 60 |
| atacgctctc | cgtaagagag | ccaacatttg | gtatgtaatg | ttgcaaatta | ttcttcaaga | 120 |
| caataaattc | aaatataatt | caatattgtc | caaatatagt | gatgtacttc | agttgtgcac | 180 |
| atagaaactc | cactaaacca | acttttagat | agatgcattc | acaaattttc | aacaatgtcg | 240 |
| cgaaagtcta | atccatcacc | agattctaac | attttaatta | ttatatttaa | ctatacatac | 300 |
| tctaatcagc | atgagtcaaa | cgtgtacaat | agcccaagca | tataataaga | ccaaagtcaa | 360 |
| actcaaataa | atgtctccaa | actcaaaact | tgaaaaagac | ctaattatta | catggtagat | 420 |
| atgactttgt | cgacaagtaa | accaactaat | cctcgaagct | accttctctt | cccagttatt | 480 |
| atgtgtgatc | gatttataaa | tctcttcttc | taataacacc | tatattttc | ttatgatgtg | 540 |
| aataaatata | aaacttttaa | ctttaaaaca | tatttatccg | aaatattgca | cttagatttc | 600 |
| aaatagataa | ataatagtac | tatctaactg | atattgaaaa | gacctaacac | ggaaaacagt | 660 |
| tttataaaaa | atcccaaatg | tgggtaatta | tcttgatttc | ttggggggaaa | cagaaaatgg | 720 |
| attaagatta | atcggagtcg | tgtcaagcag | ctcgttaata | actgtagcaa | gttgactgag | 780 |
| taagcatcaa | cgtgtcatct | ccgtaaagcc | cattatttct | agtctcgccg | cgtcttctct | 840 |
| tccacgtagc | acttcacttt | ttctctcctt | ttgtttcctt | tggaacacaa | acgtttctat | 900 |
| ttataggaat | aattacgtcg | tccgtatctg | tgtcggaaca | tagatccaaa | ttaaaagcga | 960 |
| cttacttaat | tacatatcgt | tcgtgttttt | ttcttcaaaa | a | | 1001 |

<210> SEQ ID NO 130
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter PT0743

<400> SEQUENCE: 130

| | | | | | |
|---|---|---|---|---|---|
| tcgattggcc | cgatcggccc | caaaatcaag | ctgagccgct | tcaaacttca | gcttttgaaa | 60 |
| tcaccccccaa | actcatgtcc | tcttatcatt | ataactaaag | gatctttcat | tttatttaac | 120 |
| tcatcgtctt | gcactaccca | acccaaaggt | tccaactata | cccgaagctt | tctaaaggtc | 180 |
| caaagacttt | tttttttcgag | ccagactatt | caagccaaga | aaagccaaac | cccacaagcc | 240 |
| agtacttttc | aattccatat | tataaactta | tctgtcttgt | tttagtccca | ctaaaaacaa | 300 |
| cagaatttaa | tttaggttga | gctaaaaccc | ttgacaaaag | tgtatagtcg | tcgattcagt | 360 |
| agcacactca | tcactcatca | gatttgatag | ttgacctaaa | gtatgactac | tccatttcaa | 420 |
| ctaacaaatg | aaaataaaag | agacctaagg | gttagaggat | tgaaactata | ctctcaagtc | 480 |
| ttttatcact | aggctactac | cagctagtta | acttgatgga | tttaagcaag | aaaacgtaga | 540 |
| atttatattc | gagcagattg | tttagctaaa | aaagcttggg | tttgaaattg | ccttttctcc | 600 |
| catataagca | cgtcggttcc | taaataactc | tttctagcgg | agagtgtctt | tccaataatt | 660 |
| taataaaaat | ggtgtttgta | tatcaaaaaa | aaagaaaaa | agaaactgat | cgagatagaa | 720 |
| cgtttgcagt | tttataaaca | atttaaaaaa | caaaaaaat | taaactcaat | gtatttttta | 780 |
| ttaattcaca | aacaataata | aatcatagga | tcgaatattt | acacggtatc | aaaacctact | 840 |

```
cgccgctact atataaaaat tgaagtcaaa tatcaaccgc aattattaaa ccagcaagac    900
aataattcat aaacttaata taaacataaa taaattaatg ttacacaacg atatatggtg    960
agggttatta ctatcttctt cctctcaaaa cacatctcct aaccttaagc tttagacggc   1020
ctgc                                                                1024
```

<210> SEQ ID NO 131
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0758

<400> SEQUENCE: 131

```
agctagccac atcagtgacc aaaaaagata attaacaaac caaataaaat aacaaatttt     60
gatcatttgg aataaaattt ataaaaggaa cgaaagcgcc ttctcacggg tcccatccat    120
tgaaatatat tctctctttt tgctctatat aataataacg cgtactaatt tgtagtatat    180
attattacaa agtcgatatt tgattgtttt gtgaacgttg atatattaat tttcttggat    240
gatgacaaaa aaagtcatag aaagtaacgt gtgaacatag cattaacaaa atacaaacat    300
aatatataac caaatatatg aaaataggat aaaatctcat tgaatagatc ttcttctatt    360
caaatatata aatatttgtt tgtctataaa attaacagag cattcacatt atctaaaata    420
atagtaaaat caaaataaaa ctaaataaaa ataactctgg ttttataacg attgattta     480 aatattagtt tttgttgtaa agagatcatt atatatgtct gtaatatttt tatactgagt    540
tacatgatat ttagttatta tagcgtaatt aactaagata agaaattaac taaagtgata    600
ttctgattat tattattttt gttaggacac gtacgtggaa aaactaaaca ctataggtta    660
caaaacggta taataaactc accattactg gaaaatgttt gcatttgact caataagtaa    720
cttattataa gttactgata taatgcatag ttttgaaatt cttaaataaa ttattttggt    780
ttcgcatgaa aatatgaaag gagagaaatt tattattgtc acttatatat atatacatcg    840
taatcatttt ttcgtgaata attctctctc ccattccatt atttctcagt atctctcttt    900
cttcccctta ctttattgtt gcttttaaac cttcaatttg ctcataaacc aaatatataa    960
tatcaaaaca aacaaacaaa aaatcagaat tccccctaata                        1000
```

<210> SEQ ID NO 132
<211> LENGTH: 921
<212> TYPE: DNA
<213> ORGANISM: Arabidopsis thaliana
<220> FEATURE:
<221> NAME/KEY: misc_feature
<223> OTHER INFORMATION: Ceres Promoter PT0829

<400> SEQUENCE: 132

```
aaagttttga attattggga atcaatttcg aagttttgta attctttggg ggctaatagg     60
atattttatt ttcttggttt cgtctattgt tgttttttcta tttatggttg ggcttttaga   120
actctggaca ggcccatgtc atatgttttc ccttctcctt atattttca tttttcattt    180 tgttaaatta atgcataata tccaaaaaca atttaaattt ttgaaggaac cctttagtta    240
cggctccgaa gctttcacaa gtgagaatgt gagatcaaag aaggcaaatg gaggatttta    300
aaagttaaaa tcatctttta tctgcaaaag ttgacaattt ttttgtatca aatctaaatc    360
atcaaactct cttaaactac aagagcataa caacctctat gtaatccatg aaataatctg    420
```

| | |
|---|---|
| cttgaaggac ataacataaa tcattatggc tagagtgact aacttcaatc aaatcctctt | 480 |
| aactctagct cccttacaat ggtatcgtaa aacattatgc attagggatt gttgtcctag | 540 |
| gaaaataaaa taaaaatccc cacagaccaa ctaccatttt aacttaaaaa taagcttcgt | 600 |
| ccgcgacgaa ttgttttcca tcctaaaaat agaatggtgt aatctgctaa tggtttagtt | 660 |
| ccattaactt gcaagttcta ttgaaagcct aaatgtcaat aaagatatta aaattcggag | 720 |
| tcaaaagaca aatgaatcaa aagcaacaag acaagtcagc tccattcttc actacccatc | 780 |
| ttttacaata aatcatctct cttttcacaa atttcaaact actctcattg ccctttagct | 840 |
| ttgttataga gccaacacta cagagagact cacacacttg tttcaataat taaatctgaa | 900 |
| tttggctctt cttataaact a | 921 |

<210> SEQ ID NO 133
<211> LENGTH: 763
<212> TYPE: DNA
<213> ORGANISM: Arabidopsis thaliana
<220> FEATURE:
<221> NAME/KEY: misc_feature
<223> OTHER INFORMATION: Ceres Promoter PT0837

<400> SEQUENCE: 133

| | |
|---|---|
| aactacaagg gagacataat atcaccatct ggttcctgtt atcatctgaa gatttcttgt | 60 |
| tttaccttcc agtgataaaa tgatccttat aatacatata gatatattaa attgctgtat | 120 |
| tttaagatta tagatatata aggtacatga gagtgtttat ttaaaaaaat tcacttggaa | 180 |
| ttcatgtttt gtgatacgtt agattggaat ccatttggga aaagaagaat catctgttct | 240 |
| tatgtctcaa atttttgactt cattcacttt tcttcttgtc ttttaagaaa gcttccacaa | 300 |
| tctaactgtt cgatgtgaaa actgagattc gagtaagaaa atgtgaactg tgttatactg | 360 |
| tttttttaatt agataattta gattgcactc agataaaatta ataacattcc tcgaatactt | 420 |
| ttatgtgatt ggatatatta ggtatatctg ccaaccaacc aataaactgc tatgtttaaa | 480 |
| caaattaaat aaattagtat atgtttactc aagaataaag aagatagaaa agaaaattct | 540 |
| atatgagcta aatttgctgg aggaggcatc ggacgtgggt accagacctt ccaagcaca | 600 |
| cgagtagtgc ttagccatgt catgctaaca tacaccatttt ggttcataca aaatccaaat | 660 |
| caaaatctat ttttaaaatc ttttgcacac gtctttgaaa aacacctctc atactatagc | 720 |
| tacggaagct tcaatttcaa ggtttgtcta aaagctaacg att | 763 |

<210> SEQ ID NO 134
<211> LENGTH: 751
<212> TYPE: DNA
<213> ORGANISM: Arabidopsis thaliana
<220> FEATURE:
<221> NAME/KEY: misc_feature
<223> OTHER INFORMATION: Ceres Promoter PT0838

<400> SEQUENCE: 134

| | |
|---|---|
| atactggtat gcttaaggtt gaagccaaga tctctgtctt acccaagtaa ccactttcta | 60 |
| ttagaaggga tcaacactaa gaatatggag atttaagcct aagggctaag gcggttctca | 120 |
| acaatacatg atgtgaatac aatcacagac gatttactga ggtttgttga taagatcttg | 180 |
| atcagtctct gcatcatctg ttcaacaatc tcaatctttg actgtttgct ttcggagcca | 240 |
| taaacagagg aatcccttat tccctgttat aggagcaata caccaagtat tatttccatg | 300 |
| gctgaaattc tcttatggaa acctaattgt tccattgaag ctgtaaaatc gaatctggtg | 360 |
| aatattctcg agcaaagccg catgctaatt atgtcaattc agaagagttt gattaggaga | 420 |

```
ctcgaagcga gtttgatgat ctttcttgat gttcaactcc gattgtaagg gtataattga      480
cttttcatgt attacggctc caccacctga cactaaggca ctctttgtcc atctcgttgg      540
tatcatcgga ttcggatggt aaaaataaaa agagcagagg aaacttgtta ctcatgcaag      600
cttctcaggt gccacgtcac tccattacgt gtcatcttca cacaccatct cgctcaaaac      660
cgatctcatt tttcaaacct taaaggcaga agcaactgat taagttaaca ctcttgagaa      720
gctctcgatt aagcttgaac ttggaggatc a                                     751
```

<210> SEQ ID NO 135
<211> LENGTH: 669
<212> TYPE: DNA
<213> ORGANISM: Arabidopsis thaliana
<220> FEATURE:
<221> NAME/KEY: misc_feature
<223> OTHER INFORMATION: Ceres Promoter PT0848

<400> SEQUENCE: 135

```
tctctttaaa tcagttaact aaccgtttat atatttacga taaggtttga agagattatt       60
gataaaataa tacatttcat aatcccgcgt tcaaccgttt aaagtaacat ttaagttgac      120
tatatctaat ttttttccca ttaaatatgg agctggtaaa ctttatcaac ttctaaaaag      180
tgtaacaaca aaaattaggt caatcacaat tctgtttttt ttattatttt ggattgactt      240
ccaattgcaa atagtcttag tgatcaccat tatcatacat atatacatca gtaggtttc       300 atcatgatat accacaaagt atttgacaag ccatatggtt ttggatcaaa aagtcggtcc      360
aaaattaatg ttttatgtgc aagaaccgac ccattgtaca cacgtgttaa catcttcaag      420
actttcatct ctattttttct tttggtcatt aagatacccca ttgatccgaa tctgttacat      480
tcccacctac ttttttaatt tttactatcc actccaaatt aaacacaacc gatgatttta      540
ataattggaa gcttttaaaa atatttcaaa acaagcctct ttgtgtttgt ctatatatat      600
acacgtaata agaaggtgaa tgaatctcac agcttacttg ttctaaggct tccaataacg      660
aaaacagta                                                              669
```

<210> SEQ ID NO 136
<211> LENGTH: 702
<212> TYPE: DNA
<213> ORGANISM: Arabidopsis thaliana
<220> FEATURE:
<221> NAME/KEY: misc_feature
<223> OTHER INFORMATION: Ceres Promoter PT0863

<400> SEQUENCE: 136

```
cgggaaacga caatctgatc tctagtccag tcgattggcc cgatcggccg attataaact       60
tacatgagac aagtataaat aattattata aacttattaa gtttaagatc aaggcttttg      120
tgcaatgtat caatgaatgt tagatgtgat atgatgaaag caatgtttta aacacataca      180
tagtcattga tcggaatgtg tgttattaga aatgcatgcc taagccgata gggttatcta      240
tgtttggtct tggacattat agccaaattt cgaatctaat tcttccaata tatatttttt      300 ttttttttgct tagggccact actagtattg cttatcaatt ttaagagctc atgaaaatgc      360
aacaatatag tagttgcaaa tccttgtttc aagagaaatc aaagggccac ttgtgaattg      420
aataataata atatttgcaa ataaccttc actaaccat accaacaaaa ccacacagat      480
ttggcaaaga cataaccttt gggagacgtg aaaaggctca aaatttgaca attgtcctta      540
caaattcgct cattagtgca attgtgagat ttgtttgcat ccaaatccaa ttcataactc      600
```
acactcgtct caaattcgaa aaggcctgca gggccagtgc actgggatcc aacaatgtcc    660
tccgactcgt ccaagatcaa gaggaagcgg aaccgcaccg cg    702

<210> SEQ ID NO 137
<211> LENGTH: 435
<212> TYPE: DNA
<213> ORGANISM: Arabidopsis thaliana
<220> FEATURE:
<221> NAME/KEY: misc_feature
<223> OTHER INFORMATION: Ceres Promoter PT0879

<400> SEQUENCE: 137
ttctaggaag actggtcaag ctaagctgtt tctgtttttt gttttttgtac tttactttt    60 gtttgctagt gggaactggg tttattgggc cttgaagttg ataaaagatg aataaaagac    120
atatcgccta aagcccatat gagaagcaga agacaaaaac ctccaacttt ggcataaat    180 tttgattata gttaaaagtc cagacccaat ttggcacctg gcttagttac gattctaagg    240
catgacacct gcctaatatg tttattacag aaaataaaga gaatcagcta ggtgtccctt    300
attgaacaca ttaacaaact ccaacgacac tacgtgtctt cgtgactctt actatatcca    360
aaaacctata gctaaagctg aattttccat gattagtata gtcccaacca aaaaaatact    420
gaagaaggca taagc    435

<210> SEQ ID NO 138
<211> LENGTH: 397
<212> TYPE: DNA
<213> ORGANISM: Arabidopsis thaliana
<220> FEATURE:
<221> NAME/KEY: misc_feature
<223> OTHER INFORMATION: Ceres Promoter PT0886

<400> SEQUENCE: 138
agtgtatttg aaaacgacat tgaagaatta atatattttt ttttaatttt agttttttat    60
agtacaaata ttaaaacaaa caatcctacc atatcataac atttgtaaat aacattttaa    120
gttttgtttt gagttttaat taattttcta tgacaaaaaa atgaagtcaa tagactaagt    180
gaatcatata gtataaataa acacaattta aatagtttca aataaattta gaagaataa    240 aacaaataga aatcagaagg tgtctgtttc ctcctcgcaa catacgatca aagagaaaca    300 acttgacccct ttacattgct caagagctca tctcttccct ctacaaaaat ggccgcacgt    360
ctccaacctt ctcccaactc cttcttccgc catcatc    397

<210> SEQ ID NO 139
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0007

<400> SEQUENCE: 139
agcagaacaa ctatatttat tgtgtcacat aaatctgaga tcatttataa ccaccaaaga    60
acctatacac agtaaatgac aaatgtatct ccctctatct ctattgccca tatgtagatg    120
ctaaagtaag atttctcttt ttttttaatgt acttttttt gtataaagta tattccataa    180
gaaaaaggaa aagcttgttt atggatcaat tgaccccaaa aaagttttt agatcaaagc    240 ccaatataaa aaaaaacac agtagtgaca caaggaact taaataaacc atgaattgat    300
ctataaacag tagagatcga taaggcgaac attttccatg tgaagtgtct tctttcatct    360

-continued

```
ataatatttt tgacatccaa taatttcctc tataatatca ttcacataat tgatagaaac      420
attatgttag aattgtccac atcatttgag ctgtaatata ttctgtttta acaaattata      480
tggtagttgc ttaatcttat gtccatcttc ttctatgcat cgttttcgcg cctagttgtc      540
cagtccattt caactaccta cctctaattc ttatcttaaa acaacatttt ttaatttaag      600
tattatgctc aaagactaac tagatagaaa accgttatta acattaaac  gaattaaaag      660 tcttacatgg aaaatgtagg tttataaacc acgagttatg attgacaata aaaaaaatgc      720
aaatcatcaa tcaaaagaga cttgagtgcg actctatatc aaccattgca attaaaatta      780
tctatcacaa aaattttaga cagattaagt taatttagtc taaattcact aatttatttt      840
ctataattag taattaacta tatttattta tttacacatt ttctgataat ttagaaattt      900
gcatgaataa caaatataag attttggaaa ttagtagcaa atttaattaa taattatttt      960
tgcctaaatg aaccaaacta taaaacctcc acatacacca gtcatcaaat ttacagagac     1020
aaca                                                                  1024

<210> SEQ ID NO 140
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0008

<400> SEQUENCE: 140
ctcgagagat gaagtcttag taatgtttga acaaacaata atcacgttttt ccatcaaatt       60 cgagcattta aagtttatat tactacatgc cccaagatga taccgtccat ctcatccgaa      120
aatatttctg aaattgcgct aagacaacaa tgtttgctca aattcgatca tttaaagttt      180
acaaatctct catcaatctt acaaacttct cacactaaac agaggtacat attttcttat      240
aaagacaaaa ggttcgaaca gctggcttct caactcgagt tgtttgtcag ggcctctctt      300
cactaactac aagttggtac ttcaaatatt ggtggctagc ttcacgtgat attgtctaca      360
aattaaaccc atgaaaaagc tgcattaatt gttccaagtg aaccctgagg agtgtcaata      420
gtctttgctt tagtgtgatc attaaaccaa atctctaaat tcctaatttg tactaacatt      480
tggaacgtat ttcctactct tctccctgct ccaactccca aaaataagat tagttagatt      540
tctataacta atatacatgt atactcccaa aaacagtaaa accatattaa taaagctaat      600
tttgcataga tttatttcgg taaaccggcg gttcaagttg gggaaaaaaa agacaaacgg      660
tctaaagtca tccaaagaca aaaaaccaaa gacaagttga gagagacgag accaatcaca      720
acattgcttc gtagattgcg tgacatcatc cttgacggct actttcattt gtgtcttatt      780
tggataaaac gcacgtgttt aattcacgaa ccttcatagc aataagaaat ttccattact      840
ttcatatttt caactttttt tattacccat tacatgctta aaatattaat tcacaagtct      900
ttgtcaaaat tcaatatttt ccaggttcat gaaccctttt tatctcaatc tactctataa      960
tatctcccta taaattacaa caaaacctct ttatttttca                          1000

<210> SEQ ID NO 141
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0019

<400> SEQUENCE: 141
```

```
gatataagta gaatcatttt ttgccgccgt ttctcgctaa cacaccgaaa actgaatcaa    60
atctcctagc tcttctacgc aaaatcgagt gcatcgacaa tggcggaacg tggtgtcgaa   120
cgtggtggag atcgcggcga tttcggacgt ggattcggtg gtcgcggcgg tggaagaggt   180
ggtccgagag gtcgtggtcg ccgtgcaggt cgtgctccag aggaggagaa atgggtgcca   240
gtgactaagc ttggtcgtct cgtaaaggaa ggtaagatca caaagattga gcagatctac   300
ctccattctc tcccagtcaa ggagtaccag atcatagatt tactcgtcgg tccttcattg   360
aaagacgaag tgatgaaaat catgccggtt caaaaacaaa ccagagccgg tcagagaacg   420
agattcaagg ccttcatcgt cgtcggagat agtaacggtc acgtcggatt aggagtcaaa   480
tgctccaagg aagttgcgac ggcgatcaga ggcgcgatca ttctcgcgaa attgtctgtg   540
gttccgatac gaagaggtta ttggggtaac aagattggaa accacatac ggttccgtgt    600 aaggtaaccg ggaaatgtgg atctgttact gtacgtatgg ttccagctcc gagaggttct   660
ggtattgtgg cggctagagt tcctaagaag gttcttcaat tcgctggaat tgatgatgtc   720
tttacttctt ctagaggatc caccaaaact cttggaaact tcgtcaaggt atgtactttc   780
acaatggctg ttttggtttg atgaactctg aattaggcag tgaaaaagta atcattacca   840
gttaagtgaa tttatattga agattaggat ttagctgatt gtattggttt gagcatgtga   900
gtttgtgttt aagattgctt gaattgaaat gctttaggtt gtttgattac gctaaattct   960
gactaatgta attcaaattg ttgttgtttt ttttttggtc                         999

<210> SEQ ID NO 142
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0028

<400> SEQUENCE: 142
gtcagtgaag tcgattggta gtacttgaaa cacttggttg gtttcatgta tttggcctat    60
atataaacaa acatcgtaat tatatacgga ttttttttcgg aattttacgc catatctgta   120
agtatatata acatgcatgt cgttttcaaa ttcatatgat gaacgatcca cgtaagtgct   180
actactccta caatattgca tgagagagat atgtatttat aaattttatt ttgaagaaga   240
aataagaggg aaggttactt gggtggatcg atgtgaaaac aaaagaagaa aaagcgaaac   300
ccactaagcc attacatgat atcgaccttc ttatctttt cctctttatt ttattttct     360 catcttcttt ttgtcaggac ttttttctac ttaatgaaac ctccaaacta tctaactaat   420
acactcccat gtagaataaa gaaaattata taagatattg ttgatatttt gtaactagaa   480
aatatatttg ctctgtaatt tttcgtaagt taaatcaaca ttttaaagta gaaacaaata   540
ttactgcaaa aagtaggatc attatttttg tccaaaatct cagttagcta tagggttgta   600
gtaaaaacaa aacacattct tgatttgccc caaaaaataa agagagagaa gaatattgtt   660
caaaagtggt ctcttctctc tctaattatg ttttcactaa acccaattag attcaaacag   720
tctacaaagt ccaaaagata aacatgggac aacaattcga tgcaaaaaat cctcttttca   780
tgctcttttt ttattctcta gtcttttaaa ttactaataa aaactcacaa atccaccaaa   840
cccattctct acaactcacc ttcatctaga tttaccccact cccaccgaga aacacaagaa   900
aaaaaatata catatataaa tatacaagac aacacatgat gctgatgcaa tatacacaac   960
aaagtattaa atcttagata ttgtgggtct ccctttcttc tattcatttt cttattcatt  1020
```

```
aaaa                                                                  1024

<210> SEQ ID NO 143
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0039

<400> SEQUENCE: 143
ccgttcgagt atttgaaaat tcgggtaca  cccgcctaaa taggcggacc ttatctagta    60
tatatataca tttgaactat attgtttact ttttagttga tttaggctat gtcatgacat   120
tgacataaat ctacctgtta tttatcacgt gtaattcgtg taaagtgtaa actagaaagt   180
tcaaatacgt atttgttttt gttctgttat ataggattgt catagttgta aatctacaat   240
ttattacaac atgaataagt acacaagcaa tgtaattgga tttaattgct aaactcttta   300
catggtcaat ctaaatttga taagaaatac gtcacatatt actaagactg atagtttttt   360
tgttgtcacc aattattttt gttaaattga cgaaaacaat tccaaaaact caaatgtaca   420
aaatcataca gtctcacaaa catctcatag agaaagatat aaatctccca tatgggaacg   480
ataacacgag gtcgaaatac tattcgtaaa actaaaacgc cttagttata aatcgttagt   540
tgtaaccgcg gtcgagaata catacagatc cacgaaacta ctactacaca tgctgctgaa   600
ttggaatttg gaaaagacca tcttctttag gaagagctca cccaatgagt gacaaaggtg   660
tcggtggctt gttttctacc catatgtata catcaaatgg tagtttcatt aacgtttggt   720
tttgagaaaa gtaagacttt ggctagtagc taggttcgta tataataaac tcttttgaga   780
aagttcatca ctggtggaaa atgttaaacc ggttttttct cattttttcc gccatgttaa   840
ccaccggttt aaaaagaccg taacacattg aaagattaat aagggtatat ttgtaattac   900
ggtttgctgg caattttaa ttattatttt aattagagaa aatagagaag ccctatcaat   960
gtacatggta tatatataa aggcaaaacc ctagaaaacg atactattcg actcagccgt  1020
cctt                                                                1024

<210> SEQ ID NO 144
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0050

<400> SEQUENCE: 144
aatctgatct ctagtccagt cgattggtac ttgagggaaa catcatattt ttaaaccttg    60
tctcagtaag ctaacacaca cccccttgtga ttacttatcc atgtttatcc acaagaatgc   120
agttggattg agatattttc ttctttgttg aaatcaggcc tcaaggtgtt catgtggtct   180
gcaaaaaaat tcccaaaaat aaagatagtg acatctgaaa tcgataatgg attagacgaa   240
gagtttcgtg ttattccttg gtatgggcgg gtttggggac agatattttg gcacagacga   300
ggactaggcc actgtggtcc tgcagcatta ggtgtcccct ccatgtcctg cattacatt   360
tattgatgga ttcatcaccc tatctactac aacggctaca caaactatga agagttttgt   420
ttactaataa atgcccaagt gagggtcga tcgaacccgg gacacgtttt tcagtttacc   480
atatagaatt atccttggaa cccttgatac tccatagaac atcaccacct ctgttgtcat   540
```

```
ctcaggaatc caggttcaaa cctagtctct ctctccctag tgggaggtat atggccactg    600
ggccaatgat gacaaaatgc aaaaaaaata aaatacattt gggttcatta tctaaaatat    660
ctcttgtgtt tgtaagtttt ggttgcacac tcgtgtggtt gaagtgtgtg tgagaggtac    720
tatacaatac actctgcttt tgttttgtac ctatctcttt ctcttctcca catatccaag    780
actttgggga taaagctgag atcattggtt gccatttggt tgtgtagaag caatcaccca    840
tttgctttat ccgaggttga taaatttcct cgggttctcc ttctgacacg tatgacaaat    900
tctaatagta tattcctcgt agatattacc tatatattct caatagttgc aggtacttaa    960
ggctttgtct tggcatcctc gtcctcttca gcaaaactcg tctctcttgc actccaaaaa   1020
gcaa                                                                1024
```

<210> SEQ ID NO 145
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0086

<400> SEQUENCE: 145

```
cttatccttt aacaatgaac aggttttag aggtagcttg atgattcctg cacatgtgat      60
cttggcttca ggcttaattt tccaggtaaa gcattatgag atactcttat atctcttaca    120
tacttttgag ataatgcaca agaacttcat aactatatgc tttagtttct gcatttgaca    180
ctgccaaatt cattaatctc taatatcttt gttgttgatc tttggtagac atgggtacta    240
gaaaaagcaa actacaccaa ggtaaaatac ttttgtacaa acataaactc gttatcacgg    300
aacatcaatg gagtgtatat ctaacggagt gtagaaacat ttgattattg caggaagcta    360
tctcaggata ttatcggttt atatggaatc tcttctacgc agagtatctg ttattcccct    420
tcctctagct ttcaatttca tggtgaggat atgcagtttt ctttgtatat cattcttctt    480
cttctttgta gcttggagtc aaaatcggtt ccttcatgta catacatcaa ggatatgtcc    540
ttctgaattt ttatatcttg caataaaaat gcttgtacca attgaaacac cagctttttg    600
agttctatga tcactgactt ggttctaacc aaaaaaaaaa aaatgtttaa tttacatatc    660
taaaagtagg tttagggaaa cctaaacagt aaaatatttg tatattattc gaatttcact    720
catcataaaa acttaaattg caccataaaa ttttgtttta ctattaatga tgtaatttgt    780
gtaacttaag ataaaaataa tattccgtaa gttaaccggc taaaaccacg tataaaccag    840
ggaacctgtt aaaccggttc tttactggat aaagaaatga aagcccatgt agacagctcc    900
attagagccc aaaccctaaa tttctcatct atataaaagg agtgacatta gggttttgt     960 tcgtcctctt aaagcttctc gttttctctg ccgtctctc                            999
```

<210> SEQ ID NO 146
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0088

<400> SEQUENCE: 146

```
tcgattggga ttactacttc atctagtaag gttctgaaaa cgtttgttgt tgataaggaa     60
gattcgtctc aggttattac tgttgatctt caaggtttgt gattgtgacg cttatacatg    120
tgctgaaact gtggtgttta tttattgaaa acaaaaaaaa agtctctctt gtagtttcat    180
```

```
tgtactaaat agaaaacaag aaacgttttt ttctttaatc ttctacattg ataatattgg        240
atcaaaggat tgtttctgca agacacaaca caaacatact tatactagtt tacttctact        300
aagtactaac tacataccca tacacacact tgcacctaga ctttacttct agacatcatt        360
accctaaggt agaaccaagc ttacaagcaa gttttaccga caactcttac attacaactc        420
tagtctgtag tctttaacgt agacttacta actagtcatt agtggtttaa tttttaaat         480 tttcatccat atgtttttgt tgtagatata aactaaagtc ggtcacattt ataattgtc         540 attatgtccg cgtaaaagtc aattcagcta ttggacattt atgaaatgta agattttctc        600
tctcatttcc ccgtgcgtga agacatgcat tggttttct gtaataatca acaaatccaa         660
accccttttc gatctttatt tggacattgt tagagacaaa atttctctat agtctttttc        720
ctaatttgat accatgtttt tgtttctgca caaatttact cactggttta actaactatc        780
cacttattta tgattttacc attaggcgtc agctagccct agtcaaattt gtaaacaagc        840
caagctatct acataaatcg agatgtcatt aacgttaatc gtcgttaatt cgaatttgaa        900
aacatagata gctttagcag tacaatgggc aatggtaaga agaatagcaa aaggcccaat        960
atttggtttg cagaaattaa agccttaaaa aaaagcccac agatatttgt caaagaaccc       1020
taat                                                                    1024
```

<210> SEQ ID NO 147
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0092

<400> SEQUENCE: 147

```
aaagattgag ttgagagaga tggtggagac gcagaacaga caaagggagt ttaccatata         60
gtgctctaaa gggcaatgag attgcagtga tgtggctatc cggggaatca tcgcaggtta        120
ttccttccca tgagcaacaa tcaatggatg ggttccaatt cagaggagaa acagaagaag        180
aaacgttttc agagaaccac agtagggatt ctcgatcttg cgagttgcag agagcctctg        240
aaactgcaat agaaaggaca ctgatgaaaa gaacacactg aaggagtatg ccaatcatgt        300
gaaaactcag agcttgtatt ggtcttgtgg ttgatgaagt tctcacaaaa cctttggctt        360
tgaatctccc ctcattagtc atggtgagaa caagaacaag acgagaaaca gacaaagaag        420
atgaaaaaac ttgttggcca gtgttgacta aggggggaata gccccagaca taacaaaatt        480
agacttgtcg tacatcttta atatttttt atctgtttct ttgtcctgac gctttcatta        540
ttcctgtgat caattttctc ataccattgg tccatcgtta atcctttctt aatttcattt        600
tctacgtaac atgagaggag accaagtcct atgagaacag ttgacgtaac agtggttgtt        660
aagttaagtt aaaagagga agctagtgag agtgaccgtt aggtagagaa gtgagatctt        720
taaccactct tctttctctc tctctctgct ttttttcgtcg tctttcacat ctactgttcg        780
caaactctct tatgcttcca ataatggtga taccaattga gacttgcagg agaatctcct        840
cttctccaca ctctatcaac tggtcagcca tggaatggtc gtttcagttt caatattcct        900
ggattctttt taaggattcc tgtttctctt ctgttcctgg tatattctta acgacgaaat        960
tagtatcgga tcctggtaat acattttgaa gcttttaagt accattgcac tgggatccaa       1020
caat                                                                    1024
```

<210> SEQ ID NO 148
<211> LENGTH: 1020
<212> TYPE: DNA
<213> ORGANISM: Arabidopsis thaliana
<220> FEATURE:
<221> NAME/KEY: misc_feature
<223> OTHER INFORMATION: Ceres Promoter YP0096

<400> SEQUENCE: 148

```
gaggtcagtg agtcgattgg tgcaaaattg aaaaattgaa gggtgaaaca aatttaaaga      60
taatatctat taaatcctct aattttaaaa atttagcaaa aattgtattt tcttatggat     120
ctgttagttc acacgtatct taattagtac caaatcatat ctaatgatta gtgataaaac     180
tagttagata tctatatgtg tctttaccat ttaacttgaa tccttcttct ttttttttacg    240
taaacaactt gaatccttcg ttaatacata aatttaaagc attttttctt taattctatt     300
gatcggtata tatttactat aagttttagc tcatatgcaa tttcaaatga tatgctttta     360
aattttgtct aggtgtgata gttgtatctt taacataaat cttatagcaa aattatactt     420
gatattctaa atttatctat ttgctcttgt gaacctcata ttagtctaga gaaactttga     480
aatcctttca attagttgta tgtccaatac attttttacta acatttatta gtcttttttaa   540
ttaagattat tgttagaaaa aaaaagattt tttaaaaata aataatatgt tttagataca     600
atgtgagtta ggcttcttat atttttaaaaa ataaatttat ttcatactta aaaatagttt    660
ggaatttcaa tttatttggc tgaataccat aaaatatgtc aatttgaacc ttatacccat     720
tgactatttg gtgttagaaa ccctttaaca aaaaaaaact atttggtgtt agatatcaaa     780
ataaaaaaag tttaaccatt ggtttcttat attgaattgg atattgttac atgtattaaa     840
gttttttttgg tttaattttg aaacgttgat agaaactatt aagtttaagt ttggtagtat    900
atttatttgt ggaaaattta attgccatta aatataacgt caactttttt tggttttttt     960
tgagaagtta cgttgtgatt ttgatttcct atataaagt tagattacgt cattttttaa     1020
```

<210> SEQ ID NO 149
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0097

<400> SEQUENCE: 149

```
ttcatcttta tatttaagag tttaaaaact gcaacttttg ttttctttc actaagtctt       60
atggccacag ttaattaaaa gcagatgaaa ggtggtccaa tggaaaagga gaatgtgatt     120
gggctagttg ggagagttct gatgtctagt gttgggtaca cgtgtccgtc agttacacat     180
agcattaaat cagacggcat gtcattattc aaatctagtt cacatagtac gactaatagc     240
tgataaatta atgattatac agcatatgaa ttatgaattc aaaaaaaaaa aaaaattgaa     300
aatgttaagg agatgctata ttttacaaaa ttcatcgcaa tgctttctac taatttgcta     360
agtggtcttc tccagttagt cttgtcgatt ccaagcgata ttattaaatc ttgaagcatc     420
gctcaaagca ttatagctta agataaccaa attgttatta aaacaccta gtgaaatttt      480
taaattaaaa caatttgtat atctttgtaa tatctaatac tactctttct gtgtctaaaa     540
ggattaattt tcaaaaattt cacacatatt aaaaaaaaaa aaaattact agctaaacaa      600
ttttcaataa tcataaaaca atagtaactt aataattttt ttttatttc aaaatagtcc      660
ttcaagttta caattcattt tagtattata atcaacaaaa tttgtattaa aaagttggaa     720
```

```
aattaatctt tgtggaacaa aaaaatctag aaatcatttt ttagaattag agagaggttt    780
gataaaaaaa aataaaaaaa aatagagaga ggtagtacat actaaacgat gtgatactac    840
tattgacaaa atcttaattc tcagtttagt agaataaact agaaggaatg aatgaagtaa    900
atgcgaatcc aactactaac aaaccctact tagtcatcat atttttccat atgaaatccc    960
tatataaacc catcatcatc tcccactttt ttcatatcca                         1000

<210> SEQ ID NO 150
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0101

<400> SEQUENCE: 150
ttctcgttct ctagaatatt gctggaccgg attaggtcaa tattattggg ccagattaga     60
tattgaattg tcgacgttgc ttacgttacg ttatatcttg tttaagaatt aaacctatcg    120
acttagtctt aattaagaaa acattgcctt aaattctctg gtctgcgacc gttttttttga   180 ccgttaaccc ctaattaaag aaacaaaata attatagaaa gagcactgaa atgtgattat    240
tttaacagta ctcttatgag aaaattcgta cttttttagtt tttttttttgt acaaatctct  300 aagaaaaaca ctactactaa ttaagaaacg tttcaaacaa ttttatttc gttggctcat    360 aatctttctt tctcggtccg ggactaaccg ttggcaaaaa aaaaaaaaaa gttgacaata    420
attattaaag cgtaaatcat acctctcaaa taaaaacttg aatttggaaa caaagacaac    480
taaaaaactc gaatttaaga gaattcctaa aatcaagtga agtatcatca cttggtaaaa    540
tttcataacc gttggcttct atttctatgt gtgccttggt ttgcaggaga taatatttca    600
tttccaacca atgatattcg tacacatagt caaacaaatg tttgtctttg ttattatatt    660
gagaaagaaa caagaaagag agagagagat agataagacg aaggaagtga agcttccaag    720
cgcccaccgt taaaaatctc gtgtgcaagt ttcaaataca agtggccggt ggtctccata    780
atttgatcgt catccaatta aaaggaaga aaaagcgtgt tttatacaag aaaactcatt    840
aaaatagcaa gtctagaaat atctcaacac taatctacca cgtctattac acacacacac    900
acacacactt gatcttaatt tattttcaag attcaagaaa atacccattc cattaccaca    960
acttgaccac acgcctatat ataaaacata aagcccttt cccc                     1004

<210> SEQ ID NO 151
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0102

<400> SEQUENCE: 151
atttggttga taacgttttc actcgactaa ttatatactt cagaaggata gtaatagaat     60
accaaaataa ttaaatgatt ggttagtgcc ttagtggaga cttttaaccc gattctaata    120
gactaatgat gtagctaagc atttatttgg gatcatcact gtttgaaaac gtgaaatgtg    180
ataaaagtta tgaaacgatt aaaatataaa ataaccgtac aaaacattat gtaccgtttt    240
tttctctgtt cttttggcga tttggtttag ttcgttacac tctaaatgtt attgcagata    300
tatatataat gatgcatttg catctgagga acatataatt ccggttaaca cttccaaatc    360
ttatatccgt ctaggtaggg attttataaa tcatttgtgt catcatgcgt tatgcttgtc    420
```

```
ggctttgacc ataacgcaga gatatagaac tagcttttac ttaacttttta gatttattat        480 ttgatctaga gttaagtgga gatatatagt gttttttgtta gattattggt ggatgtgaga        540
gtttgtcttt agtttcaagt tgagaatata aggcaagagg agactctgag gcaatcagag        600
gttttgattg gcaaaatatc caaaaggccc aaaccaagtc gaagcccatc tcgtacaaaa        660
aaagaaagag atctgtaaga aaaaatattc tttgatattc ttacaaaaat aagtgtaaaa        720
cttttattag tcaaaatctt caatctttaa aaactctcat cactcctacg aaagcgcgtg        780
agagttatga gacattcctt aatagcatta ctcacaagtc acaagttcaa aacgtctgac        840
tgaaacagaa acaagccttt gttgaagtct tgaagaagag acattagtac tcgtcgtata        900
gccataaaag gtaatatacg aaatttcttc gctaatctct tcaccttcct ctacgcgttt        960
cactttcact ttataaatcc aaatctccct tcgaaaacat                              1000

<210> SEQ ID NO 152
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0103

<400> SEQUENCE: 152
gttttgaaga acaatctgga tcgaaatcta acataaggtc atcgtattca agttacgcag         60
tcaaggactt gacatcatcc tactctggtc tgaggttacc acttccaaag atgggatttt        120
tcgactcggt atgcttccta agaaattcgt tttattgaac ctagcaaata tcttgtaatg        180
taagattcct gagatgatga agaaaaaaca aacttttgtt acagcaggag aacggagaga        240
aagaaaacag agaccaaaat gctcttgaag caaacagaag aagaagacac aaatccaaac        300
ttgagacttc ttctacacca gaaaaccgca gcattctggg acaacgcaaa acacgaaagt        360
gaaacgggca atgatatata tgtcttgggt gcgttacaag gcatcgtttg caactgttga        420
gttggataag tcaactgtct tctttttcctt tggttgtagt agctgccttt ttttttccttt       480 gttgctttaa gaaatagccc gaaaaaaaga atgttctaca tttcggagca gaaaactaac        540
cgaatgagtt tttggtcgga tcatcggatc gatcagatat attttgagtt acgaactgtt        600
ataaaaaaag ccataatttt gtgttgagtt tgcaaaatac cttataactt gttatttgag        660
attgcacctc catatatatt aattcgtaag agtatttatt aagtaagctt tagtataaat        720
ccttttttcc tttaaagtaa gttaatgttc tactaaataa tagtaaagtt gaagaaccgc        780
tccgttttta caccatgcac gtgttatcta acaaagaaaa tatggtacac ctaatggcta        840
atgcaaagga caacacaatg aaactaactt gactctgtgt tatagaaacc catagacatc        900
tgcatacatc ctagtatttg tataaattgg actcaaattc ctgaggacaa tcatagcaaa        960
caatcacatc atcgcaatat acataaacaa aagaggaaga aaaa                         1004

<210> SEQ ID NO 153
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0107

<400> SEQUENCE: 153
taacaatcct tgggaacatt gcatccatag atatccggtt aagatcgatc tttgaactca         60
```

```
taaaaactag tagattggtt ggttggtttc catgtaccag aaggcttacc ctattagttg    120
aaagttgaaa ctttgttccc tactcaattc ctagttgtgt aaatgtatgt atatgtaatg    180
tgtataaaac gtagtactta aatgactagg agtggttctt gagaccgatg agagatggga    240
gcagaactaa agatgatgac ataattaaga acgaatttga aaggctctta ggtttgaatc    300
ctattcgaga atgttttgt caaagatagt ggcgattttg aaccaaagaa aacatttaaa    360
aaatcagtat ccggttacgt tcatgcaaat agaaagtggt ctaggatctg attgtaattt    420
tagacttaaa gagtctctta agattcaatc ctggctgtgt acaaaactac aaataatcta    480
ttttagacta tttgggcctt aactaaactt ccactccatt atttactgag gttagagaat    540
agacttgcga ataaacacat tccccgagaa atactcatga tcccataatt agtcggaggg    600
tatgccaatc agatctaaga acacacattc cctcaaattt taatgcacat gtaatcatag    660
tttagcacaa ttcaaaaata atgtagtatt aaagacagaa atttgtagac ttttttttgg    720
cgttaaaaga agactaagtt tatacgtaca ttttatttta agtggaaaac cgaaattttc    780
catcgaaata tatgaattta gtatatatat ttctgcaatg tactattttg ctattttggc    840
aactttcagt ggactactac tttattacaa tgtgtatgga tgcatgagtt tgagtataca    900
catgtctaaa tgcatgcttt gtaaaacgta acggaccaca aaagaggatc catacaaata    960
catctcatag cttcctccat tatttttccga cacaaacaga gca                    1003
```

<210> SEQ ID NO 154
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0110

<400> SEQUENCE: 154

```
gggatgcggt tccgcttcct cttgatcttg gacgagtcgg aggacattgt tggatcccag     60
tgcaatggta atataaaaca agaaaacaag agattttata ggacaatcac taaatgacat    120
ttaattgatt aaacatttat tcattaataa ttgtatgtta ctaacttcaa catttaataa    180
ttttgtttaa gatacgttta catcagagac tattaatatt tttacaggtt gtaactttaa    240
actttgtctt gaatcgaaca tgactataga ttttgggcaa acttaaagat aacaacattt    300
ccgttttttt tcaaattatt acaaatcaaa ctgatatatt agacacaaca cgattacacg    360
taatgaaaaa agaaaagat aaaagataa aagaagggat cgattctgtt tggtctggtt    420
tagtgagatt caaagttaag ctcttccttt caagacatgc cttcttaaac cgggaatgtg    480
aacgtttgta atgtagtccg tccagttaat gcttccaaca tcaaatccaa attctctctt    540
ctcgtcctct gacatattct ccattaatct ctggggtatt gctgttatca aatctgtaaa    600
agaaaccaaa aaaaaagat gaaaactttg cgggtaccgg ttttgtctgc tctaagaatt    660
agaatgttaa tgagttctgt cttaccttcc accatagaaa gtgtatggct cataaatagt    720
agcaaggtgt ttggcttgtt caacagattt cttgcatata aactttagct tctgcatcat    780
cttactatcc actgaactca taccactcat caacccactc cgttcttgag catctctcca    840
caaatgatcc gagaaatcat caacggaatt gaaaagtttc atcaaacgca ccataatagg    900 atcacccttta gagtccatgc atggagatgt tttgtagtgg ttataaagaa gctccgctaa    960
gtcttcgaaa accagcgggt ttatcgccga agaagcgatc tgatacacgt ttatttcagg   1020
ttcc                                                                1024
```

<210> SEQ ID NO 155
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0111

<400> SEQUENCE: 155

| | | | | | |
|---|---|---|---|---|---|
| cgattggatt | tagtctatac | attatagggc | gcaagtttgt | ggatttaaga | attatataaa | 60 |
| aacttgaaat | atatagtttt | tatgcattct | cctcttgtgt | aatacataaa | ccaaatatga | 120 |
| gataggttaa | tctgtatttc | agataatatt | aaattccaaa | caatattttt | acttgttata | 180 |
| agaaggcaat | taatatctct | ctgttaatgg | caagtggtac | caagtagtat | taaactatta | 240 |
| atgcaatgga | agagtactgt | tggaaattat | aatcctctat | cacacattca | aacagatctc | 300 |
| ctgaaatctt | ctcttccaaa | cttgtacttc | tctgatccaa | atgtaggctc | caaaatatag | 360 |
| acatttacca | tttactaagt | ccacaactcc | tttcttgtct | ccttcaaaaa | tgactcttgt | 420 |
| gtaaccacca | tatgactccg | acagttcggc | attgccatga | tgagagctta | aaaattcacc | 480 |
| ttcctgagca | tttcaagtct | tcactcccctt | agcttgacct | gaaccaagat | aaaatgcctt | 540 |
| tgtcgtcccg | taatatccat | cctgctttgg | acggcatcat | agttacattc | gatccatcct | 600 |
| atttacaatg | ttattttagt | attaaaaaca | tgacaataaa | tttgttgtta | acatattca | 660 |
| aatacaatat | gattggattt | ataagtaatt | gtaatatgaa | atgtccttag | taatatgtta | 720 |
| aaaaatacat | agatacacac | acgtactaaa | agaggcaacg | cgggagatgt | cattagagga | 780 |
| agaactagga | agcagagcgt | tcatgcaaaa | tgctaccaaa | aacgttaatg | caatatctca | 840 |
| actaatcagc | acagtccatt | tcatactgag | aatgtaaaaa | ccaatcagca | tcgtccatttt | 900 |
| tttcatctaa | ttatttgtta | actcttaatt | ggccacaact | tccaaccaca | tgacgctctt | 960 |
| tctattccct | ttatatattc | ccatctcaaa | tgttcttgga | gacacaaaat | atcataaaca | 1020 |
| tata | | | | | | 1024 |

<210> SEQ ID NO 156
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0115

<400> SEQUENCE: 156

| | | | | | |
|---|---|---|---|---|---|
| gtcgattgga | tgatgaacat | tctacatata | taattattat | gtttaagcac | ttagacagca | 60 |
| taaattcttt | ctaattatat | aaatctaacc | ttgttacatt | gtacatctat | aaattacttg | 120 |
| aagaaataac | gagttctatt | tcttttttaaa | aattaaaaat | actataccat | atctcagtga | 180 |
| ttaagttgaa | ccaaaaggta | cggaggagaa | acaagcattt | gattcttcct | tatttattt | 240 |
| tattcatctc | tcactaatga | tggtggagaa | aaaagaaaa | tacctaacaa | acaaatatat | 300 |
| attgtcatac | aaaaatattt | ctatattttt | agttaattag | tttatattcc | tcactttttca | 360 |
| gggcttatat | aagaaagtga | gcaaacacaa | atcaaaatgc | agcagcaaat | actatcatca | 420 |
| cccatctcct | tagttctatt | ttataattcc | tcttcttttt | gttcatagct | ttgtaattat | 480 |
| agtcttattt | ctcttaagg | ctcaataaga | ggaggtacta | ttactacact | tctctctact | 540 |
| tttacttgta | ttttagcatt | aaaatcctaa | aatccgtttt | aaattcaaaa | ataaacttag | 600 |
| agatgtttaa | tctcgattcg | gtttttcggc | tttaggagaa | taattatatg | aaattagtat | 660 |

```
ggatatcttt actagtttcc attcaaatga ttctgattt c aatctaatac tctcactctt    720
taattaaact atatgtagtg taatttcaca ctgttaaatt tctaccatgt catgtatatt    780
agagttgcat agaaaattgt aaaacatcca tttgaattcg aatgaaacaa aatgttttaa    840
aataaaattt tggttttaa aagaaaaatc taaaactgaa ttatatcgtt taaccaagtt    900
gtaaaagtca taaaacgtag tatcttgtaa atcgctcttc cacggtccaa atagacttct    960
agtaataaac aagtaaaact aattttggtt tcttac                              996
```

<210> SEQ ID NO 157
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0117

<400> SEQUENCE: 157

```
gtcagtgagt cgattggatc acagtccttt atgataaaac aaactcataa ttattccacc     60
gacaacatgc gttttaaatt atttttttctt aaattatatt atattatatt gatatcaacc    120
tagctaaaat aattcggatg gcgaaatcgg acaattttta atagaaaaaa tgggtatgaa    180
gatagtctat gattccgttc ttagcgacta gagggacctg ctcaaatctc ccgggtgata    240
cgcgatgtca agctcaatag aaccccacaa ccgacgagac cgagaaatcc ttgatttggg    300
ctagaagatt ttgaaataaa tttaatatat tctaagtaac ttgcttaaat tttttttcaa    360
actctaaaga cataactaac ataaagtaaa aaaaaaaag ttaatacatg ggaagaaaaa     420
aattaaacta atgattagct ctctaacgtg tttaatctcg tatcaagttt tttttttaaaa   480 attatattgc tattaaaaca ttgtactatt gttctcattt tgtttagcta ttattcttgt    540
gaaatgaaaa gttgtgttta ttcaattact aaatggcaat atttatcttg gaaaactata    600
cctctaattg gattaggccc tagacatcct ctttagctta ttgacgttaa aattattccc    660
aaaactatta agtttagta gtttgaaaga tgcatcaaga cctactcaga taggtaaaag    720
tagaaaacta cagttagtgt gattatattt taaaatatat aaaacaatct tattaaacta    780
aatattcaag atatatactc aaatggaaga taaaaacatt tagtctgtta ccactaccag    840
cctagctagt cactaatagt cacttttggaa ctgagtagat atttgcatct tgagttacca    900
tggactcaaa agtccaaaaa gagaccccga gtgaaaatgc taccaactta ataacaaaga    960
agcatttaca gcggtcaaaa agtatctata aatgtttaca caacagtagt cataagcacc    1020
attg                                                                 1024
```

<210> SEQ ID NO 158
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0119

<400> SEQUENCE: 158

```
taccaaaaat aaggagtttc caaaagatgg ttctgatgag aaacagagcc catccctctc     60
cttttcccct tcccatgaaa gaaatcggat ggtcctcctt caatgtcctc cacctactct    120
tctcttcttt cttttttttct ttcttattat taaccattta attaatttcc ccttcaattt    180
cagtttctag ttctgtaaaa agaaaataca catctcactt atagatatcc atatctattt    240
```

```
atatgcatgt atagagaata aaaaagtgtg agtttctagg tatgttgagt atgtgctgtt         300
tggacaattg ttagatgatc tgtccatttt tttcttttt cttctgtgta taaatatatt          360
tgagcacaaa gaaaaactaa taaccttctg ttttcagcaa gtagggtctt ataaccttca         420
aagaaatatt ccttcaattg aaacccata aaccaaaata gatattacaa aaggaaagag          480
agatattttc aagaacaaca taattagaaa agcagaagca gcagttaagt ggtactgaga         540
taaatgatat agtttctctt caagaacagt ttctcattac ccaccttctc cttttgctg          600 atctatcgta atcttgagaa ctcaggtaag gttgtgaata ttatgcacca ttcattaacc         660
ctaaaaataa gagatttaaa ataaatgttt cttctttctc tgattcttgt gtaaccaatt         720
catgggtttg atatgtttct tggttattgc ttatcaacaa agagatttga tcattataaa         780
gtagattaat aactcttaaa cacacaaagt ttctttattt tttagttaca tccctaattc         840
tagaccagaa catggatttg atctatttct tggttatgta ttcttgatca ggaaaaggga         900
tttgatcatc aagattagcc ttctctctct ctctctagat atctttcttg aatttagaaa         960
tctttattta attatttggt gatgtcatat ataggatcaa                              1000

<210> SEQ ID NO 159
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0120

<400> SEQUENCE: 159 tagttttga tttaatctac gttttcttaa atcataaatg ggtaattatt agtttttgca          60
aaatcaaaat ccaaaaattg ttctaaacac tgcaaccatt taaggcctat atcactcaga         120
aaatttctgg tgggagaact aatcgtttgt cctttctaaa tctcacatat tagaatttag        180
aattagtgtg ctacataaga atattagttc agctcggaac aactattttt tggtaaaaca        240
gagaacttaa acaaatgcat tatttttatca acatgcattt tgaattgaat ataaaatttc       300
ataattgtaa agacataaat tacataaaat tttacatgaa aaaatagata tagaaagaaa        360
atgaaactaa ctgatgatat gctctctaaa ttttttaatc tcataacaag aattcaaatt       420
aattagttca tattttggt taatataaca tttacctgtc taagttggaa ctttcatttt        480
tttctgtttt gtttagtcag tattcttaat gtgaaacgga aagttgaatt tattcaaact      540
taaattcaat agcattaatt aaaggcgaaa gctattatct ctacatgtgg ttcaaactag      600
acatccaatt taattagctt attgacgttg aaatgttttc caaaactact atagtttggc      660
aatttgaaag atgcatcaga actactcaga caggtaaaag tagaacctct agctgtgtga      720
attgtatgtt agtccataaa gaacatcttg taaacttcat acttaagata tatattacaa      780
tatatacttg aatggtagat aaaaacgatt agtctgattg ctagcatact cacaactatt      840
tggaaatgag taagatattg gcattctaga gttactacta tggagacaaa agtcgaataa     900
aagagacctc acgtgaaaat gttacgagct agtaaaaaaa gcatttacac taacggtaaa     960
aaaagtatct ataaatgttt acacaaggta gtagtcatt                            999

<210> SEQ ID NO 160
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0121
```

<400> SEQUENCE: 160

```
ttggattttt ttttttgttga gtcagcagac catctaatct ctcttttcc accacagcct    60
gctttctatg aagcatttgg gcttacggtt gtggaatcaa tgacttgtgc actcccaacg   120
tttgctacct gtcatggtgg acccgcagag attatcgaaa acggagtttc tgggttccac   180
attgacccat atcatccaga ccaggttgca gctaccttgg tcagcttctt tgagacctgt   240
aacaccaatc caaatcattg ggttaaaatc tctgaaggag ggctcaagcg aatctatgaa   300
aggttggccc attctccttg acaggcttaa caatacaact tgtatcgctt caacaagatg   360
atggcttaat aaggattttt gcatgtatag gtacacatgg aagaagtact cagagagact   420
gcttaccctg gctggagtct atgcattctg gaaacatgtg tctaagctcg aaggagaga    480
aacacgacgt tacctagaga tgttttactc attgaaattt cgtgatttgg ttagtgtaac   540
ccactgttat tcttttgatg tctacatcta ctttacttac attattcttt tcttcggttt   600
gcaggccaat tcaatcccgc tggcaacaga tgagaactga tcatgacagg gtaggatttt   660
atttcctgca ctttctttag atcttttgtt tgtgttatct tgaataaaaa ttgttgggtt   720
tgtttccttt cagtggtttg attttggact tatttgtgtt aatgttgttt tggctgttct   780
cttaatatca ataacaaata aatttactgg ttggtatcta agatctaaca atagttacta   840
tttttagagg taaagacacc aaccttgtta tattggtcag agagctaaaa ccttgacttg   900
ttgggaaaac aaaactctaa tgacagaaaa tctgacatga tgccttataa ttcacagcct   960
catgttctac ataaatccta acaatagcac tttgtttct                           999
```

<210> SEQ ID NO 161
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0128

<400> SEQUENCE: 161

```
gataaactga taatggaaaa gaacaaagaa accagttttt aactatttgc atatgtaatt    60
tatttgttgc aaattatatt tagttaaaat gtttcctcta tttatatata tatatatcag   120
tcaagcacta tgtataagaa atgtcaattt ataaatttt acatgtcctt aacagaaag    180
aaaatgaatt tttacatgtc attcatagag agtcactcgt ttatttctta tatagagaat   240
aacacactca catgcatatg catgcaatat gatacatttt atgacaaaga taatcaacgg   300
aaacggtcaa gacataattt gataaacaac ttgcacgatg cacagatctg atcaaatata   360
taactcttta acatatccaa aatattcaaa aagaaaaact cgatccaaac tagcaacatc   420
acgctcacgc ggtaggctaa aaatttatta atctccaaaa gtctttctta tgaacactgc   480
aaacacaaca acttgaaaag tcatataggt ttagatgatg acgcgtattg gctatcgctt   540
accggagtgg ctcataaata caataaacaa tacgtaaaag tcaaagtcaa atatattag    600
tcaactataa ccattaatcg ggcaaaacct ttagctgtca aaacaacgtg aaaacgatat   660
ttgtatatat catcaagaat cagtagataa gagaatgatt taatcccctg actattacaa   720
ttttggtgta ataaacagtc tctattggtt tttattcttt gttttaattt ctcatgacct   780
atagagagaa ttaggtagtt tcgaaaattg gctaatcaac ttttgaaaac tactgtctac   840
tttgcttaaa ttctctacac ttagtttcgg ataagataat tgtcgactaa atagttaatc   900
ccttgacaat ctttgatatt ataaaaggtt tagttaatct cttctctata taaatattca   960
```

```
tacaccagct ttcaaaaata tataatccaa acaccaaaaa caaa           1004
```

<210> SEQ ID NO 162
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0137

<400> SEQUENCE: 162

```
gtggcacatg ctgaaacccc gagcatctct ccggaagaca cgcgtcgttc gctccaaaga   60
aaacagtcac agctgccgga gaatctccgc cgtcttcttc tgccaccgga aaaactctct  120
ccaccacttt cagtgcccac ctcgtgttat atccactgta tcctcgtagc accatatcag  180
cctaataaaa ttttatgtat caaattttaa gacatagccg aaactacact atactagaca  240
ataataatat gatttgtttc ctgaaaaatt atggtttcat gagaaacatt aatcatctat  300
aaaacaaatt agctatggca tcgaagagtt atcaatcaaa actgatgaat ctttacttaa  360
tatatacaac atatctttac cttgcggcgg agaagatcgg cgagagaagc accccagcca  420
ccgtcactaa aggattcttc agtgatggaa tcaccaaaga gaaaaacctt ccgtctcatc  480
atcttccaca caatcttctt gagaaaatct gagagataag aaaggtgtag tggttttgct  540
gaagtgatcg tgtttgattt agtaaagaaa tgctttattt attgttgggg aaacataaaa  600
taaataaagt aaaagtggat gcactaaatg ctttcaccca ctaatcaccg acctttcatg  660
gtttattgtg aaatacactc atagatagac atacaatacc ttatgtacgt aaataacatt  720
ttatttgtcg acacttatgt aagtaacgca tagattattt tctatgtgat tgccactctc  780
agactctcag tttcaaccaa taataacaat aactacaaca acattaatca taaacatatg  840
ctctggttta caattaaagc ttagattaag aaactgtaac aacgttacag aaaaaaaatg  900
ttatttacgt tttgtaagat tagtctctag aatcatcacc gttttttata tattaatgat  960
tctttcttat atataaaacc tttctcgaaa tacccatgaa a                     1001
```

<210> SEQ ID NO 163
<211> LENGTH: 1001
<212> TYPE: DNA
<213> ORGANISM: Arabidopsis thaliana
<220> FEATURE:
<221> NAME/KEY: misc_feature
<223> OTHER INFORMATION: Ceres Promoter YP0143

<400> SEQUENCE: 163

```
atacaacaga tggcagatat cgagttaaat acgtgaatca gccgttacga tattttaaaa   60
ctagaaaatt atttaaaaat attgcaaaat accatttaat ttcattgttc ataaaaaaaa  120
gaaattcaaa aacttaaaaa ctgattcaaa aatttggatt aattctcatt aacagtcttc  180
aacactacaa caacatgttt ctaatttatt ttatatttta ataattaaac aatatatacg  240
tctgcacatt gttgctccga cataatctag tataaaaata gttgcagcat atgtgaaaag  300
caagcagcat ttatcactca atacttttaa tttttatctgt tgtatgtatt aaggttttgt  360
agctttaaga aaacgcttat aatataaaat aacttctaaa agatatttca tgcgtataca  420
ataaatattt gtgaaaaaac atttcgaaaa cgtgtacaat atataaacta ttgtgttatc  480
ttttgacatt caaacaaatg ttgacaatgt aatttttatcc atgatatgat tggccaatta  540
gctgcgaggt aaaaatccgt atacgagtaa aagtaagata aaatttcgca agaagatttt  600
```

```
tagcaggaaa tctaagacaa gtgtcatgaa cgtgtcaatc aacaaacgaa aaggagaatt      660
atagaatcca gattcgacgt accacattaa taaatatcaa acatttat gttatttat        720 ttttgctctg gcagttacac tcttttcat tgctccaata aaaaatcac tcgcatgcat       780 gcatatatat acaccatagt aaactccgcc tcttcttcat tttaaaagta tcagtttaca     840
ctgacacaat ccttaactat tttcctttgt tcttcttcat ctttattaca catttttc       900 aaggtaacaa ataatctttt taagtcactt ttatactctt taaatcttag attgatatat    960
gaatgcatgt taatatttca agatttatag gtctaccaaa c                          1001

<210> SEQ ID NO 164
<211> LENGTH: 1003
<212> TYPE: DNA
<213> ORGANISM: Arabidopsis thaliana
<220> FEATURE:
<221> NAME/KEY: misc_feature
<223> OTHER INFORMATION: Ceres Promoter YP0144

<400> SEQUENCE: 164
aaacgttgca agattattga ttgtgagaaa gagtgctcaa ggtagtactg atttctgtaa     60
agctcacggt ggtgggaaac gatgttcttg gggagatggg aaatgtgaga aatttgcta     120 gaggaaagaa gcggtttatg cgctgcgcat aacactatta tgtctcggga gaacaaagat   180
ggaagcaaga gcggtttgat tggaccggga ctctttagtg gccttgtttt tggctctact   240
tctgatcatt ctcagtctgg agctagcgct gtctctgatt gtactgattc tgttgaacga   300
atacagtttg agaataggca gaagaacaag aagatgatga taccgatgca ggttctagta   360
ccttcatcaa tgaaatctcc aagtaattca catgaaggag aaacaaacat ctatgacttc   420
atggttccgg aggagagagt tcacggcggt gggctagtaa tgtctttact tggtggctcc   480
attgatcgaa actgaaagcc atttatggta aaagtgtcac attctcagca aaaacctgtg   540
taaagctgta aaatgtgtgg aatctccga atctgtttgt agccggttac gttatgctgg    600
atcaaaaact caagatttgt tggatattgt tatgctggat cggtggtgaa accacttccc   660
ggttgctaaa taaataaacg tttttgtttt ataatctttt tcactaaacg gcagtatggg   720
cctttagtgg gcttccttta agcgaccaat acaatcgtcg caccggaatc tactaccatt    780
tataggttta ttcatgtaaa acctcggaaa atttgagagc cacaacggtc aagagacaaa     840
aacaacttga agataaaggg ataaggaagg cttcctacat gatggacaac atttcttcc       900 acacaaattc tcataataaa aatcttataa tacaaatact tacgtcataa tcattcaatc    960
tagtccccat gttttaaggt cctgtttctt gtctgataca aat                         1003

<210> SEQ ID NO 165
<211> LENGTH: 1004
<212> TYPE: DNA
<213> ORGANISM: Arabidopsis thaliana
<220> FEATURE:
<221> NAME/KEY: misc_feature
<223> OTHER INFORMATION: Ceres Promoter YP0156

<400> SEQUENCE: 165
ttggtttgca ttgtgaagat ttgtattaac tatagaacat tgaattgatg gtgttaagtt     60
cttacacaag cgtgcttctc ggtttgaact gtttctttg tatgttgaat cagagcttag     120
tttataggaa ccagagtatc tacttagtca ttctctgatg ctaagtgcta aggttctacc   180
tagttgccct ctaggccctt atgttattga taacttatga agctatttga acacttgatt   240
cttaggagac ctaagttggt acagccagat agagtgtatg ttcttgttct ctatgtgaca   300
```

```
ggatcaagct gccacacata gttcaagggt atgctctgtg tgggtttgct cagattgagg      360
acaaatctat acaaggaagt agagtctttg acattttgat gttgtatgat aagaagaaga      420
aaggagagta ataaagaaag agaaaaggga aacagaaaca cgtgggagaa catcccaaag      480
aggaagcaca cgcggatctt catgcaaagc tccccgattc tcccatgtgg tccctttctc      540
cctttgtccc cctcctcttt cttcttttct cattttactc cttttttac cattatacaa       600 cgaatctttt ttatcataat ttttttggttt tggtttattt tccaataaca ctttcttggt     660
tacttcccat tctcactttt tcatataaga aactcacttt gggaaactta tgtttgagaa      720
tgacaagtct ttttagagaa agtgatgtaa caaatctaaa gtgattatat aataaccttg      780
cacaatgttt ttgattttt gtaagattcg aatattaggt ttattattcg tagggaataa       840
acttactttc aaaagcgttc ataagttaat actttcatat atgatcataa gtacggacac      900
tattgttttt tgtttgtttg tgtttattct aaaagaaagt agcttttaat tgaaatgtcc      960
tcggaggcac agtttaaagt tcgagtgtaa cagtttctaa ggca                      1004

<210> SEQ ID NO 166
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0158

<400> SEQUENCE: 166
ttattagatt aatagattgc attgcattgc ttgtgctttc aatttacaaa ttgtctccca       60
actccatcga cacatctctt tttgtgtata taagattcag acttgttata tttttttat      120 aaatatgtta ttagcatctt aagttaaatt gattttttat atctgcatta aggattacac      180
gactatattt gcgattgtgt gttggttaaa atataattta ggattgtctt taactacatt      240
taggattata tgactatatt tggttaaata taaaatctag ctgtgattat tagtattcaa      300
aaataagtag cctaaccaat taaaacaacg gctattgggg caaattagaa cattttagtg      360
tgtccaaaat ataatggtca ttaggtcata ttcctcctag cttcatcgca gcataattga      420
atgattgcct tatttagaag agcttttcca ctttcccaaa atctaggtgg gatcttttttg      480 ttttgacctt cattttcttt gtttaccatt tttagctaaa ttatttacga ttacaaaaga     540 tatcaaagt tggatcataa tacaatttat agacttactg tagaaaattc gtatgtacaa       600
gtacaacaaa ttcttcataa taaattttga aaattctatt acaaatgttg taagaaatag      660
aatttgaaat atatataaac taaggagaaa aaaaagaga acatgcattg ctctagtcag       720
agtggaccaa catcaacgag ataagataac ataaaaacca actcaccata actaaaaaca      780
tcccaagaga tccaacgatt catatcaaac acaaaaacat cgaacgatca gatttaaacc      840
atctctggta tctccaaaac acaaacactt ttttttttct tttgtctgaa tggaacaaaa      900
gcatgcgaca tctctgtgtc tttatcttct ctctcctctt cttgaaaaac tgaacctta      960 attctttctt cacatctcct ttagctttct gaagctgcta                           1000

<210> SEQ ID NO 167
<211> LENGTH: 1005
<212> TYPE: DNA
<213> ORGANISM: Arabidopsis thaliana
<220> FEATURE:
<221> NAME/KEY: misc_feature
<223> OTHER INFORMATION: Ceres Promoter YP0188
```

<400> SEQUENCE: 167

```
gattggtatg aaatttcgga gaccaacaaa aaaaacttta ttgagcttgg agtgaagcta      60
tatatatggg gcaagatcat aatatgttta tatcggcctt ttcgttaact gaaaataata     120
gttttgagaa atatatcaaa tggtaaacag acatcatctt tgaaaaatac catcaatgaa     180
gttaatattg ttattggcat atggtttacc catcttaatt ttaatgcaac caaacaaaca     240
agaaacaaaa actgtataag atacaaggtg ttttacgatt ttccgtctta aaaccgaaat     300
atttttgttc ctacgacttt aaacggactt tgcttaagtt gtgtgcatgt aagctcgtcg     360
tccctcgatt gtcatcaaca ttcaccaata tcagcctcta tcacacgagt gaaggtggtg     420
attcggctta atgaaaacag agaaatattt caatatgatt cctattaaat tttaaatctt     480
ttttctcaat ctctagattt tcattaaaag catcatgatt ttttttccact atgttcatat    540
atctctatca cagttttagg tacattgtag aaattggata agatacgtca tacgtctaac    600
atgaatttgg tctagcaagg aaggtttgag ataataagtg aaaagaaaac acaagataat    660
aaattataat ttataaatgc tttatagtat tgaaaaataa gatgattttt tttttttta     720
ataccggatt ggctgatcca cttatgatga ctcaaatgtt attaagtttc aagacaattt    780
atgatgacac aaatcacaat gagtcaatag tagccacgaa gccagaaaaa aaaaatgtac    840
tacaaaaaga taatgatagt acaaaatgat acgtcgtact gccacatgta cgacacaact    900
cgattaccaa aaagcagagc catccaacca taaaactcaa aacacacaga ttccactggc    960
gtgtgctctc ctcacttcac tcgtccttga aacttgaggt actga                   1005
```

<210> SEQ ID NO 168
<211> LENGTH: 1002
<212> TYPE: DNA
<213> ORGANISM: Arabidopsis thaliana
<220> FEATURE:
<221> NAME/KEY: misc_feature
<223> OTHER INFORMATION: Ceres Promoter YP0190

<400> SEQUENCE: 168

```
taaatagtga cattggtaag aagaaaaaaa acactattaa atagtgaaaa aatggtttat      60
aactctctta attaacatta cttattattg ctagcaccta aaatctccca caaaatattt     120
gttgtaaaac acaaatttac aaaatgattt tgttttttaaa ttagtaacac atgttcatat    180
atacgttaat aagaacatac cctatatgat tttatataaa aaaatttctt tgagacgtct    240
tattctttt tctttaataa tatgcaattg tgagagtttg gatttgaatg gtagcattag     300
aagcaaactt gaaccaaaca tatttcatga agtcaaactt gaaccaatgt gatcactaat    360
cacagtgttc gcagtgtaag gcatcagaaa atagaagaag ggacatagct atgaatcata    420
taatcttgac acatgtttta taggttttag gtgtgtatgc taacaaaaaa tgagacagct    480
ttcttctaat agacttaata tttgggctaa atgtaccaca gttgtgaatt tcttacaaaa    540
atgggccgag ctacaaaaaa ctacaggccc actctcaact cttatcaaac gacagcgttt    600
tacttttta aaagcacaca cttttttgttt ggtgtcggtg acggtgagtt tcgtccgctc    660
ttcctttaaa ttgaagcaac ggttttgatc cgatcaaatc caacggtgct gattacacaa    720
agcccgagac gaaaacgttg actattaagt taggttttaa tctcagccgt taatctacaa    780
atcaacggtt ccctgtaaaa cgaatcttcc ttccttcttc acttccgcgt cttctctctc    840
aatcacctca aaaaaatcga tttcatcaaa atattcaccc gcccgaattt gactctccga    900
tcatcgtctc cgaatctaga tcgacgagat caaaacccta gaaatctaaa tcggaatgag    960
```

```
aaattgattt tgatacgaat tagggatctg tgtgttgagg ac                  1002
```

<210> SEQ ID NO 169
<211> LENGTH: 995
<212> TYPE: DNA
<213> ORGANISM: Arabidopsis thaliana
<220> FEATURE:
<221> NAME/KEY: misc_feature
<223> OTHER INFORMATION: Ceres Promoter YP0212

<400> SEQUENCE: 169

```
agtcgattgg tacactctta atttaattag agtaagagat caacaaaaat atagaatttt   60
ctttatatcg aagtgctacg accttatata tatagaaaaa aaagcatagg tgaatctcta  120
aattgagatt gtgctgtagt aaacatatta agttttagt tttttaaga aatgaatctt   180
tttgttgatt aattcaaact agtagtcatt aagattccgg agattccaat ttagaaaagt  240
caaagattca agaacaagt ccaggtccac atgttgaatc cgattcatca tccactcatc   300
cttcatatct tcctccaccg tctccgccca aaaaatcaat aacaataaaa aatcctaaaa  360
aaacatattt gattttgaaa aaactttatc atatattata ttaattaaat agttatccga  420
tgactcatcc tatggtcagg gccttgctgt ctctgacgtc cttaattatc attatttta   480
aatttgtctc tctcagaaaa ttacgccaca atcttcctct ttcccttttc cgaaaacagc  540
taatatttgt ggacctaaac taaataacgt agcctctaga ttttatataa ttactaaatac  600
tatatgctac tacttgttat tatttactcc aatcatatat gataccaatc aagaatcact  660
acataagtag aaaactttgc aatgagtcca ttaattaaaa ttaagaataa acttaaaatt  720
ttatggtatt ttaagattcc ctttggattg taatgacaag aaatcagcaa attagtcgta  780
actcgtaaga ataaacaaga tcaatttta ctttctttac aaagattccg ttgtaatttt   840
agaaattttt ttttgtcact gtttttttat agattaattt atctgcatca atccgattaa  900
gaagtgtaca catgggcatc tatatatatc taacaggtaa aacgtgtatg tacatgcata  960
aggttttacg tgcttctata aatatatgtg gcagt                             995
```

<210> SEQ ID NO 170
<211> LENGTH: 1024
<212> TYPE: DNA
<213> ORGANISM: Arabidopsis thaliana
<220> FEATURE:
<221> NAME/KEY: misc_feature
<223> OTHER INFORMATION: Ceres Promoter YP0214

<400> SEQUENCE: 170

```
ccagtcgatt ggcgcctcgc atgcctatca tatttaaccg tcaataatgg atttggcggt    60
tttggtaggc cgggtcaacc ggattaaaag aaaacggttt ggagtccttc cttgcaattg   120
aattttcaca cattcgggtt ttgtgatttc tctgtcataa tgggcccggc acatatggtt   180
cataacccat gtgggcctat ggtataattt ttccaattaa aactattgtt aggtcgataa   240
aacaaaaaac aataaaaacg agtggaatac acataccaaa agaatgtga tgaacattag   300
taattttatt ttgatggtta atgaaaaaca aaataaatgc atcttggcat cttccgttgg   360
aaagcgcaaa tagggcagat tttcagacag atatcactat gatgggggt gagagaaaga   420
aaacgaggcg tacctaatgt aacactactt aattagtcgt tagttatagg acttttttt    480
tgtttgggcc tagttatagg atcataaggt aaaaatgaag aatgaatatt agattagtag   540
gagctaatga tggagttaag tatgcacgtg taagaactgg gaagtgaaac ctcctgtatg   600
gtgaagaaac tatacaacaa agccctttgt tggtgtatac gtattaattt ttattcttt    660
```

| | |
|---|---|
| atcacaagcg atacgtatct aagacataa taaatatata tcttactcat aataaatatc | 720 |
| ttaagatata tatacagtat acacctgtat atatataata aataggcata tagtagaaat | 780 |
| taatatgagt tgttgttgtt gcaaatatat aaatcaatca aaagatttaa aacccaccat | 840 |
| tcaatcttgg taagtaacga aaaaaaggg aagcaagaag aaccacagaa aagggggcta | 900 |
| acaactagac acgtagatct tcatctgccc gtccatctaa cctaccacac tctcatcttc | 960 |
| tttttcccgt gtcagtttgt tatataagct ctcactctcc ggtatatttc cccattgcac | 1020 |
| tgga | 1024 |

<210> SEQ ID NO 171
<211> LENGTH: 911
<212> TYPE: DNA
<213> ORGANISM: Arabidopsis thaliana
<220> FEATURE:
<221> NAME/KEY: misc_feature
<223> OTHER INFORMATION: Ceres Promoter YP0263

<400> SEQUENCE: 171

| | |
|---|---|
| atctagctgt ggattccacc aaaattctgg cagggccatg atctaaaaac tgagactgcg | 60 |
| cgtgttgttt tgcagtgatt tgtatttcat atttgcacca tcctacacag tccacttggt | 120 |
| atcgtaacca aacataagga gaacctaatt acattattgt tttaatttcg tcaaactggt | 180 |
| ttttacctttt tagttacata gttgattctt catttgtttt agtagttatg gagcacaata | 240 |
| atgtgcaaca aagaaagatc atagtggatt aatatgttga gaggtcagaa attcttggtt | 300 |
| aacaaaaaa agttacaagg actgagattt tgggtgggag aaagccatag cttttaaaac | 360 |
| atgattgaac ttaaaagtga tgttatggtt tgagggggaaa aaggttgatg tcaactaaga | 420 |
| tagttgaagt aatgtcttaa actaaagtaa accaccggtc caaccgtggt ccggaagcat | 480 |
| ctctggtatg atttatccta aaaatcaaaa tagtagaaac atactttaaa tatatacatt | 540 |
| gatcggacga aaattgtaaa ctagtatagt ttcaaaaact agttgaacag gttatgtacc | 600 |
| ttaaacattt atttcaaact aaacactaa agaacatata tgaatagaag tttatataaa | 660 |
| ttactatata tctaccataa atctcttata attatgatgt cacgatgagg aagtgttgaa | 720 |
| acgttaaaat gccaaaatat aagcatgcga cggaattttg gcagaagatt gtagagttgt | 780 |
| aatctgtcgc aatcattact cgtgctagca tttttcattt tcccttcatt tgtggataac | 840 |
| gcacgatata acattctaca caccaacaag attctataaa aacgcaaagg ttgtctccat | 900 |
| agaatatcgt c | 911 |

<210> SEQ ID NO 172
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0275

<400> SEQUENCE: 172

| | |
|---|---|
| aaacattaat atgtagtaac tatgggcgta tgctttactt tttaaaatgg gcctatgcta | 60 |
| taattgaatg acaaggatta aacaactaat aaaattgtag atgggttaag atgacttatt | 120 |
| tttttactta ccaatttata aatgggcttc gatgtactga aatatatcgc gcctattaac | 180 |
| gaggccattc aacgaatgtt ttaagggccc tatttcgaca ttttaaagaa cacctaggtc | 240 |
| atcattccag aaatggatat tataggattt agataatttc ccacgtttgg tttatttatc | 300 |

```
tattttttga cgttgaccaa cataatcgtg cccaaccgtt tcacgcaacg aatttatata   360
cgaaatatat atattttca  aattaagata ccacaatcaa acagctgtt gattaacaaa   420 gagatttttt ttttttggtt ttgagttaca ataacgttag aggataaggt ttcttgcaac   480
gattaggaaa tcgtataaaa taaaatatgt tataattaag tgttttattt tataatgagt   540
attaatataa ataaaacctg caaaggata  gggatattga ataataaaga gaaacgaaag   600
agcaatttta cttctttata attgaaatta tgtgaatgtt atgtttacaa tgaatgattc   660
atcgttctat atattgaagt aaagaatgag tttattgtgc ttgcataatg acgttaactt   720
cacatataca cttattacat aacatttatc acatgtgcgt cttttttttt ttttactttg   780
taaaatttcc tcacttttaa gacttttata acaattacta gtaaaataaa gttgcttggg   840
gctacaccct ttctccctcc aacaactcta tttatagata acattatatc aaaatcaaaa   900
catagtccct ttcttctata aaggttttt  cacaaccaaa tttccattat aaatcaaaaa   960
ataaaaactt aattagtttt tacagaagaa aagaaaaca                          999
```

<210> SEQ ID NO 173
<211> LENGTH: 981
<212> TYPE: DNA
<213> ORGANISM: Arabidopsis thaliana
<220> FEATURE:
<221> NAME/KEY: misc_feature
<223> OTHER INFORMATION: Ceres Promoter YP0285

<400> SEQUENCE: 173

```
gggattatat atgatagacg attgtatttg cgggacattg agatgtttcc gaaaatagtc    60
atcaaatatc aaaccagaat ttgatgtgaa acactaatt  aaaacatata attgacaact   120
agactatatc atttgttaag ttgagcgttg aaagaaaatg aaagagtgta gactgtagta   180
cgtatgagtt tcccaaaaga tggtgcttga atattattgg gaagagactt tggttggttc   240
ggttgaatga agatttttac ctgccatgtt gatagagaaa ggcaaataaa tgtaggggtc   300
gatgtctaac gtaaagactg gatcaaccaa gagtcctcct cctcgtcttc accaaaaaaa   360
aagagtcctc ctcgtggaaa cttatttctt ctccagccaa gatctcatct catctcttca   420
ctctatgaaa tataaaggaa tcttatggtt tttctaaaaa ctatagtacg tctatatacc   480
aaaggaaaca atataaaatc agttaatctg ataaattttg agtaaataat aaagttaact   540
ttgtacttac ctatatcaaa ctaattcaca aaataaagta ataataacaa gaatttttta   600
gtagatccac aatatacaca cacactatga gaaatcataa tagagaattt taatgatttt   660
gtctaactca tagcaacaag tcgctttggc cgagtggtta aggcgtgtgc ctgctaagta   720
catgggctct gcccgcgaga gttcgaatct ctcaggcgac gtttctttg ttttcggcca   780 taaaggaaaa agcccaatta acacgtctcg cttataagcc cataaagcaa acaatgggct   840
gtctctgtct cactcacaca cgcgttttcc tactttttga ctattttat aaccggcggg   900 tctgacttaa ttagggtttt ctttaataat cagacactct ctcactcgtt tcgtcaacat   960
tgaacacaga caaaaccgcg t                                             981
```

<210> SEQ ID NO 174
<211> LENGTH: 996
<212> TYPE: DNA
<213> ORGANISM: Arabidopsis thaliana
<220> FEATURE:
<221> NAME/KEY: misc_feature
<223> OTHER INFORMATION: Ceres Promoter YP0286

<400> SEQUENCE: 174

```
gaaaacaatc ataggttacg ctattatcat cgaaaggtat gtgatgcata ttcccattga    60
accagatttc catatatttt atttgtaaag tgataatgaa tcacaagatg attcaatatt   120
aaaaatgggt aactcacttt gacgtgtagt acgtggaaga atagttagct atcacgcata   180
catatatcta tgaataagtg tgtatgacat aagaaactaa atatttacc  taaagtccag   240 ttactcatac tgatttcatg catatatgta ttatttattt attttttaata aagaagcgat  300 tggtgttttc atagaaatca tgatagattg ataggtattt cagttccaca aatctagatc   360
tgtgtgctat acatgcatgt attaatttt  tccccttaaa tcatttcagt tgataatatt   420
gctctttgtt ccaactttag aaaaggtatg aaccaacctg acgattaaca agtaaacatt   480
aattaatctt tatatgagat aaaaccgagg atatatatga ttgtgttgct gtctattgat   540
gatgtgtcga tattatgctt gttgtaccaa tgctcgagcc gagcgtgatc gatgccttga   600
caaactatat atgtttcccg aattaattaa gttttgtatc ttaattagaa taacattttt   660
atacaatgta atttctcaag cagacaagat atgtatccta tattaattac tatatatgaa   720
ttgccgggca cctaccagga tgtttcaaat acgagagccc attagtttcc acgtaaatca   780
caatgacgcg acaaaatcta gaatcgtgtc aaaactctat caatacaata atatatattt   840
caagggcaat ttcgacttct cctcaactca atgattcaac gccatgaatc tctatataaa   900
ggctacaaca ccacaaagga tcatcagtca tcacaaccac attaactctt caccactatc   960
tctcaatctc tcgtttcatt tcttgacgcg tgaaaa                             996

<210> SEQ ID NO 175
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0337

<400> SEQUENCE: 175
taattttttt attttggaa  ctaacactta ttagtttagg tttccatcac ctatttaatt    60
cgtaattctt atacatgcat ataatagaga tacatatata caaatttatg atcattttg   120 cacaacatgt gatctcattc attagtatgc attatgcgaa aacctcgacg cgcaaaagac   180
acgtaatagc taataatgtt actcatttat aatgattgaa gcaagacgaa acaacaaca   240 tatatatcaa attgtaaact agatatttct taaaagtgaa aaaaacaaa  gaaatataaa   300 ggacaattttt gagtcagtct cttaatatta aacatatat  acataaataa gcacaaacgt   360
ggttacctgt cttcatgcaa tgtggacttt agtttatcta atcaaaatca aaataaaagg   420
tgtaatagtt ctcgtcattt ttcaattttt aaaaatcaga accaagtgat ttttgtttga   480
gtattgatcc attgtttaaa caatttaaca cagtatatac gtctcttgag atgttgacat   540
gatgataaaa tacgagatcg tctcttggtt ttcgaatttt gaactttaat agttttcttt   600
tttagggaaa cttaatagt  tgtttatcat aagattagtc acctaatggt tacgttgcag   660
taccgaacca atttttttacc cttttttcta aatgtggtcg tggcataatt tccaaaagag   720
atccaaaacc cggtttgctc aactgataag ccggtcggtt ctggtttgaa aaacaagaaa   780
taatctgaaa gtgtgaaaca gcaacgtgtc tcggtgtttc atgagccacc tgccacctca   840
ttcacgtcgg tcatttttgtc gtttcacggt tcacgctcta gacacgtgct ctgtccccac   900
catgactttc gctgccgact cgcttcgctt tgcaaactca acatgtgtg  tatatgtaag   960 tttcatccta ataagcatct cttaccacat taattaaaaa                         1000
```

<210> SEQ ID NO 176
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0356

<400> SEQUENCE: 176

| | | | | | |
|---|---|---|---|---|---|
| ttagttcatt | gaaacgtcaa | cttttttactt | gcaaccactt | tgtaggacca | ttaactgcaa | 60 |
| aataagaatt | ctctaagctt | cacaagggggt | tcgtttggtg | ctataaaaac | attgttttaa | 120 |
| gaactggttt | actggttcta | taaatctata | aatccaaata | tgaagtatgg | caataataat | 180 |
| aacatgttag | cacaaaaaat | actcattaaa | ttcctaccca | aaaaaaatct | ttatatgaaa | 240 |
| ctaaaactta | tatacacaat | aatagtgata | caaagtaggt | cttgatattc | aactattcgg | 300 |
| gattttctgg | tttcgagtaa | ttcgtataaa | aggtttaaga | tctattatgt | tcactgaaat | 360 |
| cttaactttg | ttttgtttcc | agttttaact | agtagaaatt | gaaattttta | aaaattgtta | 420 |
| cttacaataa | aatttgaatc | aatatcctta | atcaaaggat | cttaagacta | gcacaattaa | 480 |
| aacatataac | gtagaatatc | tgaaataact | cgaaaatatc | tgaactaagt | tagtagtttt | 540 |
| aaaatataat | cccggtttgg | accgggcagt | atgtacttca | atacttgtgg | gttttgacga | 600 |
| ttttggatcg | gattgggcgg | gccagccaga | ttgatctatt | acaaatttca | cctgtcaacg | 660 |
| ctaactccga | acttaatcaa | agattttgag | ctaaggaaaa | ctaatcagtg | atcacccaaa | 720 |
| gaaaacattc | gtgaataatt | gtttgctttc | catggcagca | aaacaaatag | gacccaaata | 780 |
| ggaatgtcaa | aaaaaagaaa | gacacgaaac | gaagtagtat | aacgtaacac | acaaaaataa | 840 |
| actagagata | ttaaaaacac | atgtccacac | atggatacaa | gagcatttaa | ggagcagaag | 900 |
| gcacgtagtg | gttagaaggt | atgtgatata | attaatcggc | ccaaatagat | tggtaagtag | 960 |
| tagccgtcta | tatcatccat | actcatcata | acttcaacct | | | 1000 |

<210> SEQ ID NO 177
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0374

<400> SEQUENCE: 177

| | | | | | |
|---|---|---|---|---|---|
| aagacacccg | taaatgttgt | catgtagaag | aaactagaaa | cgttaaacgc | atcaaatcaa | 60 |
| gaaattaaat | tgaaggtaat | ttttaacgcc | gcctttcaaa | tattcttcct | aggagaggct | 120 |
| acaagacgcg | tatttctttc | gaattctcca | aaccattacc | attttgatat | ataataccga | 180 |
| catgccgttg | ataaagtttg | tatgcaaatc | gttcattggg | tatgagcaaa | tgccatccat | 240 |
| tggttcttgt | aattaaatgg | tccaaaaata | gtttgttccc | actactagtt | actaatttgt | 300 |
| atcactctgc | aaaataatca | tgatataaac | gtatgtgcta | tttctaatta | aaactcaaaa | 360 |
| gtaatcaatg | tacaatgcag | agatgaccat | aaaagaacat | taaaacacta | cttccactaa | 420 |
| atctatgggg | tgccttggca | aggcaattga | ataaggagaa | tgcatcaaga | tgatatagaa | 480 |
| aatgctattc | agtttataac | attaatgttt | tggcggaaaa | ttttctatat | attagacctt | 540 |
| tctgtaaaaa | aaaaaaaatg | atgtagaaaa | tgctattatg | tttcaaaaat | ttcgcactag | 600 |
| tataatacgg | aacattgtag | tttacactgc | tcattaccat | gaaaaccaag | gcagtatata | 660 |

| | |
|---|---|
| ccaacattaa taaactaaat cgcgatttct agcacccca ttaattaatt ttactattat | 720 |
| acattctctt tgcttctcga aataataaac ttctctatat cattctacat aataaataag | 780 |
| aaagaaatcg acaagatcta aatttagatc tattcagctt tttcgcctga gaagccaaaa | 840 |
| ttgtgaatag aagaaagcag tcgtcatctt cccacgtttg gacgaaataa aacataacaa | 900 |
| taataaaata ataaatcaaa tatataaatc cctaatttgt ctttattact ccacaatttt | 960 |
| ctatgtgtat atatataccc acctctctct tgtgtatttg | 1000 |

```
<210> SEQ ID NO 178
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0377

<400> SEQUENCE: 178
```

| | |
|---|---|
| tataaaccat tcctataaca ccatatttaa acataacaat gaattgcttg gatttcaaac | 60 |
| tttattaaat ttggatttta aattttaatt tgattgaatt atacccccctt aattggataa | 120 |
| attcaaatat gtcaactttt tttttgtaag attttttat ggaaaaaaaa attgattatt | 180 |
| cactaaaaag atgacaggtt acttataatt taatatatgt aaaccctaaa aagaagaaaa | 240 |
| tagtttctgt tttcactttta ggtcttatta tctaaacttc tttaagaaaa tcgcaataaa | 300 |
| ttggtttgag ttcaactttt aaacacatta atatttgtgt gctatttaaa aaataattta | 360 |
| caaaaaaaaa aacaaattga cagaaaatat caggttttgt aataagatat ttcctgataa | 420 |
| atatttaggg aatataacat atcaaaagat tcaaattctg aaaatcaaga atggtagaca | 480 |
| tgtgaaagtt gtcatcaata tggtccactt tctttgctc tataacccaa aattgaccct | 540 |
| gacagtcaac ttgtacacgc ggccaaacct ttttataatc atgctatta tttccttcat | 600 |
| ttttattcta tttgctatct aactgatttt tcattaacat gataccagaa atgaatttag | 660 |
| atggattaat tctttttccat ccacgacatc tggaaacact tatctcctaa ttaaccttac | 720 |
| ttttttttta gtttgtgtgc tccttcataa aatctatatt gtttaaaaca aaggtcaata | 780 |
| aatataaata tggataagta taataaatct ttattggata tttctttttt taaaaaagaa | 840 |
| ataaatcttt tttggatatt ttcgtggcag catcataatg agagactacg tcgaaaccgc | 900 |
| tggcaaccac ttttgccgcg tttaatttct ttctgaggct tatataaata gatcaaaggg | 960 |
| gaaagtgaga tataatacag acaaaacaag agaaaaga | 998 |

```
<210> SEQ ID NO 179
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0380

<400> SEQUENCE: 179
```

| | |
|---|---|
| acaagtacca ttcactttt tacttttcaa tgtatacaat catcatgtga taaaaaaaaa | 60 |
| aatgtaacca atcaacacac tgagatacgg ccaaaaaatg gtaatacata aatgtttgta | 120 |
| ggttttgtaa tttaaatact ttagttaagt tatgatttta ttattttttgc ttatcactta | 180 |
| tacgaaatca tcaatctatt ggtatctctt aatcccgctt tttaatttcc accgcacacg | 240 |
| caaatcagca aatggttcca gccacgtgca tgtgaccaca tattgtggtc acagtactcg | 300 |
| tcctttttt ttcttttgta atcaataaat ttcaatccta aaacttcaca cattgagcac | 360 |

```
gtcggcaacg ttagctccta aatcataacg agcaaaaaag ttcaaattag ggtatatgat      420
caattgatca tcactacatg tctacataat taatatgtat tcaaccggtc ggtttgttga      480
tactcatagt taagtatata tgtgctaatt agaattagga tgaatcagtt cttgcaaaca      540
actacggttt catataatat gggagtgtta tgtacaaaat gaaagaggat ggatcattct      600
gagatgttat gggctcccag tcaatcatgt tttgctcgca tatgctatct tttgagtctc      660
ttcctaaact catagaataa gcacgttggt tttttccacc gtcctcctcg tgaacaaaag      720
tacaattaca ttttagcaaa ttgaaaataa ccacgtggat ggaccatatt atatgtgatc      780
atattgcttg tcgtcttcgt tttcttttaa atgtttacac cactacttcc tgacacgtgt      840
ccctattcac atcatccttg ttatatcgtt ttacttataa aggatcacga acaccaaaac      900
atcaatgtgt acgtcttttg cataagaaga aacagagagc attatcaatt attaacaatt      960
acacaagaca gcgagattgt aaaagagtaa gagagagag                             999
```

<210> SEQ ID NO 180
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0381

<400> SEQUENCE: 180

```
cacggtcaaa gtattgctaa catggtcatt acattgaaaa agaaaattaa ttgtctttac       60
tcatgtttat tctatacaaa taaaaatatt aaccaaccat cgcactaaca aaatagaaat      120
cttattctaa tcacttaatt gttgacaatt aaatcattga aaaatacact taaatgtcaa      180
atattcgttt tgcatacttt tcaatttaaa tacatttaaa gttcgacaag ttgcgtttac      240
tatcatagaa aactaaatct cctaccaaag cgaaatgaaa ctactaaagc gacaggcagg      300
ttacataacc taacaaatct ccacgtgtca attaccaaga gaaaaaaaga gaagataagc      360
ggaacacgtg gtagcacaaa aaagataatg tgatttaaat taaaaaacaa aaacaaagac      420
acgtgacgac ctgacgctgc aacatcccac cttacaacgt aataaccact gaacataaga      480
cacgtgtacg atcttgtctt tgttttctcg atgaaaacca cgtgggtgct caaagtcctt      540
gggtcagagt cttccatgat tccacgtgtc gttaatgcac caaacaaggg tactttcggt      600
attttggctt ccgcaaatta gacaaaacag ctttttgttt gattgatttt tctcttctct      660
ttttccatct aaattctctt tgggctctta atttcttttt gagtgttcgt tcgagatttg      720
tcggagattt tttcggtaaa tgttgaaatt ttgtgggatt tttttttatt tctttattaa      780 acttttttt attgaattta taaaagggaa aggtcgtcat taatcgaaga aatggaatct      840
tccaaaattt gatattttgc tgttttcttg ggatttgaat tgctctttat catcaagaat      900
ctgttaaaat ttctaatcta aaatctaagt tgagaaaaag agagatctct aatttaaccg      960
gaattaatat tctccgaccg aagttattat gttgcaggct                          1000
```

<210> SEQ ID NO 181
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0384

<400> SEQUENCE: 181

-continued

```
tttaaaaaat tggataaaac accgataaaa attcacattt gcaaattta  ttcagtcgga    60 atatatattt gaaacaagtt ttgaaatcca ttggacgatt aaaattcatt gttgagagga   120
taaatatgga tttgttcatc tgaaccatgt cgttgattag tgattgacta ccatgaaaaa   180
tatgttatga aaagtataac aactttgat  aaatcacatt tattaacaat aaatcaagac   240
aaaatatgtc aacaataata gtagtagaag atattaattc aaattcatcc gtaacaacaa   300
aaaatcatac cacaattaag tgtacagaaa aaccttttgg atatatttat tgtcgctttt   360
caatgatttt cgtgaaaagg atatatttgt gtaaaataag aaggatcttg acgggtgtaa   420
aaacatgcac aattcttaat ttagaccaat cagaagacaa cacgaacact tctttattat   480
aagctattaa acaaaatctt gcctattttg cttagaataa tatgaagagt gactcatcag   540
ggagtggaaa atatctcagg atttgctttt agctctaaca tgtcaaacta tctagatgcc   600
aacaacacaa agtgcaaatt cttttaatat gaaaacaaca ataatatttc taatagaaaa   660 ttaaaaggg  aaataaaata tttttttaaa atatacaaaa gaagaaggaa tccatcatca   720
aagttttata aaattgtaat ataatacaaa cttgtttgct tccttgtctc tccctctgtc   780
tctctcatct ctcctatctt ctccatatat acttcatctt cacacccaaa actccacaca   840
aaatatctct ccctctatct gcaaattttc caaagttgca tcctttcaat ttccactcct   900
ctctaatata attcacattt tcccactatt gctgattcat ttttttttgt gaattatttc   960
aaacccacat aaaaaaatct ttgtttaaat ttaaaacca                         999
```

<210> SEQ ID NO 182
<211> LENGTH: 998
<212> TYPE: DNA
<213> ORGANISM: Arabidopsis thaliana
<220> FEATURE:
<221> NAME/KEY: misc_feature
<223> OTHER INFORMATION: Ceres Promoter YP0385

<400> SEQUENCE: 182

```
actcaacaat aggacaagcc aaaaaaattc caattattgt gttactctat tcttctaaat    60
ttgaacacta atagactatg acatatgagt atataatgtg aagtcttaag atattttcat   120
gtgggagatg aataggccaa gttggagtct gcaaacaaga agctcttgag ccacgacata   180
agccaagttg atgaccgtaa ttaatgaaac taaatgtgtg tggttatata ttagggaccc   240
atggccatat acacaatttt tgtttctgtc gatagcatgc gtttatatat atttctaaaa   300
aaactaacat atttactgga tttgagttcg aatattgaca ctaatataaa ctacgtacca   360
aactacatat gtttatctat atttgattga tcgaagaatt ctgaactgtt ttagaaaatt   420
tcaatacact taacttcatc ttacaacggt aaaagaaatc accactagac aaacaatgcc   480
tcataatgtc tcgaaccctc aaactcaaga gtatacattt tactagatta gagaatttga   540
tatcctcaag ttgccaaaga attggaagct tttgttacca aacttagaaa cagaagaagc   600
cacaaaaaaa gacaaaggga gttaaagatt gaagtgatgc atttgtctaa gtgtgaaagg   660
tctcaagtct caactttgaa ccataataac attactcaca ctccctttt ttttcttttt   720 ttttcccaaa gtaccctttt taattccctc tataacccac tcactccatt ccctctttct   780
gtcactgatt caacacgtgg ccacactgat gggatccacc tttcctctta cccacctccc   840
ggtttatata aacccttcac aacacttcat cgctctcaaa ccaactctct cttctctctt   900
ctctcctctc ttctacaaga agaaaaaaaa cagagccttt acacatctca aaatcgaact   960
tactttaacc accaaatact gattgaacac acttgaaa                          998
```

<210> SEQ ID NO 183
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0396

<400> SEQUENCE: 183

| | | | | | |
|---|---|---|---|---|---|
| catagtaaaa | gtgaatttaa | tcatactaag | taaaataaga | taaaacatgt | tatttgaatt | 60 |
| tgaatatcgt | gggatgcgta | tttcggtatt | tgattaaagg | tctggaaacc | ggagctccta | 120 |
| taacccgaat | aaaaatgcat | aacatgttct | tccccaacga | ggcgagcggg | tcagggcact | 180 |
| agggtcattg | caggcagctc | ataaagtcat | gatcatctag | gagatcaaat | tgtatgtcgg | 240 |
| ccttctcaaa | attacctcta | agaatctcaa | acccaatcat | agaacctcta | aaaagacaaa | 300 |
| gtcgtcgctt | tagaatgggt | tcggtttttg | gaaccatatt | tcacgtcaat | ttaatgttta | 360 |
| gtataatttc | tgaacaacag | aattttggat | ttatttgcac | gtatacaaat | atctaattaa | 420 |
| taaggacgac | tcgtgactat | ccttacatta | agtttcactg | tcgaaataac | atagtacaat | 480 |
| acttgtcgtt | aatttccacg | tctcaagtct | ataccgtcat | ttacggagaa | agaacatctc | 540 |
| tgtttttcat | ccaaactact | attctcactt | tgtctatata | tttaaaatta | agtaaaaaag | 600 |
| actcaatagt | ccaataaaat | gatgaccaaa | tgagaagatg | gttttgtgcc | agattttagg | 660 |
| aaaagtgagt | caaggtttca | catctcaaat | ttgactgcat | aatcttcgcc | attaacaacg | 720 |
| gcattatata | tgtcaagcca | attttccatg | ttgcgtactt | ttctattgag | gtgaaaatat | 780 |
| gggtttgttg | attaatcaaa | gagtttgcct | aactaatata | actacgactt | tttcagtgac | 840 |
| cattccatgt | aaactctgct | tagtgtttca | tttgtcaaca | atattgtcgt | tactcattaa | 900 |
| atcaaggaaa | aatatacaat | tgtataattt | tcttatattt | taaaattaat | tttgatgtat | 960 |
| tacccctta | taaataggct | atcgctacaa | caccaataac | | | 1000 |

<210> SEQ ID NO 184
<211> LENGTH: 1514
<212> TYPE: DNA
<213> ORGANISM: Arabidopsis thaliana
<220> FEATURE:
<221> NAME/KEY: misc_feature
<223> OTHER INFORMATION: Ceres Promoter p13879

<400> SEQUENCE: 184

| | | | | | |
|---|---|---|---|---|---|
| tttcgatcct | cttctttttt | aggtttcttg | atttgatgat | cgccgccagt | agagccgtcg | 60 |
| tcggaagttt | cagagattaa | aaccatcacc | gtgtgagttg | gtagcgaatt | aacggaaagt | 120 |
| ctaagtcaag | atttttttaaa | aagaaattta | tgtgtgaaaa | gaagccgttg | tgtatattta | 180 |
| tataatttag | aaaatgtttc | atcattttaa | ttaaaaaatt | aataatttgt | agaagaaaga | 240 |
| agcatttttt | atacataaat | catttacctt | cttttactgtg | tttttcttca | cttacttcat | 300 |
| ttttactttt | ttacaaaaaa | gtgaaaagta | aattacgtaa | ttggtaacat | aaattcactt | 360 |
| taaatttgca | tatgttttgt | tttcttcgga | aactatatcg | aaaagcaaac | ggaaagaact | 420 |
| tcacaaaaaa | ccctagctaa | ctaaagacgc | atgtgttctt | cttattcttc | atatatcctc | 480 |
| tgtttcttgt | gttctgtttt | gagtcttaca | ttttcaatat | ctgactctga | ttactatatc | 540 |
| taaaagggaa | catgaagaac | ttgagaccat | gttaaactgt | acaatgcctt | caaacatggc | 600 |
| taactaaaga | tacattagat | ggctttacag | tgtgtaatgc | ttattatctt | taggttttt | 660 |
| aaatccctig | tattaagtta | tttaccaaat | tatgttcttg | tactgcttat | tggcttggtt | 720 |

```
gttgtgtgct tgtaaacaa cacctttggc tttatttcat cctttgtaaa cctactggtc    780
tttgttcagc tcctcttgga agtgagtttg tatgcctgga acgggtttta atggagtgtt    840
tatcgacaaa aaaaaaatgt agcttttgaa atcacagaga gtagttttat attcaaatta    900
catgcatgca actaagtagc aacaaagttg atatggccga gttggtctaa ggcgccagat    960
taaggttctg gtccgaaagg gcgtgggttc aaatcccact gtcaacattc tcttttctc    1020 aaattaatat ttttctgcct caatggttca ggcccaatta tactagacta ctatcgcgac   1080 taaaatagg actagccgaa ttgatccggc ccagtatcag ttgtgtatca ccacgttatt    1140
tcaaatttca aactaaggga taaagatgtc atttgacata tgagatattt ttttgctcca   1200
ctgagatatt tttctttgtc ccaagataaa atatcttttc tcgcatcgtc gtctttccat   1260
ttgcgcatta aaccaaaaag tgtcacgtga tatgtcccca accactacga atttaacta   1320 cagatttaac catggttaaa ccagaattca cgtaaaccga ctctaaacct agaaaatatc   1380
taaaccttgg ttaatatctc agcccccttta taaataacga gacttcgtct acatcgttct   1440
acacatctca ctgctcacta ctctcactgt aatcccttag atcttctttt caaatttcac   1500
cattgcactg gatg                                                    1514
```

<210> SEQ ID NO 185
<211> LENGTH: 1954
<212> TYPE: DNA
<213> ORGANISM: Arabidopsis thaliana
<220> FEATURE:
<221> NAME/KEY: misc_feature
<223> OTHER INFORMATION: Ceres Promoter p326

<400> SEQUENCE: 185

```
gtgggtaaaa gtatccttct ttgtgcattt ggtattttta agcatgtaat aagaaaaacc     60
aaaatagacg gctggtattt aataaaagga gactaatgta tgtatagtat atgatttgtg    120
tggaatataa taaagttgta aaatatagat gtgaagcgag tatctatctt ttgactttca    180
aaggtgatcg atcgtgttct ttgtgatagt tttggtcgtc ggtctacaag tcaacaacca    240
ccttgaagtt ttcgcgtctc ggtttcctct tcgcatctgg tatccaatag catacatata    300
ccagtgcgga aaatggcgaa gactagtggg cttgaaccat aaggtttggc cccaatacgg    360
attccaaaca acaagcctag cgcagtcttt tgggatgcat aagactaaac tgtcgcagtg    420
atagacgtaa gatatatcga cttgattgga atcgtctaag ctaataagtt taccttgacc    480
gtttatagtt gcgtcaacgt ccttatggag attgatgccc atcaaataaa cctgaaaatc    540
catcaccatg accaccataa actcccttgc tgccgctgct ttggcttgag caaggtgttt    600
ccttgtaaag ctccgatctt tggataaagt gttccacttt ttgcaagtag ctctgacccc    660
tctcagagat gtcaccggaa tcttagacag aacctcctct gccaaatcac ttggaagatc    720
ggacaatgtc atcattttg caggtaattt ctccttcgtt gctgctttgg cttgagcacg    780
gtgcttcttt gtaaagctcc gatctttgga taagagcgga tcggaatcct ctaggaggtg    840
ccagtccctt gacctattaa tttatagaag gttttagtgt attttgttcc aatttcttct    900
ctaacttaac aaataacaac tgcctcatag tcatgggctt caaattttat cgcttggtgt    960
atttcgttat ttgcaaggcc ttggcccatt ttgagcccaa taactaaatc tagccttttc   1020
agaccggaca tgaacttcgc atattggcgt aactgtgcag ttttacctttt ttcggatcag   1080 acaagatcag atttagacca cccaacaata gtcagtcata tttgacaacc taagctagcc   1140
gacactacta aaaagcaaac aaaagaagaa ttctatgttg tcatttttacc ggtggcaagt   1200
```

```
ggaccttct ataaaagagt aaagagacag cctgtgtgtg tataatctct aattatgttc   1260
accgacacaa tcacacaaac ccttctctaa tcacacaact tcttcatgat ttacgacatt   1320
aattatcatt aactctttaa attcactta catgctcaaa aatatctaat ttgcagcatt    1380
aatttgagta ccgataacta ttattataat cgtcgtgatt cgcaatcttc ttcattagat   1440
gctgtcaagt tgtactcgca cgcggtggtc cagtgaagca atccaacgg tttaaaacct    1500 tcttacattt ctagatctaa tctgaaccgt cagatatcta gatctcattg tctgaacaca   1560
gttagatgaa actgggaatg aatctggacg aaattacgat cttacaccaa ccccctcgac   1620
gagctcgtat atataaagct tatacgctcc tccttcacct tcgtactact actaccacca   1680
catttcttta gctcaacctt cattactaat ctccttttaa ggtatgttca ctttcttcg    1740 attcatactt tctcaagatt cctgcatttc tgtagaattt gaaccaagtg tcgattttg    1800 tttgagagaa gtgttgattt atagatctgg ttattgaatc tagattccaa ttttaattg    1860 attcgagttt gttatgtgtg tttatactac ttctcattga tcttgtttga tttctctgct   1920
ctgtattagg tttctttcgt gaatcagatc ggaa                               1954
```

<210> SEQ ID NO 186
<211> LENGTH: 2016
<212> TYPE: DNA
<213> ORGANISM: Arabidopsis thaliana
<220> FEATURE:
<221> NAME/KEY: misc_feature
<223> OTHER INFORMATION: Ceres Promoter p32449

<400> SEQUENCE: 186

```
gatcggcctt cttcaggtct tctctgtagc tctgttactt ctatcacagt tatcgggtat   60
ttgagaaaaa agagttagct aaatgaatt tctccatata atcatggttt actacaggtt    120
tacttgattc gcgttagctt tatctgcatc caaagttttt tccatgatgt tatgtcatat   180
gtgataccgt tactatgttt ataactttat acagtctggt tcactggagt ttctgtgatt   240
atgttgagta catactcatt catcctttgg taactctcaa gtttaggttg tttgaattgc   300
ctctgttgtg atacttattg tctattgcat caatcttcta atgcaccacc ctagactatt   360
tgaacaaaga gctgtttcat tcttaaacct ctgtgtctcc ttgctaaatg gtcatgcttt   420
aatgtcttca cctgtctttc tcttctatag atatgtagtc ttgctagata gttagttcta   480
cagctctctt ttgtagtctt gttagagagt tagttgagat attacctctt aaaagtatcc   540
ttgaacgctt tccggttatg accaatttgt tgtagctcct tgtaagtaga acttactggg   600
accagcgaga cagtttatgt gaatgttcat gcttaagtgt cgaacgtatc tatctctact   660
atagctctgt agtcttgtta gacagttagt tttatatctc catttttttg tagtcttgct   720
agttgagata ttacctcttc tcttcaaagt atccttgaac gctcaccggt tatgaaatct    780
ctacactata gctctgtagt cttgctagat agttagttct ttagctctct ttttgtagcc   840 tagttctttta gctctccttt tgtagccttg ctacagagta gatgggata ttacctcctt    900 gaacgctctc cggttatgac caatttgttg tagctccttg taagtagaac ttaggataga   960
gtgagtcaac tttaagaaag aacctagtat gtggcataac cagattgcag gctctgtctc   1020
ggctacagta acgtaactct atagctcttt gttttgttca gaaagaacca gtgattggat   1080
gattcgtcct tagaaactgg acctaacaac agtcattggc tttgaaatca agccacaaca   1140
atgcctatat gaaccgtcca tttcatttat ccgtttcaaa ccagcccatt acatttcgtc   1200
ccattgataa ccaaaagcgg ttcaatcaga ttatgtttta attttaccaa attctttatg   1260
```

```
aagtttaaat tatactcaca ttaaaaggat tattggataa tgtaaaaatt ctgaacaatt    1320
actgattttg gaaaattaac aaatattctt tgaaatagaa gaaaaagcct ttttccttttt   1380 gacaacaaca tataaaatca tactcccatt aaaaagattt taatgtaaaa ttctgaatat    1440
aagatatttt ttacaacaac aaccaaaaat atttattttt ttccttttttt acagcaacaa   1500 gaaggaaaaa ctttttttttt tgtcaagaaa aggggagatt atgtaaacag ataaaacagg   1560
gaaaataact aaccgaactc tcttaattaa catcttcaaa taaggaaaat tatgatccgc    1620
atatttagga agatcaatgc attaaaacaa cttgcacgtg gaaagagaga ctatacgctc    1680
cacacaagtt gcactaatgg tacctctcac aaaccaatca aaatactgaa taatgccaac    1740
gtgtacaaat tagggtttta cctcacaacc atcgaacatt ctcgaaacat tttaaacagc    1800
ctggcgccat agatctaaac tctcatcgac caattttttga ccgtccgatg gaaactctag   1860
cctcaaccca aaactctata taaagaaatc ttttccttcg ttattgctta ccaaatacaa    1920
accctagccg ccttattcgt cttcttcgtt ctctagtttt ttcctcagtc tctgttctta    1980
gatcccttgt agtttccaaa tcttccgata aggcct                              2016

<210> SEQ ID NO 187
<211> LENGTH: 667
<212> TYPE: DNA
<213> ORGANISM: Arabidopsis thaliana
<220> FEATURE:
<221> NAME/KEY: misc_feature
<223> OTHER INFORMATION: Ceres Promoter PD1367

<400> SEQUENCE: 187
acagttttct tttctcatct tacaacaagt ttccaggagg atagagacat aaacgaagct     60
cggattgtat cgttcttttt agcttttatt cacatccgaa agtcctgtag tttagattct    120
gttatcttgc ggttttgagt taatcagaaa cagagtaatc aatgtaatgt tgcaggctag    180
atctttcatc tttggaaatt tgttttttttc tcatgcaatt tctttagctt gaccatgagt    240
gactaaaaga tcaatcagta gcaatgattt gatttggcta agagacattt gtccacttgg    300
catcttgatt tggatggtta caacttgcaa gacccaattg gatacttgct atgacaactc    360
caactcaaga gtgtcgtgta actaagaacc ttgactaatt tgtaatttca atcccaagtc    420
atgttactat atgtttttttt gtttgtatta ttttctctcc tacaattaag ctctttgacg    480
tacgtaatct ccggaaccaa ctcctatatc caccatttac tccacgttgt ctccaattat    540
tggacgttga aacttgacac aacgtaaacg tatctacgtg gttgattgta tgtacatatg    600
tacaaacgta caccttctc ctctttcact tcatcacttg gcttgtgaat tcattaattc      660
ctgcgaa                                                              667

<210> SEQ ID NO 188
<211> LENGTH: 1836
<212> TYPE: DNA
<213> ORGANISM: Oryza sativa
<220> FEATURE:
<221> NAME/KEY: misc_feature
<223> OTHER INFORMATION: Ceres Promoter p530c10

<400> SEQUENCE: 188
gcctctcgac cacgagttta gcacttgtgc aacatatatg cgtgcgatga acatctactg     60
atgcgccatg cgaattttag cgttcgttca tgacgcttcc aacggcacag aggctgagca    120
gcagcatgca tgcatggctc ttgtgaaaac aaaaaaggtt actggtaaat gacatgctgc    180
```

```
tgtagctagc tagcagaatg caaggcccat gcatatgcaa tgctatgcga caagtacagt      240
accagcatgt atggtagcca gctaactaat ctatcagcag aggcagcaag ctcgtgcatg      300
gtgtgatgca cttctctcca gtaatctagt ggtaattttc acccaaagcg ttgctcatat      360
ggacagtaat tagtaatatt accaaggttc acaatcccgt tacctgacca atactactc      420 acgaatggta tctctggttt tcgttaaaac cgttggtaaa ccagcaaaaa tagacaaaat      480
ttgtcaaaat tttaaatttt agttttttt ttttaactta gccgggaaac cttgaagttt      540
gtgctgtcga gctgtcctgg aaggacggt tttggttggg attgtgaacc ctggttactg      600
cacttcattt ttgaacagat attagtgcaa cagacaaatg ccaacgcatt tttttctgtt      660
taccggcaag ctgaagcttt tacgatcccc atacagccgt tgctgcaaac ctgccaagaa      720
agagcagcag aaacaggtgt cattttgtgg tggaaagcca gtaaagtaa acagaagatg      780 gaagatagtg aggaccaggg agtgaggcag gggacacatg gcccacgcct ccctgcacat      840
tttcgtgtat aaatacaggt ggatgcatcg ctctcccagc atccatcggt tctctgctct      900
gttcatccat agagtttcct cctcttctcc tttagtgcaa ggtagagaag agcatgtgtg      960
tgtgtgtgtg tgtgtgaact gtgaagtgca gagtgcttct gtagttctgt gttatgtcca     1020
tagtgatctt gttaggattg ttgctatgga tgcatgatgt tatggttgat ctctgaatta     1080
cagtagggac ttttctgaga tctctggatt agtggggggt gctaaatttt tttctggttg     1140
catcagcttg ggtttctggt attggtgtgg gttcttgctc tgaattttgg ttcagaatgt     1200
cgatttgttt gtgtttgttc tctgaagttg agagtagcta tgatccatcc agcacagaac     1260
tgcaggtcct gcctgccggc tgcatataca ggacatgcca ttttgcaagc ctgggctta     1320 tggtttctct tttggagttc ttcttcttgc atgatctgtg ttctctaaca aaggaagcaa     1380
gatttagcaa ctttattcag agacaagaaa aggatctggc aaccttttgt ttctgtttta     1440
tcctactcgt aaagattgtt atttaagcaa aaatttccca aaagttttaa atataatttc     1500
catgatgtgc cactctcatg tccttgaacc tggcactcat tatgggctcc tcagaagtgc     1560
tgtagctaat gtcactaatc ttttgtatct ttgttcatag tcttgtattt tatgatgctt     1620
atccctttgt gctttccatg tttgatgtcc aaatgtcatg gcaatgtttt tgacttctag     1680
tagggttttt agtaccttt tgttagataa gtacatccaa attctgttta tttattcaaa     1740
aatcattctg tttattcact gaaaacattt gtccattcaa tggactcata aactgtctgt     1800 gttttttcagg cttgaggatc catctagaag atagca                              1836
```

<210> SEQ ID NO 189
<211> LENGTH: 3000
<212> TYPE: DNA
<213> ORGANISM: Oryza sativa
<220> FEATURE:
<221> NAME/KEY: misc_feature
<223> OTHER INFORMATION: Ceres Promoter pOsFIE2-2

<400> SEQUENCE: 189

```
gcttaacaca tgaactacca aaatatactg atcactttgt tctagtcata cataccttaa       60
gtcattttat tctgcagtgt ttggattgga gggagcattc tagcatccct tgggtcgttc      120
cagcaaatgt ggttctccaa agcagagtaa gcacaacaca gtattttagg ttatgtttcc      180
cctatctcgt cacggacagc tcacaagtta atgtgattta tctcactata gatacgaaga      240
acatggagta tcctacatcc aaaggaagtg cccatgaagt tgtggagcat cgctacgatt      300
tgtgaccaaa tttgggtgca tgtgggcaat cgtattacag ccaccctgtt gttgatctat      360
```

-continued

```
atcgactatt atccgacgat atttatcatt atattatgac tagttagttt gtagattttg    420
agagggcaac ataagaagca atccagctta acctgttatg ttcttgatgg tagattctag    480
ttcatgtgtt gaatctgttc tccctgctgt agaatgtatc gagttgctgc tctctactct    540
gtacttttag ataccttttt caatcatttg gagtcagctg attgttgtac tacttatacg    600
ccacctgatt agtcatgtca acaattaaac ttgagcactg gttaagttaa gagtggcctg    660
attgtagttg ataatcacat tttattcgta gacattgtat gctggatctt tatcagccac    720
cgtcagatca tcctctgtaa taaatcttca tcagacgtgt gtgccaatcg caaggaacac    780
gaaatgcatc cgaaatgtta ctctgagtta atcaatacta taattcttgg tcaaattaat    840
tatttatatc tataaagttt aaattaaatt taggaaaatg aattcatgca atcttgtgg    900 taagttgtca atttcataaa aaatccagct tactactccc tttttaggag tgtgttgtgg    960
ctgcacactt ctgccttttg atatatacgg ttctattctc ggtgtactcc tttattatta    1020
ttaaaacaat cccagttact tggtaagtgc taatcacgaa tcaaagtcaa cataacaaat    1080
catgtgcgta cagctataac tcgattacac aaacaacaaa attcatattt gaacataaat    1140
ccagttgtag catatctggt agtataaagt ttttttttg tatagaagag ttttaatttc     1200
tgtaagtttt ggaaagcatt taatcctaga aattgtagtg tagctcaact aaaaaataaa    1260
tgaacttgaa tcgaaattgg gttgtatcat aaatctttac cactcaaacg aatatttatc    1320
ctaaaccaca aatgactctt ttcatcaagg aatgttttgt tttcagcatt ttaaaaaaaa    1380
acttttctaa tatggttttc atgtttcgtt cttttgaaat ttaacatcta tttaatttgc    1440
acggctccat aaaattcaacg gatacatatt ctgaataatt actaaggagg catatatcgg    1500
ctctcttaat acaaccgctt gtttctcaaa atttattttg agttttgtct acacattctc    1560
aaggacggta caaacacact atagatgttc acaatttttt ttttctaaag ttgattgatg    1620
gacaaatgtt tgaacatata acatataag cactgaatat ttgcttatgc aggaggtatt     1680
tatatcaagt tcgatacttt actaccatag tccctaggac actaaaatgc cttcaatgat    1740
ctgatgaagc ctaagagaga atattgatca gtggagcgac ttgcaactac acatggcaca    1800
agtagactag acacggtata tattcatatt aacttgttaa aattttacta cttaacagtt    1860
cacttgtggt gcatccatat caattcttac ttacacaata tttgtaaaaa caacctaaca    1920
ctataggatg acctagacaa cctttatgtc aatcacactt agaagatgat cgtcttttta    1980
ataaataatg tgtactacac accatgctct ccatatagat caagatctac aaacccttcc    2040
acttataaac cttaccacca aaaactcatt aagttgcttc atttatctat gctattaaga    2100
aaaaaactta tttcgtttat gccatttcta gaaatggcta gtcacactat tcacaatatt    2160
atataataaa taaagttttc aaatattcat ccaccaaaaa tcatcaagtc gtgggactta    2220
tatgttaatt agagaagtcc ctttgggtgc aatcgatttt ggaaaccta aatttttct     2280 atacatagaa gagagagatg tctagttgca attgcttttg cgatgtgcca accacccttc    2340
tagctttcat ccacgtctac ttaattgcca ttcttcttct tcttttttctt cactattact   2400 acctcctatc ttagcgaatc ttcttcttct tcactattac tacctcccac cttagtgaat    2460
tcatcctcat tgttcacaat gacattgcta agttaactag gtatgctaag tacacaatta    2520
gaatataacc tagagccttt gtttccatca tacttaaaag atgacatttt tatatagata    2580
aagtgtgcta ctcacaaggc ttactatata tatgtatgat acacacaaac tccacaaccc    2640
aaaactcttt caagttgtgt ggccatctca tgctattaaa aagcccattt agcccatcca    2700
acatgagaaa ccctagggtt ttttccctat aaaagatacc taggttattg ttgcttttcc    2760
```

-continued

| | |
|---|---|
| accccgcccg ccgccgctcc ctattcctat ttaatcccat ctctcttcct catcaccgct | 2820 |
| ctcctctctc caggcaagag gtacgcactt tttgtttcgg atttgaaatc tttgcttcgt | 2880 |
| tttactatca ttggtcataa gttctttttt gaagatgttt gagaataagt ttatcattga | 2940 |
| gattatcgtc acttgtgata ggaagtacgc aacctcaagc cggacaagac gtgagcaaag | 3000 |

<210> SEQ ID NO 190
<211> LENGTH: 2023
<212> TYPE: DNA
<213> ORGANISM: Oryza sativa
<220> FEATURE:
<221> NAME/KEY: misc_feature
<223> OTHER INFORMATION: Ceres Promoter pOsMEA

<400> SEQUENCE: 190

| | |
|---|---|
| gagagcagaa catagtagcc gctgttttct gggggtgcaa tttgtgcaag atcgctatcc | 60 |
| ttatggacca tgcaagcacc aagcaatatt aagccaggtc caacagcggt cttggggaat | 120 |
| tcagaaatga gcttaaaaac ctccttgagc tggccagctc agccaaggag gtccatcatg | 180 |
| catgtgcatg ctcaatactt ggaattattg caaaatgatc ggtcattgac tggaagactt | 240 |
| tgcgccttc ctcagccaac cttatgtggc tgcatgcata gagtaccaac aggaaggtag | 300 |
| cgtttgttgg aataaggttt gcatccagca tgtccttgta gagcttcaaa gcctcagcac | 360 |
| cttggcccat gaaggccata tccagctaat tgcattccat gagaccacat tcttgctatc | 420 |
| catactgttg aagtgaagat gctccgagct tcggaaatgc ttccacacta tgcatacatg | 480 |
| tcaatgagca ctgtcatgac ataaacattg gccccaagt cctcctcagc gataatccta | 540 |
| tgcagccact ttcccaggga caaagctcca agctgtgcac acgctgaaag agagctagaa | 600 |
| atgatgattg gatttggtca cacgctaagt accagcattt gctcaaagag ggcaattgcc | 660 |
| atctccgtcc agccattcta ggcataccct ggtattattg cttttccatga ttccgattcc | 720 |
| gtggtcttct atggcatcgc attgaaggcc ttccttgcag actccatatc atttaaccta | 780 |
| cagtacaata tggtaattgc tgtcgacact ggagaattcg cagtaaatcc agacttgaga | 840 |
| ggaccatgta agcattgatc aagcagttca ttcccaaaca gactatacgg gatcagtgcc | 900 |
| agtgctcgag tttggcttca attccaaggc catcaaccca ataaacagat taactgatga | 960 |
| accaaccatg caattcgccg agcaaacata gattaagcat tgtaggcaac caaatctgga | 1020 |
| ttctccatca agtcaaagag acgccatgca gaattccaca tccccgctgt atacaccgag | 1080 |
| atcaaccggt cagaacatgc tcatactccg ccaaccctct cttcagaaca tgctcatact | 1140 |
| ccgccaaccc tctcttctct gcaagaggca tcctcccaa ttccccattg ttatatctgt | 1200 |
| tgctggtaag accgttgcca gcgtggttgt gtcagaccga acagactctg cactcgccat | 1260 |
| cctcacgaac gactccaggg cctccgaacc aggaagcccg gccggccatc agcgtgttcc | 1320 |
| acataacggt atccgcgac tgcacagtgt cgaacacctt gcgtgcgtgg tcacctctgg | 1380 |
| acagcatgaa gcgtacaggc tacagcttgg ccaatgcgga cgccacgaac gtgtcggcg | 1440 |
| cgtaacccgc gcgtgcagcg cgccgcgcgc gggctgcgga gtcggttgga gacgacacgc | 1500 |
| cgccgccatg agagcaatga gcgaggtggc ggcgaaggcg aaggagaagt agtcgaggca | 1560 |
| agcggaagag aaggcggcag cggagaaagc gatcggggcg gcgaggagg tgggtgggag | 1620 |
| ggagggacgc gtagcggagg tcggaggagg agggagctga ggtttccggg gcggggtcg | 1680 |
| agagggtagt gtacggaggc gagggacacg gcgaggatct ggtcgaggta gcgcagtgtg | 1740 |
| aaggaaagcg cgatgaggcg gagggcgccg gcgaagagcg gcgcggcgga tagcgggagg | 1800 |

| | |
|---|---|
| aggcggcgcc ggcggggtct catccgattg gaaacagatt gggaaggggg aggggggtagg | 1860 |
| aatacgtggc gtcggcagta ttaggtagag agagaaaccc tttccatcct ttgtctctta | 1920 |
| gccccgaagg agagagaaaa atcagaaaaa aaaaaccctc cgcgtgtggg ggaagcagag | 1980 |
| ctccggacgc tggcgccgct cgcgccaccg cacccgcacc gcc | 2023 |

<210> SEQ ID NO 191
<211> LENGTH: 2034
<212> TYPE: DNA
<213> ORGANISM: Oryza sativa
<220> FEATURE:
<221> NAME/KEY: misc_feature
<223> OTHER INFORMATION: Ceres Promoter pOsYp102

<400> SEQUENCE: 191

| | |
|---|---|
| gaacgaccca aacgcgtaaa tggtggtact ggtttccctg ctttgccgag taccagcagc | 60 |
| cacgaagaac gttacacaat cgagtacaaa atctataaga gcaagtttaa tagcatagcc | 120 |
| aaatactacc tctaaatcat ctatagccaa tttaatagtt catttattca ataattactt | 180 |
| ataaacatat actacaatca ttaatatatg gtcttacttc ttatacacat aatattttgg | 240 |
| agtccgtgtt acagctggct ataaatataa gggattttgg ttggatgtgg tacatcctat | 300 |
| tataatgaat ctagacatga aacctgtcca aattcatcgt gctaggatac gccacatcta | 360 |
| accaaaatct cttatcttta gggatggaga gagtaataat taaatgaagc taggtagagt | 420 |
| ttcccggtca atacgcttgc gtgtgcttat aagagcatgg ccaacagttt cccgatactc | 480 |
| ttcccaatat cagttttgag gagttttgtt ggaaaaaatc gctccaacag tagacctaaa | 540 |
| tcacccctaa aagcttggcg tttccaaacc cgcatatttc gttctccact tgtagggaag | 600 |
| agactcggcg cccaatcctt caaccgcatg cacttcgcgc gcgctgtgtg aaaattttcc | 660 |
| taccaggttc ttctttgtgc gttcgtctac ctgtgagtca atccatcacg ccagcagcct | 720 |
| catcttcccc gcagctgtct gggaaagcag ccatggctcc cccaagcttc cccagcgtcg | 780 |
| acatttttttt ctcagcggca gcgccagacc catctccaac ccaattgggc ggaccttcgt | 840 |
| cggcgctccc ccagcaccac caccgactcg aatcggccgt cgcccctatt catctccaat | 900 |
| cgtccctcga ccctaccgca tcctgcagca cagcctgtct ctcgcgtcag actggcgctg | 960 |
| cgctcccccc ggtaatgtgc aggcgacaaa ggcccatgc gatgcgacca gcagccggcg | 1020 |
| acaaccggag gtgcccagtc gctggccttc atcgaatcat cgtgcacctc ggtcggagtc | 1080 |
| gatttctgat tgttgctgct gctcaaatct ggagcttgct attgctgaga actgcttggt | 1140 |
| ggtggtactg gaaatttgtt gtttgctggc tgatgaaaac tgttgttctt tgctgctaaa | 1200 |
| aactgctgct tgctagtact gaaaagtact attgcagctg ctgaaatatc ttgctgcttg | 1260 |
| ctgctgaaaa cttcaagttg ttaacaccgt tcacactaaa aaagctgaaa tttttttttct | 1320 |
| gggctgaaaa ccccattgtt gatgattgca gaaccaatat ttttccatgt aaaatacagg | 1380 |
| agatcgtggt aataatcaag tgaaatatca ttttggggca aatactcaga tcgtacctga | 1440 |
| agccaatgga aacattgttc aatgcttaaa ctgtcagtta tgatgtcaaa gagattgatc | 1500 |
| actgaatgtc ctgaaaggag ccgtgaggag gatgcagcat tgcagcgtgc gcgagcgtga | 1560 |
| gtggaggaga ggaatgacga ttctgttggt agttgtcgat gtggcctact ttttttgttt | 1620 |
| tgaggattaa atttttgggaa tctcttggag ataaaaggta ttctcatacc ttaaatcctt | 1680 |
| tttagagatc taaaaaaaat gatttagggg attgaatttt gggtgctgt tggtgatgct | 1740 |
| ctaagttgca catcctgggg aaaaacctcc ctaatccatc agcaaaccga tcaaccaccc | 1800 |

```
acgacaagtc gacgccaccg ttttttttt  ctccctccta agtcctaacc ccacaaaaat    1860
cccgcgaact ttcgtctcac cacgcgccgc gtgcccccta caaataccaa acaacaccca    1920
ccacgtccac tcacaaacca cgcaggaaac ctcagaaaat caccgtacgc gacgcgggcc    1980
caagaaaacc ccgacagaaa ccgcgcagca gcaacaccac caccggcgtc ggag          2034
```

<210> SEQ ID NO 192
<211> LENGTH: 1877
<212> TYPE: DNA
<213> ORGANISM: Oryza sativa
<220> FEATURE:
<221> NAME/KEY: misc_feature
<223> OTHER INFORMATION: Ceres Promoter pOsYp285

<400> SEQUENCE: 192

```
ggcccgagtt aaacgatctt ccacgtgtca gcgaatccta gtcgttcgat gaatctgaat      60
ctgacttgtg gtggttggac ggccacgtgt taaaaagggg aaacgtccgc atcacccgat     120
gctgggacat ttgcaatttc gatccagctg tagattgacc agttgttact ctcttttttt     180
taacaccata caaacgtaat actccctctg tcccaaaata taagtatttt ttttaacctc     240
ggttcagtct tcgaggtgct actttgacca ataatattta taaaaataag atgttttaaa     300
taaagagagt tgcatattat gatagctcgt ttaatgataa acaaagtacc atcaaattta     360
catgattaat cttttttaatt tatttgctat taatagttaa aatttaaaaa gtttgacttc     420
acactgttct aaaaatactt atattttggg acggagggag tacacattag agcaggtaca     480
atagcagact agtagccagc tataaacata ttttaatgag ataaagatg agagagaaca     540 gcgggctaca gatctgtagc cagctgcagc acggactcca agacattgtg tgtgtatgac     600
aggtgggacc atatattaat agtacagtaa gtaactattg tatgaattgg ctattagatt     660
agctataggt gaattgtagc tagtagtggg ctatactatt gaacttactc ttatatctct     720
caatatctcc agaaaactag gacgatatat attgatatta acaaagtcat catagatatc     780
tcgctatcga catatatatt acctatcact gaaaaaataa ttaatcataa atgcaagcac     840
atatactacg ttcaacactg aatgtaggta gattggtaga cgggttccac cgcaagaaaa     900
gcattgcacc agtgaagaaa gaaacatcgg aatttgtatg tagtttgttg tttgatgaat     960
tcttttgatt aaaaaaaact aaaatcagag ttgattcagt taatggtgtt gcctacgata    1020
tacttccata tcatgatatc actgtagact atgaatcata tctttaatta aaactaaatc    1080
aagaaattaa gtatgagacc tcaactcaat gaagaatttc tagttgaaaa acattcctag    1140
tgtgcgttcg gatggaggta gggatcttct ctccgttcat ataaaaccgg atggttcatt    1200
agaacatgat taattaagca acagttaatc taaaaataaa ttaatatttt ttaagaaatt    1260
tttgtataga gatcttttga aaaaaataca ttggttagaa agcatactaa taaaaagaga    1320
aaaataagaa catagtacta tagtagaaaa tgagaacttg gagtatttga gaggatggga    1380
aataagaaga ttaagaagat gcgtaaagtg aacggttaac gcatgattga ttaattaaat    1440
attaattatt ttaaatttgg aaaataaatt agtatgattt ttaagcaaca tatatatata    1500
tatatatata tatatagaaa aacatagttt tagaaaatat aagcgtgtaa aacgatatgc    1560
aggaacgaaa cgttgagcat tcaaaatttc aaattgaaca tatgaatcaa gagagaataa    1620
aaaaagaggc cttctaggct ggcatggaca attggacatg ttttcaacta gggtttcaag    1680
cttcgagcat ccacttttgt ccttgcaaac tttatacggc aaggcccgtg aatctagccc    1740
cccacaccac cccacccgcc cgcgccgcgc ggccgcctcg cctcccctcc cttctcctcc    1800
```

```
tctccgcccc cgccgccagg ccgtccacct ccgccgtctc ctcccccatt cgcacccaag    1860
gcgctggcgc ggaaggc                                                   1877

<210> SEQ ID NO 193
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0565

<400> SEQUENCE: 193
caccaaatat agtgttattt caatactaaa atggtgttat ggttggagat gccctaaaga      60
taaacatgac gagacacgag atttattaat ttcttgatca accataactt ataacttaa     120 tattaatttc acttaataat ttccaattaa gtgaatcttt acttcaccaa aagttcctaa    180
cgaactctta ttttctagca tcaatattac catgaactag catcaatact atcatgaaaa    240
attcctactt cctatccaac tcttaataac aatgctagtc ttaacaatat tcatcaaaaa    300
cttgatatag accttctaac ttagccacga ctagtatcgg tgaataccaa aattaatgta    360
ttcatgagaa cttgagattt ctctaatgta ttcttgttac taaacaagta acaacactca    420
agaaatatca tgatcaaata ttttactcat aaactccata tttcacattt tgaaaatttt    480
aaacagcaaa tcacattgaa ttttcgtggt aaaagtattt aaaattgaaa aatagcagct    540
cctgatttca atgtataaat ttatctttat atggtttatg tctccaactt attttaaaaa    600
agagagaaag agcacccaaa aggtgaccgt ttgaaattcg aatttatttc cgtttgaaat    660
tcgaattcaa aaaagtaaa ccgaaccgag tctcgttact gactgtcaca cattgtttcc    720
ctaaaagcta attaacccat acgtggcgta atataacagg tcagtgatca atactaaata    780
acagacatac accttttaaaa ttcgtgcacg ctccaaaaca aaatctacac ttcaaaatca    840
acggtcacga tcattcctca aatttcaaaa aattatttaa cctcacttcc ttcgctttgt    900
ttttaaaacc tctctctctt tctctttctc tttcgccatt aaaactctgt ttccttttc     960 agagattctc agagaagatt cattttaccc taagaaaaaa                         1000

<210> SEQ ID NO 194
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0015

<400> SEQUENCE: 194
ttgagcctta ttgttgttat tgacttttag ccaatagaaa gagatggaaa ttcaataatt     60
atccacaaaa ttccaaatca ttggtgtaca aaaagatcta aggctgttat attttcaaaa    120
aagaaagaaa agaaatgcaa caaatatgga ttaaactgtg gtttgtaaat tgagctttgc    180
atgaaaactt tatcactatg atttcactac tccatattta ttgactaaag tggcactaat    240
gaatttctta atcatgaaat cttgtatcaa aaagtactaa aataaacatg acattggcaa    300
ttaggaaaat tctaaattag aaattagtaa aaatgaaagg tgaaagggaa agatgatgat    360
atgaattggt tggtgaccag gagaaatgta tcccgatttt gcagacact ttcagtgtcc     420 ccattcatat aattatggcc cacctcgtta agatttttca ttcaccacca taacaagatc    480
taagcttaga tttcatgtaa ttaaacatat aatatacttg ccaatactat ctaataaagt    540
```

```
atacttaagc aaaaattatt actctagtgt aaggcgatga aatataagtt tagttgaaaa    600
tttatgtcga tataacaaag tataatgaat taagaccttg gttttcgatt aacaaactaa    660
ttaaacacta gttttgccta ataaaaccgg gaatcgtatt caaaaccgaa cgacaaaaca    720
agggacaagt tgagagacaa aaccaaatca gcatctttct tccagaaatg tcatgaccac    780
atgacgtcat cttgacccct cttcattgtg atatctgtgg ataaagcgca cgtgtttaat    840
tcacgaacct tcgtagtaac gaaaaatcca caactttcat attttttaat tacccactaa    900
actaaaacaa atttggaaaa acatgaaaaa cttttctttt ttttccaggt tcgtgaacct    960
cgtaccctct atataaacct cttaaccacc ttccacata                            999
```

<210> SEQ ID NO 195
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0087

<400> SEQUENCE: 195

```
tgaattgagt aaaatgtgtt ttcaaacagt taggtggtag aaggtaaagg taataacatc     60
atgatcttac taaagaatt gttgcatact aactatcaat attctcaaca acataatata    120 atgtttttt aggtaattt ccatttaat ttttgtgat taaacaatta aacaactcga    180
atgatgatga taaaaaaaaa aaattaacaa ctcgaataag ttaaagtagc aatacacatg    240
tcgttcaatt caaccaataa agtaagactt atattttaa gaagttgact aatagcttaa    300
taagttggaa aacttgtgta gtttcttaat tcccacgtgc agtaagaaat aaaaatgaaa    360
aaaattatta tatccttccc actctgcgac ttttctttta ttttatcaaa tattaaaaag    420
attcatatca cagtttacac attgaaatca taaacgataa ttatgtattt tgtaataaaa    480
agttagttct gaagctcata cttggatag tcgctagtcg ctaatatgct ccttgtaata    540
attaaagtca ctacgacgca cgtcaaagcc gatatttagg gcttaattga tgcgtgtttt    600
tcttttcata taatagtaat ataaattagt actaataaag tatgatggat ggttgagaca    660
gaaaagaaaa aagatgactg tatggtcatc attcaaaga agaatgtatt cttcatgttc    720
ttaagaataa taaaatgtca cttgtaaatc aagttggtaa gcattttgag aactttgttc    780
gatgcaacgt atgatgattt atgtagacaa aagataaaac cgtatcttca actattgcca    840
agaaaagata aaacctaatc tagtcagtct ctcaacataa atacaaccca atagccaaac    900
tgtgtccaat tcggagagaa actaaactaa aacaaaacac aaaagcccaa cataagccca    960
ataaaaccca ttttataaac agaacattac taacactca                           999
```

<210> SEQ ID NO 196
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0093

<400> SEQUENCE: 196

```
atgatgaaca ttctacatat ataattatta tgtttaagca cttagacagc ataaattctt     60
tctaattata taaatctaac cttgttacat tgtacatcta taaattactt gaagaaataa    120
cgagttctat ttcttttaa aaattaaaaa tactatacca tatctcagtg attaagttga    180
accaaaaggt acggaggaga aacaagcatt tgattcttcc ttattttatt ttattcatct    240
```

```
ctcactaatg atggtggaga aaaaagaaa ataccataaca aacaaatata tattgtcata      300
caaaaatatt tctatatttt tagttaatta gtttatattc ctcactttc agggcttata       360 taagaaagtg agcaaacaca aatcaaaatg cagcagcaaa tactatcatc acccatctcc     420
ttagttctat tttataattc ctcttctttt tgttcatagc tttgtaatta tagtcttatt     480
tctctttaag gctcaataag aggaggtact attactacac ttctctctac ttttacttgt    540
attttagcat taaaatccta aaatccgttt taaattcaaa ataaaactta gagatgttta    600
atctcgattc ggttttcgg ctttaggaga ataattatat gaaattagta tggatatctt    660
tactagtttc cattcaaatg attctgattt caatctaata ctctcactct ttaattaaac   720
tatatgtagt gtaattcac actgttaaat ttctaccatg tcatgtatat tagagttgca   780
tagaaaattg taaacatcc atttgaattc gaatgaaaca aaatgttta aaataaaatt    840 ttggtttta aaagaaaaat ctaaaactga attatatcgt ttaaccaagt tgtaaaagtc   900
ataaaacgta gtatcttgta aatcgctctt ccacggtcca aatagacttc tagtaataaa  960
caagtaaaac taattttggt ttcttactaa ttttcacaga                        1000

<210> SEQ ID NO 197
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0108

<400> SEQUENCE: 197
ttagctgaac caggaaattg atctcttata ccagtttccg ggtttagatt ggtttgatgg      60
cgatttgatt aaaccccga aatttatgt cgtagttgtg catagtatta ttattctttg      120
cggacaatag acgtatcggg accaagttct gtagcaaaat tgtataagct taagtttgat   180
gaaatttaaa ggtaatcact aaaacccaaa tgggacaata aaccggtgaa gatttagagt   240
ttttaatttt gactcatgaa tctggagaaa gagccctcgt taaaggagt gaatcaatcc    300 atagggggaaa aagttttgtc ttttaaaaa ctaaagaacc aaaccttaat agaagcagct   360
caatgtgtga caactttcca ctggcactaa gataaagtga ctagcgatga gtgcaattat   420
tgaaatagta gatggtaaat attacataca agagtaaaaa tatctttatg tcaatgctta   480
attcagtgtt tctggttaac aagagaaact tctctaactt tcgtaattgg gtcttataaa   540
attttatgca attatgattt taccctttta ctacttttca ttagcttca cgaatctatt   600 ttgacaagag aaatcattag aggtaaacat gcttttggt caagggcctt aacagttcca   660
ccaatcaagc tcaaaagttg tacttaaccg acatcttctg tgaaaacata taattacatg   720
tacaaatcaa aactaccta tgaaataaat agaaatattg cagttcattt ctaatttaac   780
ctcttcaact tttaaaacta tttacatttc tttatgtcat ttctagtcat tttgatgcaa  840
attgtaccat ttatggatta tcttcacaaa tttttaagtt ggtgaaaact ttttggtggg 900
tagttaaaac ttgaaataga aatttacttt accaaaataa actaatgaaa agtaatcact  960
ccactcccta aataagatt tccaacgttc ccactaagc                            999

<210> SEQ ID NO 198
<211> LENGTH: 999
<212> TYPE: DNA
<213> ORGANISM: Arabidopsis thaliana
<220> FEATURE:
<221> NAME/KEY: misc_feature
```

<223> OTHER INFORMATION: Ceres Promoter YP0022

<400> SEQUENCE: 198

| | | |
|---|---|---|
| tagttccatt acaatttcca aatgatttgt tacaaagcta caagattatt cgaaatagga | 60 | |
| tttcatccat aagagagaat ggtgtggtcg acgctacaat gttgatttat tggttgtggt | 120 | |
| ttgcatcttg gggatgtcaa atcctaagtt tcaagttctt gtaaaaacgt tttcaggttt | 180 | |
| ctttaatata ttttaatatt aatgtaaaaa gaaaagatat agcttttgta caaaaaaatt | 240 | |
| tgtttaatca ctatgtagga ggatgcgatc aaattcatgg aatgatgtat tattagcttt | 300 | |
| tctatcctca ctctaaaaac aatactatag tgagttaaat aatttgatca tttcaatgta | 360 | |
| gattaaaatt ttattaaaag aagaaaaatt taaaagccta taacaaaata aaaaaggagg | 420 | |
| ctcgaggtat gatgggtgta gcagaagagc tggcaacagc tatcgactga gtgattacga | 480 | |
| actcagtact cagtgttctc agctcacaca ctctttttt gttctctttc ttttggacag | 540 | |
| cttttcatttt ctcttttctt ttttctattt tgtttcaaaa ttccatccat attaaaatag | 600 | |
| gcctgatcat gagaataaag gaaatactaa tgatgagttt ctcaataatg caataagatg | 660 | |
| caattattat gagctattta ctattgaaaa tgagcaaata aatgtcaaaa cacaatctgg | 720 | |
| ttaagttaga gcaactccat tgtataggat tcatgtagtt tctaagaaaa caaatgtat | 780 | |
| taatatttta cttttacatc caaaaaacca acttatatga gtaatagaaa cgatcctaat | 840 | |
| attaggaatt ttagagattt tctctcatct gtttcttaac ttttcaatat ttttattttt | 900 | |
| taaaattgta tgagtttcta ctaagaaact actgctggag ttggtcttag cttcccaatg | 960 | |
| cttctccacc tatatatatg catatctcct tcttaaaac | 999 | |

<210> SEQ ID NO 199
<211> LENGTH: 999
<212> TYPE: DNA
<213> ORGANISM: Arabidopsis thaliana
<220> FEATURE:
<221> NAME/KEY: misc_feature
<223> OTHER INFORMATION: Ceres Promoter YP0080

<400> SEQUENCE: 199

| | | |
|---|---|---|
| aagcggcaat ttagtaagaa gtactcaaag tatcatttac caaaagtata tggttttggg | 60 | |
| aagagttgtt agggatgtat tctttctaaa cagatgatat gacgatgttc ttgaaaacta | 120 | |
| atgttaaaga cggaatctct ggcatcttca ctcgggagat atattaaacc gttgattgta | 180 | |
| gttagccatg tacttagctt agtgcacaaa taatctgctg caagaaatct tttctatta | 240 | |
| taatatctct catttaaaca ttagaacata ttgtttaact tgttcttcta gaaataaaac | 300 | |
| tgctaatttc ttatggtaaa ctattttcct ttagattgca caatcgaact cgaaaatcta | 360 | |
| gtggagacta tgtgactatg tttatatata tgaaacctaa atcaaattat cccaataatt | 420 | |
| gggagacaca aagaaaaat tacgaaagaa aacaggaaat caaatcaaaa gataaagaga | 480 | |
| aggtaaaaaa aggcaagaag cactaatgtt taatatttat agttttctcc attaaagaaa | 540 | |
| aagcgatgat gtgtgttctc atctttgtg aaagtatata tattgctttt gcttttctca | 600 | |
| aaagcaaaag actcatccaa caagaacaaa aaaaaaaact aaagctcaat ccaaaagacg | 660 | |
| aagaatgcat tggatactac aacttctttt tcacttttct ttcaaattta caattatgat | 720 | |
| tttcacaata cagttttattc aaaaataaat aaaaaaacga ggcatgaaaa taatgattat | 780 | |
| cctcttcact tattaagcca ctcactataa gcagagcaac tccagaacat agtgagcccc | 840 | |
| caaaacatta agcatgatg atgtctaatg atgatgatct tcttcgttcc atttctctaa | 900 | |

| attttttggga tttctgcgaa gacccttctt ctctttctct tctctgaact tcaagattcg | 960 |
| tgtcggacaa atttttgttt ttatttttct gatgttaca | 999 |

<210> SEQ ID NO 200
<211> LENGTH: 3000
<212> TYPE: DNA
<213> ORGANISM: Arabidopsis thaliana
<220> FEATURE:
<221> NAME/KEY: misc_feature
<223> OTHER INFORMATION: Ceres Promoter PR0924

<400> SEQUENCE: 200

| atctataacg agttaacatg ttgccagttt gaatcaagaa gcttggatga tgaatgaatg | 60 |
| gatcggtttg tggtacaatt cttaaaattg tagtagagga gacagagaaa aaacatgata | 120 |
| agactttggt atttacaact tgacggagac aagacagtaa gccaaatctg tcacaaaaac | 180 |
| actcaaactc ttttctcagt gttttgagtt taaagagaga cttattcact tcccctttcg | 240 |
| taacacttat ttgtctccca accaaacagt ttctgtcctt tcccttgtcc tcccacgtgc | 300 |
| atctttatat ctcatgactt ttcgtttcta gatcttgaat aatgtcttag tggattaggt | 360 |
| ttgttgtcgg taaattaggt gaccgttttt ttcttatatt tggaagatcg cgggatgaag | 420 |
| cagatactga gtttcagggc atacacacct aatttgaaaa tcattgttag tccaatttca | 480 |
| ctttaatctt gtttacaaaa aaattgatct gaaaatgttg atgggataag taaaaatgta | 540 |
| agttttgcta gtagtcatga tataataata gcaaaaccag atcaattttg agcaaaagga | 600 |
| agaaacaaaa aacagatcga tcccacgagc aagactaagt gtaaagtggt tcccacaaga | 660 |
| gccatatgga tatggtcctt caacttttaa agcccattac ttcagtggtc gacccgacat | 720 |
| tacgccacga gtagtcacgc acgcacgact ccgttcacgt gacattcacg ttgatatttc | 780 |
| cccctctact ctcttctgct tggttgatct aaaaaacatg aagagaccaa cctaatttca | 840 |
| tattaatata tgatatagac ttcatactca acagtcactt tcgtaatcca aatccatatc | 900 |
| ttacgaaatt agttcttaat aaaggttgtg gattaagtta taatattgtg ttaagagtta | 960 |
| agacacagca tataaccttg taccaacagt gctttattct taaatggaaa caaaacatat | 1020 |
| gtcaatgtca agcatacagc taaaatatca ttatctaata ttaagagtaa aacaagataa | 1080 |
| ttaaaaattg aaacaacacc atatttttat agctttactt atcgtatttt tctagtcttc | 1140 |
| atggtaattg tgttgcttta ttttgtttat aaatgaattt ggttcgacca gatagtctaa | 1200 |
| tatcagtttt taaacactgg ttttaataaa atcatatgtc ggcaattcaa cctgttacgt | 1260 |
| tgtatgattg tatcctagtc aaataggga ggaggtacta gtcgtttcaa ttagtttacg | 1320 |
| taatcaatcc aaagaaacta taagctataa agatcctcaa tttgttggtt acaataaaaa | 1380 |
| caacagttgt caaaatttat gtttataaaa agtaataact atgttccttc ccatatagag | 1440 |
| caaagtacct caggataggc aaaccgtact taatagccct tattcataat ttgatccaac | 1500 |
| tcttccccac aaaattgcaa ctgatgaagt caatacttgt atagtgagtc aagctataaa | 1560 |
| tgtctagtga tagttttgtc tcttaaaagg ttaacaaaag ttatgacaag ctgaaaaatc | 1620 |
| agagtttgct aggagtatta cttacagtta tcagtttaag tatcacattt atagtattgt | 1680 |
| atacaatgat tcttaaattc cacctttttcc gtgcgaaacc aaattttcta ttggaaacat | 1740 |
| agaatgtaaa caaaaatatg ggacgttgtc cgttccaaca ttaaccaaac ttgtctatta | 1800 |
| ctaatattcg tgttggtttg atgttggatg tctaaattcg ttgaatcatg tgtctcttga | 1860 |
| cgaaatatgc atcttcttat ttcttagtat agatgcactt tatcattctt ttagtacatg | 1920 |

-continued

| | |
|---|---|
| cttaatttttt tttttttaaaa tatgttgatt gtcatattgc caaaagtatg aattaaagac | 1980 |
| gcacatctaa cacaagttag cagccgtaaa tccttccata aatttatttt gcaagttttg | 2040 |
| ctcattatat aatgagcgga atttatgata taatcgtttg taataatgtt atgttttgat | 2100 |
| caaaatttga aattaaaagt aggtgagaac ttgttataca gtgtagataa ggtggatctt | 2160 |
| gaatataaaa ataaaattta taagatgtat ttaaagcaga aaagcataaa actttagata | 2220 |
| aaataatgta aaaatgtgtt agcatcaatg ttgggatatt ggccgacccg aacttaatca | 2280 |
| atgtcggaag ccattacttc tctcccaaaa gaccttttc cttcggagaa ctaggaactt | 2340 |
| cctcactacc tttcgcttaa cgtgaaagcc ataaatttca tatattcata aaaatcagaa | 2400 |
| aatctaaaac tgtttagtat cacctgtttt tggtatagac tattggtttt gtgttacttc | 2460 |
| ctaaactata tgatttcgta cttcattgga tcttatagag atgaatattc gtaaaaagat | 2520 |
| aagttatctg gtgaaacgtt acttcagtca tgttgggtct agatttacat actactatga | 2580 |
| aacattttaa gataataatt atcctagcca actatatgtt ctatattatg ggccaagaag | 2640 |
| atatagaact aaaagttcag aatttaacga tataaattac tagtatattc taatacttga | 2700 |
| atgattactg ttttagttgt ttagaataaa tagtagcgtg ttggttaaga taccatctat | 2760 |
| ccacatctat atttgtgtgg gttacataaa atgtacataa tattatatac atatatatgt | 2820 |
| atattttga taaagccata tattactcct tgacctctgc ccccatttcc ttttactata | 2880 |
| aataggaata ctcatgatcc tctaattcag caatcaacac caacgaacac aacctttttcc | 2940 |
| aaagccaata ataaaagaac aaaagcttttt agtttcatca aagacgaagc tgccttagaa | 3000 |

<210> SEQ ID NO 201
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter YP0388

<400> SEQUENCE: 201

| | |
|---|---|
| agaagtattc acgcaccaag gttatatttg tagtgacata ttctacaatt atcacatttt | 60 |
| tctcttatgt ttcgtagtcg cagatggtca attttttcta taataatttg tccttgaaca | 120 |
| caccaaactt tagaaacgat gatatatacc gtattgtcac gctcacaatg aaacaaacgc | 180 |
| gatgaatcgt catcaccagc taaaagccta aacaccatc ttagttttca ctcagataaa | 240 |
| aagattattt gtttccaacc tttctattga attgattagc agtgatgacg taattagtga | 300 |
| tagtttatag taaaacaaat ggaagtggta ataaatttac acaacaaaat atggtaagaa | 360 |
| tctataaaat aagaggttaa gagatctcat gttatattaa atgattgaaa gaaaaacaaa | 420 |
| ctattggttg atttccatat gtaatagtaa gttgtgatga aagtgatgac gtaattagtt | 480 |
| gtatttatag taaaacaaat taaaatggta aggtaaattt ccacaacaaa acttggtaaa | 540 |
| aatcttaaaa aaaaaaaaag aggtttagag atcgcatgcg tgtcatcaaa ggttcttttt | 600 |
| cactttaggt ctgagtagtg ttagactttg attggtgcac gtaagtgttt cgtatcgcga | 660 |
| tttaggagaa gtacgttta cacgtggaca caatcaacgg tcaagatttc gtcgtccaga | 720 |
| tagaggagcg atacgtcacg ccattcaaca atctcctctt cttcattcct tcattttgat | 780 |
| tttgagtttt gatctgcccg ttcaaaagtc tcggtcatct gcccgtaaat ataaagatga | 840 |
| ttatatttat ttatatcttc tggtgaaaga agctaatata aagcttccat ggctaatctt | 900 |
| gtttaagctt ctcttcttct tctctctcct gtgtctcgtt cactagtttt ttttcggggg | 960 |

```
agagtgatgg agtgtgtttg ttgaatagtt ttgacgatca                    1000
```

<210> SEQ ID NO 202
<211> LENGTH: 283
<212> TYPE: DNA
<213> ORGANISM: Arabidopsis thaliana
<220> FEATURE:
<221> NAME/KEY: misc_feature
<223> OTHER INFORMATION: Ceres Promoter PD0901

<400> SEQUENCE: 202

```
caaagtattt gacaagccat atggttttgg atcaaaaagt cggtccaaaa ttaatgtttt    60
atgtgcaaga accgacccat tgtacacacg tgttaacatc ttcaagactt tcatctctat   120
ttttcttttg gtcattaaga tacccattga tccgaatctg ttacattccc acctactttt   180
ttaattttta ctatccactc caaattaaac acaccgatg attttaataa ttggaagctt    240
tttaaaatat ttctccacgt gcctctttgt gtttgtctat ata                     283
```

<210> SEQ ID NO 203
<211> LENGTH: 1000
<212> TYPE: DNA
<213> ORGANISM: Arabidopsis thaliana
<220> FEATURE:
<221> NAME/KEY: misc_feature
<223> OTHER INFORMATION: Ceres Promoter PT0623

<400> SEQUENCE: 203

```
aaagttattg acattttgaa aggaccgtaa atattaccaa aaaactgacg gagttaggat    60
cggccacgta gaagggaca aagagagaac agtcacggac tcggccagac taagtatggg   120
cctgtctgaa tccaaactca gctaagttcc aaaagcataa agagagatgt gtaatgaaat   180
gaacgtattc tagaaacgaa agcaatgtta tgctttgttt ttgagccaca tgttttgtgg   240
agatggagag aatctttttt acgtttttaa cctaacccac ttggcacttg gccaaaaaag   300
tgagaagaaa ctgtggcgaa tgagtaggcc acgccatgga ctttgttcct tgtccttcaa   360
aagttaaatt tatgttatgc gtggggacaa tctaagcaac gtggttcctt taaatatcgc   420
agcttcctct tttacacttt tggagcctac gtgttttgtt ttggaccggc caaatacacg   480
agtcagtcag tttagaaata atttggatgt ccaaaaatct tggagatcca aataaaataa   540
ttagcatgtt ttagttcata agaatatgaa atgtagataa actgtctata ttaattttc    600
catagaattg gctttttatc gaggtgatgt acttaatgac tttgttgatt actactcgta   660
taacaataaa gaatatgata ctatgtgaga cttataatga atttggtgtg tgttaattaa   720
tccagttgaa acagtttaat aacaaatcag aataaaaatt gtagtaagaa aatttgaacg   780
ctgatccttc aacctagata gtgaacctt caaatactat atgattcacg tgtaatgttt    840
ttgaccgttg gttatttttg tgtgaactat attaacttat caatatcgaa aggctaaata   900
agtaaataac taaagaaag ttcaggaaac aactcgacct aatgacctat catttctgat    960
cacccgtcct ataaatacat acgtaagatc attcgttact                        1000
```

<210> SEQ ID NO 204
<211> LENGTH: 33
<212> TYPE: PRT
<213> ORGANISM: Artificial Sequence
<220> FEATURE:
<223> OTHER INFORMATION: Truncated version of Ceres CLONE ID no.
      100021733
<220> FEATURE:
<221> NAME/KEY: misc_feature
<223> OTHER INFORMATION: Ceres CLONE ID no. 100021733_T

```
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 204

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 205
<211> LENGTH: 33
<212> TYPE: PRT
<213> ORGANISM: Artificial Sequence
<220> FEATURE:
<223> OTHER INFORMATION: Truncated version of Ceres CLONE ID no. 1036726
<220> FEATURE:
<221> NAME/KEY: misc_feature
<223> OTHER INFORMATION: Ceres CLONE ID no. 1036726_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 205

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 206
<211> LENGTH: 33
<212> TYPE: PRT
<213> ORGANISM: Artificial Sequence
<220> FEATURE:
<223> OTHER INFORMATION: Truncated version of Ceres CLONE ID no. 1482731
<220> FEATURE:
<221> NAME/KEY: misc_feature
<223> OTHER INFORMATION: Ceres CLONE ID no. 1482731_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 206

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys
```

```
<210> SEQ ID NO 207
<211> LENGTH: 80
<212> TYPE: PRT
<213> ORGANISM: Artificial Sequence
<220> FEATURE:
<223> OTHER INFORMATION: Truncated version of Ceres CLONE ID no. 1554560
<220> FEATURE:
<221> NAME/KEY: misc_feature
<223> OTHER INFORMATION: Ceres CLONE ID no. 1554560_T
<220> FEATURE:
<221> NAME/KEY: misc_feature
<222> LOCATION: (17)..(78)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 207

Met Ala Leu Ala Glu Ala Asp Asp Gly Ala Val Val Phe Gly Glu Glu
1               5                   10                  15

Gln Glu Ala Leu Val Leu Lys Ser Trp Ala Val Met Lys Lys Asp Ala
            20                  25                  30

Ala Asn Leu Gly Leu Arg Phe Phe Leu Lys Val Phe Glu Ile Ala Pro
        35                  40                  45

Ser Ala Lys Gln Met Phe Ser Phe Leu Arg Asp Ser Asp Val Pro Leu
    50                  55                  60

Glu Lys Asn Pro Lys Leu Lys Thr His Ala Met Ser Val Phe Val Met
65                  70                  75                  80

<210> SEQ ID NO 208
<211> LENGTH: 77
<212> TYPE: PRT
<213> ORGANISM: Artificial Sequence
<220> FEATURE:
<223> OTHER INFORMATION: Truncated version of Ceres CLONE ID no. 1802327
<220> FEATURE:
<221> NAME/KEY: misc_feature
<223> OTHER INFORMATION: Ceres CLONE ID no. 1802327_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 208

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Asn His Ala Met Ser Val Phe Val Met
65                  70                  75

<210> SEQ ID NO 209
<211> LENGTH: 77
<212> TYPE: PRT
```

```
<213> ORGANISM: Artificial Sequence
<220> FEATURE:
<223> OTHER INFORMATION: Truncated version of Ceres CLONE ID no. 1876458
<220> FEATURE:
<221> NAME/KEY: misc_feature
<223> OTHER INFORMATION: Ceres CLONE ID no. 1876458_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 209

Met Ala Leu Ala Glu Gly Asn Val Ile Phe Gly Glu Glu Gln Glu Ala
1               5                   10                  15

Leu Val Leu Lys Ser Trp Ala Leu Met Lys Lys Asp Ser Ala Asp Leu
            20                  25                  30

Gly Leu Arg Phe Phe Leu Lys Ile Phe Glu Ile Ala Pro Ser Ala Lys
        35                  40                  45

Gln Met Phe Ser Phe Leu Arg Asp Ser Asp Val Pro Leu Glu Lys Asn
    50                  55                  60

Pro Lys Leu Lys Thr His Ala Met Ser Val Phe Val Met
65                  70                  75

<210> SEQ ID NO 210
<211> LENGTH: 79
<212> TYPE: PRT
<213> ORGANISM: Artificial Sequence
<220> FEATURE:
<223> OTHER INFORMATION: Truncated version of Ceres CLONE ID no. 1879148
<220> FEATURE:
<221> NAME/KEY: misc_feature
<223> OTHER INFORMATION: Ceres CLONE ID no. 1879148_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 210

Met Ala Leu Ala Asp Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
            20                  25                  30

Asp Leu Gly Leu Arg Phe Phe Leu Lys Ile Phe Glu Ile Ala Pro Ser
        35                  40                  45

Ala Lys Gln Met Phe Ser Phe Leu Arg Asp Ser Asp Val Pro Leu Glu
    50                  55                  60

Lys Asn Pro Lys Leu Lys Thr His Ala Met Ser Val Phe Val Met
65                  70                  75

<210> SEQ ID NO 211
<211> LENGTH: 33
<212> TYPE: PRT
<213> ORGANISM: Artificial Sequence
<220> FEATURE:
<223> OTHER INFORMATION: Truncated version of Ceres CLONE ID no. 1884696
<220> FEATURE:
<221> NAME/KEY: misc_feature
```

```
<223> OTHER INFORMATION: Ceres CLONE ID no. 1884696_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 211

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 212
<211> LENGTH: 76
<212> TYPE: PRT
<213> ORGANISM: Artificial Sequence
<220> FEATURE:
<223> OTHER INFORMATION: Truncated version of Ceres CLONE ID no. 1916866
<220> FEATURE:
<221> NAME/KEY: misc_feature
<223> OTHER INFORMATION: Ceres CLONE ID no. 1916866_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 212

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 213
<211> LENGTH: 33
<212> TYPE: PRT
<213> ORGANISM: Artificial Sequence
<220> FEATURE:
<223> OTHER INFORMATION: Truncated version of Ceres CLONE ID no. 1950105
<220> FEATURE:
<221> NAME/KEY: misc_feature
<223> OTHER INFORMATION: Ceres CLONE ID no. 1950105_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 213
```

```
Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
                20                  25                  30

Lys
```

<210> SEQ ID NO 214
<211> LENGTH: 79
<212> TYPE: PRT
<213> ORGANISM: Artificial Sequence
<220> FEATURE:
<223> OTHER INFORMATION: Truncated version of Ceres CLONE ID no. 1990746
<220> FEATURE:
<221> NAME/KEY: misc_feature
<223> OTHER INFORMATION: Ceres CLONE ID no. 1990746_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 214

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
        50                  55                  60

Lys Asn Pro Lys Leu Lys Thr His Ala Met Ser Val Phe Val Met
65                  70                  75
```

<210> SEQ ID NO 215
<211> LENGTH: 79
<212> TYPE: PRT
<213> ORGANISM: Artificial Sequence
<220> FEATURE:
<223> OTHER INFORMATION: Truncated version of Ceres CLONE ID no. 2033803
<220> FEATURE:
<221> NAME/KEY: misc_feature
<223> OTHER INFORMATION: Ceres CLONE ID no. 2033803_T
<220> FEATURE:
<221> NAME/KEY: misc_feature
<222> LOCATION: (16)..(77)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 215

```
Met Ala Leu Ala Glu Gly Asn Gly Ala Ala Ile Phe Gly Glu Glu Gln
1               5                   10                  15

Glu Ala Leu Val Leu Lys Ser Trp Ala Leu Met Lys Lys Asp Ser Ala
                20                  25                  30

Asp Leu Gly Leu Arg Phe Phe Leu Lys Ile Phe Glu Ile Ala Pro Ser
            35                  40                  45

Ala Lys Gln Met Phe Ser Phe Leu Arg Asp Ser Asp Val Pro Leu Glu
        50                  55                  60
```

```
Lys Asn Pro Lys Leu Lys Thr His Ala Met Ser Val Phe Val Met
 65                  70                  75
```

```
<210> SEQ ID NO 216
<211> LENGTH: 33
<212> TYPE: PRT
<213> ORGANISM: Artificial Sequence
<220> FEATURE:
<223> OTHER INFORMATION: Truncated version of Ceres CLONE ID no. 2034916
<220> FEATURE:
<221> NAME/KEY: misc_feature
<223> OTHER INFORMATION: Ceres CLONE ID no. 2034916_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 216

Met Gln Ile Phe Val Lys Thr Leu Thr Gly Lys Thr Ile Thr Leu Glu
 1               5                  10                  15

Val Glu Ser Ser Asp Thr Ile Asp Asn Val Lys Ala Lys Ile Gln Asp
                20                  25                  30

Lys
```

```
<210> SEQ ID NO 217
<211> LENGTH: 33
<212> TYPE: PRT
<213> ORGANISM: Artificial Sequence
<220> FEATURE:
<223> OTHER INFORMATION: Truncated version of Ceres CLONE ID no. 513071
<220> FEATURE:
<221> NAME/KEY: misc_feature
<223> OTHER INFORMATION: Ceres CLONE ID no. 513071_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
<221> NAME/KEY: misc_feature
<223> OTHER INFORMATION: Functional homolog of Ceres Clone ID no. 2403
      given in SEQ ID NO: 40

<400> SEQUENCE: 217

Met Gln Ile Phe Val Lys Thr Leu Thr Gly Lys Thr Ile Thr Leu Glu
 1               5                  10                  15

Val Glu Ser Ser Asp Thr Val Asp Asn Val Lys Ala Lys Ile Gln Asp
                20                  25                  30

Lys
```

```
<210> SEQ ID NO 218
<211> LENGTH: 33
<212> TYPE: PRT
<213> ORGANISM: Artificial Sequence
<220> FEATURE:
<223> OTHER INFORMATION: Truncated version of Ceres CLONE ID no. 522921
<220> FEATURE:
<223> OTHER INFORMATION: Ceres CLONE ID no. 522921_T
<220> FEATURE:
<221> NAME/KEY: misc_feature
<222> LOCATION: (1)..(33)
<223> OTHER INFORMATION: Pfam Name: ubiquitin
      Pfam Description: Ubiquitin family
<220> FEATURE:
```

```
<221> NAME/KEY: misc_feature
<223> OTHER INFORMATION: Functional homolog of Ceres Clone ID no. 2403
      given in SEQ ID NO: 40

<400> SEQUENCE: 218

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ala Lys Ile Gln Asp
            20                  25                  30

Lys

<210> SEQ ID NO 219
<211> LENGTH: 76
<212> TYPE: PRT
<213> ORGANISM: Artificial Sequence
<220> FEATURE:
<223> OTHER INFORMATION: Truncated version of Ceres CLONE ID no. 546001
<220> FEATURE:
<221> NAME/KEY: misc_feature
<223> OTHER INFORMATION: Ceres CLONE ID no. 546001_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 219

Met Thr Thr Thr Leu Glu Arg Gly Phe Ser Glu Glu Gln Glu Ala Leu
1               5                   10                  15

Val Val Lys Ser Trp Asn Val Met Lys Lys Asn Ser Gly Glu Leu Gly
            20                  25                  30

Leu Lys Phe Phe Leu Lys Ile Phe Glu Ile Ala Pro Ser Ala Gln Lys
        35                  40                  45

Leu Phe Ser Phe Leu Arg Asp Ser Thr Val Pro Leu Glu Gln Asn Pro
    50                  55                  60

Lys Leu Lys Pro His Ala Val Ser Val Phe Val Met
65                  70                  75

<210> SEQ ID NO 220
<211> LENGTH: 76
<212> TYPE: PRT
<213> ORGANISM: Artificial Sequence
<220> FEATURE:
<223> OTHER INFORMATION: Truncated version of Ceres CLONE ID no. 651581
<220> FEATURE:
<221> NAME/KEY: misc_feature
<223> OTHER INFORMATION: Ceres CLONE ID no. 651581_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 220

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
            20                  25                  30
```

-continued

```
Leu Lys Leu Phe Ile Lys Ile Phe Glu Ile Ala Pro Thr Ala Lys Lys
         35                  40                  45

Leu Phe Ser Phe Leu Arg Asp Ser Pro Ile Pro Ala Glu Gln Asn Pro
 50                  55                  60

Lys Leu Lys Pro His Ala Met Ser Val Phe Val Met
 65                  70                  75

<210> SEQ ID NO 221
<211> LENGTH: 77
<212> TYPE: PRT
<213> ORGANISM: Artificial Sequence
<220> FEATURE:
<223> OTHER INFORMATION: Truncated version of Ceres CLONE ID no. 839727
<220> FEATURE:
<221> NAME/KEY: misc_feature
<223> OTHER INFORMATION: Ceres CLONE ID no. 839727_T
<220> FEATURE:
<221> NAME/KEY: misc_feature
<222> LOCATION: (14)..(75)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 221

Met Ser Ala Ala Glu Gly Ala Val Val Phe Ser Glu Glu Lys Glu Ala
 1               5                  10                  15

Leu Val Leu Lys Ser Trp Ala Ile Met Lys Lys Asp Ser Ala Asn Leu
                 20                  25                  30

Gly Leu Arg Phe Phe Leu Lys Ile Phe Glu Ile Ala Pro Ser Ala Arg
         35                  40                  45

Gln Met Phe Pro Phe Leu Arg Asp Ser Asp Val Pro Leu Glu Thr Asn
 50                  55                  60

Pro Lys Leu Lys Thr His Ala Val Ser Val Phe Val Met
 65                  70                  75

<210> SEQ ID NO 222
<211> LENGTH: 76
<212> TYPE: PRT
<213> ORGANISM: Artificial Sequence
<220> FEATURE:
<223> OTHER INFORMATION: Truncated version of Public GI ID no. 11095158
<220> FEATURE:
<221> NAME/KEY: misc_feature
<223> OTHER INFORMATION: Public GI ID no. 11095158_T
<220> FEATURE:
<221> NAME/KEY: misc_feature
<222> LOCATION: (13)..(76)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 222

Met Gly Thr Leu Asp Thr Lys Gly Phe Thr Glu Glu Gln Glu Ala Leu
 1               5                  10                  15

Val Val Lys Ser Trp Asn Ala Met Lys Lys Asn Ser Ala Glu Leu Gly
                 20                  25                  30

Leu Lys Leu Phe Leu Lys Ile Phe Glu Ile Ala Pro Ser Ala Gln Lys
         35                  40                  45

Leu Phe Ser Phe Leu Lys Asp Ser Lys Val Pro Leu Glu Gln Asn Thr
 50                  55                  60
```

-continued

Lys Leu Lys Pro His Ala Met Ser Val Phe Leu Met
 65                  70                  75

<210> SEQ ID NO 223
<211> LENGTH: 71
<212> TYPE: PRT
<213> ORGANISM: Artificial Sequence
<220> FEATURE:
<223> OTHER INFORMATION: Truncated version of Public GI ID no. 12963875
<220> FEATURE:
<221> NAME/KEY: misc_feature
<223> OTHER INFORMATION: Public GI ID no. 12963875_T
<220> FEATURE:
<221> NAME/KEY: misc_feature
<222> LOCATION: (8)..(69)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 223

Met Ser Ser Phe Ser Glu Glu Gln Glu Ala Leu Val Val Lys Ser Trp
 1               5                  10                  15

Gly Ser Met Lys Lys Asp Ala Gly Glu Trp Gly Leu Lys Phe Phe Leu
             20                  25                  30

Lys Ile Phe Glu Ile Ala Pro Ser Ala Lys Lys Met Phe Ser Phe Leu
         35                  40                  45

Lys Asp Ser Asn Val Pro Leu Asp Gln Asn Pro Lys Leu Lys Ile His
     50                  55                  60

Ala Lys Ser Val Leu Val Met
 65                  70

<210> SEQ ID NO 224
<211> LENGTH: 84
<212> TYPE: PRT
<213> ORGANISM: Artificial Sequence
<220> FEATURE:
<223> OTHER INFORMATION: Truncated version of Public GI ID no. 14701800
<220> FEATURE:
<221> NAME/KEY: misc_feature
<223> OTHER INFORMATION: Public GI ID no. 14701800_T
<220> FEATURE:
<221> NAME/KEY: misc_feature
<222> LOCATION: (21)..(82)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 224

Met Ala Leu Val Glu Gly Asn Asn Gly Val Ser Gly Gly Ala Val Ser
 1               5                  10                  15

Phe Ser Glu Glu Gln Glu Ala Leu Val Leu Lys Ser Trp Ala Ile Met
             20                  25                  30

Lys Lys Asp Ser Ala Asn Ile Gly Leu Arg Phe Phe Leu Lys Ile Phe
         35                  40                  45

Glu Val Ala Pro Ser Ala Ser Gln Met Phe Ser Phe Leu Arg Asn Ser
     50                  55                  60

Asp Val Pro Leu Glu Lys Asn Pro Lys Leu Lys Thr His Ala Met Ser
 65                  70                  75                  80

Val Phe Val Met

<210> SEQ ID NO 225
<211> LENGTH: 76
<212> TYPE: PRT
<213> ORGANISM: Artificial Sequence
<220> FEATURE:
<223> OTHER INFORMATION: Truncated version of Public GI ID no. 15226675
<220> FEATURE:
<221> NAME/KEY: misc_feature
<223> OTHER INFORMATION: Public GI ID no. 15226675_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 225

Met Glu Ser Glu Gly Lys Ile Val Phe Thr Glu Glu Gln Ala Leu
1               5                   10                  15

Val Val Lys Ser Trp Ser Val Met Lys Lys Asn Ser Ala Glu Leu Gly
                20                  25                  30

Leu Lys Leu Phe Ile Lys Ile Phe Glu Ile Ala Pro Thr Thr Lys Lys
                35                  40                  45

Met Phe Ser Phe Leu Arg Asp Ser Pro Ile Pro Ala Glu Gln Asn Pro
    50                  55                  60

Lys Leu Lys Pro His Ala Met Ser Val Phe Val Met
65                  70                  75

<210> SEQ ID NO 226
<211> LENGTH: 76
<212> TYPE: PRT
<213> ORGANISM: Artificial Sequence
<220> FEATURE:
<223> OTHER INFORMATION: Truncated version of Public GI ID no. 15824736
<220> FEATURE:
<221> NAME/KEY: misc_feature
<223> OTHER INFORMATION: Public GI ID no. 15824736_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 226

Met Ala Thr Tyr Glu Gly Lys Val Phe Thr Glu Glu Gln Ala Leu
1               5                   10                  15

Val Val Lys Ser Trp Thr Val Met Lys Lys Thr Ala Glu Leu Gly
                20                  25                  30

Leu Lys Phe Phe Leu Lys Ile Phe Glu Ile Ala Pro Ser Ala Lys Lys
                35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75

<210> SEQ ID NO 227
<211> LENGTH: 76
<212> TYPE: PRT

<213> ORGANISM: Artificial Sequence
<220> FEATURE:
<223> OTHER INFORMATION: Truncated version of Public GI ID no. 30909306
<220> FEATURE:
<221> NAME/KEY: misc_feature
<223> OTHER INFORMATION: Public GI ID no. 30909306_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 227

Met Glu Ser Glu Gly Lys Ile Val Phe Thr Glu Glu Gln Glu Ala Leu
1               5                   10                  15

Val Val Lys Ser Trp Ser Val Met Lys Lys Asn Ser Ala Asp Leu Gly
                20                  25                  30

Leu Lys Leu Phe Ile Lys Ile Phe Glu Ile Ala Pro Thr Ala Lys Lys
            35                  40                  45

Leu Phe Ser Phe Leu Arg Asp Ser Pro Ile Pro Ala Glu Gln Asn Pro
        50                  55                  60

Lys Leu Lys Pro His Ala Met Ser Val Phe Val Met
65                  70                  75

<210> SEQ ID NO 228
<211> LENGTH: 73
<212> TYPE: PRT
<213> ORGANISM: Artificial Sequence
<220> FEATURE:
<223> OTHER INFORMATION: Truncated version of Public GI ID no. 37903656
<220> FEATURE:
<221> NAME/KEY: misc_feature
<223> OTHER INFORMATION: Public GI ID no. 37903656_T
<220> FEATURE:
<221> NAME/KEY: misc_feature
<222> LOCATION: (10)..(71)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 228

Met Glu Gly Lys Val Phe Thr Glu Glu Gln Glu Thr Leu Val Val Lys
1               5                   10                  15

Ser Trp Gly Val Met Lys Lys Asn Ala Ala Glu Leu Gly Leu Lys Phe
                20                  25                  30

Phe Leu Lys Ile Phe Glu Ile Ala Pro Ser Ala Gln Lys Leu Phe Ser
            35                  40                  45

Phe Leu Arg Asp Ser Asp Ile Pro Leu Glu Lys Asn Pro Lys Leu Lys
        50                  55                  60

Pro His Ala Met Ser Val Phe Val Met
65                  70

<210> SEQ ID NO 229
<211> LENGTH: 76
<212> TYPE: PRT
<213> ORGANISM: Artificial Sequence
<220> FEATURE:
<223> OTHER INFORMATION: Truncated version of Public GI ID no. 62548111
<220> FEATURE:
<221> NAME/KEY: misc_feature -continued

```
<223> OTHER INFORMATION: Public GI ID no. 62548111_T
<220> FEATURE:
<221> NAME/KEY: misc_feature
<222> LOCATION: (13)..(74)
<223> OTHER INFORMATION: Pfam Name: Globin
      Pfam Description: Globin
<220> FEATURE:
<221> NAME/KEY: misc_feature
<223> OTHER INFORMATION: Functional homolog of Ceres Clone ID no. 30469
      given in SEQ ID NO: 7

<400> SEQUENCE: 229

Met Ala Thr Tyr Glu Gly Lys Val Phe Thr Glu Glu Gln Glu Ala Leu
1               5                   10                  15

Val Val Lys Ser Trp Thr Val Met Lys Lys Asn Ala Ala Glu Leu Gly
            20                  25                  30

Leu Lys Phe Phe Leu Lys Ile Phe Glu Ile Ala Pro Ser Ala Lys Lys
        35                  40                  45

Leu Phe Ser Phe Leu Arg Asp Ser Asn Val Pro Leu Glu Gln Asn Thr
    50                  55                  60

Lys Leu Lys Pro His Ala Met Ser Val Phe Val Met
65                  70                  75
```

NUCLEOTIDE SEQUENCES AND POLYPEPTIDES ENCODED THEREBY USEFUL FOR MODIFYING PLANT CHARACTERISTICS IN RESPONSE TO COLD

This application is a divisional of application Ser. No. 11/779,266 filed on Jul. 17, 2007 (pending), which application is a Continuation-In-Part of application Ser. No. 11/778,060 filed on Jul. 15, 2007 (abandoned), which is a Continuation-In-Part of application Ser. No. 11/248,547 filed on Oct. 12, 2005 (now U.S. Pat. No. 7,244,879), and application Ser. No. 11/779,266 is also a Continuation-In-Part of application Ser. No. 11/248,547 filed on Oct. 12, 2005 (now U.S. Pat. No. 7,244,879), the entire contents of which are hereby incorporated by reference and for which priority is claimed under 35 U.S.C. § 120.

FIELD OF THE INVENTION

The present invention relates to isolated polynucleotides, polypeptides encoded thereby, and the use of those products for making transgenic plants with improved tolerances to environmental stresses such as low or chilling temperatures.

BACKGROUND OF THE INVENTION

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a process for increasing the growth potential in plants under low temperature, chilling or cold conditions, characterized by expression of recombinant DNA molecules stably integrated into the plant genome.

SUMMARY OF THE INVENTION

The present invention, therefore, relates to isolated polynucleotides, polypeptides encoded thereby and the use of those products for making transgenic plants with improved cold tolerance.

The present invention also relates to processes for increasing the growth potential in plants due to cold acclimation, recombinant nucleic acid molecules and polypeptides used for these processes and their uses, as well as to plants with an increased growth potential due to improved cold acclimation. Unless otherwise defined, all scientific and technical terms used herein have the same meaning as commonly understood by one of ordinary skilled in the art to which this invention belongs.

BRIEF DESCRIPTION OF THE FIGURES

FIG. 1 is an alignment of ME01451. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE (Edgar (2004) Nuc. Acids Res. 32(5):1792-1797).

FIG. 2 is an alignment of ME02779.
FIG. 3 is an alignment of truncated mutant of ME02779.
FIG. 4 is an alignment of ME03944.
FIG. 5 is an alignment of ME05304.

FIG. 6 is an alignment of truncated mutant of ME05304.
FIG. 7 is an alignment of ME03186.

DETAILED DESCRIPTION OF THE INVENTION

1. Definitions

The following terms are utilized throughout this application:

Amino acid: As used herein, "amino acid" refers to one of the twenty biological occurring amino acids and to synthetic amino acids, including D/L optical isomers.

Cell type-preferential promoter or Tissue-preferential promoter: As used herein, these phrases refer to a promoter that drives expression preferentially in a target cell type or tissue, respectively, but may also lead to some transcription in other cell types or tissues as well.

Cold: Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress can not be generalized. However, cold tolerant plants are characterized by their ability to retain their normal appearance or recover quickly from low temperature conditions. Such cold tolerant plants produce higher biomass and yield than plants that are not cold tolerant. Differences in physical appearance, recovery and yield can be quantified and statistically analyzed using well known measurement and analysis methods.

Plant seeds vary considerably in their ability to germinate under cold conditions. Seeds of many plant species will not germinate at temperatures less than 10° C. Once seeds have imbibed water they become very susceptible to disease, water and chemical damage. Seeds that are tolerant to cold stress during germination can survive for relatively long periods under which the temperature is too low to germinate. Since plant species vary in their capacity to tolerate cold during germination, the precise environmental conditions that cause cold stress during germination can not be generalized. However, plants that tolerate cold during germination are characterized by their ability to remain viable or recover quickly from low temperature conditions. Such cold tolerant plants germinate, become established, grow more quickly and ultimately produce more biomass and yield than plants that are not cold tolerant. Differences in germination rate, appearance, recovery and yield can be quantified and statistically analyzed using well known measurement and analysis methods.

Constitutive Promoter: Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region, the 1' or 2' promoter derived from T-DNA of *Agrobacterium tumefaciens* and other transcription initiation regions from various plant genes, such as the maize ubiquitin-1 promoter, known to those of skill.

Control Plant: "Control plant" refers to a plant that does not contain the exogenous nucleic acid present in the transgenic plant of interest, but otherwise has the same of similar genetic background as such a transgenic plant. A suitable control plant can be a non-transgenic segregant from a transformation experiment, or a transgenic plant that contains an exogenous nucleic acid other than the exogenous nucleic acid of interest.

Domain: "Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Down-regulation: "Down-regulation" refers to regulation that decreases production of expression products (mRNA, polypeptide, or both) relative to basal or native states.

Endogenous: The term "endogenous," within the context of the current invention refers to any polynucleotide, polypeptide or protein sequence which is a natural part of a cell or organism regenerated from said cell.

Exogenous: "Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Expression: As used herein, "expression" refers to the process of converting genetic information of a polynucleotide into RNA through transcription, which is catalyzed by an enzyme, RNA polymerase, and into protein, through translation of mRNA on ribosomes.

Functionally Comparable Proteins: This phrase describes those proteins that have at least one characteristic in common. Such characteristics include sequence similarity, biochemical activity, transcriptional pattern similarity and phenotypic activity. Typically, the functionally comparable proteins share some sequence similarity or at least one biochemical. Within this definition, homologs, orthologs and analogs are considered to be functionally comparable. In addition, functionally comparable proteins generally share at least one biochemical and/or phenotypic activity.

Functionally comparable proteins will give rise to the same characteristic to a similar, but not necessarily the same, degree. Typically, comparable proteins give the same characteristics where the quantitative measurement due to one of the comparables is at least 20% of the other; more typically, between 30 to 40%; even more typically, between 50-60%; even more typically between 70 to 80%; even more typically between 90 to 100% of the other.

Heterologous polypeptide: "Heterologous polypeptide" as used herein refers to a polypeptide that is not a naturally occurring polypeptide in a plant cell, e.g., a transgenic *Panicum* plant transformed with and expressing the coding sequence for a nitrogen transporter from a *Zea* plant.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other. On the other hand, these same elements remain operatively linked but become heterologous if other filler sequence is placed between them. Thus, the promoter and coding sequences of a corn gene expressing an amino acid transporter are not heterologous to each other, but the promoter and coding sequence of a corn gene operatively linked in a novel manner are heterologous.

Inducible Promoter: An "inducible promoter" in the context of the current invention refers to a promoter which is regulated under certain conditions, such as light, chemical concentration, protein concentration, conditions in an organism, cell, or organelle, etc. A typical example of an inducible promoter which can be utilized with the polynucleotides of the present invention is rd29a, the promoter from an *Arabidopsis* gene and which is induced by cold or dehydration (Baker et al. (1994) *Plant Mol. Biol.* 24:701). Examples of environmental conditions that may affect transcription by inducible promoters include anaerobic conditions, elevated temperature and/or the presence of light.

Isolated nucleic acid: "Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

Masterpool: The "master pools" discussed in these experiments are a pool of seeds from five independent transformation events of the same exogenous nucleotide sequence.

Modulation: As used herein, "Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

Misexpression: The term "misexpression" refers to an increase or a decrease in the transcription of a coding region into a complementary RNA sequence as compared to the wild-type. This term also encompasses expression of a gene or coding region for a different time period as compared to the wild-type and/or from a non-natural location within the plant genome.

Nucleic acid and polynucleotide: "Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

Operably linked: As used herein, "operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

Percentage of sequence identity: "Percentage of sequence identity," as used herein, is determined by comparing two optimally aligned sequences over a comparison window defined by the length of the longest sequence, where the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman (1981) *Add. APL. Math.* 2:482, by the homology alignment algorithm of Needleman and Wunsch (1970) *J. Mol. Biol.* 48:443), by the search for similarity method of Pearson and Lipman (1988) *Proc. Natl. Acad. Sci.* (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Query nucleic acid and amino acid sequences were searched against subject nucleic acid or amino acid sequences residing in public or proprietary databases. Such searches were done using the Washington University Basic Local Alignment Search Tool Version 1.83 (WU-Blast2) program. The WU-Blast2 program is available on the internet from Washington University. A WU-Blast2 service for *Arabidopsis* can also be found on the internet. Typically the following parameters of WU-Blast2 were used: Filter options were set to "default," Output format was set to "gapped alignments," the Comparison Matrix was set to "BLOSUM62," Cutoff Score (S value) was set to "default," the Expect (E threshold) was set to "default," the Number of best alignments to show was set to "100," and the "Sort output" option was set to sort the output by "pvalue."

Plant Promoter: A "plant promoter" is a promoter capable of initiating transcription in plant cells and can drive or facilitate transcription of a nucleotide sequence or fragment thereof of the instant invention. Such promoters need not be of plant origin. For example, promoters derived from plant viruses, such as the CaMV35S promoter or from *Agrobacterium tumefaciens*, such as the T-DNA promoters, can be plant promoters. A typical example of a plant promoter of plant origin is the maize ubiquitin-1 (ubi-1) promoter known to those of skill.

Polypeptide: "Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

Progeny: As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

Regulatory region: As used herein, "regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

Specific Promoter: In the context of the current invention, "specific promoters" refers to promoters that have a high preference for being active in a specific tissue or cell and/or at a specific time during development of an organism. By "high preference" is meant at least a 3-fold, preferably 5-fold, more preferably at least 10-fold still more preferably at least a 20-fold, 50-fold or 100-fold increase in transcription in the desired tissue over the transcription in any other tissue. Typical examples of temporal and/or tissue specific promoters of plant origin that can be used with the polynucleotides of the present invention, are: SH-EP from *Vigna mungo* and EP-C1 from *Phaseolus vulgaris* (Yamauchi et al. (1996) *Plant Mol Biol.* 30:321-9.); RCc2 and RCc3, promoters that direct root-specific gene transcription in rice (Xu et al. (1995) *Plant Mol. Biol.* 27:237) and TobRB27, a root-specific promoter from tobacco (Yamamoto et al. (1991) *Plant Cell* 3:371).

Stringency: "Stringency" as used herein is a function of probe length, probe composition (G+C content), salt concentration, organic solvent concentration and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m-5°$ C. to $T_m-10°$ C. Medium or moderate stringency conditions are those providing $T_m-20°$ C. to $T_m-29°$ C. Low stringency conditions are those providing a condition of $T_m-40°$ C. to $T_m-48°$ C. The relationship of hybridization conditions to $T_m$ (in ° C.) is expressed in the mathematical equation $$T_m = 81.5 - 16.6(\log_{10}[Na^+]) + 0.41(\% \text{ G+C}) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log\{[Na^+]/(1+0.7[Na^+])\} + 0.41(\% \text{ G+C}) - 500/L \, 0.63(\% \text{ formamide}) \quad (2)$$

where L is the length of the probe in the hybrid (P. Tijessen, "Hybridization with Nucleic Acid Probes" In Laboratory Techniques in Biochemistry and Molecular Biology, P. C. vand der Vliet, ed., c. 1993 by Elsevier, Amsterdam.) The $T_m$ of equation (2) is affected by the nature of the hybrid; for DNA-RNA hybrids $T_m$ is 10-15° C. higher than calculated, for RNA-RNA hybrids $T_m$ is 20-25° C. higher. Because the $T_m$ decreases about 1° C. for each 1% decrease in homology when a long probe is used (Bonner et al., (1973) *J. Mol. Biol.* 81:123), stringency conditions can be adjusted to favor detection of identical genes or related family members.

Equation (2) is derived assuming equilibrium. Therefore, hybridizations according to the present invention are most preferably performed under conditions of probe excess and for sufficient time to achieve equilibrium. The time required to reach equilibrium can be shortened by using a hybridization buffer that includes a hybridization accelerator such as dextran sulfate or another high volume polymer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5-8° C. below $T_m$, medium or moderate stringency is 26-29° C. below $T_m$ and low stringency is 45-48° C. below $T_m$.

Superpool: As used in the context of the current invention, a "superpool" refers to a mixture of seed from 100 different "master pools." The master pools are of 5 different events with the same exogenous nucleotide sequence transformed into them. Thus, while the superpool contains an equal amount of seed from 500 different events, it only represents 100 transgenic plants with a distinct exogenous nucleotide sequence transformed into them.

$T_0$: As used in the current application, the term "$T_0$" refers to the whole plant, explant or callus tissue inoculated with the transformation medium.

$T_1$: As used in the current application, the term $T_1$ refers to either the progeny of the $T_0$ plant, in the case of whole-plant transformation, or the regenerated seedling in the case of explant or callous tissue transformation.

$T_2$: As used in the current application, the term $T_2$ refers to the progeny of the $T_1$ plant. $T_2$ progeny are the result of self-fertilization or cross pollination of a $T_1$ plant.

$T_3$: As used in the current application, the term $T_3$ refers to second generation progeny of the plant that is the direct result of a transformation experiment. $T_3$ progeny are the result of self-fertilization or cross pollination of a $T_2$ plant.

Up-regulation: "Up-regulation" refers to regulation that increases the level of an expression product (mRNA, polypeptide, or both) relative to basal or native states.

Vector: "Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

2. Important Characteristics of the Polynucleotides of the Invention

The genes and polynucleotides of the present invention are of interest because when they are misexpressed (i.e. when expressed at a non-natural location or in an increased or decreased amount) they produce plants with improved low temperature, chilling or cold tolerance as discussed below and as evidenced by the results of various experiments. These traits can be used to exploit or maximize plant products. For example, the genes and polynucleotides of the present invention are used to increase the expression of genes that render the plant more tolerant to low temperature, chilling or cold conditions. As a consequence, such transgenic plants do better and grow faster under low temperature, chilling or cold conditions, leading to reduced costs for the farmer and, better yield under low temperatures.

3. The Polynucleotides and Polypeptides of the Invention

The polynucleotides of the invention and the proteins expressed thereby are set forth in the Sequence Listing. Such Sequence Listing consists of functionally comparable proteins.

Functionally comparable proteins are those proteins that have at least one characteristic in common. Such characteristics can include sequence similarity, biochemical activity and phenotypic activity. Typically, the functionally comparable proteins share some sequence similarity. Within this definition homologs, orthologs and analogs are considered to be functionally comparable.

Also, these comparables generally share at least one biochemical and/or phenotypic activity. For example, biochemical activity comparables are proteins that act on the same reactant to give the same product.

Another class of comparables is phenotypic comparables that both give the same physical characteristic, such as increased low temperature, chilling or cold tolerance. Proteins can be considered phenotypic comparables even if the proteins give rise to the same physical characteristic, but to a different degree.

4. Use of the Polynucleotides and Polypeptides to Make Transgenic Plants

To use the sequences of the present invention or a combination of them or parts and/or mutants and/or fusions and/or variants of them, recombinant DNA constructs are prepared which comprise the polynucleotide sequences of the invention inserted into a vector and which are suitable for transformation of plant cells. The construct can be made using standard recombinant DNA techniques (see Sambrook et al., Molecular Cloning: A Laboratory Manual, Second Edition, Cold Spring Harbor Laboratory Press, 1989, New York) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs and vectors of the sort described by (a) BAC: Shizuya et al. (1992) *Proc. Natl. Acad. Sci. USA* 89: 8794-8797; Hamilton et al. (1996) *Proc. Natl. Acad. Sci. USA* 93: 9975-9979;

(b) YAC: Burke et al. (1987) *Science* 236:806-812;

(c) PAC: Sternberg N. et al. (1990) *Proc Natl Acad Sci USA*. January; 87:103-7;

(d) Bacteria-Yeast Shuttle Vectors: Bradshaw et al. (1995) *Nucl Acids Res* 23: 4850-4856;

(e) Lambda Phage Vectors: Replacement Vector, e.g., Frischauf et al. (1983) *J. Mol Biol* 170: 827-842; or Insertion vector, e.g., Huynh et al., In: Glover N M (ed) DNA Cloning: A practical Approach, Vol. 1 Oxford: IRL Press (1985); T-DNA gene fusion vectors: Walden et al. (1990) *Mol Cell Biol* 1: 175-194; and (g) Plasmid vectors: Sambrook et al., infra.

Typically, the construct comprises a vector containing a sequence of the present invention with any desired transcriptional and/or translational regulatory sequences such as promoters, UTRs, and 3' end termination sequences. Vectors can also include origins of replication, scaffold attachment regions (SARs), markers, homologous sequences, introns, etc. The vector may also comprise a marker gene that confers a selectable phenotype on plant cells. The marker typically encodes biocide resistance, particularly antibiotic resistance, such as resistance to kanamycin, bleomycin, or hygromycin, or herbicide resistance, such as resistance to glyphosate, chlorosulfuron or phosphinotricin.

A plant promoter is used that directs transcription of the gene in all tissues of a regenerated plant and may be a constitutive promoter, such as the Cauliflower Mosaic Virus 35S. Alternatively, the plant promoter directs transcription of a sequence of the invention in a specific tissue (tissue-specific promoters) or is otherwise under more precise environmental or developmental control (inducible promoters). Typically, preferred promoters to use in the present invention are cold inducible promoters. Many cold-inducible genes, including the cis-elements which confer cold induction, have been identified (Shinozaki et al. (2003) *Curr. Opin. Plant Biol.* 6:410). Examples of such cold-inducible genes include RD29A (Yamaguchi-Shinozaki and Shinozaki (1994) *Plant Cell* 6:251) and CBF/DREB1 (Stockinger et al. (1997) *PNAS* 94:1035. Another preferred embodiment of the present invention is to use seedling specific promoters, endosperm specific promoters and leaf specific promoters. Various plant promoters, including constitutive, tissue-specific and inducible, are known to those skilled in the art and can be utilized in the present invention.

Alternatively, misexpression can be accomplished using a two component system, whereby the first component consists of a transgenic plant comprising a transcriptional activator operatively linked to a promoter and the second component consists of a transgenic plant that comprises sequence of the invention operatively linked to the target-binding sequence/region of the transcriptional activator. The two transgenic plants are crossed and the sequence of the invention is expressed in their progeny. In another alternative, the misexpression can be accomplished by having the sequences of the two component system transformed in one transgenic plant line.

Transformation

Nucleotide sequences of the invention are introduced into the genome or the cell of the appropriate host plant by a variety of techniques. These techniques for transforming a wide variety of higher plant species are well known and described in the technical and scientific literature. See, e.g. Weising et al. (1988) *Ann. Rev. Genet.* 22:421; and Christou (1995) *Euphytica, v.* 85, n. 1-3:13-27.

Processes for the transformation of monocotyledonous and dicotyledonous plants are known to the person skilled in the art. A variety of techniques is available for the introduction of DNA into a plant host cell. These techniques include transformation of plant cells by injection, microinjection, electroporation of DNA, PEG, use of biolistics, fusion of cells or protoplasts, and via T-DNA using *Agrobacterium tumefaciens* or *Agrobacterium rhizogenes* or other bacterial hosts, as well as further possibilities.

In addition, a number of non-stable transformation methods that are well known to those skilled in the art may be desirable for the present invention. Such methods include, but are not limited to, transient expression and viral transfection.

Seeds are obtained from the transformed plants and used for testing stability and inheritance. Generally, two or more generations are cultivated to ensure that the phenotypic feature is stably maintained and transmitted.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The nucleic acids of the invention can be used to confer the trait of increased tolerance to low temperature, chilling or cold conditions without reduction in fertility on essentially any plant, including chilling sensitive crop plants such as corn, soybean, rice and cotton.

The nucleotide sequences according to the invention encode appropriate proteins from any organism, in particular from plants, fungi, bacteria or animals.

The process according to the invention can be applied to any plant, preferably higher plants, pertaining to the classes of Angiospermae and Gymnospermae. Plants of the subclasses of the Dicotylodenae and the Monocotyledonae are particularly suitable. Dicotyledonous plants belong to the orders of the Magniolales, Illiciales, Laurales, Piperales Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Monocotyledonous plants belong to the orders of the Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales. Plants belonging to the class of the Gymnospermae are Pinales, Ginkgoales, Cycadales and Gnetales.

The process is preferably used with plants that are important or interesting for agriculture, horticulture, biomass for bioconversion and/or forestry. Examples are tobacco, oilseed rape, sugar beet, potatoes, tomatoes, cucumbers, peppers, beans, peas, citrus fruits, avocados, peaches, apples, pears, berries, plumbs, melons, eggplants, cotton, soybean, sunflowers, roses, poinsettia, petunia, guayule, cabbages, spinach, alfalfa, artichokes, corn, wheat, rice, rye, barley, grasses such as switch grass or turf grass, millet, hemp, bananas, poplars, eucalyptus trees and conifers.

Homologs Encompassed by the Invention

It is well known in the art that one or more amino acids in a native sequence can be substituted with other amino acid(s), the charge and polarity of which are similar to that of the native amino acid, i.e. a conservative amino acid substitution, resulting in a silent change. Conservative substitutes for an amino acid within the native polypeptide sequence can be selected from other members of the class to which the amino acid belongs. Amino acids can be divided into the following four groups: (1) acidic (negatively charged) amino acids, such as aspartic acid and glutamic acid; (2) basic (positively charged) amino acids, such as arginine, histidine, and lysine; (3) neutral polar amino acids, such as serine, threonine, tyrosine, asparagine, and glutamine; and (4) neutral nonpolar (hydrophobic) amino acids such as glycine, alanine, leucine, isoleucine, valine, proline, phenylalanine, tryptophan, cysteine, and methionine.

In a further aspect of the present invention, nucleic acid molecules of the present invention can comprise sequences that differ from those encoding a protein or fragment thereof selected from the group consisting of SEQ ID NOs: 2-5, 7, 9-18, 20-32, 34-38, 40 and 42-46 due to the fact that the different nucleic acid sequence encodes a protein having one or more conservative amino acid changes.

Polypeptides

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 20, as described in more detail herein. In some embodiments, cold tolerance-modulating polypeptides have greater than 80% identity to SEQ ID NOs: 2, 7, 9, 20, 34, 40, and 42, as described in more detail herein.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the cold tolerance-modulating activity of a truncated polypeptide. In some embodiments, a truncated polypeptide is a dominant negative polypeptide. SEQ ID NOs 7 and 40 set forth the amino sequences of cold tolerance-modulating polypeptides that are truncated at the 3' end relative to the naturally occurring polypeptides SEQ ID NOs 9 and 34, respectively. Expression in a plant of such a truncated polypeptide confers a difference in the level of cold tolerance in a tissue of the plant as compared to the corresponding level in tissue of a control plant that does not comprise the truncation.

A. Functional Homologs Identified by Reciprocal BLAST

In some embodiments, one or more functional homologs of a reference cold tolerance-modulating polypeptide defined by one or more of the pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at the Wellcome Trust Sanger Institute and HMMI janelia farm research campus. A description of the information included at the Pfam database is described in Sonnhammer et al., *Nucl. Acids Res.*, 26:320-322 (1998); Sonnhammer et al., Proteins, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Figure 7:
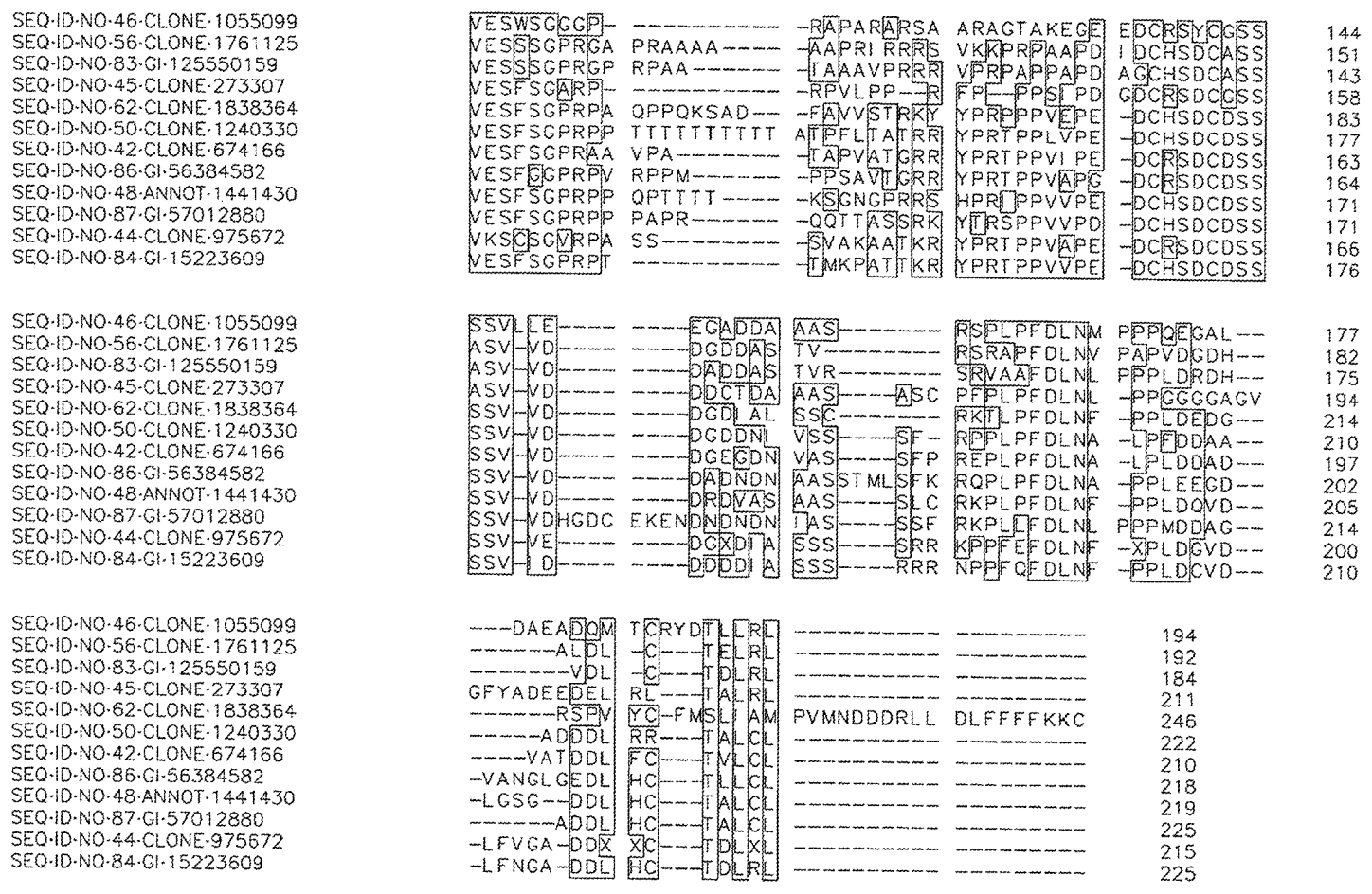

Amino acid sequences of functional homologs of the polypeptide set forth in SEQ ID NOs 2, 7, 9, 20, 34, 40 and 42 are provided in FIGS. 1-7, respectively. In some cases, a functional homolog of SEQ ID NOs 2, 7, 9, 20, 34, 40 and 42 has an amino acid sequence with at least 80% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in the Sequence Listing.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in any one of FIGS. 1-7. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

B. Functional Homologs Identified by HMMER

In some embodiments, useful cold tolerance-modulating polypeptides include those that fit a Hidden Markov Model based on the polypeptides set forth in any one of FIGS. 1-7. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, - -consistency REPS of 2; -ir, - -iterative-refinement REPS of 100; -pre, - -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as the HMMER page on the HHMI janelia farm research campus website; the Eddy Lab Home page on the HHMI janelia farm research campus website; and HMMER 2.3.2 download available on the Fish & Richardson website. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in one of Table 7. In some embodiments, a cold tolerance-modulating polypeptide discussed below fits the indicated HMM with an HMM bit score greater than 20, and has a domain indicative of an cold tolerance-modulating polypeptide. In some embodiments, a cold tolerance-modulating polypeptide discussed below fits the indicated HMM with an HMM bit score greater than 20, and has 80% or greater sequence identity (e.g., 75%, 80%, 85%, 90%, 95%, or 100% sequence identity) to an amino acid sequence shown in any one of FIGS. 1-7.

Polypeptides are shown in Table 7 that have HMM bit scores greater than 20 when fitted to an HMM generated from the amino acid sequences set forth in FIGS. 1-7, respectively.

In another aspect, biologically functional equivalents of the proteins or fragments thereof of the present invention can have about 10 or fewer conservative amino acid changes, more preferably about 7 or fewer conservative amino acid changes and most preferably about 5 or fewer conservative amino acid changes. In a preferred embodiment, the protein has between about 5 and about 500 conservative changes, more preferably between about 10 and about 300 conservative changes, even more preferably between about 25 and about 150 conservative changes, and most preferably between about 5 and about 25 conservative changes or between 1 and about 5 conservative changes.

Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a cold tolerance-modulating polypeptide, and the other strand of the stem portion of the double stranded RNA comprises a sequence that is similar or identical to the sequence that is complementary to the 3' or 5' untranslated region, respectively, of the mRNA encoding the cold tolerance-modulating polypeptide. In other embodiments, one strand of the stem portion of a double stranded RNA comprises a sequence that is similar or identical to the sequence of an intron in the pre-mRNA encoding a cold tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a cold tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

In some embodiments, nucleic acid based inhibition of gene expression does not require transcription of the nucleic acid.

Identification of Useful Nucleotide Sequences

The nucleotide sequences of the invention were identified by use of a variety of screens under low temperature, chilling or cold conditions recognized by those skilled in the art to be predictive of nucleotide sequences that provide plants with improved tolerance to low temperature, chilling or cold conditions. One or more of the following screens were, therefore, utilized to identify the nucleotide (and amino acid) sequences of the invention.

1. Cold Germination Superpool Screen 0.5×MS Media is prepared and the pH adjusted to 5.7 using 10N KOH. Seven g/l of Phytagar is added prior to autoclaving.

Individual superpool and control seeds are sterilized in a 30% bleach solution for 5 minutes. Seeds are then rinsed repeatedly with sterile water to eliminate all bleach solution. Seeds are sown on media plates in a monolayer, including wild-type and positive controls. Plates are wrapped in aluminum foil and placed at 4° C. for three days to stratify. At the end of this time, the foil is removed and plates are transferred to an 8° C. Percival with fluorescent bulbs emitting a light intensity of ~100 µEinsteins.

Approximately 10 days after transfer to 8° C., seeds are examined microscopically to identify those that have germinated (defined as cotyledon emergence and expansion). Seedlings with more expanded and greener cotyledons compared to the wild-type population in the same plate are collected. DNA from these candidate seedlings is extracted and the transgene amplified using PCR. The PCR product is sequenced to determine the identity of the transgene and consequently the ME line from which the candidate is derived.

2. Cold Germination Assay

Independent transformation events of the ME lines identified in the Superpool screen are assayed in two generations to validate the cold tolerance phenotype. Media is prepared and seeds sterilized as described above for the Cold Germination Superpool Screen.

Two events with 27 seeds from each event are sown in a Latin square layout on square Petri dishes together with 27 wild-type control seeds. Following 3 days of stratification at 4° C., plates are transferred to 8° C. in the light and grown as above. Approximately 10 days after transfer, plates are imaged on a flat-bed scanner. Plate images are analyzed using WinRhizo software to determine the area of each seedling. Subsequently, plates are transferred to 22° C. for several days of growth and then sprayed with Finale™ to identify transgenic seedlings. Seedling area and transgene status data are entered into a database. Events are considered positive for the low temperature, chilling or cold-tolerant phenotype if the seedling area of the transgenic plants within an event is significantly different by a one-tailed student's t-test than the seedling area of the pooled non-transgenic seedlings across all the events for that ME line.

References:

Levitt (1980) Chilling injury and resistance. In T T Kozlowsky, ed, Chilling, Freezing, and High Temperature Stresses: Responses of Plant to Environmental Stresses, Vol 1. Academic Press, New York, pp 23-64.

Graham and Patterson (1982) *Annu Rev Plant Physiol* 33: 347-372.

Guy (1990) *Annu Rev Plant Physiol Plant Mol Biol* 41: 187-223.

Nishida and Murata (1996) *Annu Rev Plant Physiol Plant Mol Biol* 47: 541-568.

EXAMPLES

Summary

| | |
|---|---|
| Trait area(s) | Cold |
| Sub-trait Area | Cold - germination and vigor |
| Coding sequence/ Species of Origin | 1. Vector Construct Sequence Identifier 14298746 corresponding to Clone 30087 - ME01451; encodes a 164 amino acid protein of unknown function from *Arabidopsis*. 2. Vector Construct Sequence Identifier 14298770 corresponding to Clone 30469 - ME02779 encodes a 78 amino acid protein with identity to the N-terminal half of an *Arabidopsis* class I nonsymbiotic hemoglobin. 3. Vector Construct Sequence Identifier 14301197 corresponding to Clone 271922 - ME03944 encodes a 92 amino acid 60s ribosomal protein L37a protein from *Arabidopsis*. 4. Vector Construct Sequence Identifier 14296769 corresponding to Clone 2403 - ME05304 encodes a truncated ubiquitin-like protein from *Arabidopsis*. 5. Vector Construct Sequence Identifier 14301334 corresponding to Clone 674166 -ME03186 from *Glycine max* encodes a 210 amino acid protein with similarity to the ethylene-responsive element binding protein (ERF) family. |
| Species in which Clone was Tested | *Arabidopsis thaliana* |
| Promoter | 35S, a strong constitutive promoter |
| Insert DNA type | cDNA |

Introduction:

How plants respond to stress in the environment dictates their ability to survive and reproduce. There are probably many mechanisms by which plants regulate the temperatures under which they will germinate (Lu and Hills, 2003). Finding genes that result in stress tolerance when overexpressed has proved difficult because of the large amount of cross-talk and regulation among gene families.

Over-expression of these genes could be useful for increasing low temperature, chilling or cold tolerance in crops. If successfully deployed, low temperature, chilling or cold tolerant genes could enhance crop productivity following intermittent or sustained low temperature, chilling or cold periods that occur early in the growing season when seeds are germinating. Assuming conservation of processes controlling vegetative physiology across species, these genes and proteins are likely to function similarly in other species.

Assays described here focus on low temperature, chilling or cold tolerance in germinating seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these genes, the result could be very valuable in agriculture in many crops and environments and make a significant contribution to sustainable farming. Furthermore, low temperature, chilling or cold tolerance may be modulated by expressing these clones under the control of a low temperature, chilling or cold inducible promoter.

Materials and Methods:
Generation and Phenotypic Evaluation of $T_1$ Events.

Wild-type *Arabidopsis* Wassilewskija (Ws) plants were transformed with a Ti plasmid containing different Clones in the sense orientation relative to the 35S promoter, by *Agrobacterium*-Mediated Transformation. The Ti plasmid vector used for this construct, CRS 338, contains the Ceres-constructed, plant selectable marker gene phosphinothricin acetyltransferase (PAT) which confers herbicide resistance to transformed plants. Ten independent transformation events were selected and evaluated for their qualitative phenotype in the $T_1$ generation by selecting Finale™-resistant plants and observing their physical characteristics.

Screening for Low Temperature, Chilling or Cold Germination Candidates.

All superpools (n=91) were screened for cold germination by plating seeds on MS media and germinating them at 8° C. Candidates were chosen based on a comparison to wild-type controls. The candidates were processed as follows.

Process Flow:
Procedure for 1) identifying the candidate from a cold germination superpool screen, 2) confirming the phenotype in the second and third generations and 3) determining the lack of significant negative phenotypes.
1. Superpools screened for Cold Germination
2. Cold tolerant candidates identified
3. Independent events tested for Cold Germination and Finale™ resistance in two generations
4. For all candidates, at least 2 Events were significantly tolerant to cold in 2 generations
5. Tested positive events for negative phenotypes Growth Conditions and Planting Schema Under Cold Germination.

Up to five independent $T_2$ transformation events were evaluated for each line under cold conditions. Subsequently, $T_3$ generation seeds for up to five events were evaluated under cold germination conditions. In these assays, the seedling area (a measure of timing of germination and cotyledon expansion) for transgenic plants within an event was compared to the seedling area for non-transgenic segregants pooled across all plates for that line.

Preparation of plates and seed sowing were performed by sowing seeds on 0.5×MS plates and grown at 8° C. Plates were scored on day 10, and analyzed for cotyledon area. After the Cold Germination Assay was complete, plates were transferred to 22° C. and insert-containing plants were identified by spraying the seedlings with Finale™. Transgenic plants are Finale™ resistant.

Screening for Negative Phenotypes.

The events described in this report were analyzed for negative phenotypes. None of the events had (a) reduction in germination of more than 25%, (b) delay in onset of flowering more than 4 days in 50% or more of plants relative to in-flat control, (c) reduction in fertility as evidenced by visual observation of reduction in silique fill or silique number, (d) a reduction in seed dry weight by 25% or more relative to control, or (e) more than 30% reduction in rosette diameter at maturity.

Results:

Example 1: ME01451

TABLE 1-1

| Construct | Event/Generation | Plant Stage | Assay | Result |
|---|---|---|---|---|
| 35S:: 30087 | -01/$T_2$ Finale resistant plants | Seedling | Cold Germination | Significant at p ≤ .05 |
| 35S:: 30087 | -05/$T_2$ Finale resistant plants | Seedling | Cold Germination | Significant at p ≤ .05 |
| 35S:: 30087 | -01/$T_3$ Finale resistant plants | Seedling | Cold Germination | Significant at p ≤ .05 |
| 35S:: 30087 | -05/$T_3$ Finale resistant plants | Seedling | Cold Germination | Significant at p ≤ .05 |

Ectopic expression of Clone 30087 under the control of the 35S promoter induces the following phenotypes:

Early germination at 8° C. resulting in larger seedlings after 10 days of growth in the cold.

Plants from Events -01 and -05 which are heterozygous or homozygous for Clone 30087 do not show any negative phenotypes under long-day conditions.

The gene corresponding to Clone 30087 is up-regulated in developing seedlings, seeds and siliques and down-regulated in drought, heat and ABA.

Two Events of ME01451 Showed Significant Early Germination Under Cold Conditions in Both Generations.

All five events of ME01451 were sown as described in the Cold Germination Assay in both the $T_2$ and the $T_3$ generations. Two events, -01 and -05, were significant in both generations at p=0.05 using a one-tailed t-test assuming unequal variance (Table 1-2). ME01451 transgenic seedlings were significantly larger than the pooled non-transgenic segregants.

TABLE 1-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME01451 | ME01451-01 | 0.0086 | 0.0005 | 25 | 0.0067 | 0.0006 | 54 | 0.00702 |
| ME01451 | ME01451-01-99 | 0.0106 | 0.0006 | 22 | 0.0079 | 0.0010 | 14 | 0.01374 |
| ME01451 | ME01451-05 | 0.0104 | 0.0006 | 18 | 0.0067 | 0.0006 | 54 | 0.00002 |
| ME01451 | ME01451-05-99 | 0.0125 | 0.0007 | 25 | 0.0079 | 0.0010 | 14 | 0.00035 |

Two Events of ME01451 Show 3:1 and 15:1 Segregation for Finale™ Resistance.

Events -01 and -05 segregated 15:1 and 3:1 (R:S), respectively, for Finale™ resistance in the $T_2$ generation (data not shown).

Qualitative Analysis of the $T_1$ Plants:

The physical appearance of all ten $T_1$ plants was identical to the controls.

Qualitative and Quantitative Analysis of the $T_2$ Plants:

Events -01 and -05 of ME01451 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls Example 2: ME02779

Ectopic expression of Clone 30469 under the control of the 35S promoter induces the following phenotypes:

Early germination at 8° C. resulting in larger seedlings after 10 days at 8° C.

Plants from Events -01 and -03 which are heterozygous or homozygous for Clone 30469 do not show any negative phenotypes under long-day conditions.

The gene corresponding to Clone 30469 is down-regulated in ABA, heat, and germinating seeds and up-regulated in high nitrogen and most cold and drought treatments.

Clone 30469 encodes a class I nonsymbiotic hemoglobin. These proteins can play a role in acclimation to hypoxic conditions, possibly explaining the cold tolerance phenotype (Hunt et al., 2001). Clone 30469 is a splice variant of a gene that encodes a longer protein.

Two Events of ME02779 Showed Significant Early Germination Under Cold Conditions in Both Generations.

Five events of ME02779 were sown as described in the Cold Germination Assay in both the $T_2$ and the $T_3$ generations. Two events, -01 and -03 were significant in both generations at p=0.05 using a one-tailed t-test assuming unequal variance (Table 2-2). ME02779 transgenic seedlings were significantly larger than the pooled non-transgenic segregants.

TABLE 2-1

| Construct | Event/Generation | Plant Stage | Assay | Result |
|---|---|---|---|---|
| 35S:: 30469 | -01/$T_2$ Finale resistant plants | Seedling | Cold Germination | Significant at p ≤ .05 |
| 35S:: 30469 | -03/$T_2$ Finale resistant plants | Seedling | Cold Germination | Significant at p ≤ .05 |
| 35S:: 30469 | -01/$T_3$ Finale resistant plants | Seedling | Cold Germination | Significant at p ≤ .05 |
| 35S:: 30469 | -03/$T_3$ Finale resistant plants | Seedling | Cold Germination | Significant at p ≤ .05 |

TABLE 2-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME02779 | ME02779-01 | 0.0077 | 0.0007 | 12 | 0.0040 | 0.0014 | 3 | 0.01738 |
| ME02779 | ME02779-01-99 | 0.0051 | 0.0005 | 21 | 0.0034 | 0.0002 | 29 | 0.00077 |
| ME02779 | ME02779-03 | 0.0111 | 0.0007 | 19 | 0.0085 | 0.0007 | 40 | 0.00433 |
| ME02779 | ME02779-03-99 | 0.0052 | 0.0006 | 20 | 0.0034 | 0.0002 | 29 | 0.00293 |

Two Events of ME02779 Show 3:1 Segregation for Finale™ Resistance.

Events -01 and -03 segregated 3:1 (R:S) for Finale™ resistance in the $T_2$ generation (data not shown).

Qualitative Analysis of the $T_1$ Plants:

The physical appearance of nine of the ten $T_1$ plants was identical to the controls except for Event -09, which exhibited small rosettes and reduced fertility.

Qualitative and Quantitative Analysis of the $T_2$ Plants:

Events -01 and -03 of ME02779 exhibited no statistically relevant negative phenotypes.

Germination

No detectable reduction in germination rate.

General morphology/architecture

Plants appeared wild-type in all instances.

Days to flowering

No observable or statistical differences between experimentals and controls.

Rosette area 7 days post-bolting

No observable or statistical differences between experimentals and controls.

Fertility (silique number and seed fill)

No observable or statistical differences between experimentals and controls

Example 3: ME03944

TABLE 3-1

| Construct | Event/Generation | Plant Stage | Assay | Result |
|---|---|---|---|---|
| 35S:: 271922 -02/$T_2$ Finale resistant plants | | Seedling | Cold Germination | Significant at p ≤ .05 |
| 35S:: 271922 -06/$T_2$ Finale resistant plants | | Seedling | Cold Germination | Significant at p ≤ .05 |
| 35S:: 271922 -02/$T_3$ Finale resistant plants | | Seedling | Cold Germination | Significant at p ≤ .05 |
| 35S:: 271922 -06/$T_3$ Finale resistant plants | | Seedling | Cold Germination | Significant at p ≤ .05 |

Ectopic expression of Clone 271922 under the control of the 35S promoter induces the following phenotypes:

Early germination at 8° C. resulting in larger seedlings after 10 days at 8° C.

Plants from Events -02 and -06 which are heterozygous or homozygous for Clone 271922 do not show any negative phenotypes under long-day conditions.

The gene corresponding to Clone 271922 shows little differential regulation in transcription profiling experiments on wildtype.

Clone 271922 encodes a 60s ribosomal protein L37a.

Two Events of ME03944 Showed Significant Early Germination Under Cold Conditions in Both Generations.

Four events of ME03944 were sown as described in the Cold Germination Assay in both the $T_2$ and the $T_3$ generations. Two events, -02 and -06, were significant in both generations at p≤0.05 using a one-tailed t-test assuming unequal variance (Table 3-2). The $T_3$ lines are indicated as -99 which indicates that the seeds are the bulked progeny from several $T_2$ plants. ME03944 transgenic seedlings were significantly larger than the pooled non-transgenic segregants.

TABLE 3-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME03944 | ME03944-02 | 0.0115 | 0.0004 | 23 | 0.0069 | 0.0006 | 35 | 3.4023E−08 |
| ME03944 | ME03944-02-99 | 0.0070 | 0.0008 | 15 | 0.0051 | 0.0004 | 29 | 0.0173 |
| ME03944 | ME03944-06 | 0.0106 | 0.0006 | 18 | 0.0069 | 0.0006 | 35 | 2.7850E−05 |
| ME03944 | ME03944-06-99 | 0.0077 | 0.0007 | 21 | 0.0051 | 0.0004 | 29 | 0.0011 |

Two Events of ME03944 Show 3:1 Segregation for Finale™ Resistance.

Events -02 and -06 segregated 3:1 (R:S) for Finale™ resistance in the $T_2$ generation (data not shown).

Qualitative Analysis of the $T_1$ Plants:

The physical appearance of five of the six $T_1$ plants was identical to the controls. Event -03 exhibited a small rosette and curled leaves.

Other Characteristics:

Seedlings from ME03944-06 exhibited elongated hypocotyls. This phenotype co-segregated with Finale™ resistance.

Qualitative and Quantitative Analysis of the $T_2$ Plants:
Events -02 and -06 of ME03944 exhibited no statistically relevant negative phenotypes.

Germination
  No detectable reduction in germination rate.
General morphology/architecture
  Plants appeared wild-type in all instances.
Days to flowering
  No observable or statistical differences between experimentals and controls.
Rosette area 7 days post-bolting
  No observable or statistical differences between experimentals and controls.
Fertility (silique number and seed fill)
  No observable or statistical differences between experimentals and controls Example 4: ME05304

TABLE 4-1

| Construct | Event/Generation | Plant Stage | Assay | Result |
|---|---|---|---|---|
| 35S:: 2403 | -01/$T_2$ Finale resistant plants | Seedling | Cold Germination | Significant at $p \leq .05$ |
| 35S:: 2403 | -04/$T_2$ Finale resistant plants | Seedling | Cold Germination | Significant at $p \leq .05$ |
| 35S:: 2403 | -01/$T_3$ Finale resistant plants | Seedling | Cold Germination | Significant at $p \leq .05$ |
| 35S:: 2403 | -04/$T_3$ Finale resistant plants | Seedling | Cold Germination | Significant at $p \leq .05$ |

Ectopic expression of Clone 2403 under the control of the 35S promoter induces the following phenotypes:

Early germination at 8° C. resulting in larger seedlings after 10 days at 8° C.

Plants from Events -01 and -04 which are heterozygous or homozygous for Clone 2403 do not show any negative phenotypes under long-day conditions.

The gene corresponding to Clone 2403 shows little differential regulation in transcript profiling experiments on wildtype.

Clone 2403 encodes a truncated ubiquitin-like protein.

Two Events of ME05304 Showed Significant Early Germination Under Cold Conditions in Both Generations.

Four events of ME05304 were sown as described in the Cold Germination Assay in both the $T_2$ and the $T_3$ generations. Two events, -01 and -04 were significant in both generations at p≤0.05 using a one-tailed t-test assuming unequal variance (Table 4-2). The $T_3$ lines are indicated as -99 which indicates that the seeds are the bulked progeny from several $T_2$ plants.

TABLE 4-2

T-test comparison of seedling area between transgenic seedlings and pooled non-transgenic segregants after 10 days at 8° C.

| | | Transgenic | | | Pooled Non-Transgenics | | | t-test |
|---|---|---|---|---|---|---|---|---|
| Line | Events | Avg | SE | N | Avg | SE | N | p-value |
| ME05304 | ME05304-01 | 0.0142 | 0.0009 | 20 | 0.0079 | 0.0006 | 39 | 0.0000 |
| ME05304 | ME05304-01-99 | 0.0061 | 0.0005 | 17 | 0.0049 | 0.0003 | 27 | 0.0213 |
| ME05304 | ME05304-04 | 0.0101 | 0.0007 | 15 | 0.0079 | 0.0006 | 39 | 0.0099 |
| ME05304 | ME05304-04-99 | 0.0067 | 0.0005 | 22 | 0.0049 | 0.0003 | 27 | 0.0014 |

Two Events of ME05304 Show 3:1 Segregation for Finale™ Resistance.

Events -01 and -04 segregated 3:1 (R:S) for Finale™ resistance in the $T_2$ generation (data not shown).

Qualitative Analysis of the $T_1$ Plants:

The physical appearance of seven of the ten $T_1$ plants was identical to the controls. The other three events exhibited the following phenotypes: late flowering (Events -01, -02 and -08), dark green rosette leaves (Events -01 and -08) and shorter petioles (Events -02 and -08). Event -01 did not reproduce the late-flowering phenotype in the $T_2$ generation.

Qualitative and Quantitative Analysis of the $T_2$ Plants:

Events -01 and -04 of ME05304 exhibited no statistically relevant negative phenotypes.

Germination
   No detectable reduction in germination rate.
General morphology/architecture
   Plants appeared wild-type in all instances.
Days to flowering
   No observable or statistical differences between experimentals and controls.
Rosette area 7 days post-bolting
   No observable or statistical differences between experimentals and controls.
Fertility (silique number and seed fill)
   No observable or statistical differences between experimentals and controls.

Example 5: ME03186

TABLE 5-1

| Construct | Event/Generation | Plant Stage | Assay | Result |
|---|---|---|---|---|
| 35S::674166 | -04/$T_3$ Finale resistant plants | Seedling | Cold Germination | Significant at $p \leq .05$ |
| 35S::674166 | -04/$T_4$ Finale resistant plants | Seedling | Cold Germination | Significant at $p \leq .05$ |
| 35S::674166 | -05/$T_2$ Finale resistant plants | Seedling | Cold Germination | Significant at $p \leq .05$ |
| 35S::674166 | -05/$T_3$ Finale resistant plants | Seedling | Cold Germination | Significant at $p \leq .05$ |

Ectopic expression of Clone 674166 under the control of the 35S promoter results in early germination at 8° C. resulting in larger seedlings after 10 days at 8° C.

Plants from Events -04 and -05 which are hemizygous or homozygous for Clone 674166 do not show any negative phenotypes under long-day conditions.

Two Events of ME03186 Showed Significant Early Germination Under Cold Conditions in Both Generations.

Two events, -04 and -05 were significant in two generations at $p \leq 0.05$ using a one-tailed t-test assuming unequal variance (Table 5-2). '-99' signifies that seeds were pooled from several plants.

TABLE 5-2

T-test comparison of seedling area between transgenic seedlings and control non-transgenic segregants after 10 days at 8° C.

| Events | Event-Gen | Transgenic Avg | Transgenic SE | Transgenic N | Control Non-Transgenics[a] Avg | Control Non-Transgenics[a] SE | Control Non-Transgenics[a] N | t-test p-value |
|---|---|---|---|---|---|---|---|---|
| ME03186-04-99[b] | 04-T3 | 0.0045 | 0.0003 | 35 | 0.0030 | 0.0002 | 31 | 1.37E−05 |
| ME03186-04-99 | 04-T3 | 0.0092 | 0.0003 | 48 | 0.0051 | 0.0005 | 12 | 3.72E−10 |
| ME03186-04-99-03 | 04-T4 | 0.0107 | 0.0002 | 70 | 0.0083 | 0.0005 | 34 | 2.72E−05 |
| ME03186-04-99-04 | 04-T4 | 0.0120 | 0.0004 | 62 | 0.0083 | 0.0005 | 34 | 3.61E−08 |
| ME03186-04-99-07 | 04-T4 | 0.0107 | 0.0003 | 69 | 0.0083 | 0.0005 | 34 | 4.91E−05 |
| ME03186-04-99-08 | 04-T4 | 0.0110 | 0.0003 | 69 | 0.0083 | 0.0005 | 34 | 5.53E−06 |
| ME03186-05[b] | 05-T2 | 0.0051 | 0.0005 | 22 | 0.0038 | 0.0005 | 6 | 0.0332 |
| ME03186-05 | 05-T2 | 0.0067 | 0.0003 | 53 | 0.0054 | 0.0005 | 9 | 0.0106 |
| ME03186-05-04 | 05-T3 | 0.0050 | 0.0003 | 50 | 0.0037 | 0.0003 | 9 | 0.0008 |

[a] Transgenic seedlings were compared to non-transgenic segregants within a seed line except for the $T_4$ generation of Event-04. Since these seed lines were homozygous, they were compared to pooled non-transgenic segregants from another $T_4$ generation event that was grown in the same flat as the $T_4$ generation of Event-04.

[b] These events were sown twice. The first time was to identify ME03186 as a hit. They were repeated the second time with two generations to identify ME03186 as a candidate.

Two Events of ME03186 Show 3:1 Segregation for Finale™ Resistance.

Event -05 segregated 3:1 (R:S) for Finale™ resistance in the $T_2$ generation. $T_2$ generation seed was not available for Event -04. However, the $T_3$ generation seeds that were pooled from several $T_2$ plants segregated approximately 2:1 in a manner consistent with a single insert (see Table 5-2). Qualitative and Quantitative Analysis of the $T_2$ Plants (Screening for Negative Phenotypes):
Events -04 and -05 of ME03186 exhibited no statistically significant negative phenotypes.
  Germination
    No detectable reduction in germination rate.
  General morphology/architecture
    Plants appeared wild-type in all instances.
  Days to flowering
    No observable or statistical differences between experimentals and controls.
  Rosette area 7 days post-bolting
References:
Hunt et al, (2001) *Plant Mol Biol* 47: 677-692.
Lu and Hills (2002) *Plant Physiol.* 129:1352-8

Example 6: Clone 1055099 (SEQ ID NO: 46)—ME 24967

In the same manner as Example 5, transgenics made with a construct of 35S—Clone 1055099 were screened for cold tolerance. Clone 1055099 (SEQ ID NO: 46) is a wheat functional homolog of clone 674166 (SEQ ID NO: 42), and showed the following results in the seedling cold tolerance assay.

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

TABLE 6-1

Cold Germination Assay results for ME24967.

| Event | p-values | | Avg. Seedling Area | | | Sample No. | | |
|---|---|---|---|---|---|---|---|---|
| | Internal[a] | Pooled[b] | Transgenic | Internal | Pooled | Transgenic | Internal | Pooled |
| ME03186-04-99[c] | 0.00224438 | 0.00224438 | 0.0032 | 0.0017 | 0.0017 | 30 | 40 | 40 |
| ME24967-02 | 0.12660455 | 0.45511103 | 0.0053 | 0.0071 | 0.0054 | 29 | 5 | 83 |
| ME24967-03[d] | 0.01488322 | 0.04610112 | 0.0069 | 0.0031 | 0.0054 | 31 | 3 | 83 |
| ME24967-05[d] | 0.08783497 | 3.0406E-08 | 0.0115 | 0.0092 | 0.0054 | 23 | 12 | 83 |
| ME24967-10 | 0.40686041 | 0.25206736 | 0.0049 | 0.0053 | 0.0054 | 28 | 6 | 83 |
| ME24967-11 | 0.19290195 | 0.40123421 | 0.0051 | 0.0038 | 0.0054 | 5 | 25 | 83 |
| ME24967-12 | 0.3021565 | 0.00329335 | 0.0032 | 0.0050 | 0.0054 | 27 | 2 | 83 |
| ME24967-13 | 0.24672812 | 0.31347649 | 0.0060 | 0.0077 | 0.0054 | 23 | 7 | 83 |
| ME24967-14 | 0.17548824 | 0.29369895 | 0.0050 | 0.0032 | 0.0054 | 26 | 5 | 83 |
| ME24967-15 | 0.29278326 | 0.38586196 | 0.0057 | 0.0048 | 0.0054 | 22 | 11 | 83 |
| ME24967-16 | | 0.05451794 | 0.0041 | 0.0018 | 0.0054 | 34 | 1 | 83 |
| ME24967-17 | 0.27484717 | 0.13660585 | 0.0044 | 0.0058 | 0.0054 | 26 | 6 | 83 |

[a]Internal controls are segregating non-transgenic seedlings within an Event.
[b]Pooled controls are all of the segregating non-transgenic seedlings from all of the Events within a line.
[c]ME03186 is a positive control to verify that the experimental conditions were appropriate.
[d]These events show significantly improved seedling area for at least internal or pooled controls.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 2, 7, 9, 20, 34, 40 and 42 are shown in FIGS. 1-7, respectively. The BLAST percent identities and E-values of functional homologs to SEQ ID NOs: 2, 7, 9, 20, 34, 40 and 42 are shown in the Sequence Listing. The BLAST sequence identities and E-values given in the Sequence Listing were taken from the forward search round of the Reciprocal BLAST process.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in each of FIGS. 1-7 as input. Additional sequences were input into the model, and the HMM bit scores for the additional sequences are shown in the Sequence Listing. The results indicate that these additional sequences are functional homologs of SEQ ID NOs: 2, 7, 9, 20, 34, 40 and 42, respectively. The bit score results are provided in Table 7.

TABLE 7

| Query Identifier | Functional Homolog | Sequence Type | Species | Seq Id No | Length | Pfam |
|---|---|---|---|---|---|---|
|  | Ceres CLONE ID no. 30087 | DNA | Arabidopsis thaliana | 1 | 828 |  |
| Ceres CLONE ID no. 30087 | Ceres CLONE ID no. 30087 | PRT | Arabidopsis thaliana | 2 | 164 |  |
| Ceres Clone ID no. 30087 | Ceres CLONE ID no. 947579 | PRT | Brassica napus | 3 | 155 |  |
| Ceres Clone ID no. 30087 | Public GI no. 62526422 | PRT | Brassica napus | 4 | 152 |  |
| Ceres Clone ID no. 30087 | Ceres CLONE ID no. 1606506 | PRT | Parthenium argentatum | 5 | 150 |  |
|  | Ceres CLONE ID no. 30469 | DNA | Artificial Sequence | 6 | 586 |  |
| Ceres CLONE ID no. 30469 | Ceres CLONE ID no. 30469 | PRT | Artificial Sequence | 7 | 78 | Globin |
|  | Ceres CLONE ID no. 30469_FL | DNA | Arabidopsis thaliana | 8 | 483 |  |
| Ceres Clone ID no. 30469 | Ceres CLONE ID no. 30469_FL | PRT | Arabidopsis thaliana | 9 | 160 | Globin |
| Ceres Clone ID no. 30469 | Public GI no. 30909306 | PRT | Raphanus sativus | 10 | 160 | Globin |
| Ceres Clone ID no. 30469 | Public GI no. 37903656 | PRT | Arabidopsis thaliana | 11 | 158 | Globin |
| Ceres Clone ID no. 30469 | Public GI no. 15824736 | PRT | Arabidopsis thaliana | 12 | 163 | Globin |
| Ceres Clone ID no. 30469 | Ceres CLONE ID no. 546001 | PRT | Glycine max | 13 | 161 | Globin |
| Ceres Clone ID no. 30469 | Public GI no. 11095158 | PRT | Glycine max | 14 | 160 | Globin |
| Ceres Clone ID no. 30469 | Public GI no. 12963875 | PRT | Glycine max | 15 | 152 | Globin |
| Ceres Clone ID no. 30469 | Ceres CLONE ID no. 1554560 | PRT | Zea mays | 16 | 165 | Globin |
| Ceres Clone ID no. 30469 | Ceres CLONE ID no. 839727 | PRT | Triticum aestivum | 17 | 162 | Globin |
| Ceres Clone ID no. 30469 | Public GI no. 14701800 | PRT | Triticum aestivum | 18 | 169 | Globin |
|  | Ceres CLONE ID no. 271922 | DNA | Arabidopsis thaliana | 19 | 416 |  |
| Ceres CLONE ID no. 271922 | Ceres CLONE ID no. 271922 | PRT | Arabidopsis thaliana | 20 | 92 | Ribosomal_L37ae; |
| Ceres Clone ID no. 271922 | Public GI no. 4090257 | PRT | Arabidopsis thaliana | 21 | 92 | Ribosomal_L37ae |
| Ceres Clone ID no. 271922 | Public GI no. 4741896 | PRT | Arabidopsis thaliana | 22 | 92 | Ribosomal_L37ae |
| Ceres Clone ID no. 271922 | Ceres CLONE ID no. 36046 | PRT | Arabidopsis thaliana | 23 | 92 | Ribosomal_L37ae |
| Ceres Clone ID no. 271922 | Public GI no. 6016699 | PRT | Arabidopsis thaliana | 24 | 92 | Ribosomal_L37ae |
| Ceres Clone ID no. 271922 | Ceres CLONE ID no. 664936 | PRT | Glycine max | 25 | 92 | Ribosomal_L37ae |
| Ceres Clone ID no. 271922 | Ceres CLONE ID no. 658438 | PRT | Glycine max | 26 | 92 | Ribosomal_L37ae |
| Ceres Clone ID no. 271922 | Ceres CLONE ID no. 1049262 | PRT | Glycine max | 27 | 92 | Ribosomal_L37ae |
| Ceres Clone ID no. 271922 | Ceres CLONE ID no. 632613 | PRT | Triticum aestivum | 28 | 92 | Ribosomal_L37ae |
| Ceres Clone ID no. 271922 | Ceres CLONE ID no. 1390976 | PRT | Zea mays | 29 | 92 | Ribosomal_L37ae |
| Ceres Clone ID no. 271922 | Ceres CLONE ID no. 1457185 | PRT | Zea mays | 30 | 92 | Ribosomal_L37ae |
| Ceres Clone ID no. 271922 | Public GI no. 56202147 | PRT | Zea mays | 31 | 92 | Ribosomal_L37ae |
| Ceres Clone ID no. 271922 | Public GI no. 58578274 | PRT | Zea mays | 32 | 92 | Ribosomal_L37ae |
|  | Ceres CLONE ID no. 2403_FL | DNA | Arabidopsis thaliana | 33 | 632 |  |
| Ceres CLONE ID no. 2403 | Ceres CLONE ID no. 2403_FL | PRT | Arabidopsis thaliana | 34 | 154 | ubiquitin; |
| Ceres CLONE ID no. 2403 | Ceres CLONE ID no. 2403_FL | PRT | Arabidopsis thaliana | 34 | 154 | ubiquitin; |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 1482731 | PRT | Zea mays | 35 | 169 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 522921 | PRT | Glycine max | 36 | 154 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 1036726 | PRT | Brassica napus | 37 | 160 | ubiquitin |
| Ceres Clone ID no. 2403 | Ceres CLONE ID no. 513071 | PRT | Glycine max | 38 | 188 | ubiquitin |
| Ceres Clone ID no. 2403 | Ceres CLONE ID no. 513071 | PRT | Glycine max | 38 | 188 | ubiquitin |
|  | Ceres CLONE ID no. 2403 | DNA | Artificial Sequence | 39 | 620 |  |
| Ceres CLONE ID no. 2403 | Ceres CLONE ID no. 2403 | PRT | Artificial Sequence | 40 | 33 | ubiquitin; |
|  | Ceres CLONE ID no. 674166 | DNA | Glycine max | 41 | 1106 |  |
| Ceres CLONE ID no. 674166 | Ceres CLONE ID no. 674166 | PRT | Glycine max | 42 | 210 | AP2; |
| Ceres Clone ID no. 674166 | Public GI no. 12322345 | PRT | Glycine max | 43 | 225 | AP2 |
| Ceres Clone ID no. 674166 | Ceres CLONE ID no. 975672 | PRT | Brassica napus | 44 | 215 | AP2 |

TABLE 7-continued

| | | | | | | |
|---|---|---|---|---|---|---|
| Ceres Clone ID no. 674166 | Ceres CLONE ID no. 273307 | PRT | Zea mays | 45 | 211 | AP2 |
| Ceres Clone ID no. 674166 | Ceres CLONE ID no. 1055099 | PRT | Triticum aestivum | 46 | 194 | AP2 |
| | Ceres ANNOT ID no. 1441430 | DNA | Populus balsamifera subsp. trichocarpa | 47 | 660 | |
| Ceres CLONE ID no. 674166 | Ceres ANNOT ID no. 1441430 | PRT | Populus balsamifera subsp. trichocarpa | 48 | 219 | AP2 |
| | Ceres CLONE ID no. 1240330 | DNA | Glycine max | 49 | 985 | |
| Ceres CLONE ID no. 674166 | Ceres CLONE ID no. 1240330 | PRT | Glycine max | 50 | 222 | AP2 |
| | Ceres CLONE ID no. 1382611 | DNA | Zea mays | 51 | 726 | |
| Ceres CLONE ID no. 30087 | Ceres CLONE ID no. 1382611 | PRT | Zea mays | 52 | 156 | |
| | Ceres CLONE ID no. 1627907 | DNA | Papaver somniferum | 53 | 580 | |
| Ceres CLONE ID no. 271922 | Ceres CLONE ID no. 1627907 | PRT | Papaver somniferum | 54 | 92 | Ribosomal_L37ae |
| | Ceres CLONE ID no. 1761125 | DNA | Panicum virgatum | 55 | 983 | |
| Ceres CLONE ID no. 674166 | Ceres CLONE ID no. 1761125 | PRT | Panicum virgatum | 56 | 192 | AP2 |
| | Ceres CLONE ID no. 1783890 | DNA | Panicum virgatum | 57 | 594 | |
| Ceres CLONE ID no. 271922 | Ceres CLONE ID no. 1783890 | PRT | Panicum virgatum | 58 | 92 | Ribosomal_L37ae |
| | Ceres CLONE ID no. 1802327 | DNA | Panicum virgatum | 59 | 880 | |
| Ceres Clone ID no. 30469 | Ceres CLONE ID no. 1802327 | PRT | Panicum virgatum | 60 | 162 | Globin |
| | Ceres CLONE ID no. 1838364 | DNA | Gossypium hirsutum | 61 | 1017 | |
| Ceres CLONE ID no. 674166 | Ceres CLONE ID no. 1838364 | PRT | Gossypium hirsutum | 62 | 246 | AP2 |
| | Ceres CLONE ID no. 1876458 | DNA | Panicum virgatum | 63 | 708 | |
| Ceres Clone ID no. 30469 | Ceres CLONE ID no. 1876458 | PRT | Panicum virgatum | 64 | 162 | Globin |
| | Ceres CLONE ID no. 1879148 | DNA | Panicum virgatum | 65 | 712 | |
| Ceres Clone ID no. 30469 | Ceres CLONE ID no. 1879148 | PRT | Panicum virgatum | 66 | 164 | Globin |
| | Ceres CLONE ID no. 1884696 | DNA | Gossypium hirsutum | 67 | 1129 | |
| Ceres CLONE ID no. 2403 | Ceres CLONE ID no. 1884596 | PRT | Gossypium hirsutum | 68 | 153 | ubiquitin |
| Ceres CLONE ID no. 2403 | Ceres CLONE ID no. 1884696 | PRT | Gossypium hirsutum | 68 | 153 | ubiquitin |
| | Ceres CLONE ID no. 1916866 | DNA | Gossypium hirsutum | 69 | 679 | |
| Ceres Clone ID no. 30469 | Ceres CLONE ID no. 1916866 | PRT | Gossypium hirsutum | 70 | 163 | Globin |
| | Ceres CLONE ID no. 1950105 | DNA | Panicum virgatum | 71 | 1003 | |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| Ceres CLONE ID no. 2403 | Ceres CLONE ID no. 1950105 | PRT | Panicum virgatum | 72 | 229 | ubiquitin |
| | Ceres CLONE ID no. 1990746 | DNA | Panicum virgatum | 73 | 724 | |
| Ceres Clone ID no. 30469 | Ceres CLONE ID no. 1990746 | PRT | Panicum virgatum | 74 | 164 | Globin |
| | Ceres CLONE ID no. 2007485 | DNA | Panicum virgatum | 75 | 696 | |
| Ceres CLONE ID no. 674166 | Ceres CLONE ID no. 2007485 | PRT | Panicum virgatum | 76 | 201 | AP2 |
| | Ceres CLONE ID no. 2033803 | DNA | Panicum virgatum | 77 | 698 | |
| Ceres Clone ID no. 30469 | Ceres CLONE ID no. 2033803 | PRT | Panicum virgatum | 78 | 156 | Globin |
| | Ceres CLONE ID no. 2034916 | DNA | Panicum virgatum | 79 | 724 | |
| Ceres CLONE ID no. 2403 | Ceres CLONE ID no. 2034916 | PRT | Panicum virgatum | 80 | 213 | ubiquitin |
| Ceres CLONE ID no. 2403 | Ceres CLONE ID no. 2034916 | PRT | Panicum virgatum | 80 | 213 | ubiquitin |
| Ceres CLONE ID no. 2403 | Ceres CLONE ID no. 2034916 | PRT | Panicum virgatum | 80 | 213 | ubiquitin |
| | Ceres CLONE ID no. 651581 | DNA | Glycine max | 81 | 1194 | |
| Ceres CLONE ID no. 674166 | Ceres CLONE ID no. 651581 | PRT | Glycine max | 82 | 224 | AP2 |
| Ceres CLONE ID no. 674166 | Public GI ID no. 125550159 | PRT | Oryza sativa subsp. indica | 83 | 184 | AP2 |
| Ceres CLONE ID no. 674166 | Public GI ID no. 15223609 | PRT | Arabidopsis thaliana | 84 | 225 | AP2 |
| Ceres CLONE ID no. 30087 | Public GI ID no. 30683885 | PRT | Arabidopsis thaliana | 85 | 164 | |
| Ceres CLONE ID no. 674166 | Public GI ID no. 56384582 | PRT | Pisum sativum | 86 | 218 | AP2 |
| Ceres CLONE ID no. 674166 | Public GI ID no. 57012880 | PRT | Nicotiana tabacum | 87 | 225 | AP2 |
| Ceres Clone ID no. 30469 | Public GI ID no. 62548111 | PRT | Gossypium hirsutum | 88 | 163 | Globin |
| Ceres CLONE ID no. 2403 | Ceres CLONE ID no. 100021733 | PRT | Gossypium hirsutum | 89 | 153 | ubiquitin |
| Ceres CLONE ID no. 2403 | Ceres CLONE ID no. 100021733 | PRT | Gossypium hirsutum | 89 | 153 | ubiquitin |
| | Ceres CLONE ID no. 947579 | DNA | Brassica napus | 90 | 775 | |
| | Ceres CLONE ID no. 36046 | DNA | Arabidopsis thaliana | 91 | 1032 | |
| | Ceres CLONE ID no. 1606506 | DNA | Parthenium argentatum | 92 | 492 | |
| | Ceres CLONE ID no. 546001 | DNA | Glycine max | 93 | 970 | |
| | Ceres CLONE ID no. 1554560 | DNA | Zea mays | 94 | 604 | |
| | Ceres CLONE ID no. 839727 | DNA | Triticum aestivum | 95 | 846 | |
| | Ceres CLONE ID no. 664936 | DNA | Glycine max | 96 | 440 | |
| | Ceres CLONE ID no. 658438 | DNA | Glycine max | 97 | 463 | |
| | Ceres CLONE ID no. 1049262 | DNA | Glycine max | 98 | 458 | |
| | Ceres CLONE ID no. 632613 | DNA | Triticum aestivum | 99 | 600 | |
| | Ceres CLONE ID no. 1390976 | DNA | Zea mays | 100 | 546 | |
| | Ceres CLONE ID no. 1457185 | DNA | Zea mays | 101 | 550 | |
| | Ceres CLONE ID no. 1482731 | DNA | Zea mays | 102 | 668 | |
| | Ceres CLONE ID no. 522921 | DNA | Glycine max | 103 | 752 | |
| | Ceres CLONE ID no. 1036726 | DNA | Brassica napus | 104 | 484 | |
| | Ceres CLONE ID no. 513071 | DNA | Glycine max | 105 | 580 | |
| | Ceres CLONE ID no. 975672 | DNA | Brassica napus | 106 | 987 | |
| | Ceres CLONE ID no. 273307 | DNA | Zea mays | 107 | 1034 | |
| | Ceres CLONE ID no. 1055099 | DNA | Triticum aestivum | 108 | 911 | |
| Ceres Clone ID no. 30469 | Ceres GI ID no. GI_15226675 | PRT | Arabidopsis thaliana | 109 | 160 | Globin |
| | Ceres Promoter 21876 | DNA | Arabidopsis thaliana | 110 | 1823 | |
| | Ceres Promoter PT0668 | DNA | Arabidopsis thaliana | 111 | 1000 | |
| | Ceres Promoter PT0535 | DNA | Arabidopsis thaliana | 112 | 1000 | |
| | Ceres Promoter PT0585 | DNA | Arabidopsis thaliana | 113 | 999 | |
| | Ceres Promoter PT0613 | DNA | Arabidopsis thaliana | 114 | 1000 | |

TABLE 7-continued

| Ceres Promoter PT0625 | DNA | *Arabidopsis thaliana* | 115 | 351 |
|---|---|---|---|---|
| Ceres Promoter PT0633 | DNA | *Arabidopsis thaliana* | 116 | 1022 |
| Ceres Promoter PT0650 | DNA | *Arabidopsis thaliana* | 117 | 1000 |
| Ceres Promoter PT0660 | DNA | *Arabidopsis thaliana* | 118 | 998 |
| Ceres Promoter PT0665 | DNA | *Arabidopsis thaliana* | 119 | 1000 |
| Ceres Promoter PT0672 | DNA | *Arabidopsis thaliana* | 120 | 998 |
| Ceres Promoter PT0676 | DNA | *Arabidopsis thaliana* | 121 | 1000 |
| Ceres Promoter PT0678 | DNA | *Arabidopsis thaliana* | 122 | 998 |
| Ceres Promoter PT0683 | DNA | *Arabidopsis thaliana* | 123 | 1000 |
| Ceres Promoter PT0688 | DNA | *Arabidopsis thaliana* | 124 | 1000 |
| Ceres Promoter PT0695 | DNA | *Arabidopsis thaliana* | 125 | 1000 |
| Ceres Promoter PT0708 | DNA | *Arabidopsis thaliana* | 126 | 1000 |
| Ceres Promoter PT0710 | DNA | *Arabidopsis thaliana* | 127 | 1000 |
| Ceres Promoter PT0723 | DNA | *Arabidopsis thaliana* | 128 | 1002 |
| Ceres Promoter PT0740 | DNA | *Arabidopsis thaliana* | 129 | 1001 |
| Ceres Promoter PT0743 | DNA | *Arabidopsis thaliana* | 130 | 1024 |
| Ceres Promoter PT0758 | DNA | *Arabidopsis thaliana* | 131 | 1000 |
| Ceres Promoter PT0829 | DNA | *Arabidopsis thaliana* | 132 | 921 |
| Ceres Promoter PT0837 | DNA | *Arabidopsis thaliana* | 133 | 763 |
| Ceres Promoter PT0838 | DNA | *Arabidopsis thaliana* | 134 | 751 |
| Ceres Promoter PT0848 | DNA | *Arabidopsis thaliana* | 135 | 669 |
| Ceres Promoter PT0863 | DNA | *Arabidopsis thaliana* | 136 | 702 |
| Ceres Promoter PT0879 | DNA | *Arabidopsis thaliana* | 137 | 435 |
| Ceres Promoter PT0886 | DNA | *Arabidopsis thaliana* | 138 | 397 |
| Ceres Promoter YP0007 | DNA | *Arabidopsis thaliana* | 139 | 1024 |
| Ceres Promoter YP0008 | DNA | *Arabidopsis thaliana* | 140 | 1000 |
| Ceres Promoter YP0019 | DNA | *Arabidopsis thaliana* | 141 | 999 |
| Ceres Promoter YP0028 | DNA | *Arabidopsis thaliana* | 142 | 1024 |
| Ceres Promoter YP0039 | DNA | *Arabidopsis thaliana* | 143 | 1024 |
| Ceres Promoter YP0050 | DNA | *Arabidopsis thaliana* | 144 | 1024 |
| Ceres Promoter YP0086 | DNA | *Arabidopsis thaliana* | 145 | 999 |
| Ceres Promoter YP0088 | DNA | *Arabidopsis thaliana* | 146 | 1024 |
| Ceres Promoter YP0092 | DNA | *Arabidopsis thaliana* | 147 | 1024 |
| Ceres Promoter YP0096 | DNA | *Arabidopsis thaliana* | 148 | 1020 |
| Ceres Promoter YP0097 | DNA | *Arabidopsis thaliana* | 149 | 1000 |
| Ceres Promoter YP0101 | DNA | *Arabidopsis thaliana* | 150 | 1004 |
| Ceres Promoter YP0102 | DNA | *Arabidopsis thaliana* | 151 | 1000 |
| Ceres Promoter YP0103 | DNA | *Arabidopsis thaliana* | 152 | 1004 |
| Ceres Promoter YP0107 | DNA | *Arabidopsis thaliana* | 153 | 1003 |
| Ceres Promoter YP0110 | DNA | *Arabidopsis thaliana* | 154 | 1024 |
| Ceres Promoter YP0111 | DNA | *Arabidopsis thaliana* | 155 | 1024 |
| Ceres Promoter YP0115 | DNA | *Arabidopsis thaliana* | 156 | 996 |
| Ceres Promoter YP0117 | DNA | *Arabidopsis thaliana* | 157 | 1024 |
| Ceres Promoter YP0119 | DNA | *Arabidopsis thaliana* | 158 | 1000 |
| Ceres Promoter YP0120 | DNA | *Arabidopsis thaliana* | 159 | 999 |
| Ceres Promoter YP0121 | DNA | *Arabidopsis thaliana* | 160 | 999 |
| Ceres Promoter YP0128 | DNA | *Arabidopsis thaliana* | 161 | 1004 |
| Ceres Promoter YP0137 | DNA | *Arabidopsis thaliana* | 162 | 1001 |
| Ceres Promoter YP0143 | DNA | *Arabidopsis thaliana* | 163 | 1001 |
| Ceres Promoter YP0144 | DNA | *Arabidopsis thaliana* | 164 | 1003 |
| Ceres Promoter YP0156 | DNA | *Arabidopsis thaliana* | 165 | 1004 |
| Ceres Promoter YP0158 | DNA | *Arabidopsis thaliana* | 166 | 1000 |
| Ceres Promoter YP0188 | DNA | *Arabidopsis thaliana* | 167 | 1005 |
| Ceres Promoter YP0190 | DNA | *Arabidopsis thaliana* | 168 | 1002 |
| Ceres Promoter YP0212 | DNA | *Arabidopsis thaliana* | 169 | 995 |
| Ceres Promoter YP0214 | DNA | *Arabidopsis thaliana* | 170 | 1024 |
| Ceres Promoter YP0263 | DNA | *Arabidopsis thaliana* | 171 | 911 |
| Ceres Promoter YP0275 | DNA | *Arabidopsis thaliana* | 172 | 999 |
| Ceres Promoter YP0285 | DNA | *Arabidopsis thaliana* | 173 | 981 |
| Ceres Promoter YP0286 | DNA | *Arabidopsis thaliana* | 174 | 996 |
| Ceres Promoter YP0337 | DNA | *Arabidopsis thaliana* | 175 | 1000 |
| Ceres Promoter YP0356 | DNA | *Arabidopsis thaliana* | 176 | 1000 |
| Ceres Promoter YP0374 | DNA | *Arabidopsis thaliana* | 177 | 1000 |
| Ceres Promoter YP0377 | DNA | *Arabidopsis thaliana* | 178 | 998 |
| Ceres Promoter YP0380 | DNA | *Arabidopsis thaliana* | 179 | 999 |
| Ceres Promoter YP0381 | DNA | *Arabidopsis thaliana* | 180 | 1000 |
| Ceres Promoter YP0384 | DNA | *Arabidopsis thaliana* | 181 | 999 |
| Ceres Promoter YP0385 | DNA | *Arabidopsis thaliana* | 182 | 998 |
| Ceres Promoter YP0396 | DNA | *Arabidopsis thaliana* | 183 | 1000 |
| Ceres Promoter p13879 | DNA | *Arabidopsis thaliana* | 184 | 1514 |
| Ceres Promoter p326 | DNA | *Arabidopsis thaliana* | 185 | 1954 |
| Ceres Promoter p32449 | DNA | *Arabidopsis thaliana* | 186 | 2016 |
| Ceres Promoter PD1367 | DNA | *Arabidopsis thaliana* | 187 | 667 |
| Ceres Promoter p530c10 | DNA | *Oryza sativa* | 185 | 1836 |
| Ceres Promoter pOsFIE2-2 | DNA | *Oryza sativa* | 189 | 3000 |
| Ceres Promoter pOsMEA | DNA | *Oryza sativa* | 190 | 2023 |
| Ceres Promoter pOsYp102 | DNA | *Oryza sativa* | 191 | 2034 |
| Ceres Promoter pOsYp285 | DNA | *Oryza sativa* | 192 | 1877 |
| Ceres Promoter PT0565 | DNA | *Arabidopsis thaliana* | 193 | 1000 |
| Ceres Promoter YP0015 | DNA | *Arabidopsis thaliana* | 194 | 999 |

TABLE 7-continued

| | | | | | | | | |
|---|---|---|---|---|---|---|---|---|
| | Ceres Promoter YP0087 | DNA | *Arabidopsis thaliana* | 195 | 999 | | | |
| | Ceres Promoter YP0093 | DNA | *Arabidopsis thaliana* | 196 | 1000 | | | |
| | Ceres Promoter YP0108 | DNA | *Arabidopsis thaliana* | 197 | 999 | | | |
| | Ceres Promoter YP0022 | DNA | *Arabidopsis thaliana* | 198 | 999 | | | |
| | Ceres Promoter YP0080 | DNA | *Arabidopsis thaliana* | 199 | 999 | | | |
| | Ceres Promoter PR0924 | DNA | *Arabidopsis thaliana* | 200 | 3000 | | | |
| | Ceres Promoter YP0388 | DNA | *Arabidopsis thaliana* | 201 | 1000 | | | |
| | Ceres Promoter PD0901 | DNA | *Arabidopsis thaliana* | 202 | 283 | | | |
| | Ceres Promoter PT0623 | DNA | *Arabidopsis thaliana* | 203 | 1000 | | | |
| Ceres Clone ID no. 2403 | Truncated version of Ceres CLONE ID no. 100021733 | PRT | Artificial Sequence | 204 | 33 | ubiquitin | | |
| Ceres Clone ID no. 2403 | Truncated version of Ceres CLONE ID no. 1036726 | PRT | Artificial Sequence | 205 | 33 | ubiquitin | | |
| Ceres Clone ID no. 2403 | Truncated version of Ceres CLONE ID no. 1482731 | PRT | Artificial Sequence | 206 | 33 | ubiquitin | | |
| Ceres Clone ID no. 30469 | Truncated Version of Ceres CLONE ID no. 1554560 | PRT | Artificial Sequence | 207 | 80 | Globin | | |
| Ceres Clone ID no. 30469 | Truncated Version of Ceres CLONE ID no. 1802327 | PRT | Artificial Sequence | 208 | 77 | Globin | | |
| Ceres Clone ID no. 30469 | Truncated Version of Ceres CLONE ID no. 1876458 | PRT | Artificial Sequence | 209 | 77 | Globin | | |
| Ceres Clone ID no. 30469 | Truncated Version of Ceres CLONE ID no. 1879148 | PRT | Artificial Sequence | 210 | 79 | Globin | | |
| Ceres Clone ID no. 2403 | Truncated version of Ceres CLONE ID no. 1884696 | PRT | Artificial Sequence | 211 | 33 | ubiquitin | | |
| Ceres Clone ID no. 30469 | Truncated Version of Ceres CLONE ID no. 1916866 | PRT | Artificial Sequence | 212 | 76 | Globin | | |
| Ceres Clone ID no. 2403 | Truncated version of Ceres CLONE ID no. 1950105 | PRT | Artificial Sequence | 213 | 33 | ubiquitin | | |
| Ceres Clone ID no. 30469 | Truncated Version of Ceres CLONE ID no. 1990746 | PRT | Artificial Sequence | 214 | 79 | Globin | | |
| Ceres Clone ID no. 30469 | Truncated Version of Ceres CLONE ID no. 2033803 | PRT | Artificial Sequence | 215 | 79 | Globin | | |
| Ceres Clone ID no. 2403 | Truncated version of Ceres CLONE ID no. 2034916 | PRT | Artificial Sequence | 216 | 33 | ubiquitin | | |
| Ceres Clone ID no. 2403 | Truncated version of Ceres CLONE ID no. 513071 | PRT | Artificial Sequence | 217 | 33 | ubiquitin | | |
| Ceres Clone ID no. 2403 | Truncated version of Ceres CLONE ID no. 522921 | PRT | Artificial Sequence | 218 | 33 | ubiquitin | | |
| Ceres Clone ID no. 30469 | Truncated Version of Ceres CLONE ID no. 546001 | PRT | Artificial Sequence | 219 | 76 | Globin | | |
| Ceres Clone ID no. 30469 | Truncated Version of Ceres CLONE ID no. 651581 | PRT | Artificial Sequence | 220 | 76 | Globin | | |
| Ceres Clone ID no. 30469 | Truncated Version of Ceres CLONE ID no. 839727 | PRT | Artificial Sequence | 221 | 77 | Globin | | |
| Ceres Clone ID no. 30469 | Truncated Version of Public GI ID no. 11095158 | PRT | Artificial Sequence | 222 | 76 | Globin | | |
| Ceres Clone ID no. 30469 | Truncated Version of Public GI ID no. 12963875 | PRT | Artificial Sequence | 223 | 71 | Globin | | |
| Ceres Clone ID no. 30469 | Truncated Version of Public GI ID no. 14701800 | PRT | Artificial Sequence | 224 | 84 | Globin | | |
| Ceres Clone ID no. 30469 | Truncated Version of Public GI ID no. 15226675 | PRT | Artificial Sequence | 225 | 76 | Globin | | |
| Ceres Clone ID no. 30469 | Truncated Version of Public GI ID no. 15824736 | PRT | Artificial Sequence | 226 | 76 | Globin | | |
| Ceres Clone ID no. 30469 | Truncated Version of Public GI ID no. 30909306 | PRT | Artificial Sequence | 227 | 76 | Globin | | |
| Ceres Clone ID no. 30469 | Truncated Version of Public GI ID no. 37903656 | PRT | Artificial Sequence | 228 | 73 | Globin | | |
| Ceres Clone ID no. 30469 | Truncated Version of Public GI ID no. 62548111 | PRT | Artificial Sequence | 229 | 76 | Globin | | |

| Query Identifier | Functional Homolog | Pfam Description | Start | End | Profile | HMM Bit Score | FL_Profile | FL_Score |
|---|---|---|---|---|---|---|---|---|
| Ceres CLONE ID no. 30087 | Ceres CLONE ID no. 30087 | | | | Y | | | |
| Ceres Clone ID no. 30087 | Ceres CLONE ID no. 947579 | | | | Y | | | |
| Ceres Clone ID no. 30087 | Public GI no. 62526422 | | | | | | | |
| Ceres Clone ID no. 30087 | Ceres CLONE ID no. 1606506 | | | | Y | | | |
| Ceres CLONE ID no. 30469 | Ceres CLONE ID no. 30469 | Globin | 13 | 74 | Y | 184.6 | | 66 |
| Ceres Clone ID no. 30469 | Ceres CLONE ID no. 30469_FL | Globin | 13 | 152 | | 184.6 | Y | 404.9 |
| Ceres Clone ID no. 30469 | Public GI no. 30909306 | Globin | 13 | 152 | | 185.7 | Y | 410.4 |
| Ceres Clone ID no. 30469 | Public GI no. 37903656 | Globin | 10 | 149 | | 172.6 | | 387.2 |
| Ceres Clone ID no. 30469 | Public GI no. 15824736 | Globin | 13 | 152 | | 184.2 | | 405.4 |
| Ceres Clone ID no. 30469 | Ceres CLONE ID no. 546001 | Globin | 13 | 152 | | 182.8 | Y | 402.3 |
| Ceres Clone ID no. 30469 | Public GI no. 11095158 | Globin | 13 | 152 | | 167.8 | | 387.2 |
| Ceres Clone ID no. 30469 | Public GI no. 12963875 | Globin | 8 | 147 | | 145.8 | | 337.1 |

TABLE 7-continued

| | | | | | | | | |
|---|---|---|---|---|---|---|---|---|
| Ceres Clone ID no. 30469 | Ceres CLONE ID no. 1554560 | Globin | 17 | 157 | | 185.7 | Y | 404.5 |
| Ceres Clone ID no. 30469 | Ceres CLONE ID no. 839727 | Globin | 14 | 154 | | 187.8 | Y | 415.2 |
| Ceres Clone ID no. 30469 | Public GI no. 14701800 | Globin | 21 | 161 | | 170.1 | | 386.9 |
| Ceres CLONE ID no. 271922 | Ceres CLONE ID no. 271922 | Ribosomal L37ae protein family | 2 | 91 | Y | 266.3 | | |
| Ceres Clone ID no. 271922 | Public GI no. 4090257 | Ribosomal L37ae protein family | 2 | 91 | | 265.8 | | |
| Ceres Clone ID no. 271922 | Public GI no. 4741896 | Ribosomal L37ae protein family | 2 | 91 | | 264 | | |
| Ceres Clone ID no. 271922 | Ceres CLONE ID no. 36046 | Ribosomal L37ae protein family | 2 | 91 | | 257.8 | | |
| Ceres Clone ID no. 271922 | Public GI no. 6016699 | Ribosomal L37ae protein family | 2 | 91 | | 257.4 | | |
| Ceres Clone ID no. 271922 | Ceres CLONE ID no. 664936 | Ribosomal L37ae protein family | 2 | 91 | Y | 268.8 | | |
| Ceres Clone ID no. 271922 | Ceres CLONE ID no. 658438 | Ribosomal L37ae protein family | 2 | 91 | | 269 | | |
| Ceres Clone ID no. 271922 | Ceres CLONE ID no. 1049262 | Ribosomal L37ae protein family | 2 | 91 | | 268.9 | | |
| Ceres Clone ID no. 271922 | Ceres CLONE ID no. 632613 | Ribosomal L37ae protein family | 2 | 91 | Y | 269 | | |
| Ceres Clone ID no. 271922 | Ceres CLONE ID no. 1390976 | Ribosomal L37ae protein family | 2 | 91 | Y | 269 | | |
| Ceres Clone ID no. 271922 | Ceres CLONE ID no. 1457185 | Ribosomal L37ae protein family | 2 | 91 | | 269 | | |
| Ceres Clone ID no. 271922 | Public GI no. 56202147 | Ribosomal L37ae protein family | 2 | 91 | | 269 | | |
| Ceres Clone ID no. 271922 | Public GI no. 58578274 | Ribosomal L37ae protein family | 2 | 91 | | 267.2 | | |
| Ceres CLONE ID no. 2403 | Ceres CLONE ID no. 2403_FL | Ubiquitin family | 1 | 74 | | 118.7 | | 416.2 |
| Ceres CLONE ID no. 2403 | Ceres CLONE ID no. 2403_FL | Ubiquitin family | 77 | 150 | | 118.7 | Y | 416.2 |
| Ceres Clone ID no. 2403 | Ceres CLONE ID no. 1482731 | Ubiquitin family | 1 | 74 | | 118.3 | Y | 417 |
| Ceres Clone ID no. 2403 | Ceres CLONE ID no. 1482731 | Ubiquitin family | 77 | 150 | | 118.3 | Y | 417 |
| Ceres Clone ID no. 2403 | Ceres CLONE ID no. 522921 | Ubiquitin family | 1 | 74 | | 118.7 | Y | 418.4 |
| Ceres Clone ID no. 2403 | Ceres CLONE ID no. 522921 | Ubiquitin family | 77 | 150 | | 118.7 | Y | 418.4 |
| Ceres Clone ID no. 2403 | Ceres CLONE ID no. 1036726 | Ubiquitin family | 1 | 74 | | 118.7 | Y | 384.4 |
| Ceres Clone ID no. 2403 | Ceres CLONE ID no. 1036726 | Ubiquitin family | 77 | 142 | | 118.7 | Y | 384.4 |
| Ceres Clone ID no. 2403 | Ceres CLONE ID no. 513071 | Ubiquitin family | 1 | 74 | | 114.3 | | 408.6 |
| Ceres Clone ID no. 2403 | Ceres CLONE ID no. 513071 | Ubiquitin family | 77 | 150 | | 114.3 | | 408.6 |
| Ceres CLONE ID no. 2403 | Ceres CLONE ID no. 2403 | Ubiquitin family | 1 | 33 | Y | 87.6 | | −83.1 |
| Ceres CLONE ID no. 674166 | Ceres CLONE ID no. 674166 | AP2 domain | 26 | 89 | Y | 491.8 | | |
| Ceres Clone ID no. 674166 | Public GI no. 12322345 | AP2 domain | 26 | 89 | | 522.4 | | |
| Ceres Clone ID no. 674166 | Ceres CLONE ID no. 975672 | AP2 domain | 21 | 84 | Y | 481.7 | | |
| Ceres Clone ID no. 674166 | Ceres CLONE ID no. 273307 | AP2 domain | 17 | 80 | Y | 419.7 | | |
| Ceres Clone ID no. 674166 | Ceres CLONE ID no. 1055099 | AP2 domain | 20 | 83 | Y | 358.4 | | |
| Ceres ANNOT ID no. 1441430 | Ceres ANNOT ID no. 1441430 | AP2 domain | 29 | 92 | Y | 504.4 | | |
| Ceres CLONE ID no. 674166 | Ceres CLONE ID no. 1240330 | AP2 domain | 24 | 87 | | 483.3 | | |
| Ceres CLONE ID no. 30087 | Ceres CLONE ID no. 1382611 | | | | Y | | | |
| Ceres CLONE ID no. 271922 | Ceres CLONE ID no. 1627907 | Ribosomal L37ae protein family | 2 | 91 | Y | 268.1 | | |
| Ceres CLONE ID no. 674166 | Ceres CLONE ID no. 1761125 | AP2 domain | 13 | 76 | Y | 363 | | |
| Ceres CLONE ID no. 271922 | Ceres CLONE ID no. 1783890 | Ribosomal L37ae protein family | 2 | 91 | Y | 269 | | |

TABLE 7-continued

| | | | | | | | | |
|---|---|---|---|---|---|---|---|---|
| Ceres Clone ID no. 30469 | Ceres CLONE ID no. 1802327 | Globin | 14 | 154 | | 191.4 | Y | 417.9 |
| Ceres CLONE ID no. 674166 | Ceres CLONE ID no. 1838364 | AP2 domain | 28 | 91 | Y | 484.1 | | |
| Ceres Clone ID no. 30469 | Ceres CLONE ID no. 1876458 | Globin | 14 | 154 | | 191.9 | | 415.3 |
| Ceres Clone ID no. 30469 | Ceres CLONE ID no. 1879148 | Globin | 16 | 156 | | 185.7 | | 411.2 |
| Ceres CLONE ID no. 2403 | Ceres CLONE ID no. 1884696 | Ubiquitin family | 1 | 74 | | 175.2 | Y | 408 |
| Ceres CLONE ID no. 2403 | Ceres CLONE ID no. 1884696 | Ubiquitin family | 77 | 150 | | 175.2 | Y | 408 |
| Ceres Clone ID no. 30469 | Ceres CLONE ID no. 1916866 | Globin | 13 | 152 | | 188.3 | Y | 409.8 |
| Ceres CLONE ID no. 2403 | Ceres CLONE ID no. 1950105 | Ubiquitin family | 1 | 74 | | 262.8 | | 504.1 |
| Ceres CLONE ID no. 2403 | Ceres CLONE ID no. 1950105 | Ubiquitin family | 77 | 150 | | 262.8 | | 504.1 |
| Ceres CLONE ID no. 2403 | Ceres CLONE ID no. 1950105 | Ubiquitin family | 153 | 226 | | 262.8 | | 504.1 |
| Ceres Clone ID no. 30469 | Ceres CLONE ID no. 1990746 | Globin | 16 | 156 | | 184.9 | | 405.6 |
| Ceres CLONE ID no. 674166 | Ceres CLONE ID no. 2007485 | AP2 domain | 17 | 80 | | 271.2 | | 369.2 |
| Ceres Clone ID no. 30469 | Ceres CLONE ID no. 2033803 | Globin | 16 | 148 | | 184.9 | | 369.2 |
| Ceres CLONE ID no. 2403 | Ceres CLONE ID no. 2034916 | Ubiquitin family | 1 | 74 | | 259.2 | Y | 460.4 |
| Ceres CLONE ID no. 2403 | Ceres CLONE ID no. 2034916 | Ubiquitin family | 77 | 150 | | 259.2 | Y | 460.4 |
| Ceres CLONE ID no. 2403 | Ceres CLONE ID no. 2034916 | Ubiquitin family | 153 | 213 | | 259.2 | Y | 460.4 |
| Ceres CLONE ID no. 674166 | Ceres CLONE ID no. 651581 | AP2 domain | 24 | 87 | | 469.5 | | |
| Ceres CLONE ID no. 674166 | Public GI ID no. 125550159 | AP2 domain | 7 | 70 | Y | 344 | | |
| Ceres CLONE ID no. 674166 | Public GI ID no. 15223609 | AP2 domain | 26 | 89 | Y | 522.4 | | |
| Ceres CLONE ID no. 30087 | Public GI ID no. 30683885 | | | | | | | |
| Ceres CLONE ID no. 674166 | Public GI ID no. 56384582 | AP2 domain | 21 | 84 | Y | 484.2 | | |
| Ceres CLONE ID no. 674166 | Public GI ID no. 57012880 | AP2 domain | 26 | 89 | Y | 521.4 | | |
| Ceres Clone ID no. 30469 | Public GI ID no. 62548111 | Globin | 13 | 152 | | 188.3 | | 409.8 |
| Ceres CLONE ID no. 2403 | Ceres CLONE ID no. 100021733 | Ubiquitin family | 1 | 74 | | 175.2 | | 410.3 |
| Ceres CLONE ID no. 2403 | Ceres CLONE ID no. 100021733 | Ubiquitin family | 77 | 150 | | 175.2 | | 410.3 |
| | Ceres CLONE ID no. 947579 | | | | | | | |
| | Ceres CLONE ID no. 36046 | | | | | | | |
| | Ceres CLONE ID no. 1606506 | | | | | | | |
| | Ceres CLONE ID no. 546001 | | | | | | | |
| | Ceres CLONE ID no. 1554560 | | | | | | | |
| | Ceres CLONE ID no. 839727 | | | | | | | |
| | Ceres CLONE ID no. 664936 | | | | | | | |
| | Ceres CLONE ID no. 658438 | | | | | | | |
| | Ceres CLONE ID no. 1049262 | | | | | | | |
| | Ceres CLONE ID no. 632613 | | | | | | | |
| | Ceres CLONE ID no. 1390976 | | | | | | | |
| | Ceres CLONE ID no. 1457185 | | | | | | | |
| | Ceres CLONE ID no. 1482731 | | | | | | | |
| | Ceres CLONE ID no. 522921 | | | | | | | |
| | Ceres CLONE ID no. 1036726 | | | | | | | |
| | Ceres CLONE ID no. 513071 | | | | | | | |
| | Ceres CLONE ID no. 975672 | | | | | | | |
| | Ceres CLONE ID no. 273307 | | | | | | | |
| | Ceres CLONE ID no. 1055099 | | | | | | | |
| Ceres Clone ID no. 30469 | Ceres GI ID no. GI_15226675 | Globin | 13 | 152 | | 184.6 | | 404.9 |
| | Ceres Promoter 21876 | | | | | | | |
| | Ceres Promoter PT0668 | | | | | | | |
| | Ceres Promoter PT0535 | | | | | | | |
| | Ceres Promoter PT0585 | | | | | | | |
| | Ceres Promoter PT0613 | | | | | | | |
| | Ceres Promoter PT0625 | | | | | | | |
| | Ceres Promoter PT0633 | | | | | | | |
| | Ceres Promoter PT0650 | | | | | | | |
| | Ceres Promoter PT0660 | | | | | | | |
| | Ceres Promoter PT0665 | | | | | | | |
| | Ceres Promoter PT0672 | | | | | | | |
| | Ceres Promoter PT0676 | | | | | | | |
| | Ceres Promoter PT0678 | | | | | | | |
| | Ceres Promoter PT0683 | | | | | | | |
| | Ceres Promoter PT0688 | | | | | | | |
| | Ceres Promoter PT0695 | | | | | | | |
| | Ceres Promoter PT0708 | | | | | | | |
| | Ceres Promoter PT0710 | | | | | | | |
| | Ceres Promoter PT0723 | | | | | | | |
| | Ceres Promoter PT0740 | | | | | | | |
| | Ceres Promoter PT0743 | | | | | | | |
| | Ceres Promoter PT0758 | | | | | | | |
| | Ceres Promoter PT0829 | | | | | | | |
| | Ceres Promoter PT0837 | | | | | | | |

TABLE 7-continued

| | | | | | | |
|---|---|---|---|---|---|---|
| | Ceres Promoter PT0838 | | | | | |
| | Ceres Promoter PT0848 | | | | | |
| | Ceres Promoter PT0863 | | | | | |
| | Ceres Promoter PT0879 | | | | | |
| | Ceres Promoter PT0886 | | | | | |
| | Ceres Promoter YP0007 | | | | | |
| | Ceres Promoter YP0008 | | | | | |
| | Ceres Promoter YP0019 | | | | | |
| | Ceres Promoter YP0028 | | | | | |
| | Ceres Promoter YP0039 | | | | | |
| | Ceres Promoter YP0050 | | | | | |
| | Ceres Promoter YP0086 | | | | | |
| | Ceres Promoter YP0088 | | | | | |
| | Ceres Promoter YP0092 | | | | | |
| | Ceres Promoter YP0096 | | | | | |
| | Ceres Promoter YP0097 | | | | | |
| | Ceres Promoter YP0101 | | | | | |
| | Ceres Promoter YP0102 | | | | | |
| | Ceres Promoter YP0103 | | | | | |
| | Ceres Promoter YP0107 | | | | | |
| | Ceres Promoter YP0110 | | | | | |
| | Ceres Promoter YP0111 | | | | | |
| | Ceres Promoter YP0115 | | | | | |
| | Ceres Promoter YP0117 | | | | | |
| | Ceres Promoter YP0119 | | | | | |
| | Ceres Promoter YP0120 | | | | | |
| | Ceres Promoter YP0121 | | | | | |
| | Ceres Promoter YP0128 | | | | | |
| | Ceres Promoter YP0137 | | | | | |
| | Ceres Promoter YP0143 | | | | | |
| | Ceres Promoter YP0144 | | | | | |
| | Ceres Promoter YP0156 | | | | | |
| | Ceres Promoter YP0158 | | | | | |
| | Ceres Promoter YP0188 | | | | | |
| | Ceres Promoter YP0190 | | | | | |
| | Ceres Promoter YP0212 | | | | | |
| | Ceres Promoter YP0214 | | | | | |
| | Ceres Promoter YP0263 | | | | | |
| | Ceres Promoter YP0275 | | | | | |
| | Ceres Promoter YP0285 | | | | | |
| | Ceres Promoter YP0286 | | | | | |
| | Ceres Promoter YP0337 | | | | | |
| | Ceres Promoter YP0356 | | | | | |
| | Ceres Promoter YP0374 | | | | | |
| | Ceres Promoter YP0377 | | | | | |
| | Ceres Promoter YP0380 | | | | | |
| | Ceres Promoter YP0381 | | | | | |
| | Ceres Promoter YP0384 | | | | | |
| | Ceres Promoter YP0385 | | | | | |
| | Ceres Promoter YP0396 | | | | | |
| | Ceres Promoter p13879 | | | | | |
| | Ceres Promoter p326 | | | | | |
| | Ceres Promoter p32449 | | | | | |
| | Ceres Promoter PD1367 | | | | | |
| | Ceres Promoter p530c10 | | | | | |
| | Ceres Promoter pOsFIE2-2 | | | | | |
| | Ceres Promoter pOsMEA | | | | | |
| | Ceres Promoter pOsYp102 | | | | | |
| | Ceres Promoter pOsYp285 | | | | | |
| | Ceres Promoter PT0565 | | | | | |
| | Ceres Promoter YP0015 | | | | | |
| | Ceres Promoter YP0087 | | | | | |
| | Ceres Promoter YP0093 | | | | | |
| | Ceres Promoter YP0108 | | | | | |
| | Ceres Promoter YP0022 | | | | | |
| | Ceres Promoter YP0080 | | | | | |
| | Ceres Promoter PR0924 | | | | | |
| | Ceres Promoter YP0388 | | | | | |
| | Ceres Promoter PD0901 | | | | | |
| | Ceres Promoter PT0623 | | | | | |
| Ceres Clone ID no. 2403 | Truncated version of Ceres CLONE ID no. 100021733 | Ubiquitin family | 1 | 33 | | 87.6 | −83.1 |
| Ceres Clone ID no. 2403 | Truncated version of Ceres CLONE ID no. 1036726 | Ubiquitin family | 1 | 33 | Y | 87.6 | −83.1 |
| Ceres Clone ID no. 2403 | Truncated version of Ceres CLONE ID no. 1482731 | Ubiquitin family | 1 | 33 | Y | 87.1 | −85 |
| Ceres Clone ID no. 30469 | Truncated Version of Ceres CLONE ID no. 1554560 | Globin | 17 | 78 | Y | 185.7 | 61.3 |
| Ceres Clone ID no. 30469 | Truncated Version of Ceres CLONE ID no. 1802327 | Globin | 14 | 75 | Y | 191.4 | 67.2 |

TABLE 7-continued

| Ceres Clone ID no. 30469 | Truncated Version of Ceres CLONE ID no. 1876458 | Globin | 14 | 75 | | 191.9 | 67.7 |
|---|---|---|---|---|---|---|---|
| Ceres Clone ID no. 30469 | Truncated Version of Ceres CLONE ID no. 1879148 | Globin | 16 | 77 | | 185.7 | 61.3 |
| Ceres Clone ID no. 2403 | Truncated version of Ceres CLONE ID no. 1884696 | Ubiquitin family | 1 | 33 | Y | 87.6 | 65 |
| Ceres Clone ID no. 30469 | Truncated Version of Ceres CLONE ID no. 1916866 | Globin | 13 | 74 | Y | 188.3 | 65 |
| Ceres Clone ID no. 2403 | Truncated version of Ceres CLONE ID no. 1950105 | Ubiquitin family | 1 | 33 | Y | 87.6 | 60.7 |
| Ceres Clone ID no. 30469 | Truncated Version of Ceres CLONE ID no. 1990746 | Globin | 16 | 77 | | 184.9 | 60.7 |
| Ceres Clone ID no. 30469 | Truncated Version of Ceres CLONE ID no. 2033803 | Globin | 16 | 77 | | 184.9 | 60.7 |
| Ceres Clone ID no. 2403 | Truncated version of Ceres CLONE ID no. 2034916 | Ubiquitin family | 1 | 33 | | 87.6 | 63.3 |
| Ceres Clone ID no. 2403 | Truncated version of Ceres CLONE ID no. 513071 | Ubiquitin family | 1 | 33 | | 85.9 | 44.7 |
| Ceres Clone ID no. 2403 | Truncated version of Ceres CLONE ID no. 522921 | Ubiquitin family | 1 | 33 | Y | 87.6 | 22.4 |
| Ceres Clone ID no. 30469 | Truncated Version of Ceres CLONE ID no. 546001 | Globin | 13 | 74 | Y | 182.8 | 59.6 |
| Ceres Clone ID no. 30469 | Truncated Version of Ceres CLONE ID no. 651581 | Globin | 13 | 74 | | 185.7 | 63.9 |
| Ceres Clone ID no. 30469 | Truncated Version of Ceres CLONE ID no. 839727 | Globin | 14 | 75 | Y | 187.8 | 63.3 |
| Ceres Clone ID no. 30469 | Truncated Version of Public GI ID no. 11095158 | Globin | 13 | 76 | | 167.8 | 44.7 |
| Ceres Clone ID no. 30469 | Truncated Version of Public GI ID no. 12963875 | Globin | 8 | 69 | | 145.8 | 22.4 |
| Ceres Clone ID no. 30469 | Truncated Version of Public GI ID no. 14701800 | Globin | 21 | 82 | | 170.1 | 45.8 |
| Ceres Clone ID no. 30469 | Truncated Version of Public GI ID no. 15226675 | Globin | 13 | 74 | | 184.6 | 63 |
| Ceres Clone ID no. 30469 | Truncated Version of Public GI ID no. 15824736 | Globin | 13 | 74 | | 184.2 | 60.9 |
| Ceres Clone ID no. 30469 | Truncated Version of Public GI ID no. 30909306 | Globin | 13 | 74 | Y | 185.7 | 63.9 |
| Ceres Clone ID no. 30469 | Truncated Version of Public GI ID no. 37903656 | Globin | 10 | 71 | | 172.6 | 49.6 |
| Ceres Clone ID no. 30469 | Truncated Version of Public GI ID no. 62548111 | Globin | 13 | 74 | | 188.3 | 65 |

The invention claimed is:

1. A method of producing a transgenic plant with increased cold tolerance, said method comprising:
   growing plant cells transformed with an exogenous nucleic acid, wherein said exogenous nucleic acid comprising a polynucleotide having a nucleotide sequence encoding a polypeptide having at least 95% amino acid sequence identity to SEQ ID NO: 2, and wherein said nucleotide sequence is operably linked to a heterologous promoter;
   producing transgenic plants from said transformed plant cells; and
   selecting for a transgenic plant from said transgenic plants that overexpresses said polypeptide in the selected transgenic plant and which exhibits an increased level of cold tolerance as compared to a control plant of the same plant species that does not comprise said exogenous nucleic acid.

2. The method of claim 1, wherein said polypeptide comprises the amino acid sequence of SEQ ID NO: 2.

3. The method of claim 1, wherein said nucleotide sequence has at least 95% nucleotide sequence identity to the nucleotide sequence of SEQ ID NO: 1.

4. The method of claim 1, wherein said polypeptide has at least 97% amino acid sequence identity to the amino acid sequence of SEQ ID NO: 2.

5. The method of claim 1, wherein said polypeptide has at least 99% amino acid sequence identity to the amino acid sequence of SEQ ID NO: 2.

6. The method of claim 1, wherein said nucleotide sequence has the nucleotide sequence of SEQ ID NO: 1.

7. The method of claim 1, wherein said transgenic plant is a member of a species selected from the group consisting of *Panicum virgatum, Sorghum bicolor, Miscanthus giganteus, Saccharum* sp., *Populus balsamifera, Zea mays, Glycine max, Brassica napus, Triticum aestivum, Gossypium hirsutum, Oryza sativa, Helianthus annuus, Medicago sativa, Beta vulgaris*, and *Pennisetum glaucum*.

* * * * *